(12) United States Patent
Purkayastha et al.

(10) Patent No.: US 8,236,565 B2
(45) Date of Patent: Aug. 7, 2012

(54) TAGGING REAGENTS AND METHODS FOR HYDROXYLATED COMPOUNDS

(75) Inventors: Subhasish Purkayastha, Acton, MA (US); Subhakar Dey, N. Billerice, MA (US); Sasi Pillai, Littleton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 1372 days.

(21) Appl. No.: 11/754,929

(22) Filed: May 29, 2007

(65) Prior Publication Data

US 2008/0014642 A1 Jan. 17, 2008

Related U.S. Application Data

(60) Provisional application No. 60/809,133, filed on May 26, 2006.

(51) Int. Cl.
*G01N 37/00* (2006.01)
(52) U.S. Cl. ............ 436/56; 560/330; 544/59; 544/171; 544/399; 546/248
(58) Field of Classification Search .................. 544/400
See application file for complete search history.

(56) References Cited

U.S. PATENT DOCUMENTS

| | | | |
|---|---|---|---|
| 2,429,171 A | | 10/1947 | Ruzicka et al. |
| 4,036,850 A | * | 7/1977 | Enders ...................... 548/321.1 |
| 4,707,226 A | * | 11/1987 | Dapperheld ................. 205/440 |
| 5,705,610 A | | 1/1998 | Zuckermann et al. |
| 5,800,992 A | | 9/1998 | Foder et al. |
| 6,027,890 A | | 2/2000 | Van Ness et al. |
| 6,270,976 B1 | | 8/2001 | Schmidt et al. |
| 6,287,780 B1 | | 9/2001 | Schmidt et al. |
| 6,475,807 B1 | | 11/2002 | Geysen et al. |
| 7,355,045 B2 | * | 4/2008 | Dey et al. .................... 544/399 |
| 7,910,059 B2 | * | 3/2011 | Pappin et al. ................ 422/430 |
| 7,947,513 B2 | * | 5/2011 | Pappin et al. ................ 436/544 |
| 2004/0220412 A1 | * | 11/2004 | Pappin et al. ................ 548/542 |
| 2005/0148087 A1 | * | 7/2005 | Pappin et al. ................ 436/86 |

FOREIGN PATENT DOCUMENTS

| | | |
|---|---|---|
| WO | WO 98/31830 A | 7/1998 |
| WO | WO 2004/019000 A | 3/2004 |
| WO | WO 2004/070352 A | 8/2004 |
| WO | WO 2004/090525 A | 10/2004 |
| WO | WO 2005/068446 A | 7/2005 |

OTHER PUBLICATIONS

H.T. Vakos et al., Journal of Protein Chemistry, 19(3), 231-237 (2000).*
P. Zlatoidsky et al., Eur. J. Med. Chem. 34, 1023-1034 (1999).*
P.V. Vodicka et al, Chirality, 17, 378-387 (2005).*
Bottari P et al: "Design and Synthesis of Visible Isotope-Coded Affinity Tags for the Absolute Quantification of Specific proteins in Complex Mixtures" Bioconjugate Chemistry, ACS, Washington, D.C., U.S. vol. 15, No. 2, Feb. 21, 2004, pp. 380-388.
Dunayevskiy, Yuriy M.: "Application of Capillary Electrophoresis-Electrospray ionization Mass Spectrometry in the Determination of Molecular Diversity"; PNAS 1996, Proc. Natl. Acad. Sci. USA 93—Boston, MA, Jan. 30, 1996, pp. 6152-6157.
Gygi S P et al: "Quantitative Analysis of Complex Protein Mixtures using Isotope-Coded Affinity Tags" Nature Biotechnology, nature Publishing Group, New York, NY, U.S. vol. 17, No. 10, Oct. 1, 1999, pp. 994-999.
Database Beilstein [online] Beilstein Institute for Organic Chemistry, Frankfurt-Main, DE; XP002468229 accession No. BRN: 6136406 abstract & S.V. Baires et al: BULL. Acad.Sci.USSR Div.Chem.Sci., vol. 35, No. 1, 1986, pp. 203-206.
Fredline V. F. et al: A Reference Method for the Analysis of Aldosterone in Blood by High-Performance Liquid Chromatography-Atmospheric Pressure Chemical Ionization-Tandem Mass Spectrometry; Analystical Biochemistry, Academic Press, San Diego, CA, US, vol. 252, No. 2, 1997, pp. 208-313, XP002289527 ISSN: 0003-2697.
Kissmeyer A-M et al: Determination of the Vitamin D Analog EB 1089 (Seocalcitol) in Human and Pig Serum Using Liquid Chromatography-Tandem Mass Spectrometry; Journal of Chromatography. Biomedical Applications, Elsevier, Amsterdam, NL, vol. 740, No. 1, Mar. 2000, pp. 117-128, XP004193057 ISSN: 0378-4347.
Vogeser M et al: Determination of Serum Cortisol by Isotope-Dilution Liquid-Chromatography Electrospray Ionization Tandem Mass Spectrometry With On-Line Extraction; Clinical Chemistry and Laboratory Medicine, Walter De Gruyter Und Co, DE, vol. 39, No. 10, Oct. 2001, pp. 944-947, XP009034269 ISSN: 1434-6621.

* cited by examiner

*Primary Examiner* — James O Wilson
*Assistant Examiner* — Alexander R Pagano

(57) ABSTRACT

In various aspects, the present teachings provide labeling reagents and sets of labeling reagents for the relative quantitation, absolute quantitation, or both, of hydroxylated compounds including, but not limited to, hydroxylated ring containing compounds, steroids and sterols. In various aspects, the present teachings also provide methods for the analysis hydroxylated compounds including, but not limited to, hydroxylated ring containing compounds, steroids and sterols my MS/MS methods.

22 Claims, 93 Drawing Sheets

Cholesterol

Androsterone

Estradiol

Prednisone

Testosterone (17–β)
EpiTestosterone (17–α)

Vitamin D

25(OH) Vitamin D 1,25(OH)$_2$-Vitamin D

Prostaglandin E2

Prostaglandin E1

Prostaglandin F2a

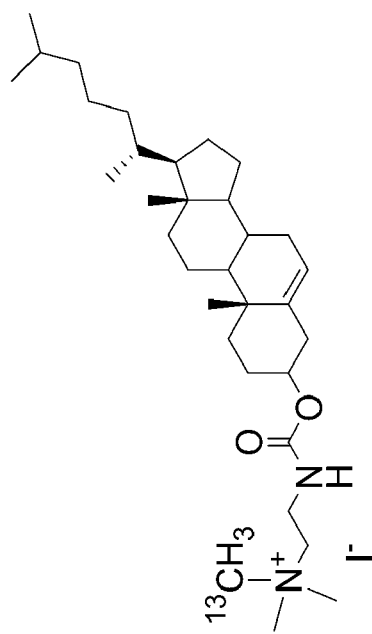
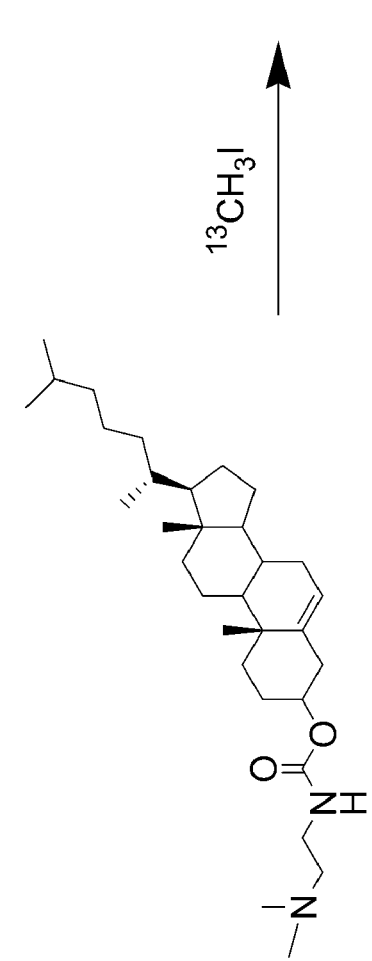
FIGURE 6C

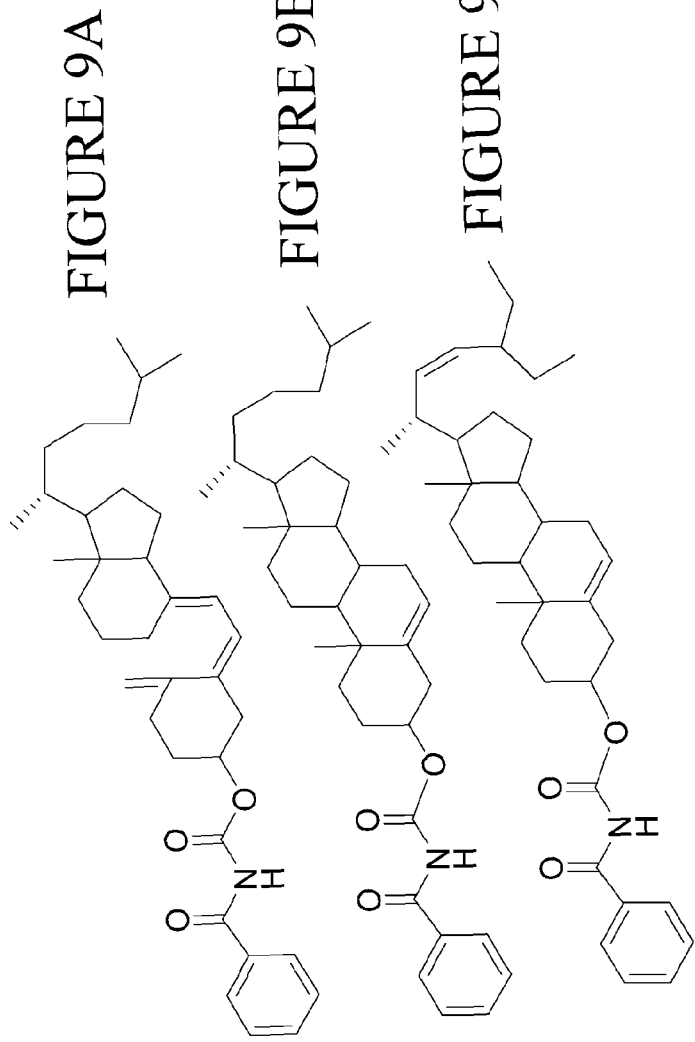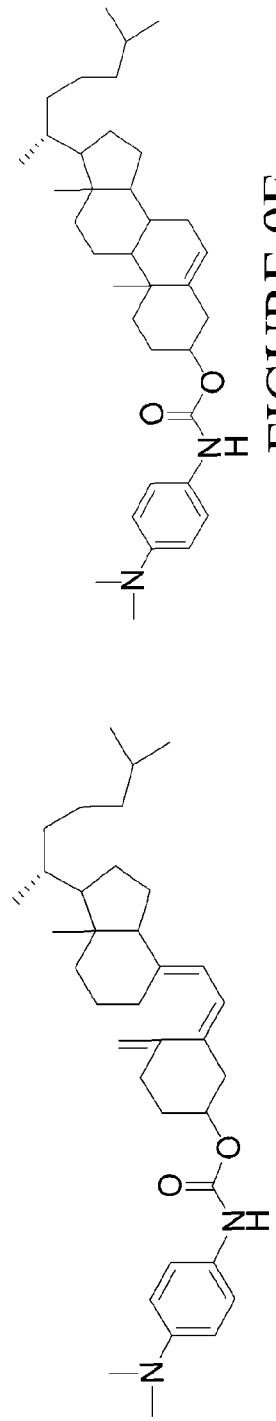
FIGURE 9A
FIGURE 9B
FIGURE 9C
FIGURE 9D
FIGURE 9E

FIGURE 11
Scheme 1101
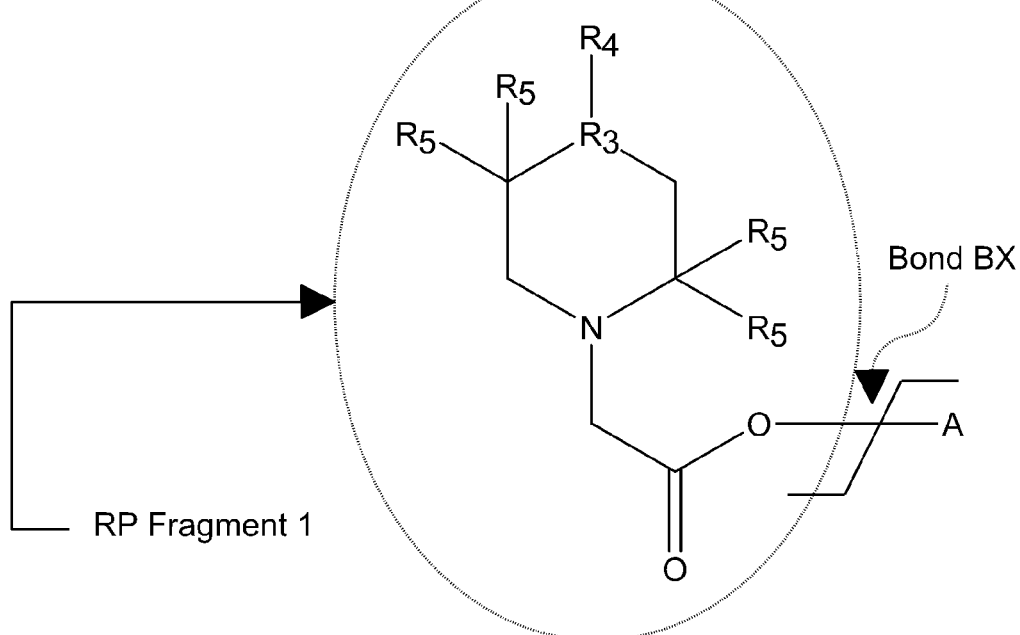
RP Fragment 1
Scheme 1102
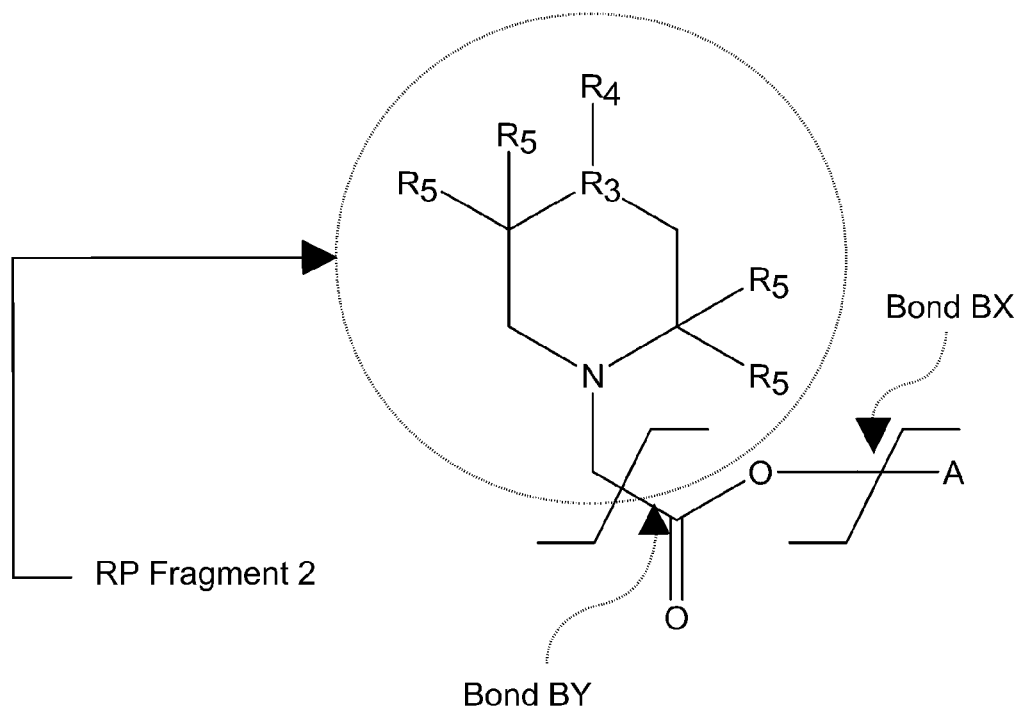
RP Fragment 2
= Fragmentation of bond

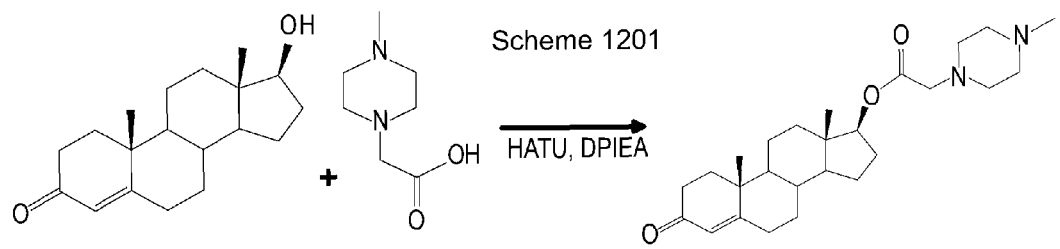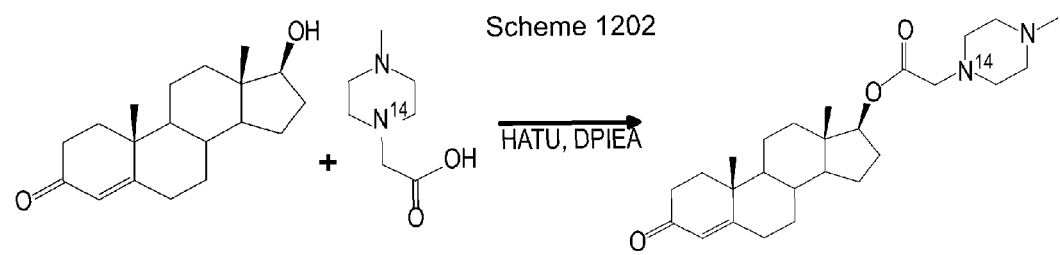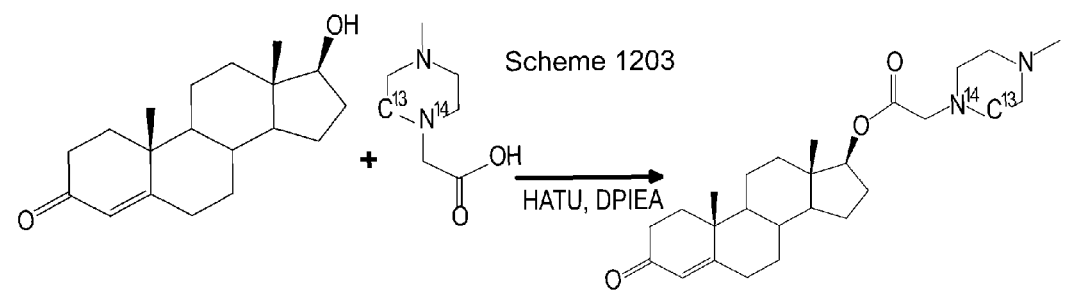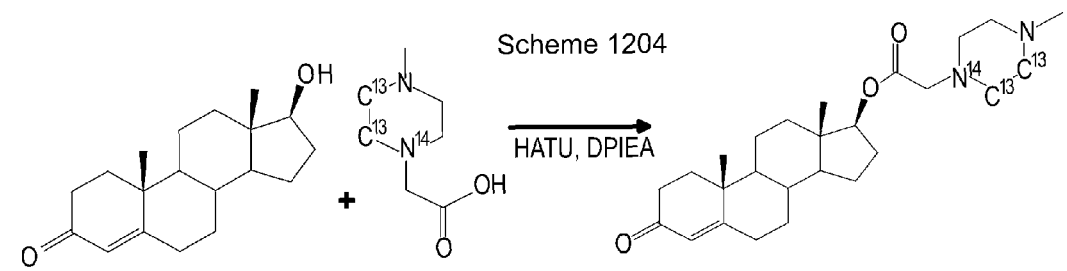
FIGURE 12A

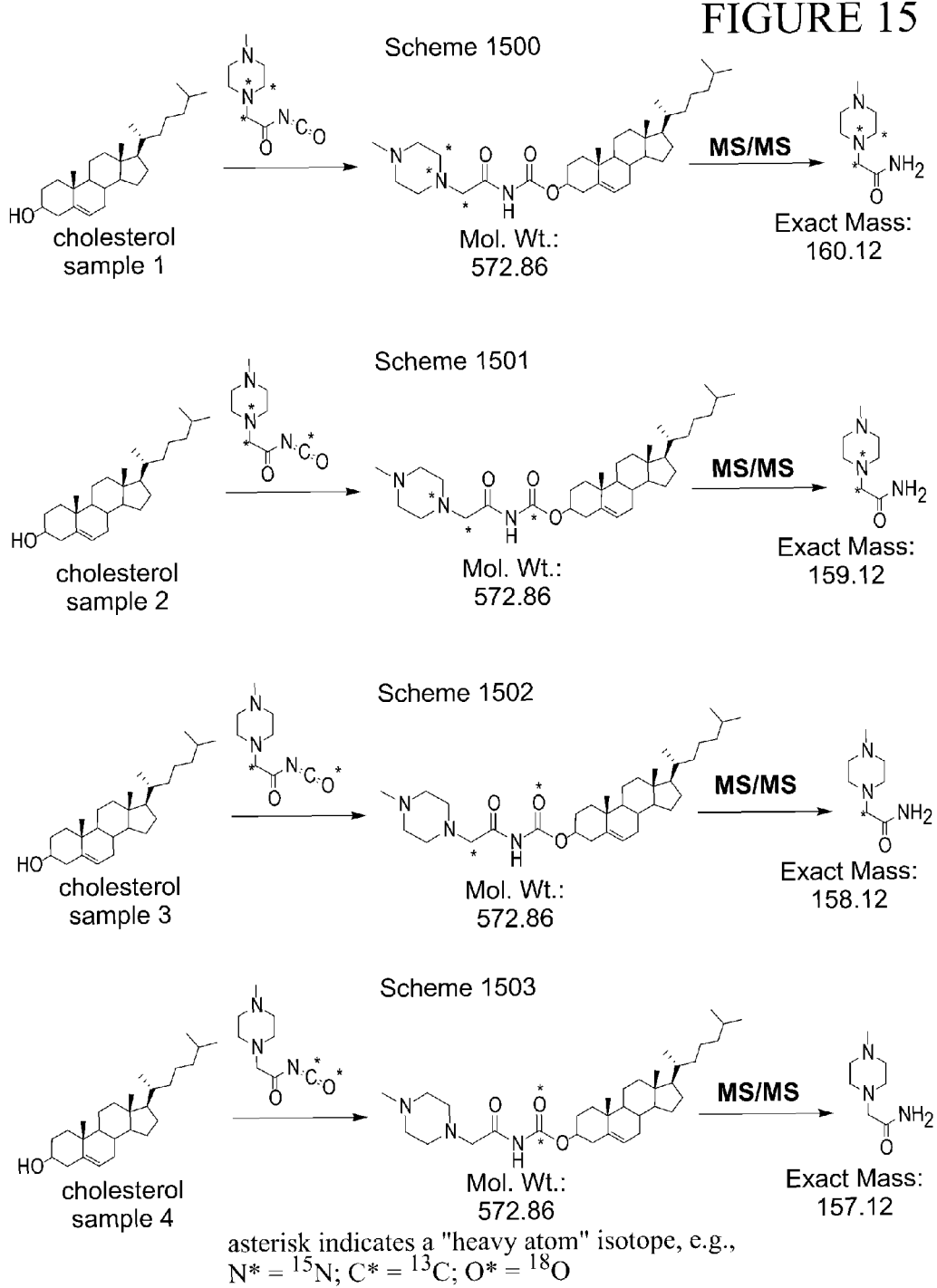

Scheme 1800
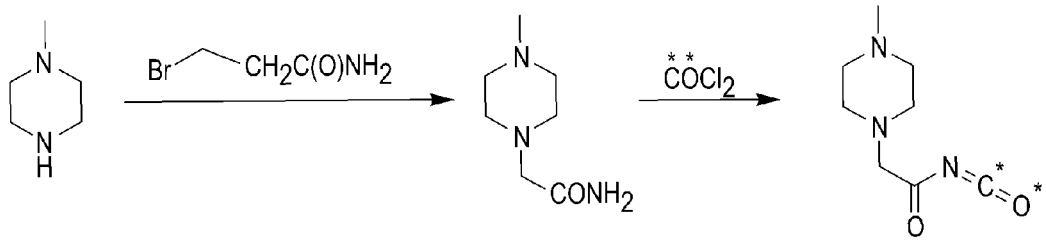
Scheme 1801
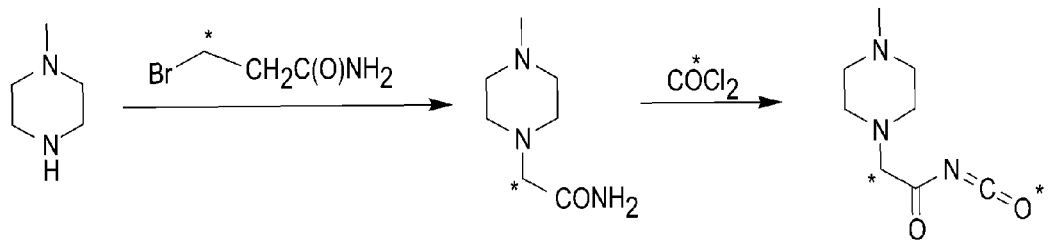
Scheme 1802
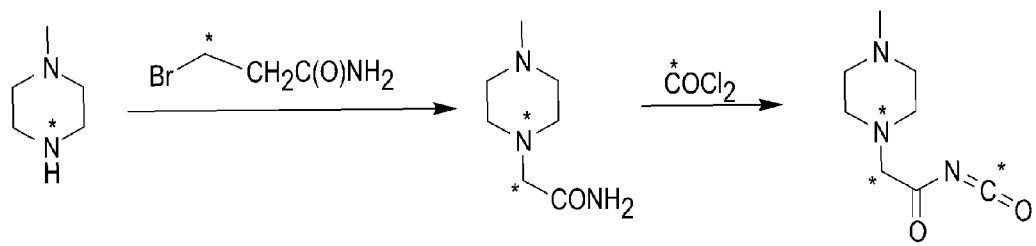
Scheme 1803
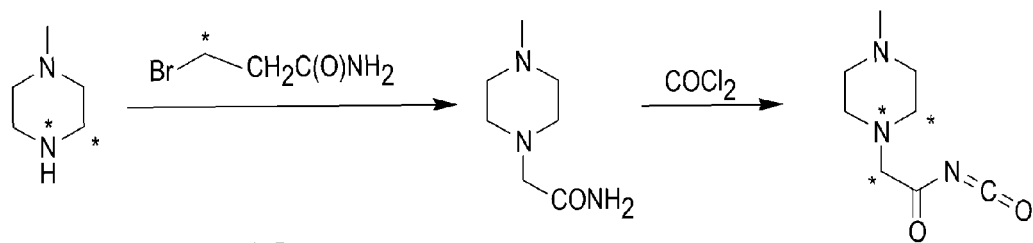
FIGURE 18
asterisk indicates a "heavy atom" isotope, e.g.,
N* = $^{15}$N; C* = $^{13}$C; O* = $^{18}$O

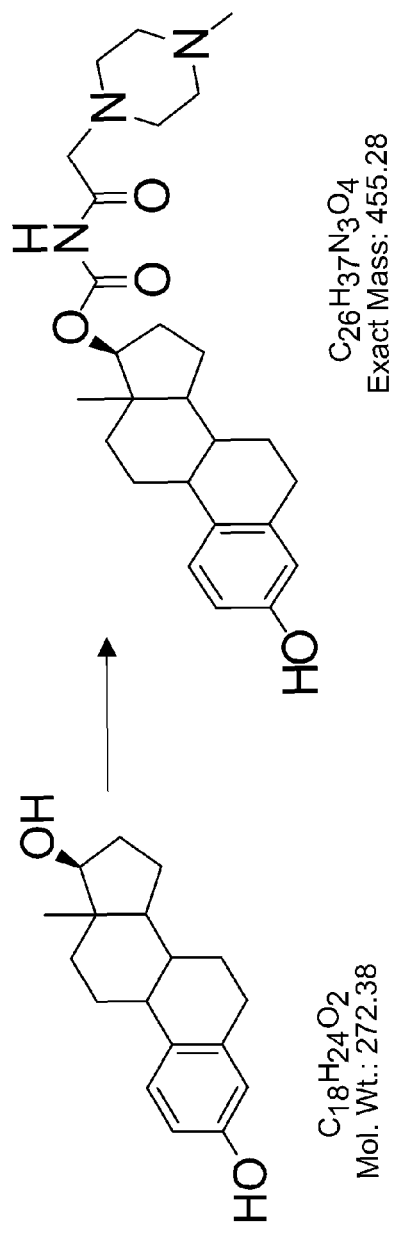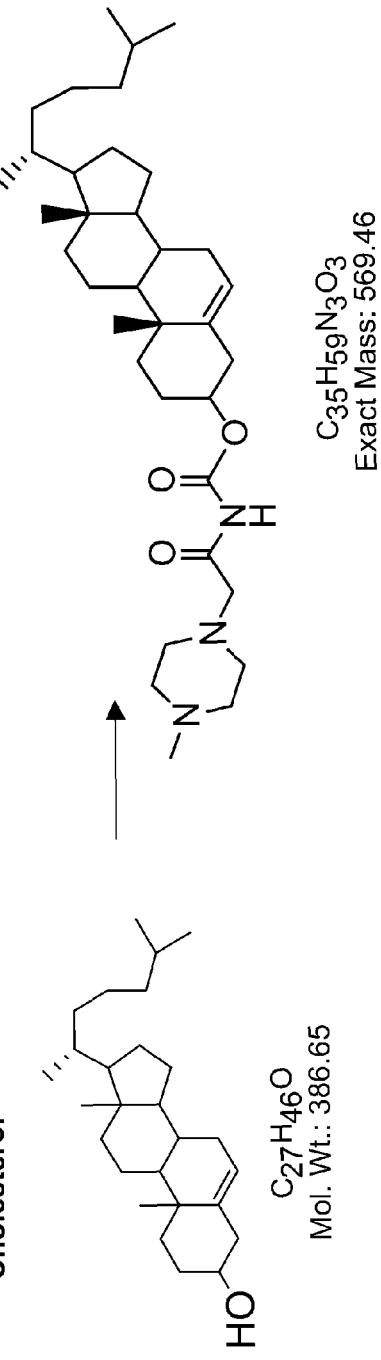

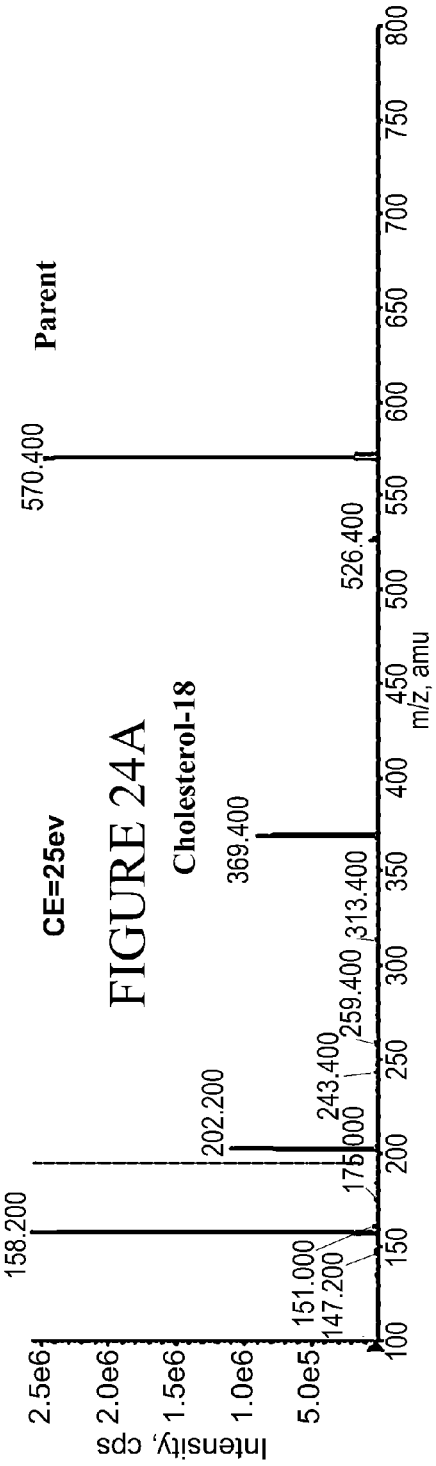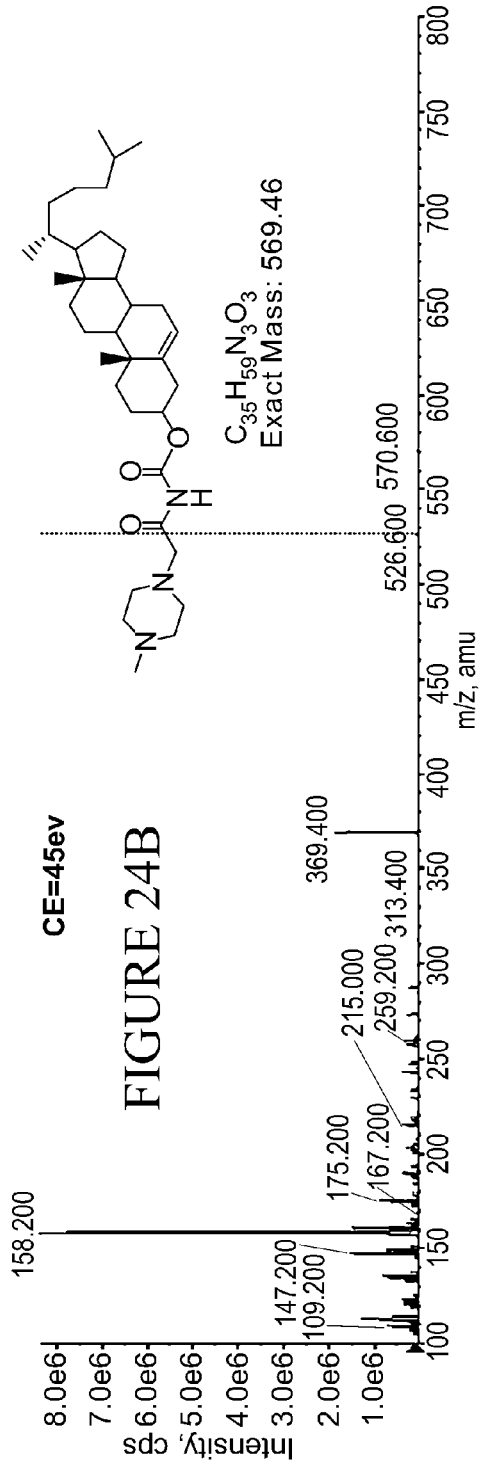
FIGURE 24A
FIGURE 24B

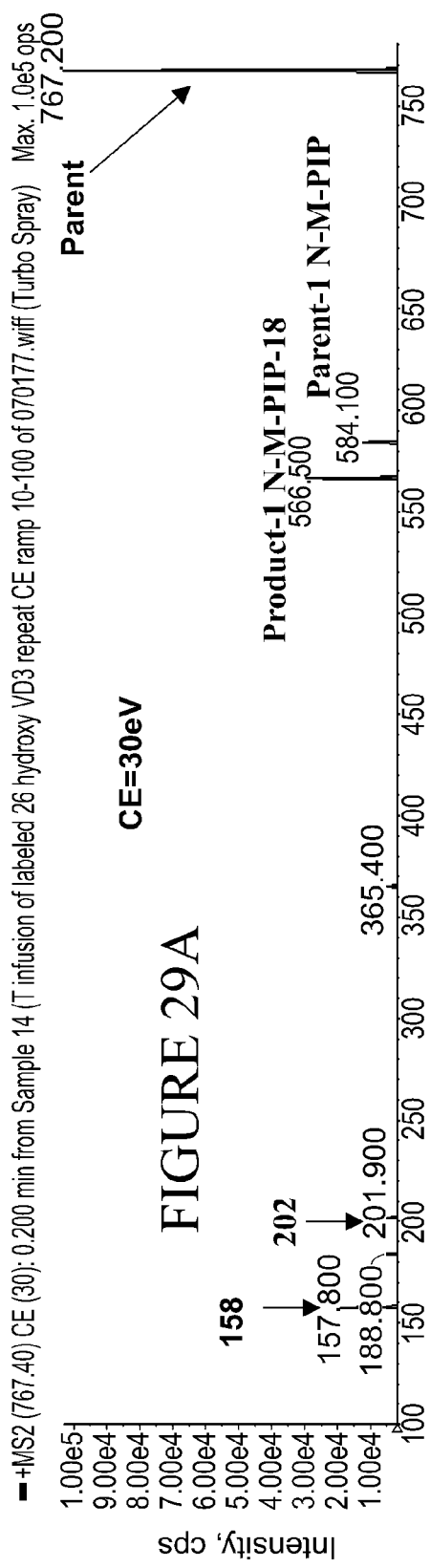
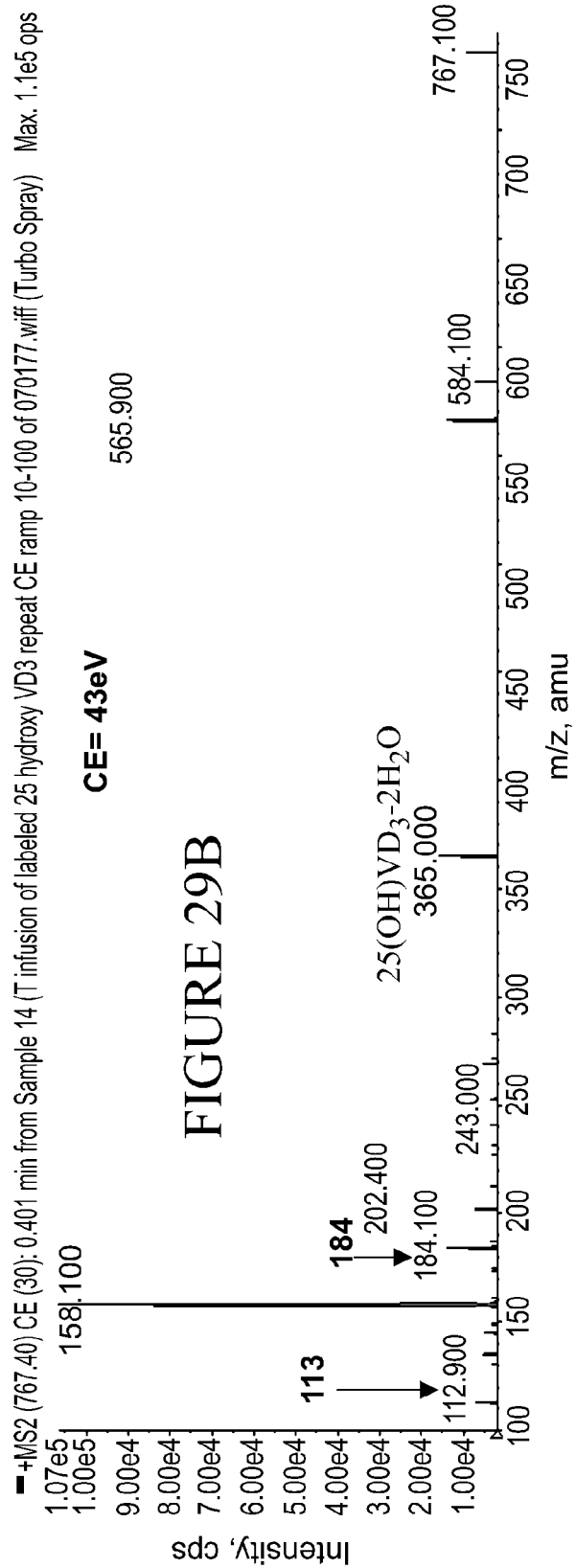
FIGURE 29A
FIGURE 29B

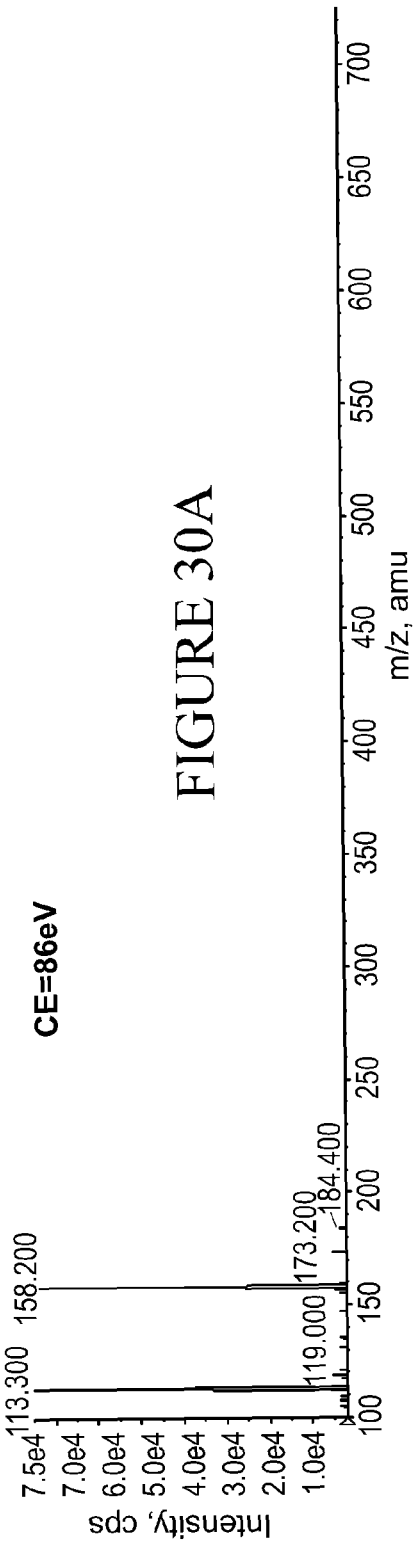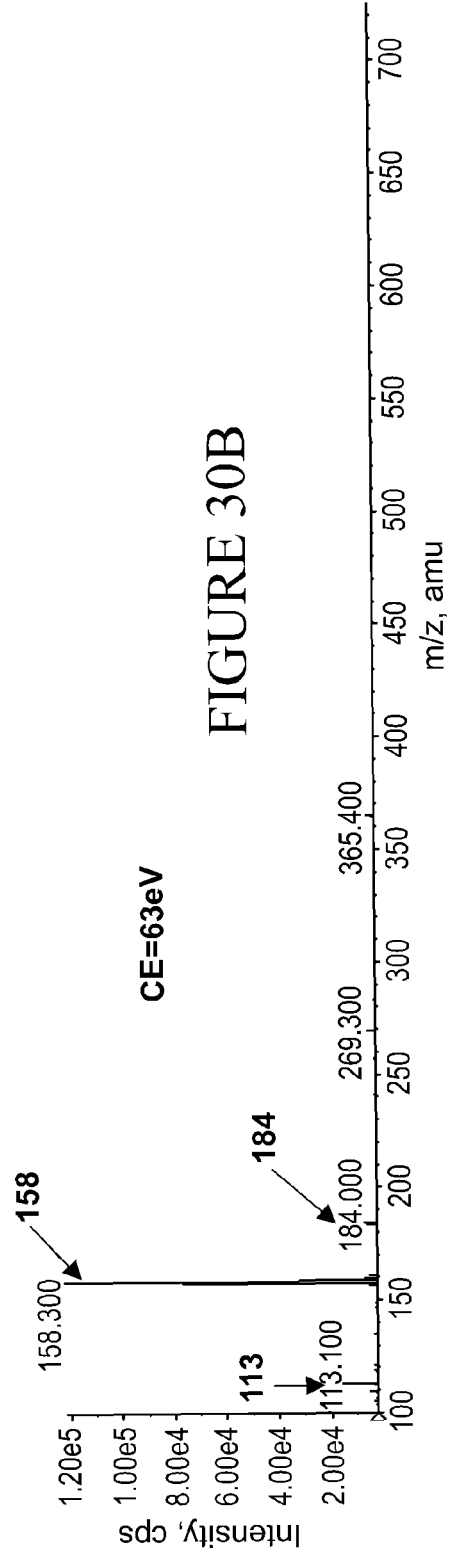
FIGURE 30A
FIGURE 30B $C_{51}H_{83}N_9O_9$
Exact Mass: 965.63

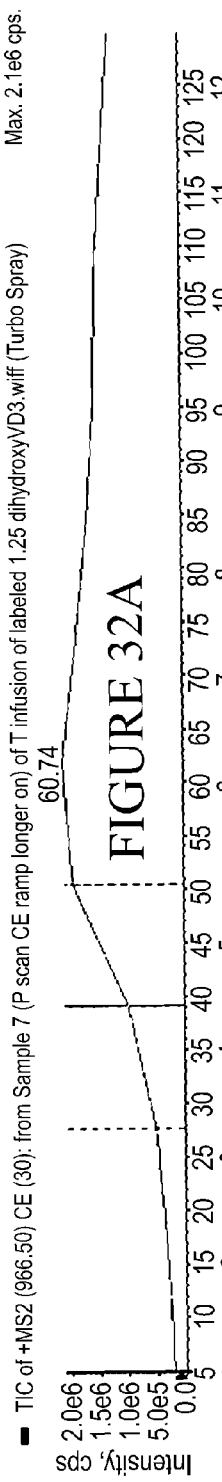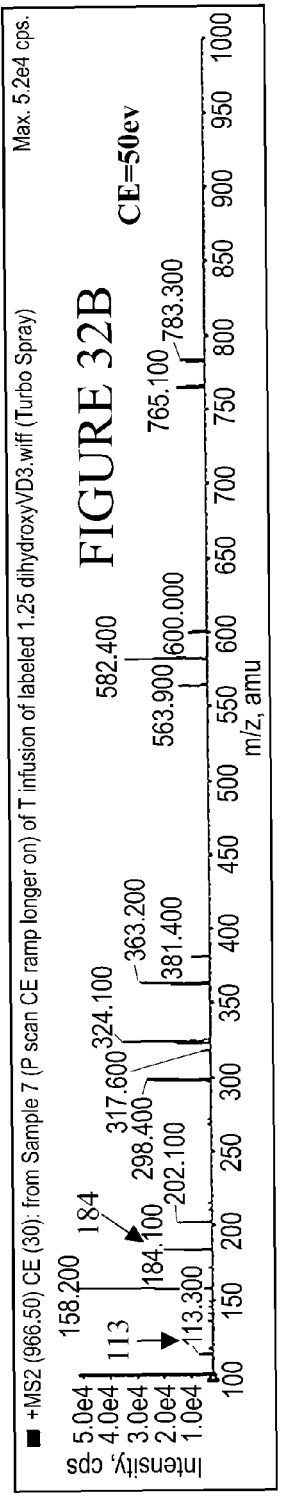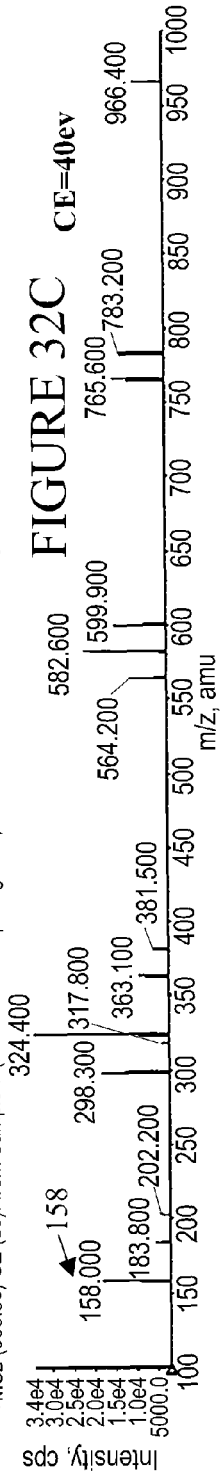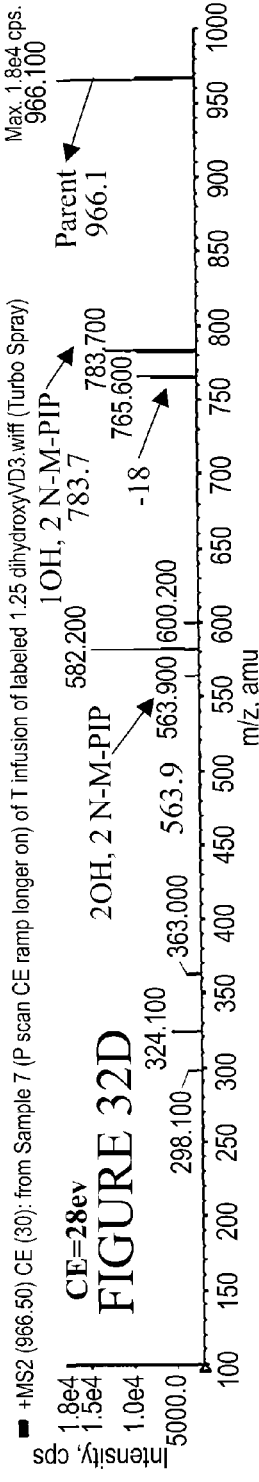

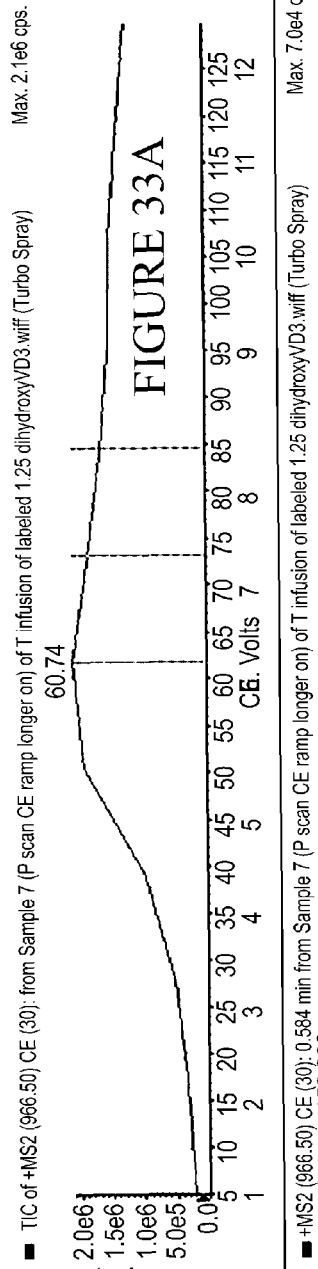
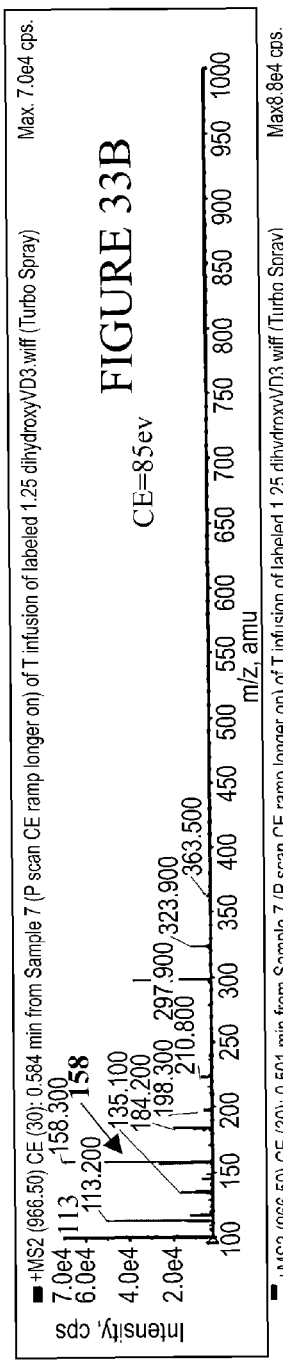
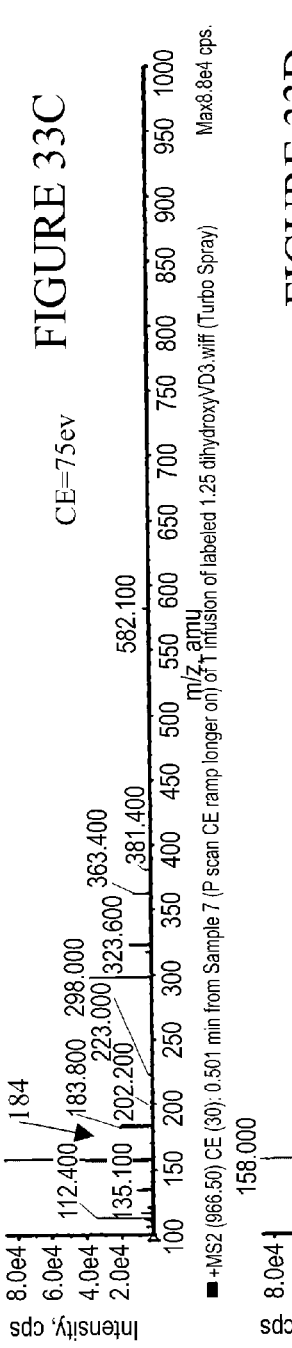
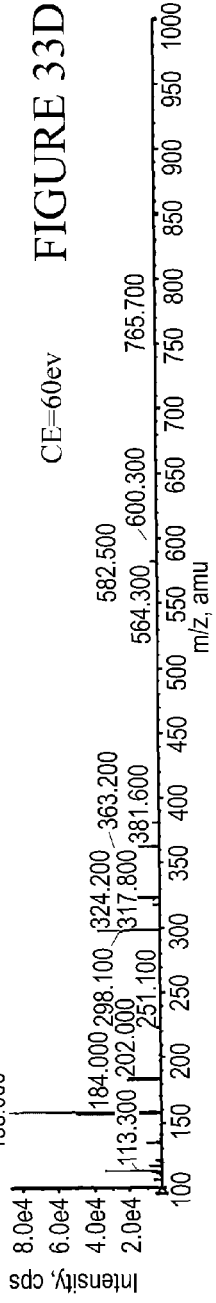
FIGURE 33A
FIGURE 33B
FIGURE 33C
FIGURE 33D

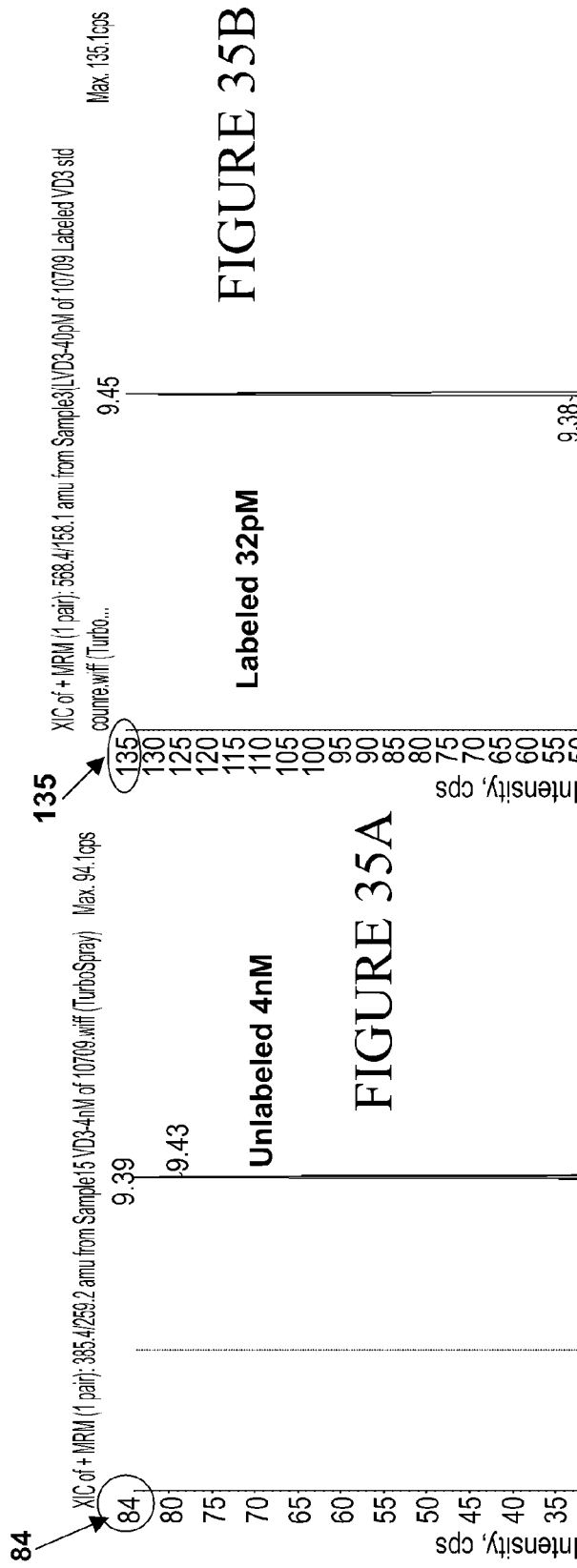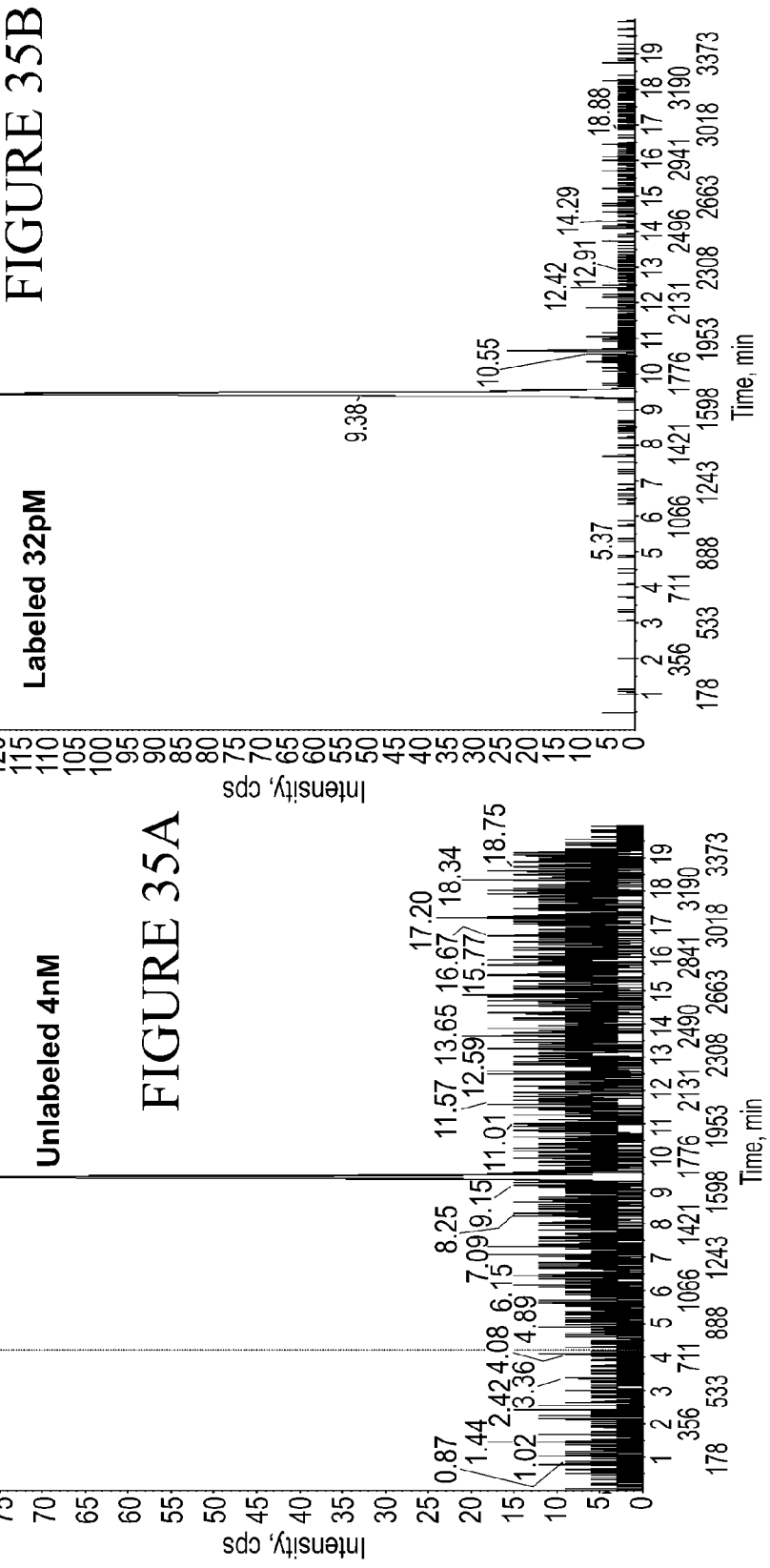

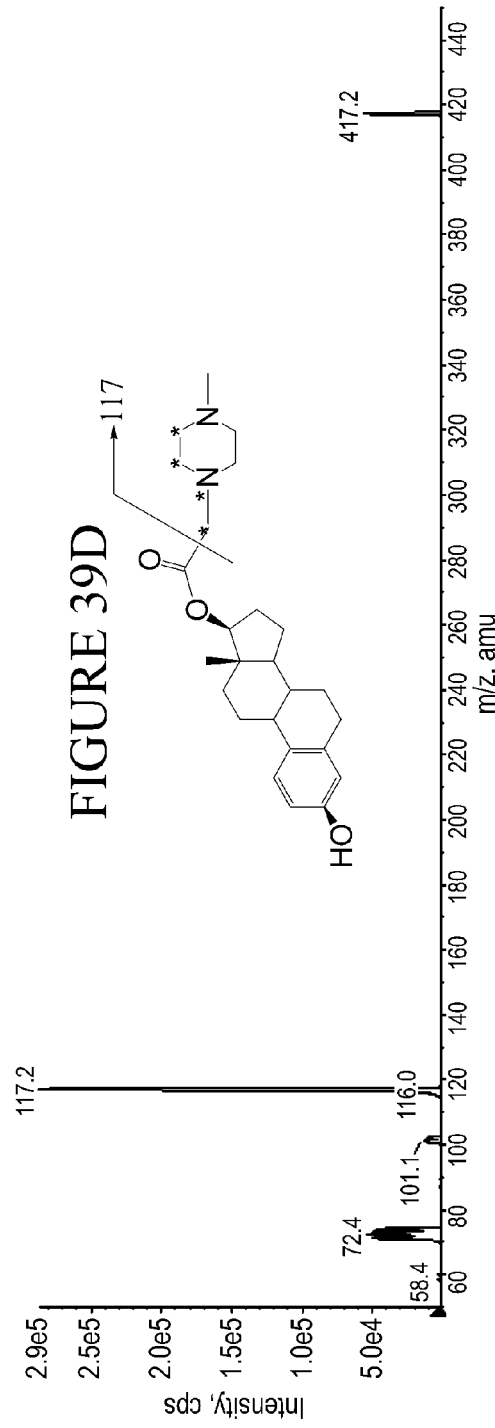
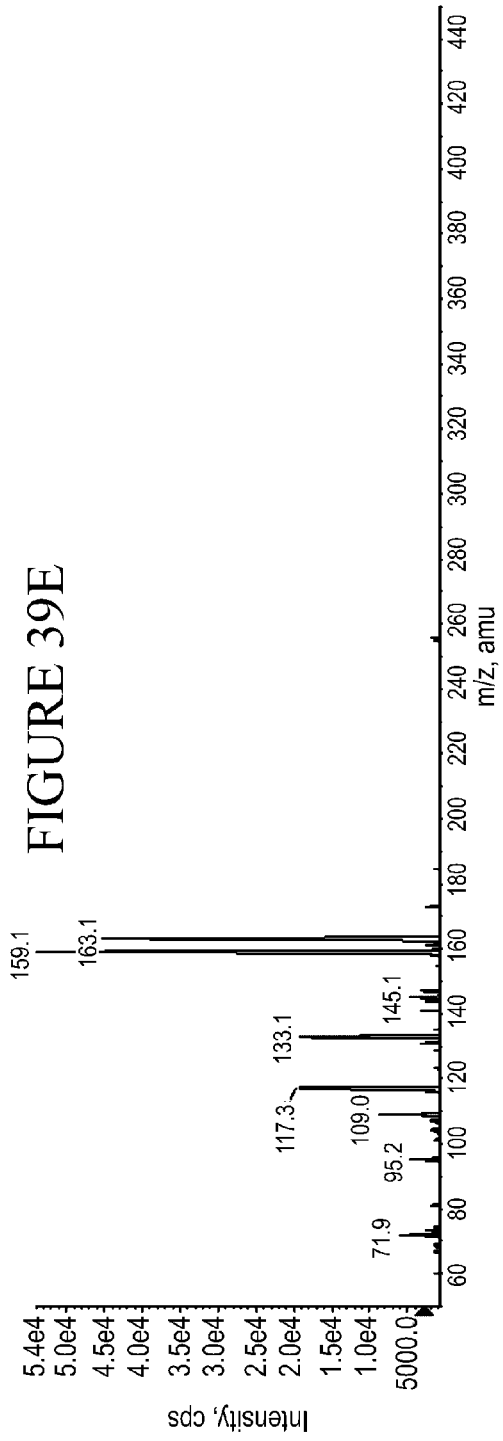
FIGURE 39D
FIGURE 39E

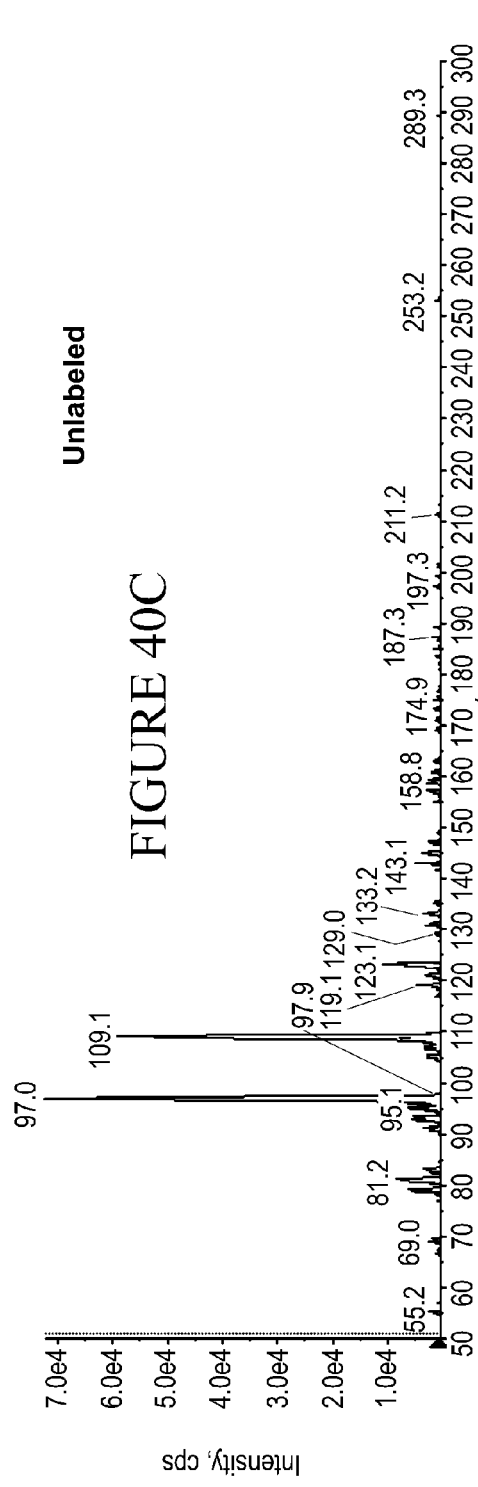
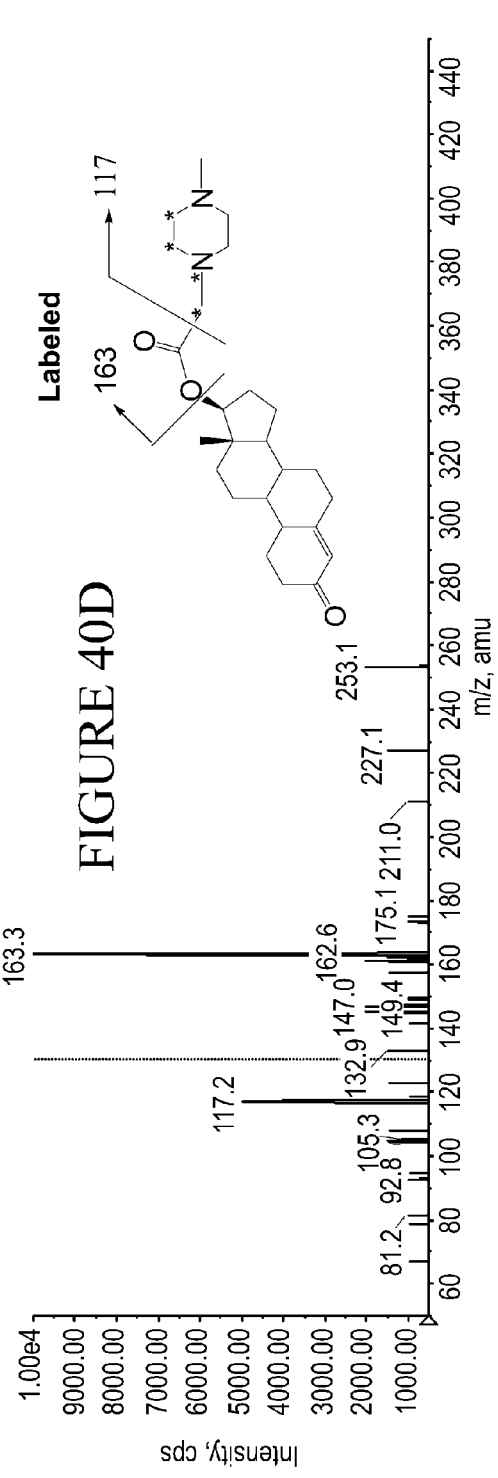
FIGURE 40C
FIGURE 40D

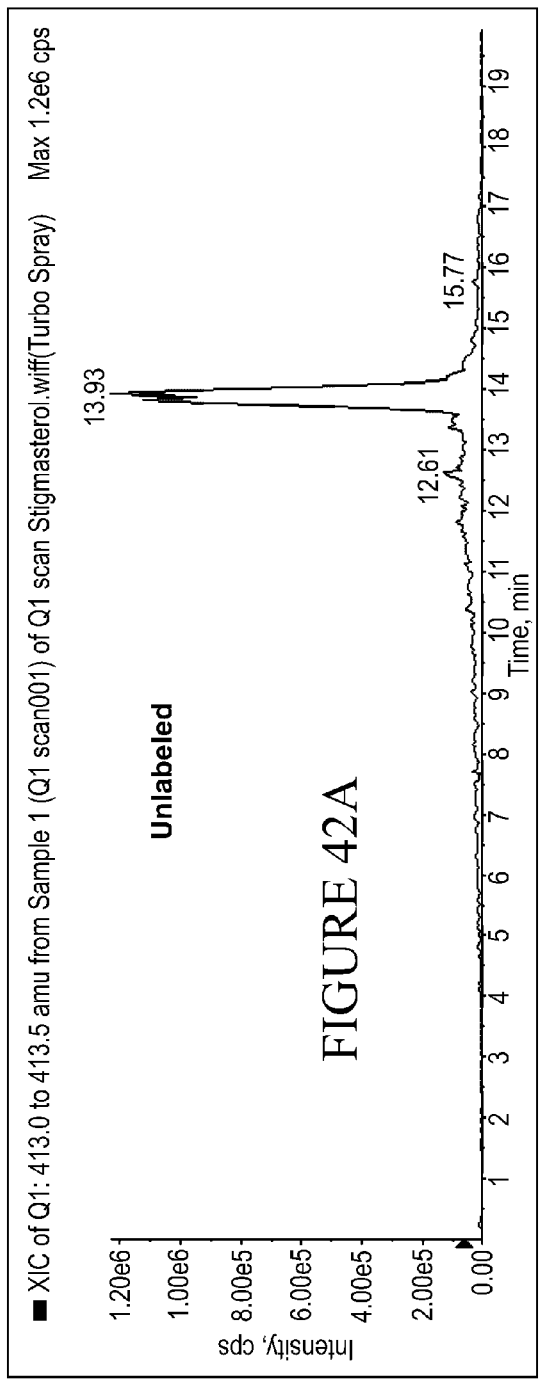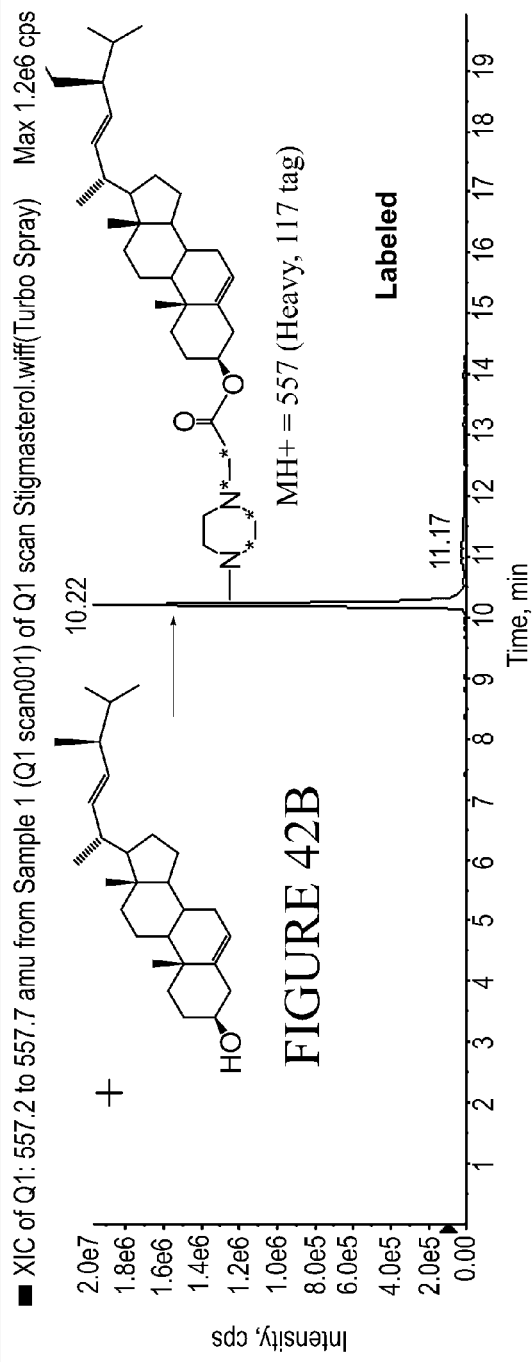
FIGURE 42A
FIGURE 42B

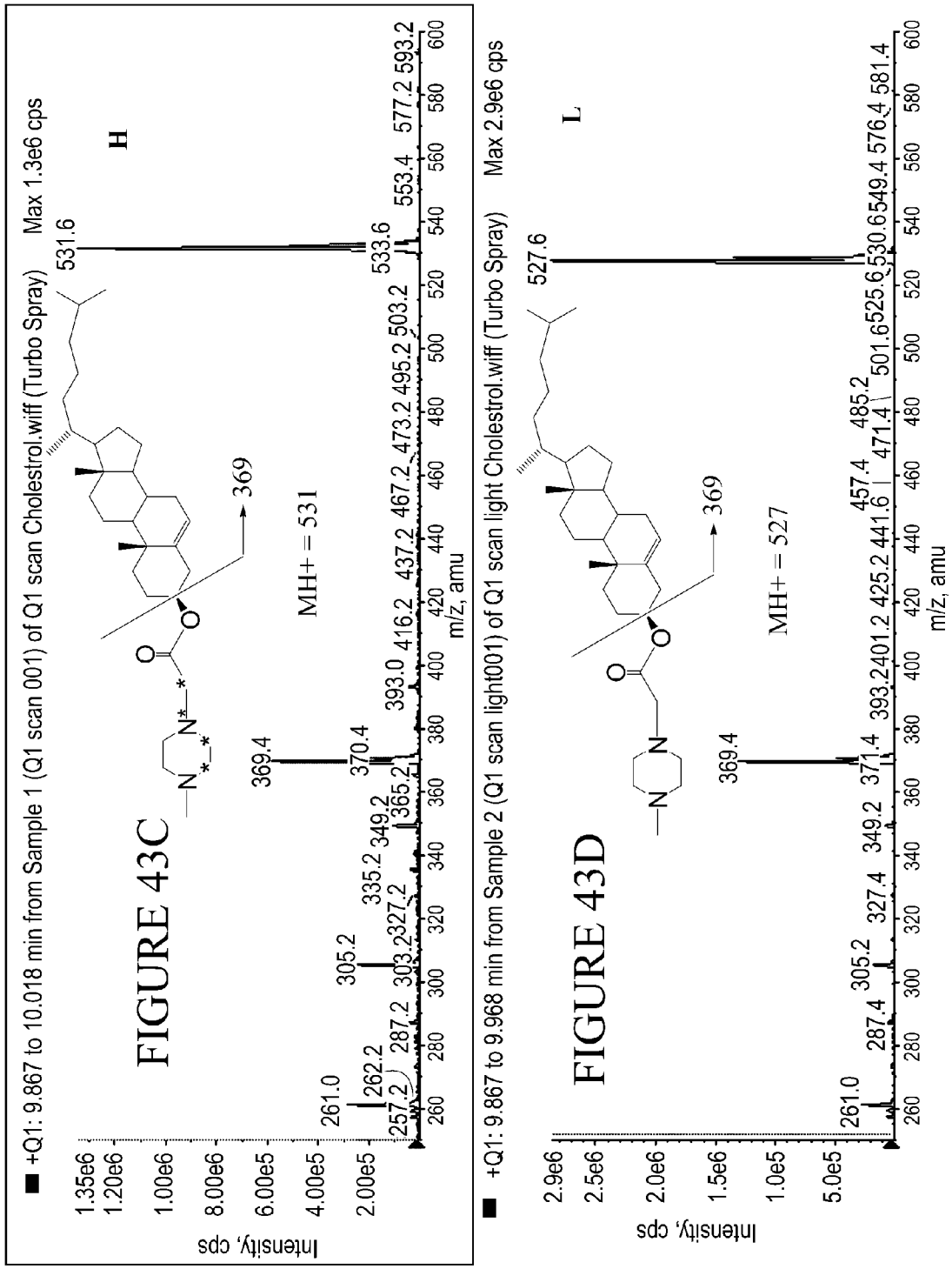

TAGGING REAGENTS AND METHODS FOR HYDROXYLATED COMPOUNDS

CROSS-REFERENCE TO RELATED APPLICATIONS

The present application claims the benefit of and priority to copending U.S. provisional application No. 60/809133 filed May 26, 2006, the entire contents of which are herein incorporated by reference.

INTRODUCTION

The ability to rapidly screen and/or analyze a large number of biological samples is of great interest to many fields. Mass spectrometry is one technique that can provide rapid sample analysis. However, detection of many physiologically important molecules by mass spectrometry can be problematic due to mass interferences and low sample concentrations. In addition, some classes of compounds are not amiable to the traditional chemistry and/or conditions often used to prepare the sample for mass spectrometric analysis.

One class of physiologically important compounds are steroids. Traditional methods for the quantitation of steroids in a sample include immunoassays, high performance liquid chromatography (HPLC) with ultra-violet (UV) fluorescent, and liquid chromatography in conjunction with mass spectrometry (LC/MS) and/or tandem mass spectrometry (MS/MS).

Absolute quantitation of steroids by the above-mentioned methods can be problematic. Immunoassays used in modern clinical laboratories lack sensitivity and are subject to interference by cross-reacting substances. Traditional approaches employing LC or HPLC followed by UV, MS or MS/MS detection, also suffer from a lack of sensitivity. For example, in order to analyze many steroids by HPLC, a difficult and time-consuming derivatization step must be performed before analysis occurs. In addition, HPLC has the drawbacks of long analysis times, high run-to-run deviations, a lack of multiplexing capability and non-specificity.

The more recent use LC/MS and MS/MS for the detection and quantitation of compounds offers the advantage of increased speed and specificity and the ability to rapidly measure multiple compounds in one sample; however, these techniques also lack a multiplexing capability and can suffer from a lack of sensitivity. In order to perform absolute quantitation, expensive isotopically enriched compounds are used as internal standards, which are incompatible with some tandem mass spectrometry methods. In addition, these isotopically enriched internal standards do not increase sensitivity for detection of the analyte compound.

SUMMARY

The present teachings provide reagents and methods for the analysis of samples containing one or more hydroxylated compounds. In various embodiments, these reagents and methods provided can be used to determine the relative concentration, absolute concentration, or both, of one or more steroids in one or more samples. The present teachings can be for used for isobaric labeling reagents and methods; as well as mass differential labeling reagents and methods by appropriate choice of isotopic substitution of the reagents. As used herein, the terms "label" and "tag" are used interchangeably. Examples of methods for synthesizing isotopically enriched compounds can be found in U.S. Patent Application Publication No. 2005/0148774, the entire contents of which are herein incorporated by reference.

The hydroxylated compounds, to which various embodiments of the present teachings can be applied, can come from a wide variety of sources such as, for example, physiological fluid samples, cell or tissue lysate samples, protein samples, cell culture samples, fermentation broth media samples, agricultural product samples, animal product samples, animal feed samples, samples of food or beverage for human consumption, and combinations thereof. The present teachings, in various embodiments, can be applied to both naturally produced as well as synthetic steroids. A wide variety of steroids, including, but not limited to, cortisol, 11-desoxycortisol (compound S), corticosterone, DHT, testosterone, epitestosterone, desoxymethyltestosterone (DMT), tetrahydrogestrinone (THG), estradiol, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, D4A (delta 4 androstenedione), stigmasterol, and cholesterol, can be analyzed in various embodiments of the present teachings.

In various aspects, the present teachings provide reagents and methods for the analysis of samples containing one or more hydroxylated compounds using mass differential tags. In various embodiments, provided are sets of mass differential labels where one or more labels of the set contains one or more heavy atom isotopes. A set of mass differential labels can be provided by preparing labels with different overall mass and different primary reporter ion mass. It is to be understood that not every member of a set of mass differential tags is heavy atom isotopically enriched according to the present teaching. In various embodiments, the present teachings provide reagents and methods for the analysis of one or more hydroxylated compounds in one or more samples using mass differential labels and parent-daughter ion transition monitoring (PDITM). In various embodiments, the present teachings can be used for qualitative and quantitative analysis of hydroxylated compounds using mass differential tagging reagents and mass spectroscopy. The mass differential tags include, but are not limited to, non-isobaric isotope coded reagents. In various embodiments, the present teachings provide reagents and methods for the absolute quantitation of hydroxylated compounds without the use of an isotopically enriched standard compound. In various embodiments, the hydroxylated compounds comprise hydroxylated ring containing compounds. In various embodiments, the hydroxylated ring containing compounds comprise hydroxylated polycyclic ring containing compounds.

In various aspects, the present teachings provide reagents and methods for the analysis of samples containing one or more hydroxylated compounds using isotopically enriched isobaric tags. In various embodiments, provided are sets of isobaric labels where each label of the set comprises one or more heavy atom isotopes. A set of isobaric labels can be provided by preparing labels where each label has substantially the same mass but where each label has a primary reporter ion of a different mass. In various embodiments, a set of isobaric tagging reagents can be used for qualitative and quantitative analysis of hydroxylated compounds using mass spectroscopy. For example, in various embodiments, provided are methods that use isotopically enriched isobaric tags and parent-daughter ion transition monitoring (PDITM) to determine the presence and/or concentration of one or more hydroxylated compounds in a sample. In various embodiments, the hydroxylated compounds comprise hydroxylated ring containing compounds. In various embodiments, the hydroxylated ring containing compounds comprise hydroxylated polycyclic ring containing compounds.

In various aspects, the present teachings provide labeling reagents and sets of labeling reagents for the relative quantitation, absolute quantitation, or both, of hydroxylated compounds including, but not limited to, hydroxylated ring containing compounds, where the label reagents can be represented by general formula (I):

(I), and can be provided and/or used in a salt or hydrate form. In general formula (I): (a) Z represents a substituted or unsubstituted straight, branched or cyclic alkyl; a substituted or unsubstituted aryl; a substituted or unsubstituted hetero aryl; a substituted or unsubstituted amino; or a substituted or unsubstituted thio; (b) $R_1$ represents a substituted or unsubstituted

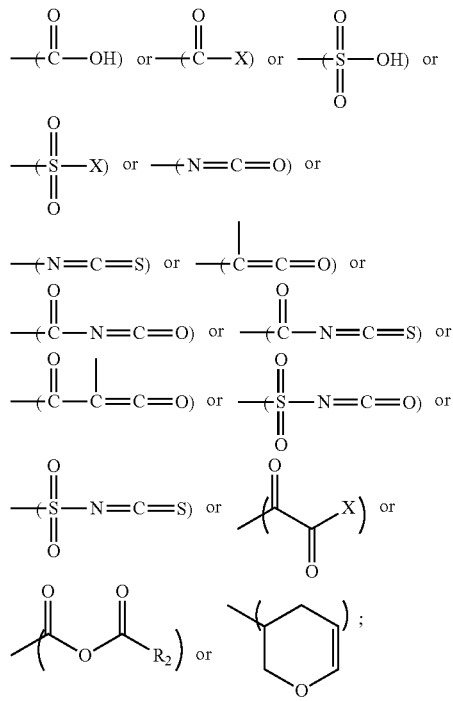

(c) X represents Cl, Br, I or an acetyl; and (e) $R_2$ represents a substituted or unsubstituted alkyl; a substituted or unsubstituted halogenated alkyl; or a substituted or unsubstituted aryl.

In various aspects, the present teachings provide labeled analytes, wherein the analyte comprised at least one hydroxyl group to labeling with a label of the present teachings. In various embodiments, the labeled compounds can be represented by the general formula (II):

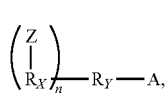

(II)

and can be provided and/or used as a salt or hydrate form thereof In general formula (II): (a) Z can be as given for formula (I); (b) A represents the compound that contained one or more hydroxyl groups prior to formation of the labeled compound; (c) $R_Y$ represents an oxygen atom forming a bond to a carbon atom of A that contained a hydroxyl group prior to formation of the labeled compound; (d) n represents an integer from 1 up to the number of hydroxyl groups in A prior to formation of the labeled compound; and (e) $R_X$ represents a substituted or unsubstituted

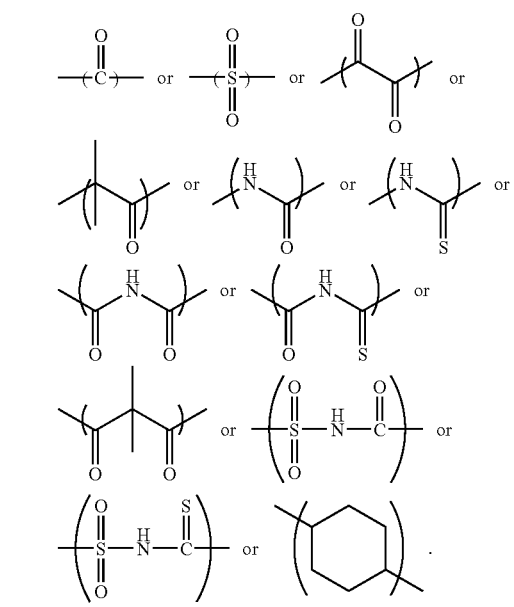

The present teachings are not limited to the analysis of hydroxylated compounds, but can be applied to non-hydroxylated carbonyl bearing compounds by reduction of the carbonyl group prior to labeling with a tag of an embodiments of the present teachings; by reduction in situ with the labeling reaction; or combinations thereof.

In various embodiments, the labeled analyte compound comprises a tetracyclic ring. In various embodiments, the tetracyclic ring can be represented by the general formula (III)

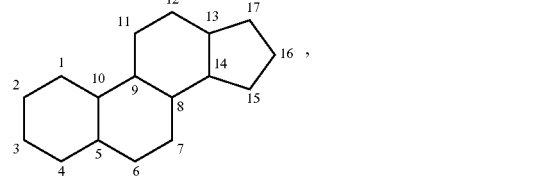

(III)

wherein one or more of the positions on the tetracyclic ring that do not form a bond with $R_Y$ are each independently substituted with a hydrogen, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, alkoxyl, cyano, alkylaryl, or an aromatic or heteroaromatic group. The numbers given in general formula (III) are for positional reference purposes only. In various embodiments, the hydroxylated compound from which A derives comprises a polycyclic ring structure of formula (III) hydroxylated at the 3 position, the 17 position or both.

In various embodiments, the present teachings can provide reagents and methods for the analysis of one or more steroids in one or more samples using mass differential labels, isobaric labels, or both, and parent-daughter ion transition monitoring (PDITM). In various aspects, the present teachings can provide methods for determining the relative concentration, absolute concentration, or both, of one or more steroids in one or more samples. In various embodiments, the present teachings can provide methods whereby the relative concentration, absolute concentration, or both, of multiple steroids in a sample, one or more steroids in multiple samples, or combinations thereof, can be determined in a multiplex fashion. In various embodiments, the present teachings can be used for qualitative and/or quantitative analysis of steroids using mass differential tagging reagents, isobaric tagging reagents, or both, and mass spectroscopy.

Referring to FIG. 1, a label of a set of labels represented by the general formula (I) comprises a linker group portion (102) and at least one reporter group portion (104); that can be used, e.g., to label a hydroxyl containing analyte (106).

In embodiments providing sets of isobaric labels, the heavy atom substitutions of the linker group portion (LG) and reporter group portion (RP) are chosen such that each reporter group portion has a different mass while the masses of each of the isobaric tags is substantially equal. In embodiments comprising sets of isobaric labels, the linker group portion can be referred to as a balance group. For example, referring to FIG. 2, in various embodiments a set of four isobaric labels are added to a set of one or more analytes (202) and combined to form a combined sample (204) that is subjected to MS/MS analysis to fragment the labeled analyte compounds and produce 4 reporter ions of different mass (206). The labels can be made isobaric by an appropriate combination of heavy atom substitutions of a reporter portion (RP) and a balance group portion (BG); for example in FIG. 2 the RP and BG masses are such that the mass of each label in the set is about 186 amu.

In embodiments providing sets of mass differential labels, the heavy atom substitutions of the reporter group portion (RP) (104) are chosen such that each reporter group portion has a different mass. In various embodiments, on label of a set of mass differential labels contains substantially no heavy atom substitutions.

In various embodiments of the present teachings, the linker group portion is chosen such that upon subjecting a labeled analyte (108) to fragmentation, fragmentation occurs by breaking of at least the bond (110) between a nitrogen of the reporter group portion (104) and the balance group (102).

In various embodiments, the heavy atom isotope distribution in each of the labels can be designed to result in the generation of a different reporter ion signal when analyzed in a mass spectrometer (MS). Accordingly, in various embodiments, the ion signals associated with various labeled components of a mixture (e.g., different analytes, analytes from different samples, standards, etc.) can be deconvoluted by use of the reporter ion signal associated with the respective label. Deconvolution can include, for example, determining the relative and/or absolute amount (often expressed in concentration or quantity) of one or more labeled components in the mixture. Examples of various experimental analyses for which the labeling reagents of the present teachings can be used include, but are not limited to, time course studies, biomarker analysis, multiplex analysis, affinity pull-downs, and multiple control experiments.

In various aspects, the present teachings provide methods for analyzing one or more hydroxylated ring containing compounds in one or more samples using labels of formula (I) and parent-daughter ion transition monitoring (PDITM).

The term "parent-daughter ion transition monitoring" or "PDITM" refers to, for example, a measurement using mass spectrometry whereby the transmitted mass-to-charge (m/z) range of a first mass separator (often referred to as the first dimension of mass spectrometry) is selected to transmit a molecular ion (often referred to as "the parent ion" or "the precursor ion") to an ion fragmentor (e.g. a collision cell, photodissociation region, etc.) to produce fragment ions (often referred to as "daughter ions") and the transmitted m/z range of a second mass separator (often referred to as the second dimension of mass spectrometry) is selected to transmit one or more daughter ions to a detector which measures the daughter ion signal. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal".

For example, one embodiment of parent-daughter ion transition monitoring is multiple reaction monitoring (MRM) (also referred to as selective reaction monitoring). In various embodiments of MRM, the monitoring of a given parent-daughter ion transition comprises using as the first mass separator (e.g., a first quadrupole parked on the parent ion m/z of interest) to transmit the parent ion of interest and using the second mass separator (e.g., a second quadrupole parked on the daughter ion m/z of interest) to transmit one or more daughter ions of interest. In various embodiments, a PDITM can be performed by using the first mass separator (e.g., a quadrupole parked on a parent ion m/z of interest) to transmit parent ions and scanning the second mass separator over a m/z range including the m/z value of the one or more daughter ions of interest.

For example, a tandem mass spectrometer (MS/MS) instrument or, more generally, a multidimensional mass spectrometer (MS$^n$) instrument, can be used to perform PDITM, e.g., MRM. Examples of suitable mass analyzer systems include, but are not limited to, those that comprise on or more of a triple quadrupole, a quadrupole-linear ion trap, a quadrupole TOF, and a TOF-TOF.

In various embodiments, for analyzing one or more hydroxylated compounds in one or more samples using labels of the present teachings comprises the steps of: (a) labeling one or more hydroxylated compounds each with a different label from a set of labels of formula (I) to provide labeled analyte compounds of formula (II), the labeled analyte compounds each having a reporter ion portion; (b) combining at least a portion of each of the labeled analyte compounds to produce a combined sample; (c) subjecting at least a portion of the combined sample to parent-daughter ion transition monitoring; (d) measuring the ion signal of one or more of the transmitted reporter ions; and (e) determining the concentration of one or more of the labeled analyte compounds based at least on a comparison of the measured ion signal of the corresponding reporter ion to one or more measured ion signals of a standard compound. Accordingly, in various embodiments, the concentration of multiple hydroxylated compounds in one or more samples can be determined in a multiplex fashion, for example, by combining two or more labeled analyte compounds to produce a combined sample and subjecting the combined sample to PDITM, and monitoring the reporter ions of two or more of labeled analyte compounds.

In various embodiments, the step of determining the concentration of one or more labeled analyte compounds comprises determining the absolute concentration of one or more of the labeled analyte compounds, determining the relative concentration of one or more of the labeled analyte compounds, or both.

In various embodiments, the chromatographic column is used to separate two or more labeled analyte compounds. For example, in various embodiments, a first labeled analyte compound found in one or more of the samples is separated by the chromatographic column from a second labeled analyte compound found in one or more of the samples.

In various embodiments, one or more of the samples of interest comprises a standard sample containing one or more standard compounds, wherein the measured ion signal of a reporter ion corresponding to a standard compound in the method corresponds to the measured reporter ion signal of one or more labeled standard compounds in the standard sample.

In various embodiments of the present teachings, a concentration curve of a standard compound can be generated by: (a) providing a non-isotopically enriched standard compound having a first concentration; (b) labeling the standard compound with a label from a set of labels of formula (I), or salt or hydrate forms thereof, the labeled standard compound having a reporter ion portion; (c) loading at least a portion of the labeled standard compound on a chromatographic column; (d) subjecting at least a portion of the eluent from the chromatographic column to parent-daughter ion transition monitoring; (e) measuring the ion signal of the transmitted reporter ions; (f) repeating steps (a)-(e) for one or more different standard compound concentrations; and (g) generating a concentration curve for the standard compound based at least on the measured ion signal of the transmitted reporter ions at two or more standard compound concentrations.

The standard compound can be contained in a standard sample, and a standard sample can contain more than one standard compound. In various embodiments of the present teachings, a concentration curve of a standard compound can be generated by: (a) providing a standard sample comprising one or more non-isotopically enriched standard compounds having first concentrations; (b) adding a label of formula (I), or a salt or a hydrate form thereof, to the standard sample to label one or more of the standard compounds in the sample, the labeled standard compounds each having a reporter ion portion; (c) loading at least a portion of the labeled sample on a chromatographic column; (d) subjecting at least a portion of the eluent from the chromatographic column to parent-daughter ion transition monitoring; (e) measuring the ion signal of the transmitted reporter ions; (f) repeating steps (a)-(e) for one or more different standard samples containing different concentrations of one or more of the standard compounds; and (g) generating a concentration curve for one or more of the standard compounds based at least on the measured ion signal of the transmitted reporter ions for the corresponding standard compound at two or more standard compound concentrations. In various embodiments, the step of adding a label of formula (I), or a salt or a hydrate form thereof, to the standard sample to label one or more of the standard compounds in the sample comprises a two step reaction where a first portion of the label (e.g., a moiety comprising portion $R_1$ in formula (I)) followed by a second step adding a second portion of the label (e.g., a moiety comprising portion Z in formula (I)) to effect the labeling of a standard compound.

The forgoing and other aspects, embodiments, and features of the teachings can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the teachings.

BRIEF DESCRIPTIONS OF THE DRAWINGS

Figure 1:
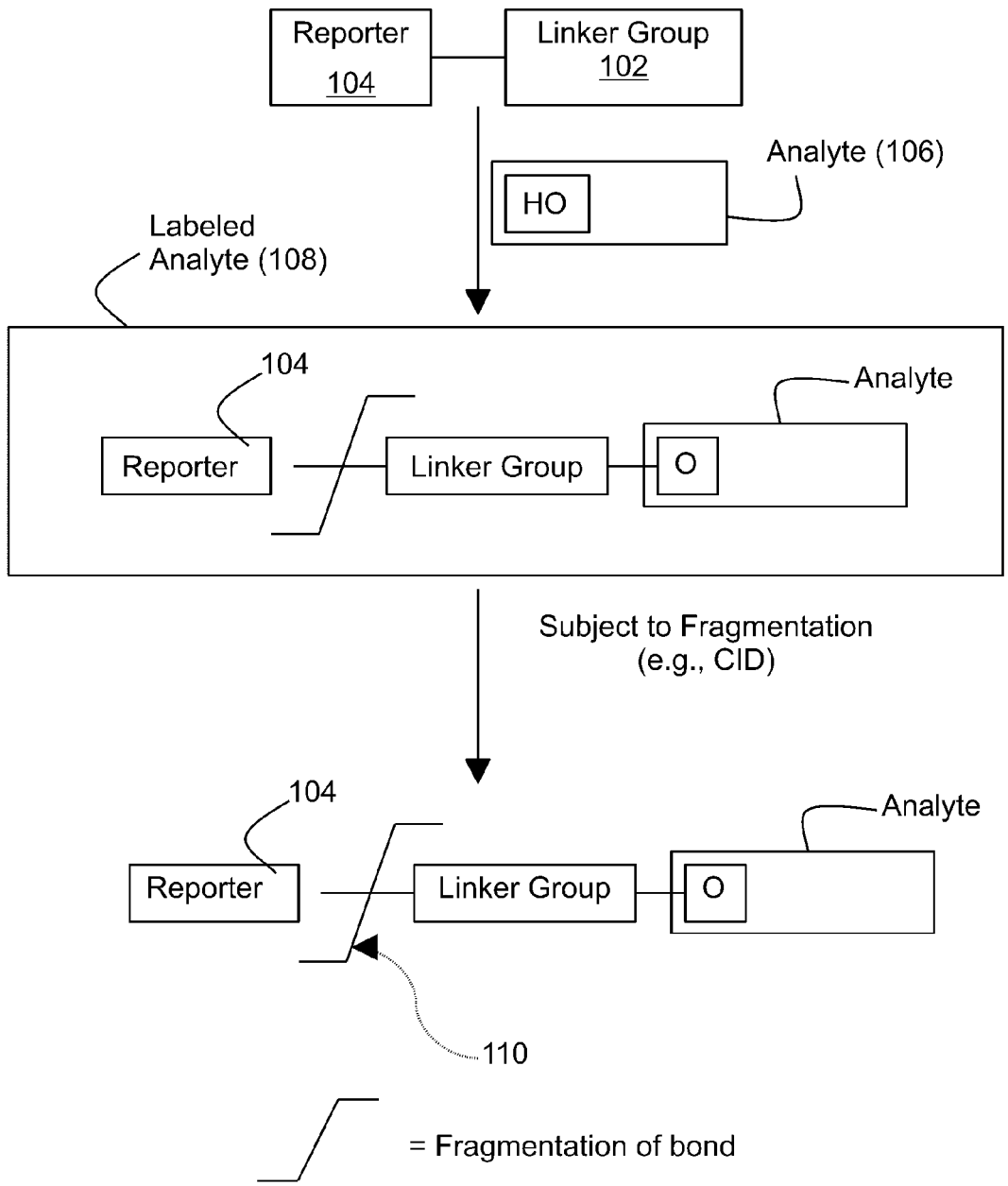
FIG. 1 is a schematic diagram a label, labeling reaction, labeled analyte compound, and generation of a reporter ion according to various embodiments of the present teachings.
Figure 2:
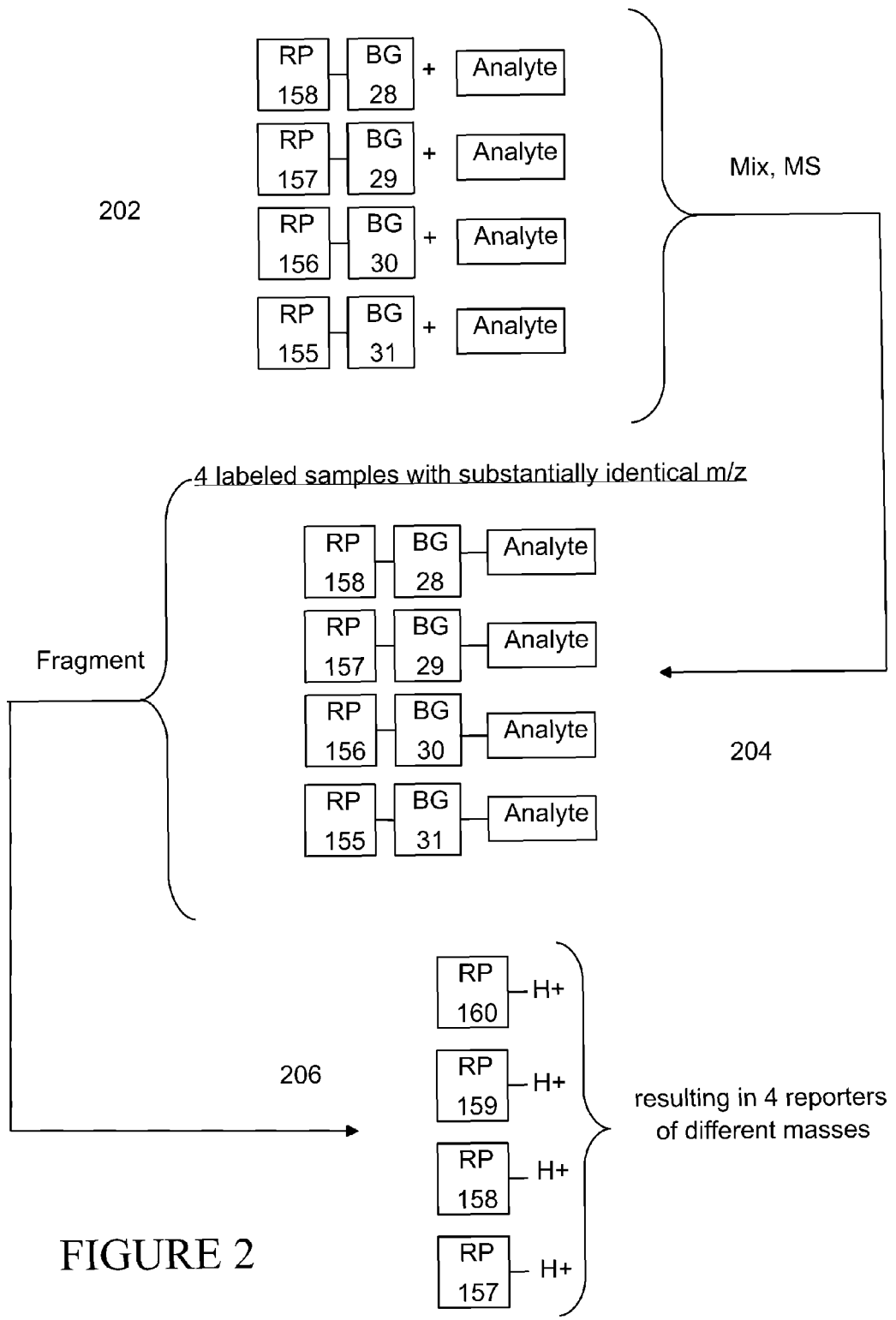
FIG. 2 is a schematic diagram of various embodiments of methods of analyzing one or more hydroxylated compounds in one or more samples using isobaric labeling reagents of the present teachings.
Figure 3A:
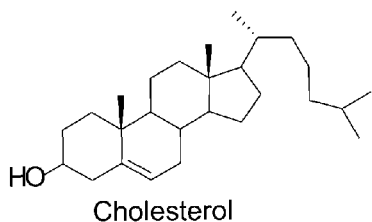
Figure 3B:
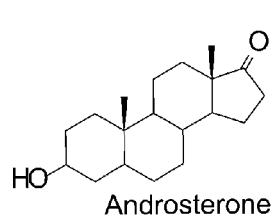
Figure 3C:
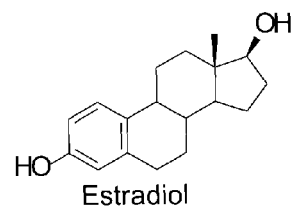
Figure 3D:
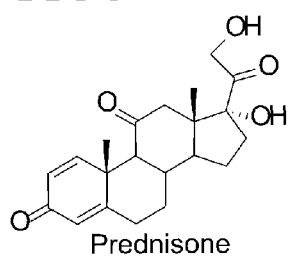
Figure 3E:
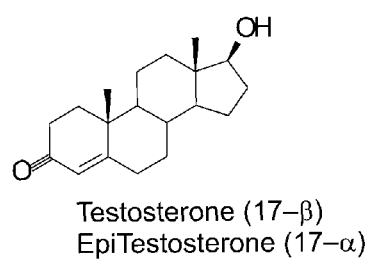
Figure 3F:
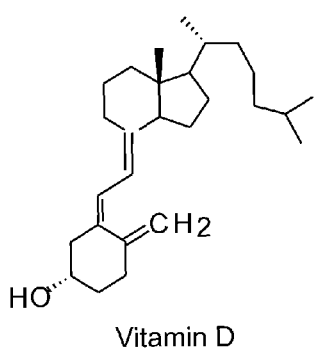
Figure 3G:
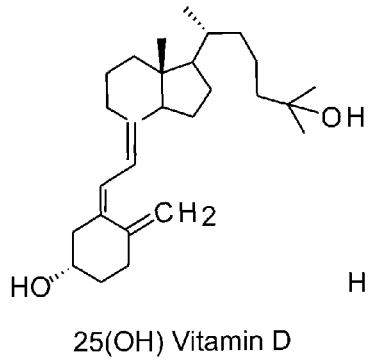
Figure 3H:
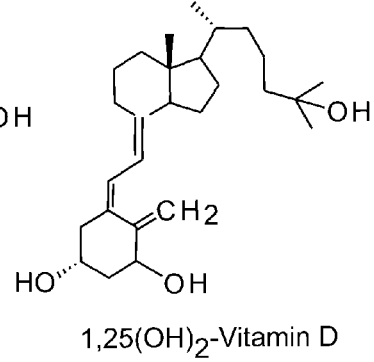
Figure 3J:
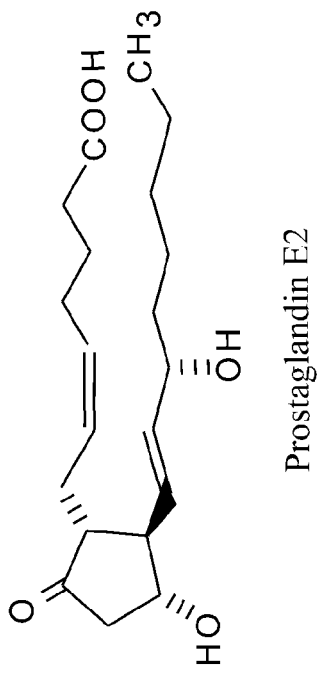
Figure 3I:
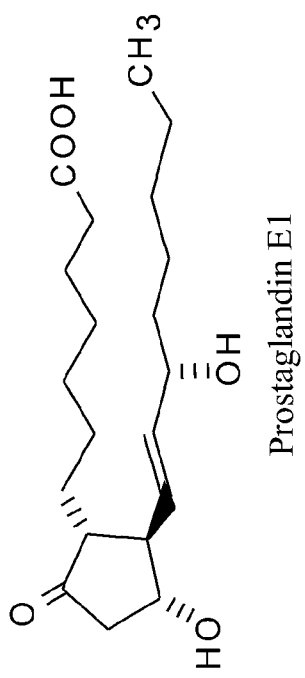
Figure 3K:
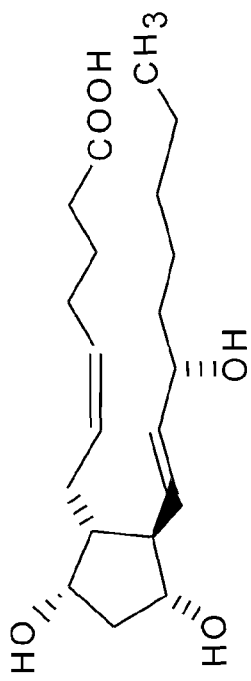

FIGS. 3A-3K schematically depict the structure of various hydroxylated ring containing compounds; FIGS. 3A-3E schematically depicting steroids, 3F-3H schematically depicting vitamin $D_3$ and various metabolites, and analogs thereof, and FIGS. 3I-3K schematically depicting various hydroxylated compounds amenable to analysis by various embodiments the present teachings.

Figure 4A:
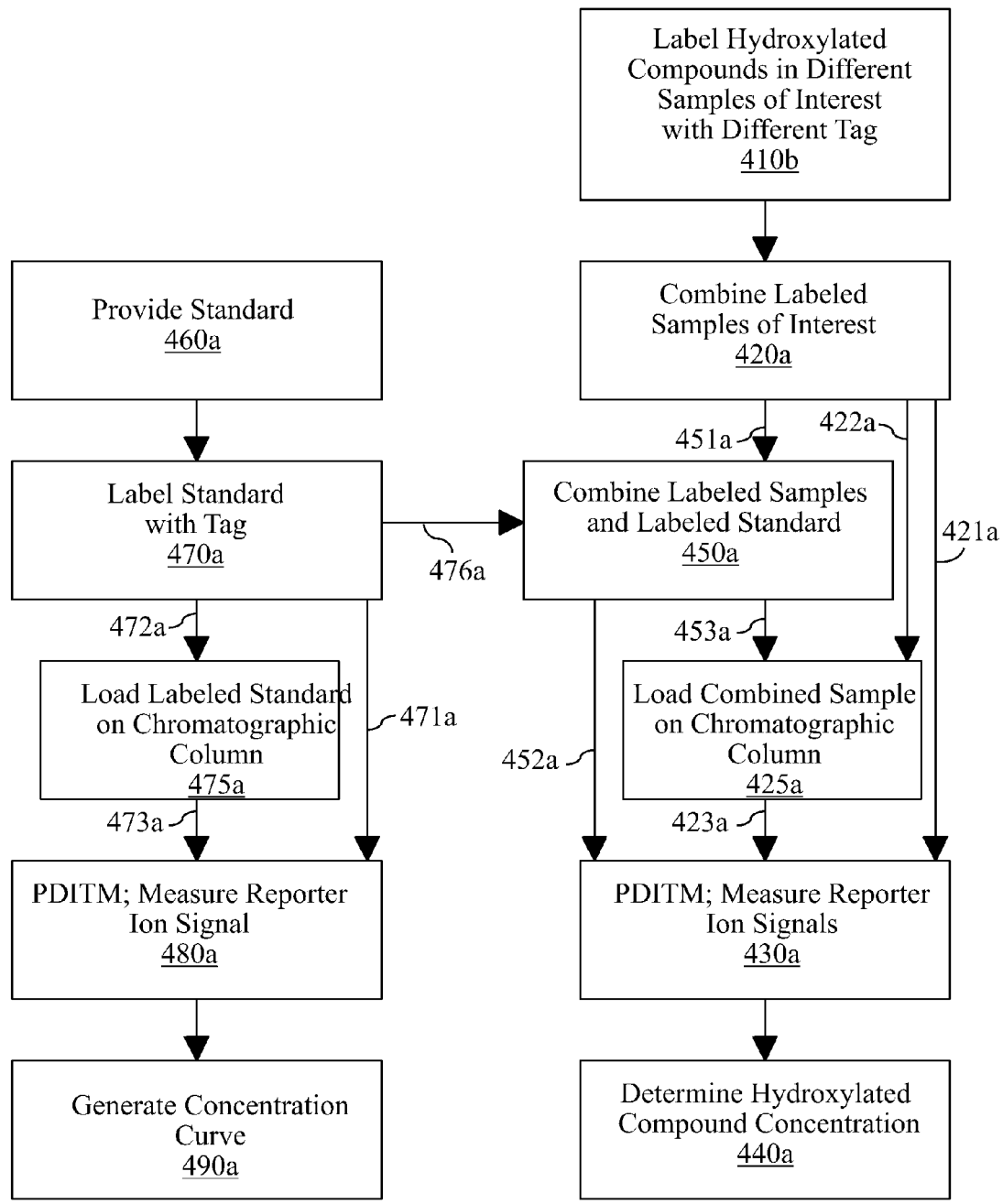
Figure 4B:
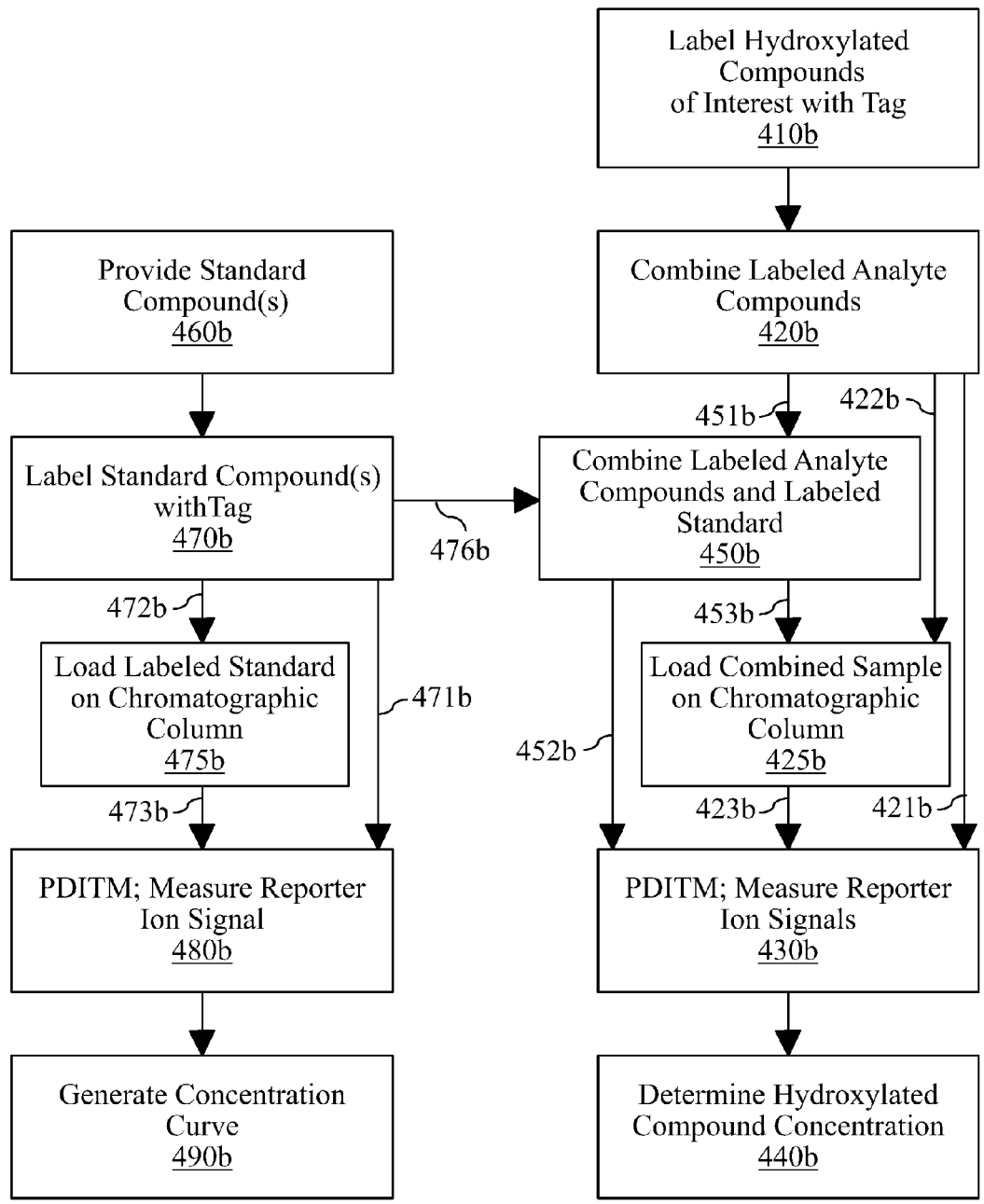

FIGS. 4A and 4B are schematic diagrams of various embodiments of methods of analyzing one or more hydroxylated compounds in one or more samples.

Figure 5:
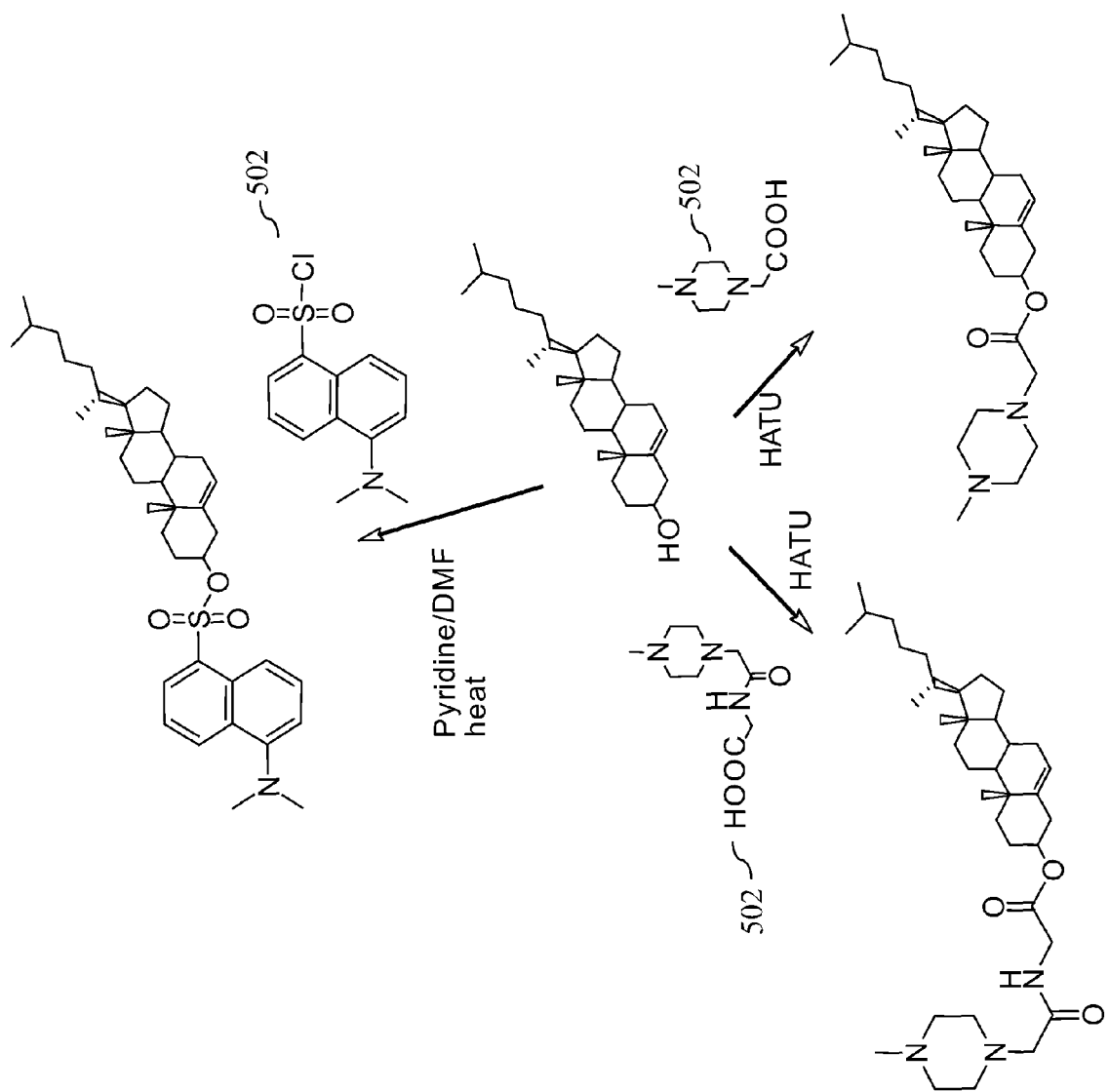

FIG. 5 schematically depicts examples of labeling of cholesterol with various embodiments of labels of the present teachings and examples of the resultant labeled analyte compounds.

Figure 6A:
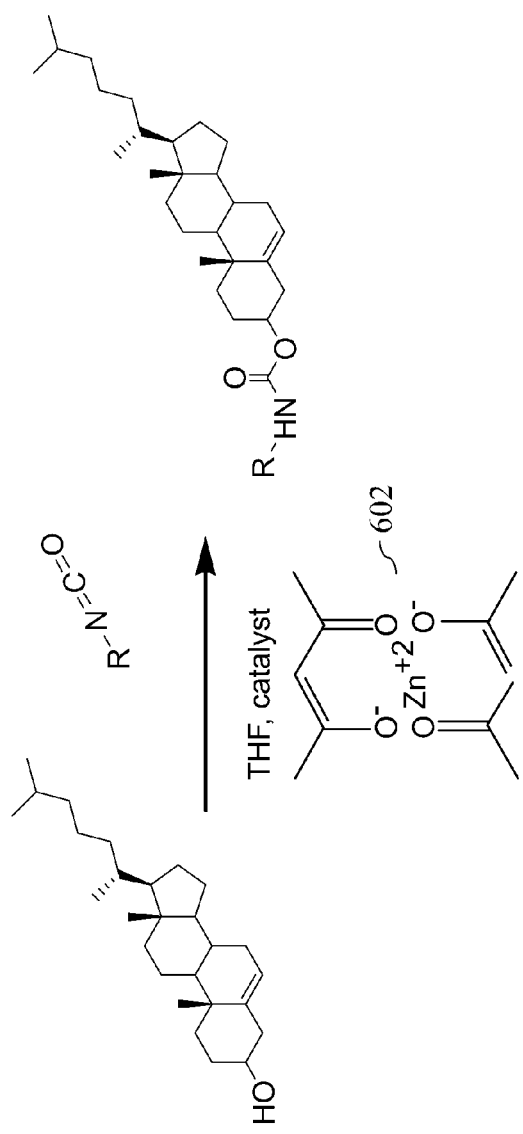
Figure 6B:
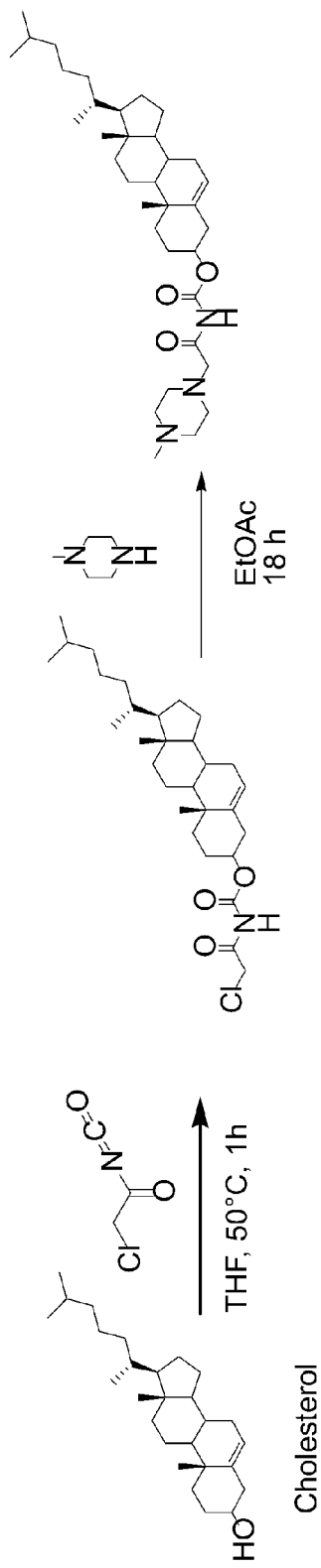

FIGS. 6A-6C schematically illustrates various embodiments of labeling with a tag of the present teachings having a isocyanate $R_1$ portion for a compound of general formula (I); FIG. 6A illustrating a general reaction, FIG. 6B a two-step labeling reaction with a piperzine isocyanate, and FIG. 6C the creation of a trimethyl isocyanate labeled analyte, where the labeled analyte is an iodine salt.

Figure 7B:
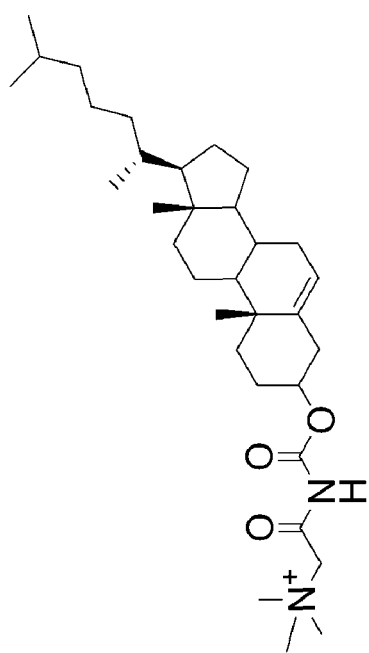
Figure 7A:
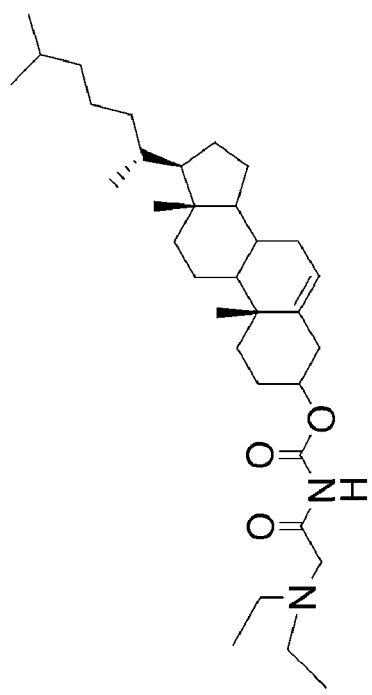

FIGS. 7A-7B schematically illustrates various embodiments of labeled analytes, where the hydroxylated compound, cholesterol, has been labeled with a diethylammonia (FIG. 7A) or trimethylammonium (FIG. 7B) tag.

Figure 8A:
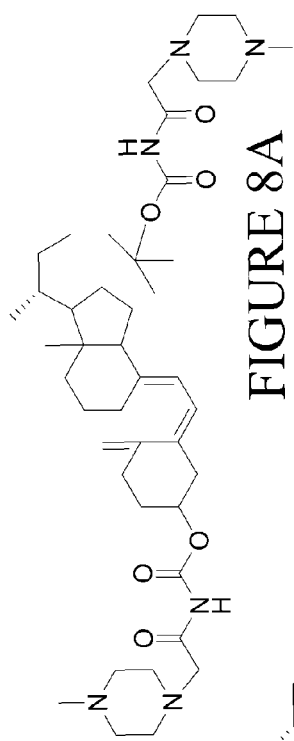
Figure 8B:
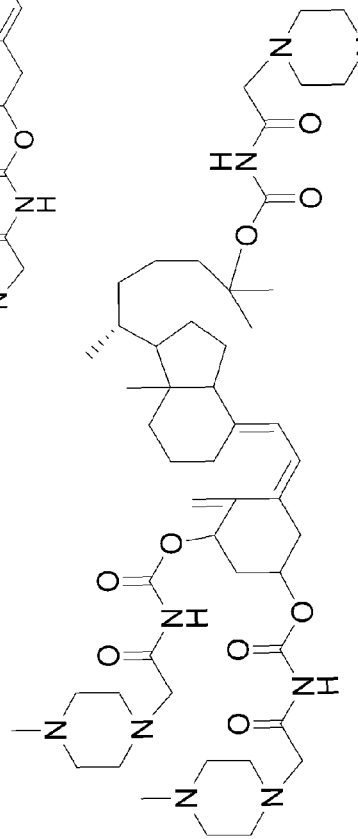
Figure 8D:
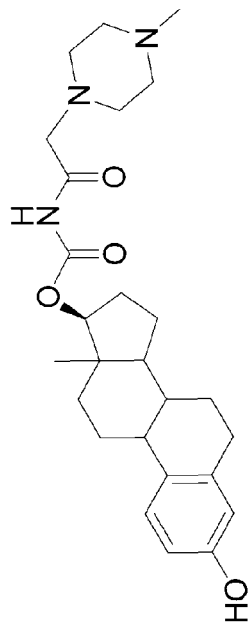
Figure 8E:
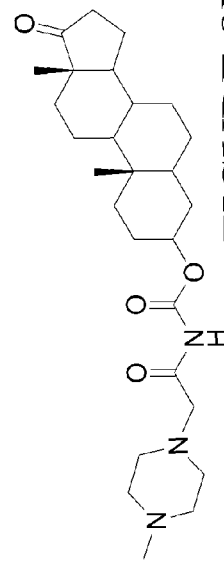
Figure 8C:
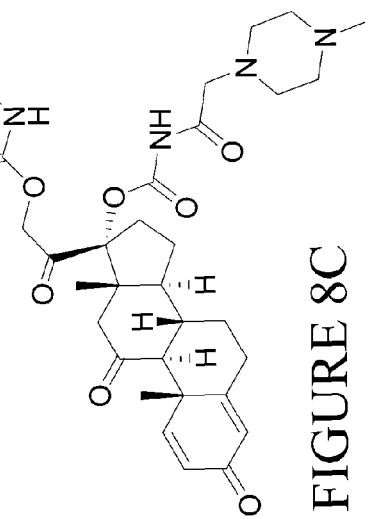

FIGS. 8A-8E schematically illustrates various embodiments of labeled analytes with a tag of the present teachings having a piperzine Z portion for a compound of general formula (I); FIGS. 8A-8C illustrating the labeling of multiple hydroxyls on the analyte.

FIGS. 9A-9E schematically illustrates various embodiments of labeled analytes with a tag of the present teachings having a benzoyl or substituted phenyl Z portion for a compound of general formula (I); FIGS. 9A-9C illustrating the labeling by direct reaction of a benzoyl isocyanate with the analyte.

Figure 10:
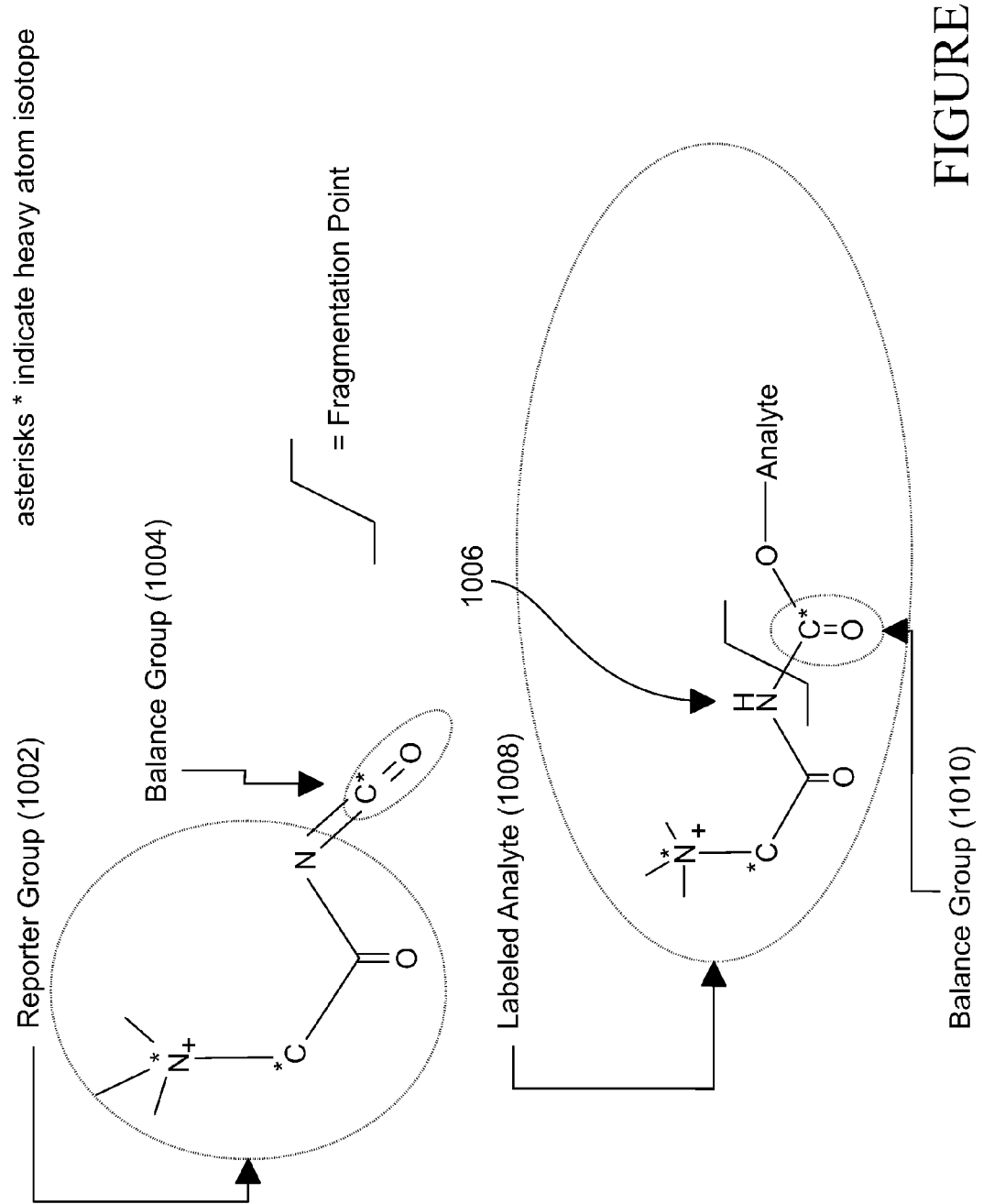

FIG. 10 is a schematic representation of various embodiments of an ammonium labeling reagent and an analyte labeled with the reagent.

FIG. 11 is a schematic representation of various embodiments of a labeled analyte and examples of multiple fragmentation points.

Figure 12B:
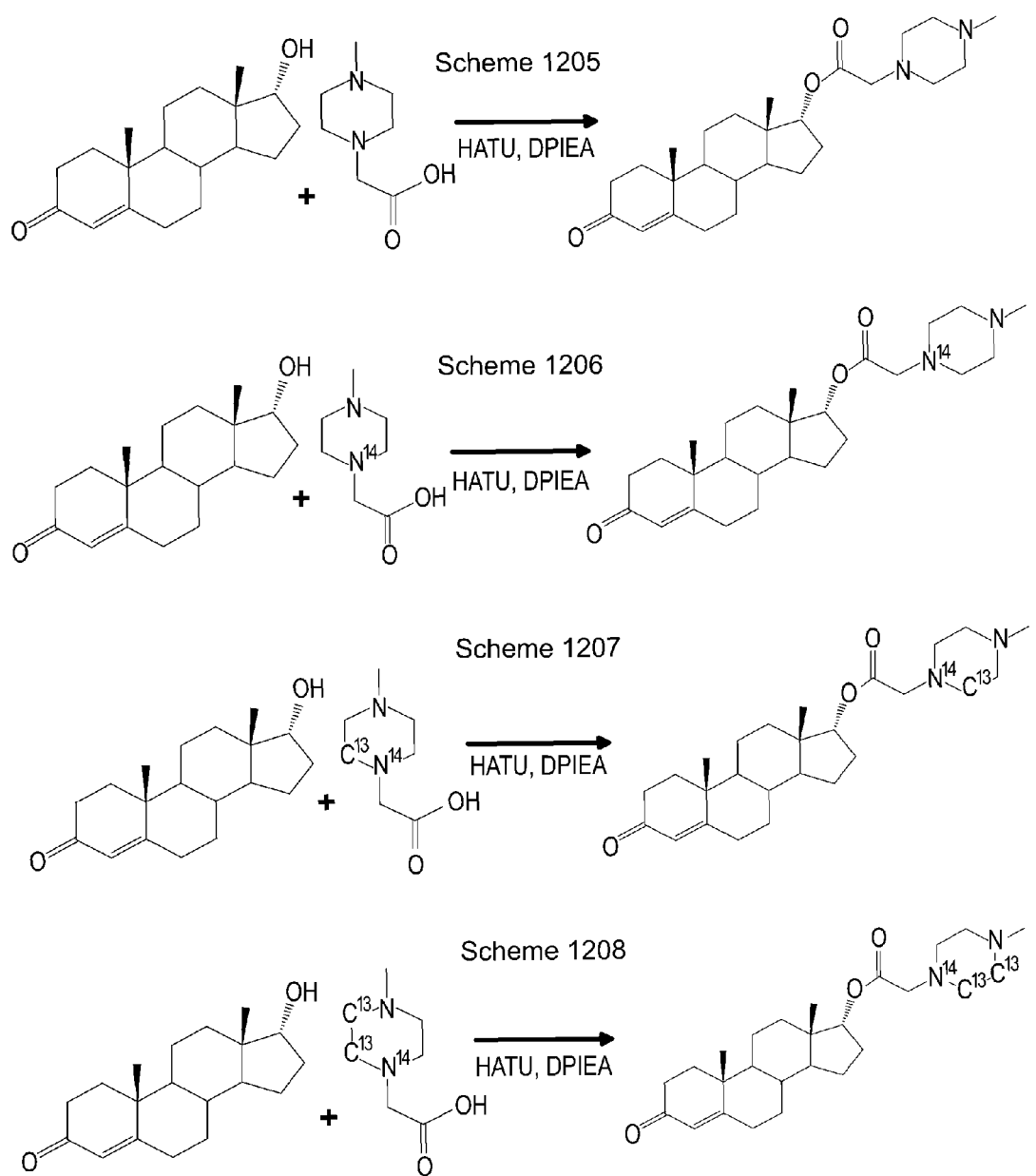

FIGS. 12A-12B are schematic representations of various embodiments of methods of labeling a hydroxylated compound with a mass differential tag.

Figure 13:
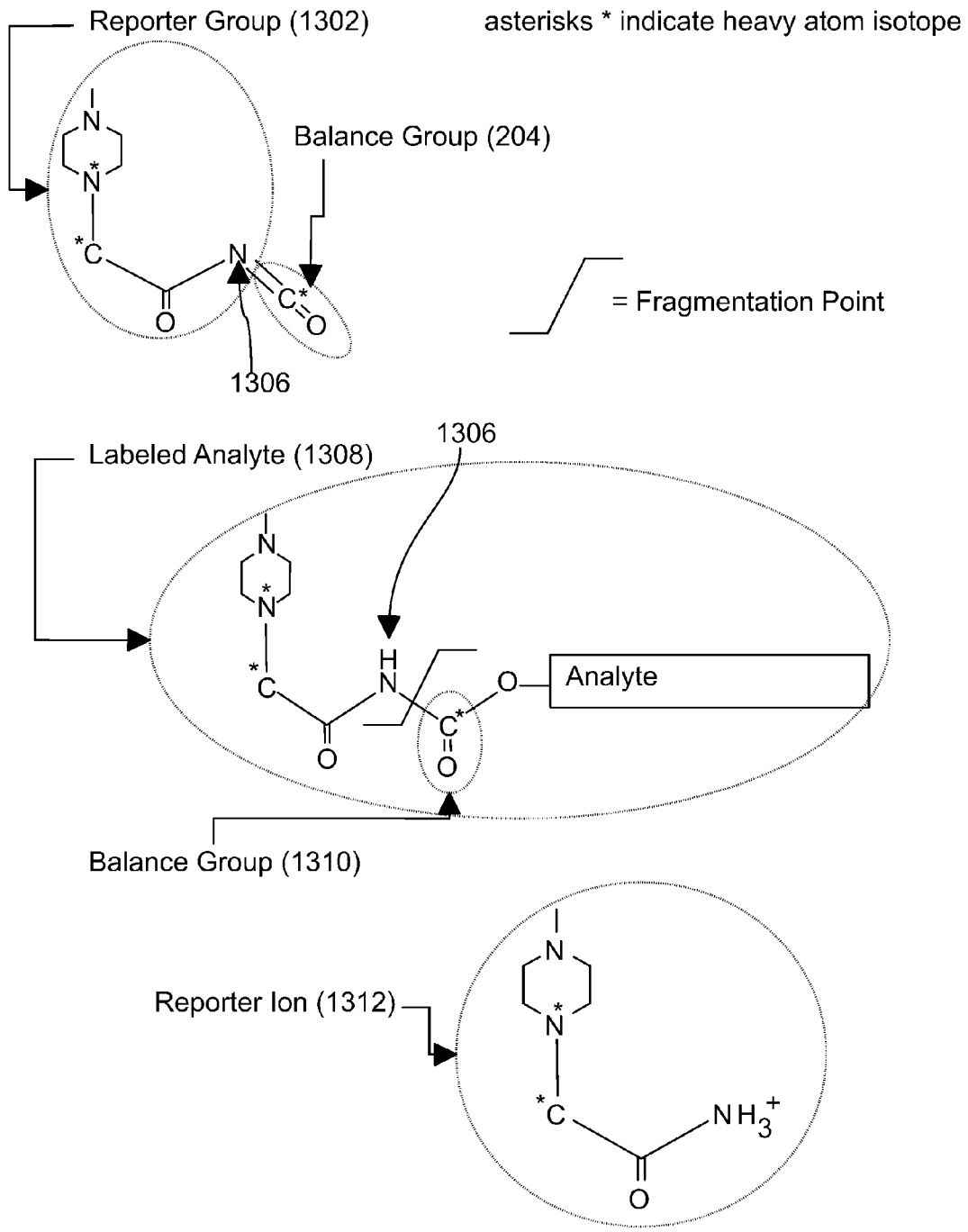

FIG. 13 is a schematic representation of various embodiments of piperzine labeling reagent, a labeled analyte, and a reporter ion.

Figure 14:
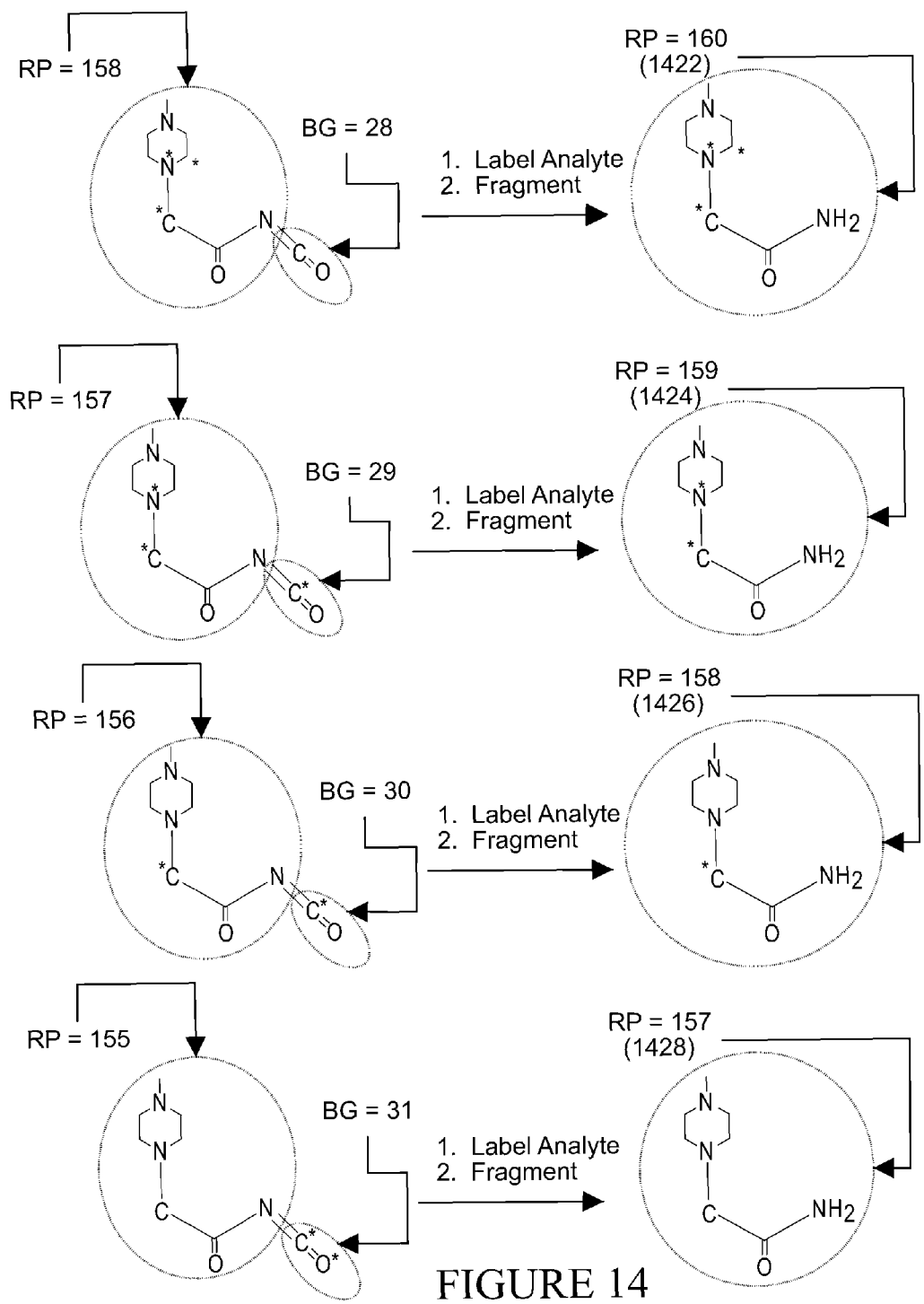

FIG. 14 schematically illustrates various embodiments of isobaric tags of the present teachings and their associated reporter ions.

FIG. 15 schematically illustrates various embodiments of isobaric tags of the present teachings, their reaction with a cholesterol to produce a labeled cholesterol and associated reporter ions for the labeled cholesterol subjected to an MS/MS analysis.

Figure 16A:
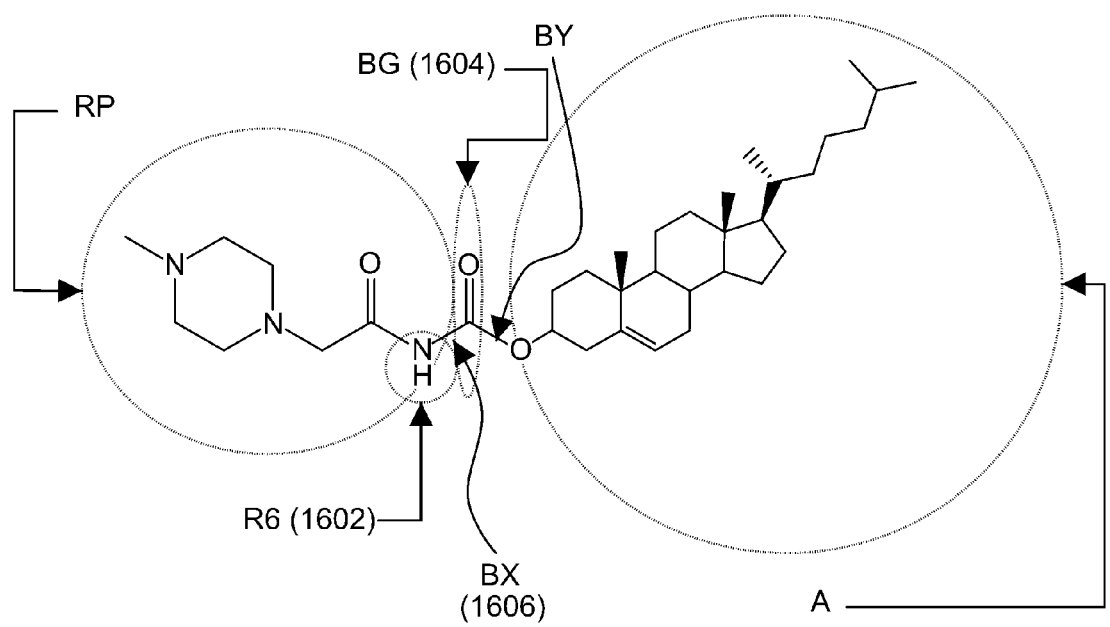
Figure 16B:
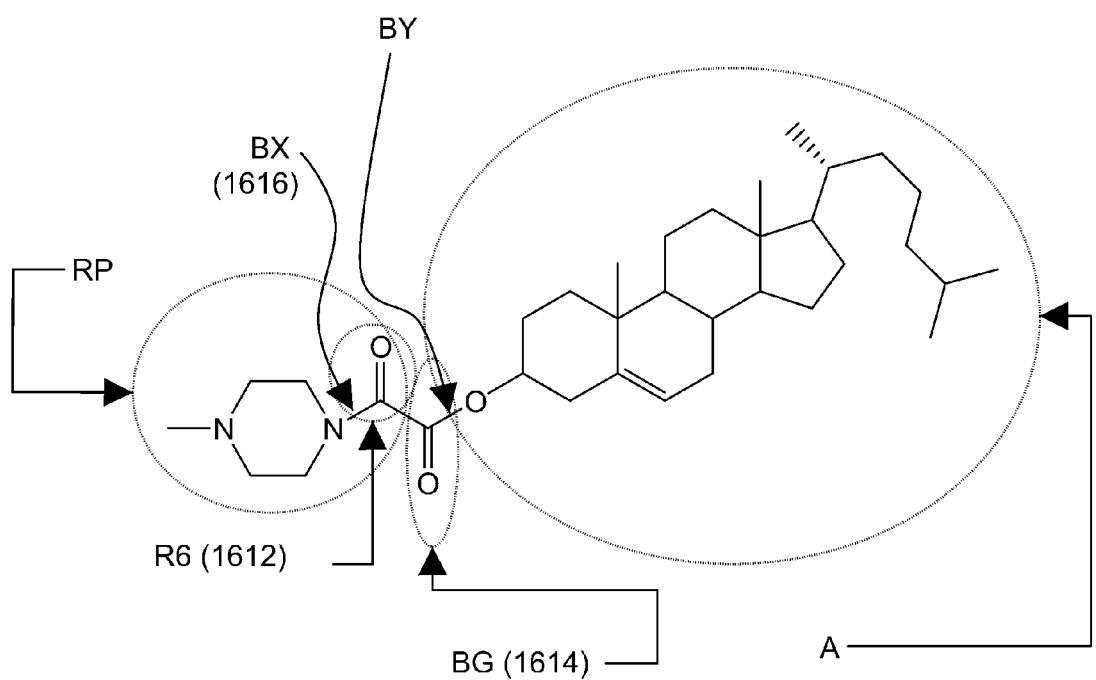

FIGS. 16A-16B schematically illustrates various embodiments of labeled compounds of the present teachings.

Figure 17:
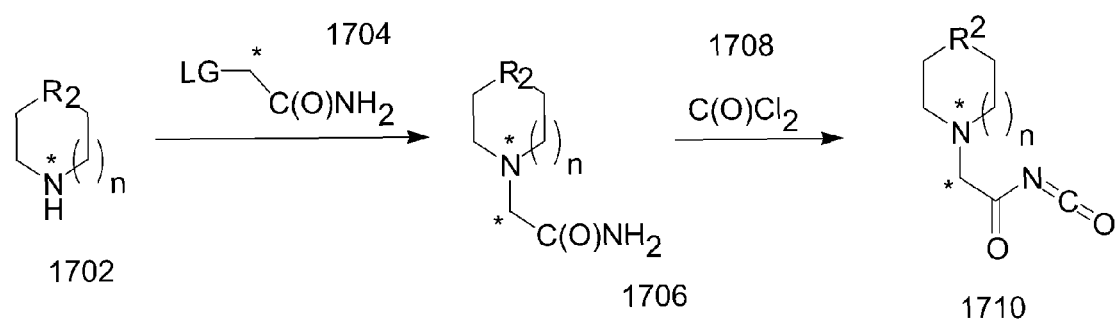

FIGS. 17 and 18 schematically illustrates of various embodiments of methods of forming labeling reagents of the present teachings.

Figure 19:
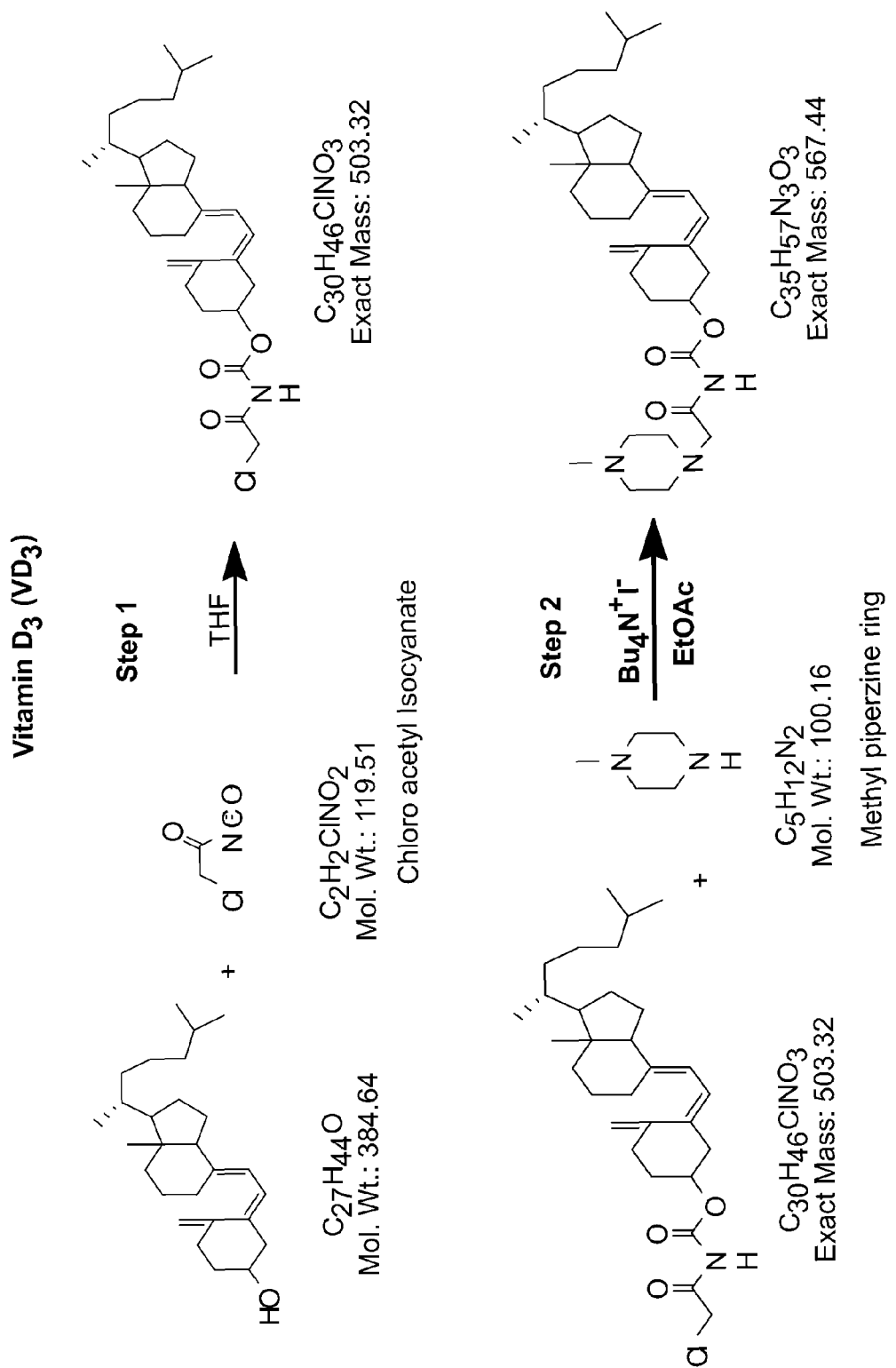

FIGS. 19 and 20 schematically illustrates reactions for forming the various labeled analytes of Examples 1-4.

Figure 21:
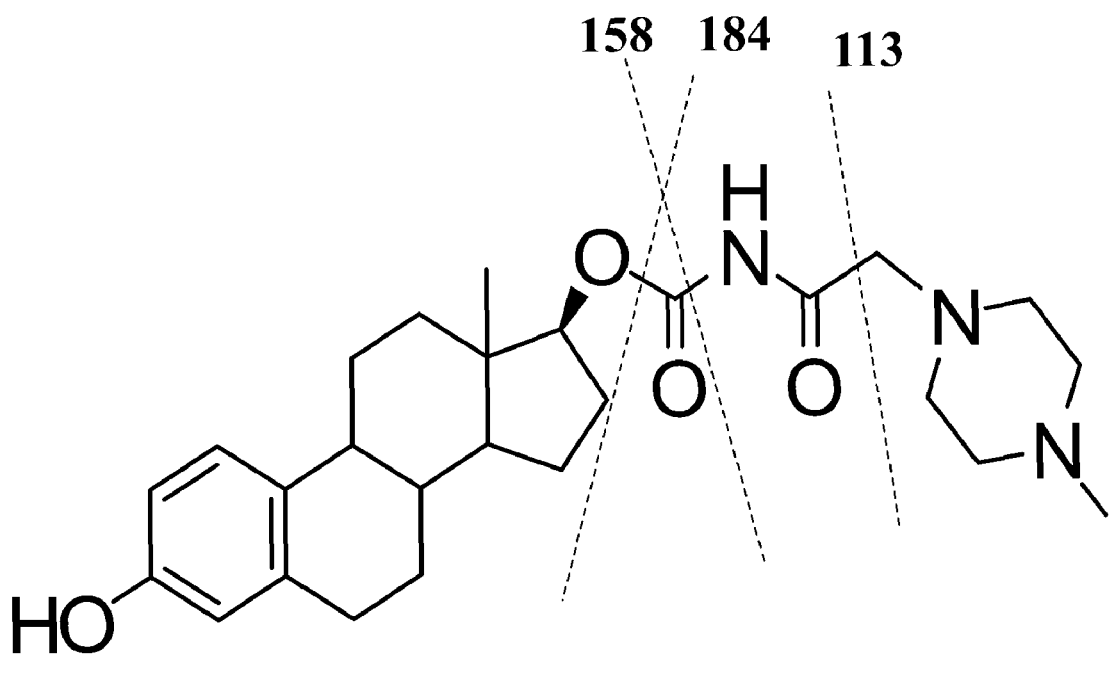

FIG. 21 schematically illustrates for Example 1 various theoretical fragmentation points (dashed lines) of labeled analytes and the potential reporter ion rough base mass resulting from fragmentation at that point (number associated with dashed line).

Figure 22A:
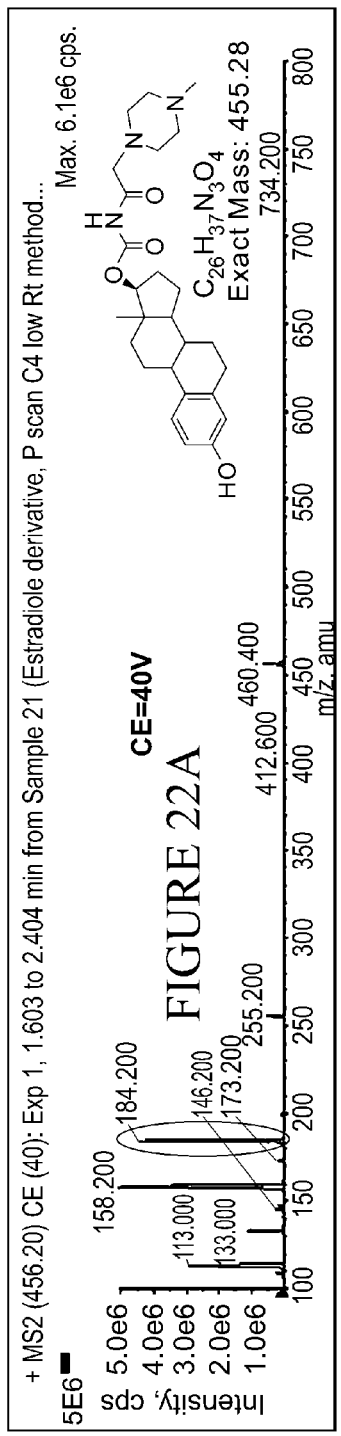
Figure 22B:
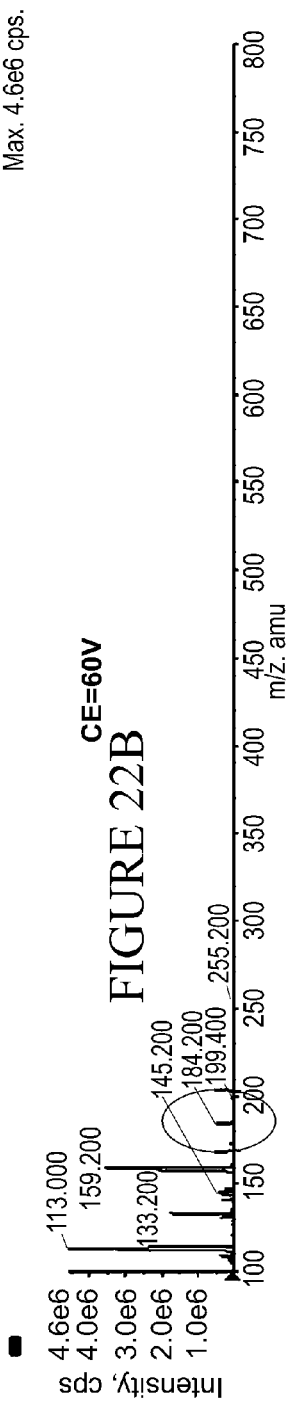
Figure 22C:

FIGS. 22A-C schematically depict experimental LC/MS/MS data of Example 1 for various collision energies (CE).

Figure 23:
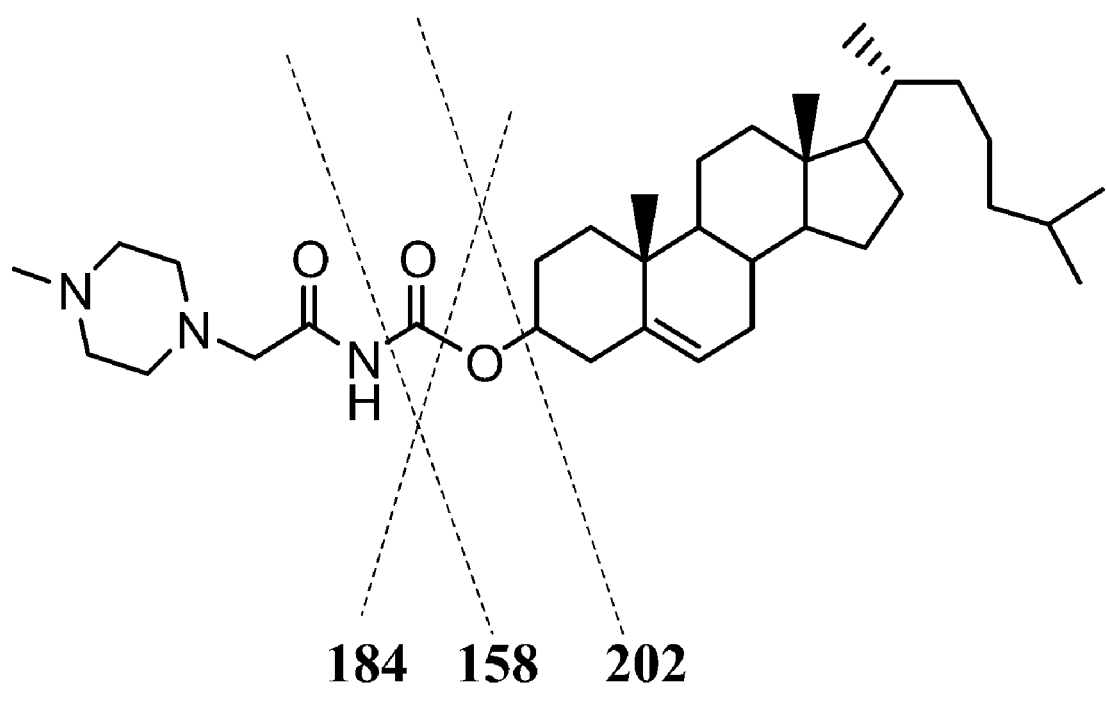

FIG. 23 schematically illustrates for Example 2 various theoretical fragmentation points (dashed lines) of labeled analytes and the potential reporter ion rough base mass resulting from fragmentation at that point (number associated with dashed line).

FIGS. 24A-B schematically depict experimental LC/MS/MS data of Example 2 for various collision energies (CE).

Figure 25:
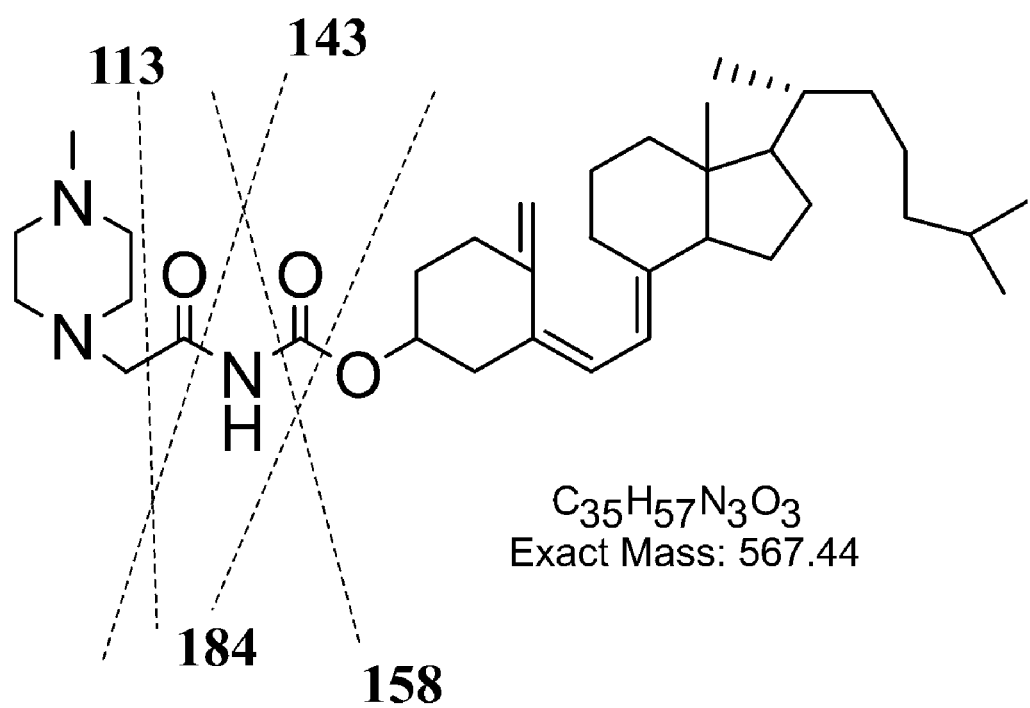

FIG. 25 schematically illustrates for Example 3 various theoretical fragmentation points (dashed lines) of labeled analyte of that example (Vitamin D3) and the potential reporter ion rough base mass resulting from fragmentation at that point (number associated with dashed line).

Figure 26:
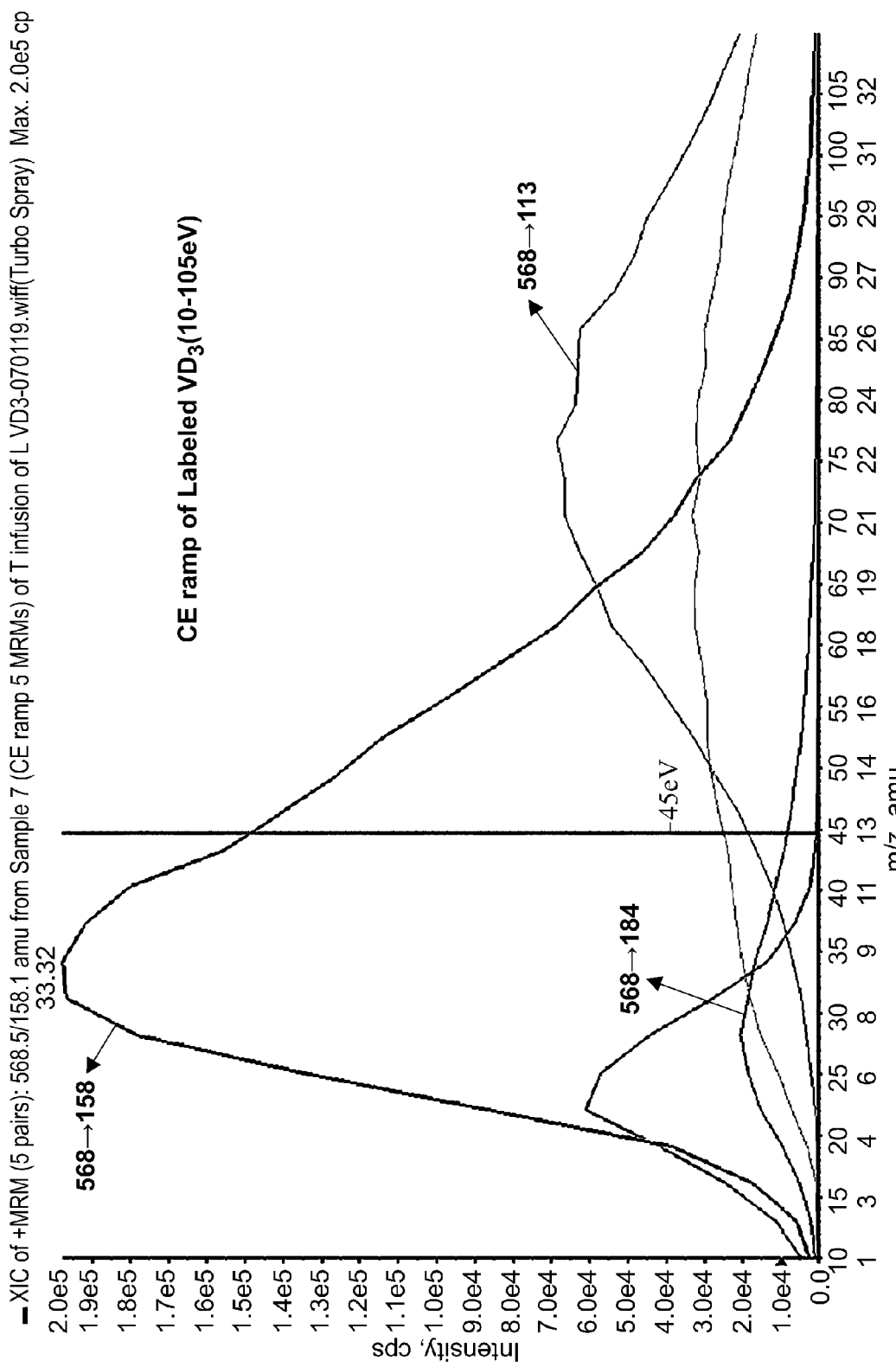

FIG. 26 schematically depicts experimental data of Example 3 on the signal intensity (y-axis) for various MRM (parent-daughter ion transitions) as a function of collision energy (x-axis) given in electron volts (eV).

Figure 27:
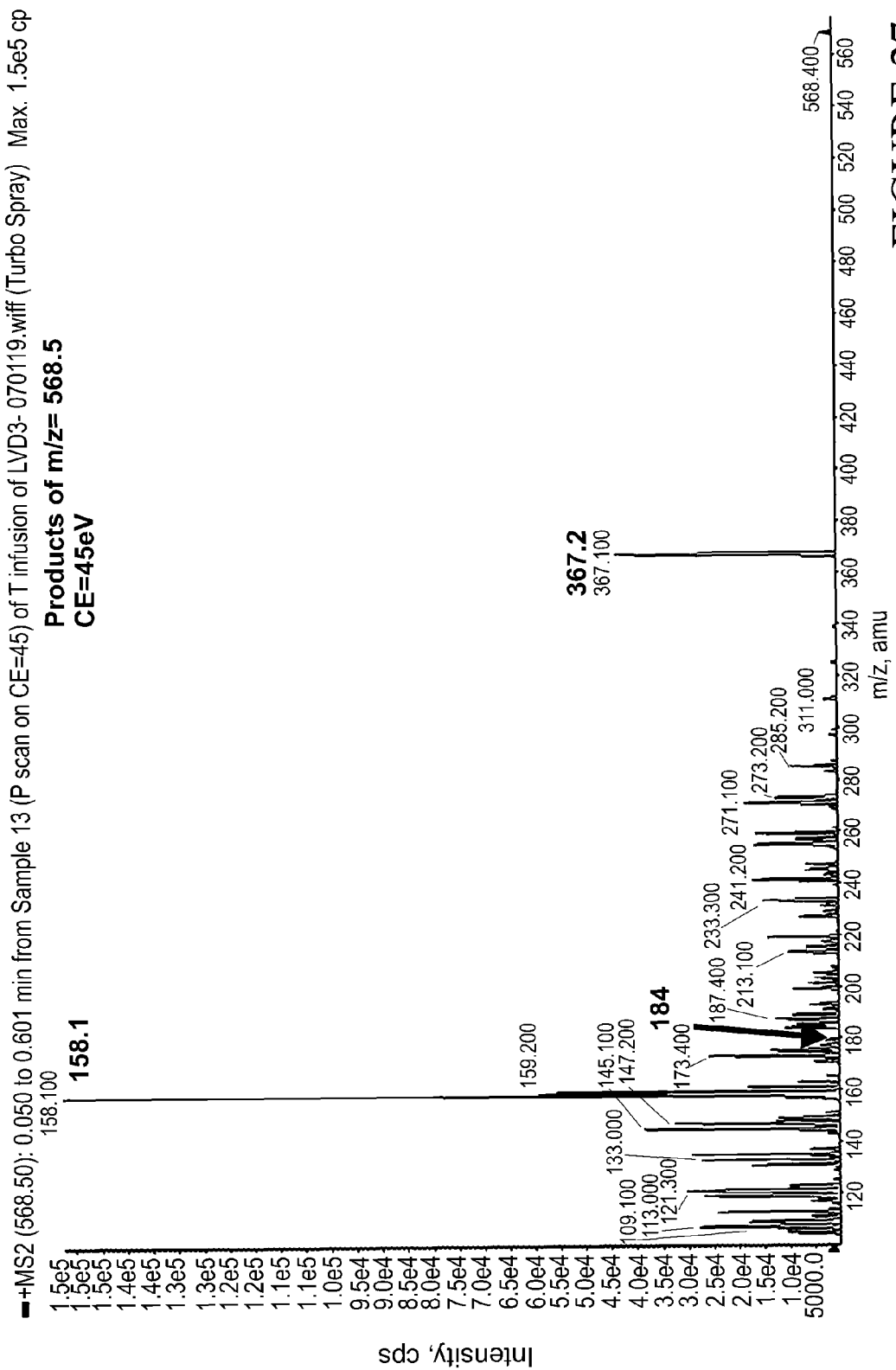

FIG. 27 schematically depicts experimental LC/MS/MS data of Example 3 at a collision energy of 45 eV.

Figure 28:
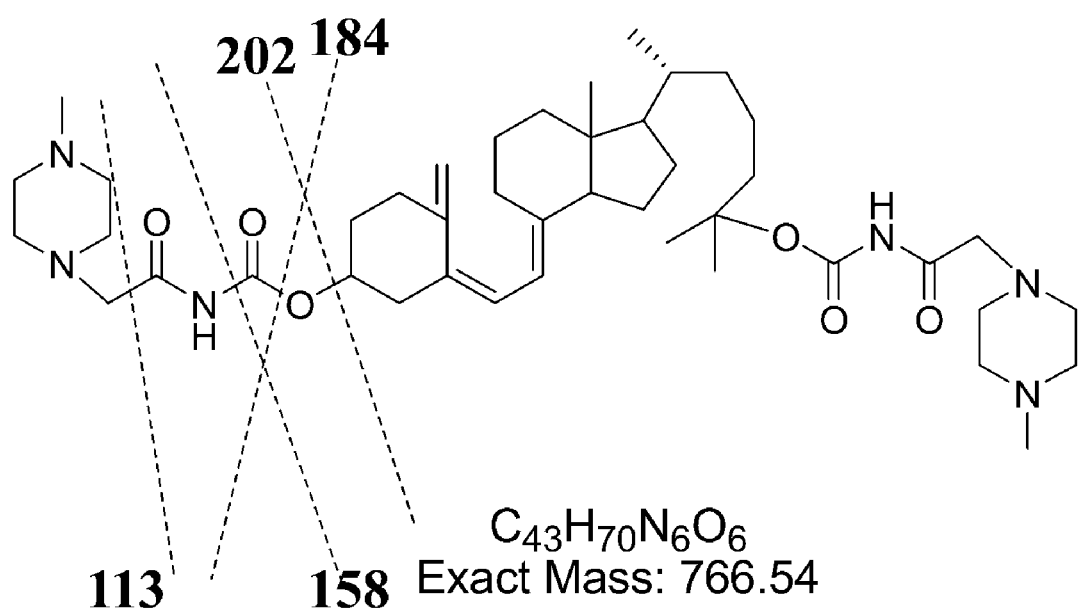

FIG. 28 schematically illustrates for Example 3 various theoretical fragmentation points (dashed lines) of a labeled analyte of that example (25(OH) Vitamin D3) and the potential reporter ion rough base mass resulting from fragmentation at that point (number associated with dashed line).

FIGS. 29A-B and 30A-B schematically depict experimental LC/MS/MS data of Example 3 for various collision energies (CE).

Figure 31:
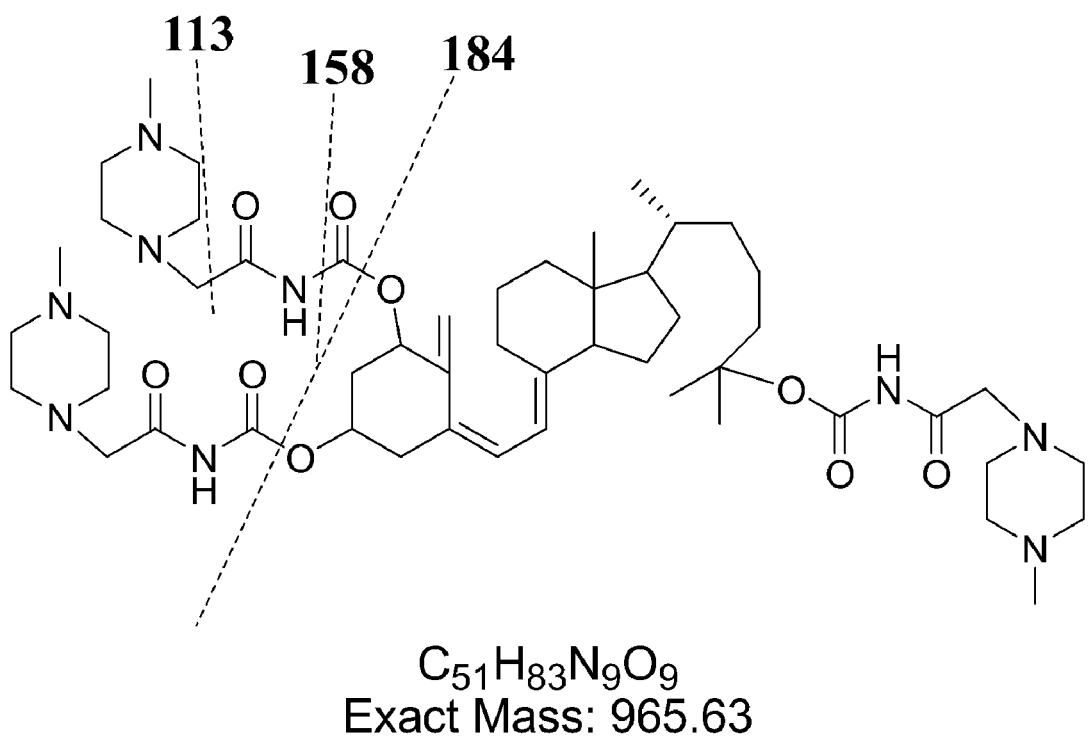

FIG. 31 schematically illustrates for Example 3 various theoretical fragmentation points (dashed lines) of a labeled analyte of that example (1,25(OH)$_2$ Vitamin D3) and the potential reporter ion rough base mass resulting from fragmentation at that point (number associated with dashed line).

FIGS. 32A-D and 33A-D schematically depict experimental data of Example 3; FIGS. 32A and 33A depicting total ion current (TIC) as a function of collision energy (CE); and FIGS. 32B-D and 33B-D depicting experimental LC/MS/MS data for various collision energies (CE).

FIGS. 34-38 schematically depict experimental data of Example 4 on improved signal and/or detection limit of analytes labeled with labels of various embodiments of the present teaching versus unlabeled analytes.

Figure 39A:
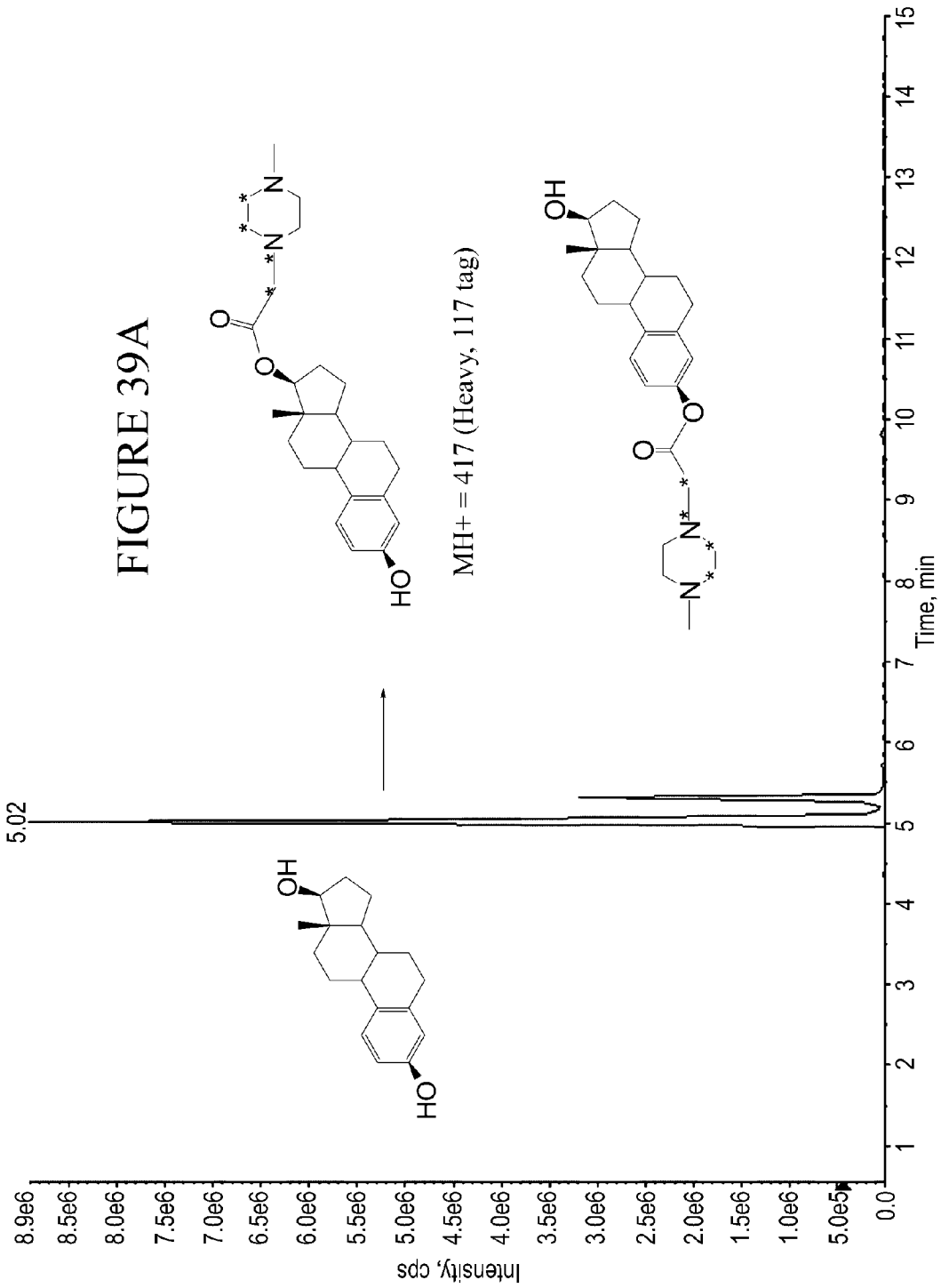
Figure 39B:
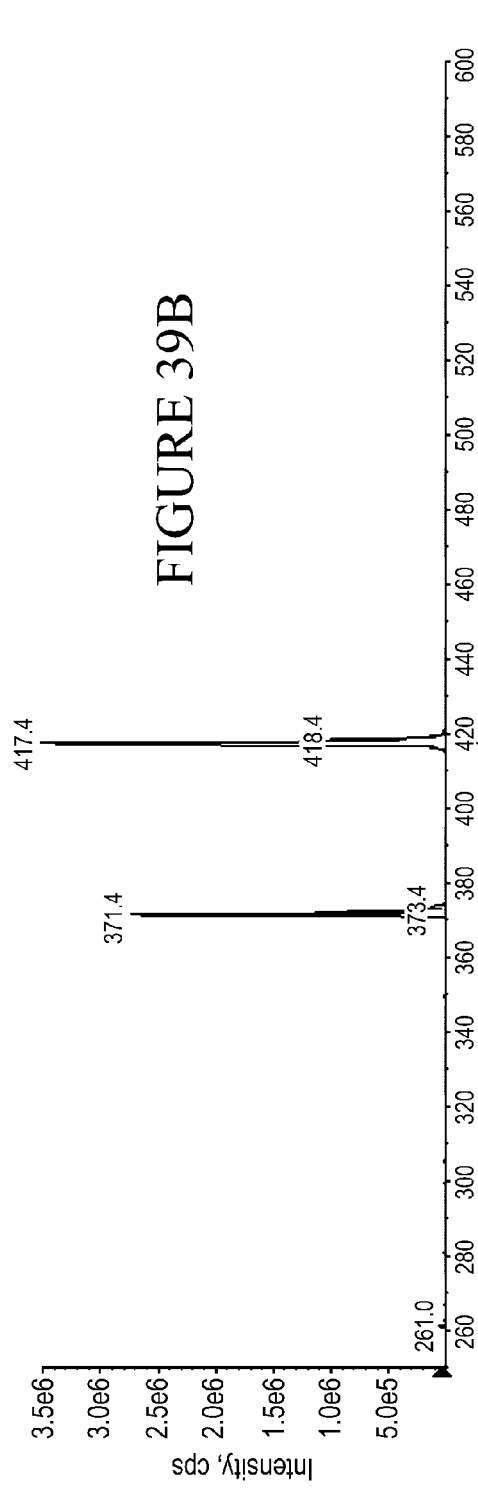
Figure 39C:
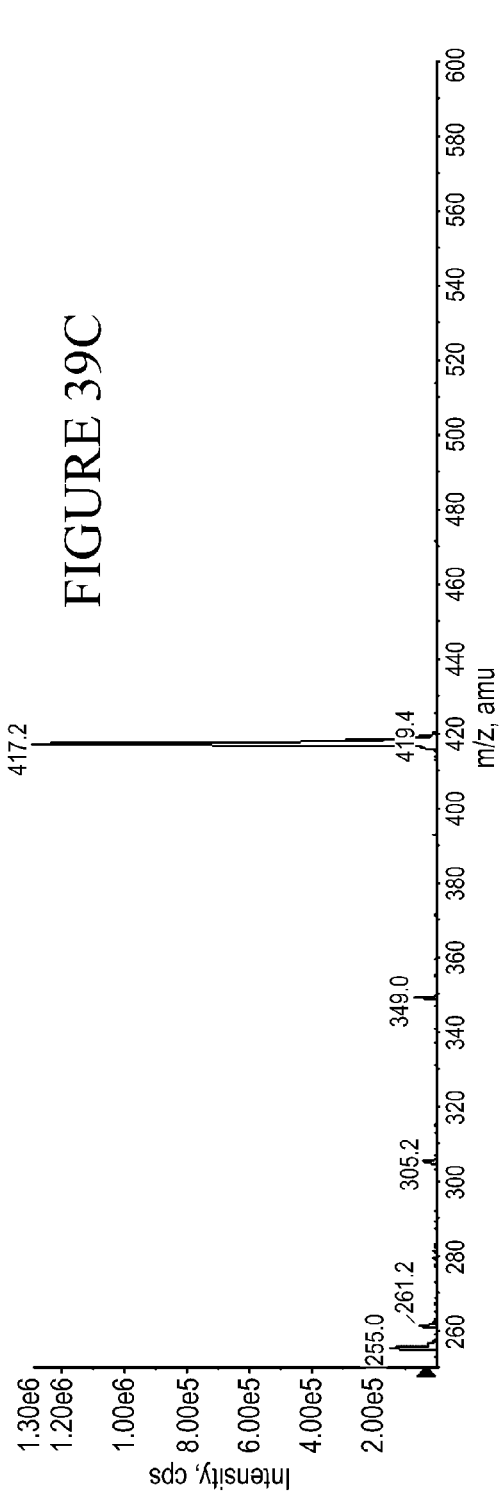
Figure 39F:
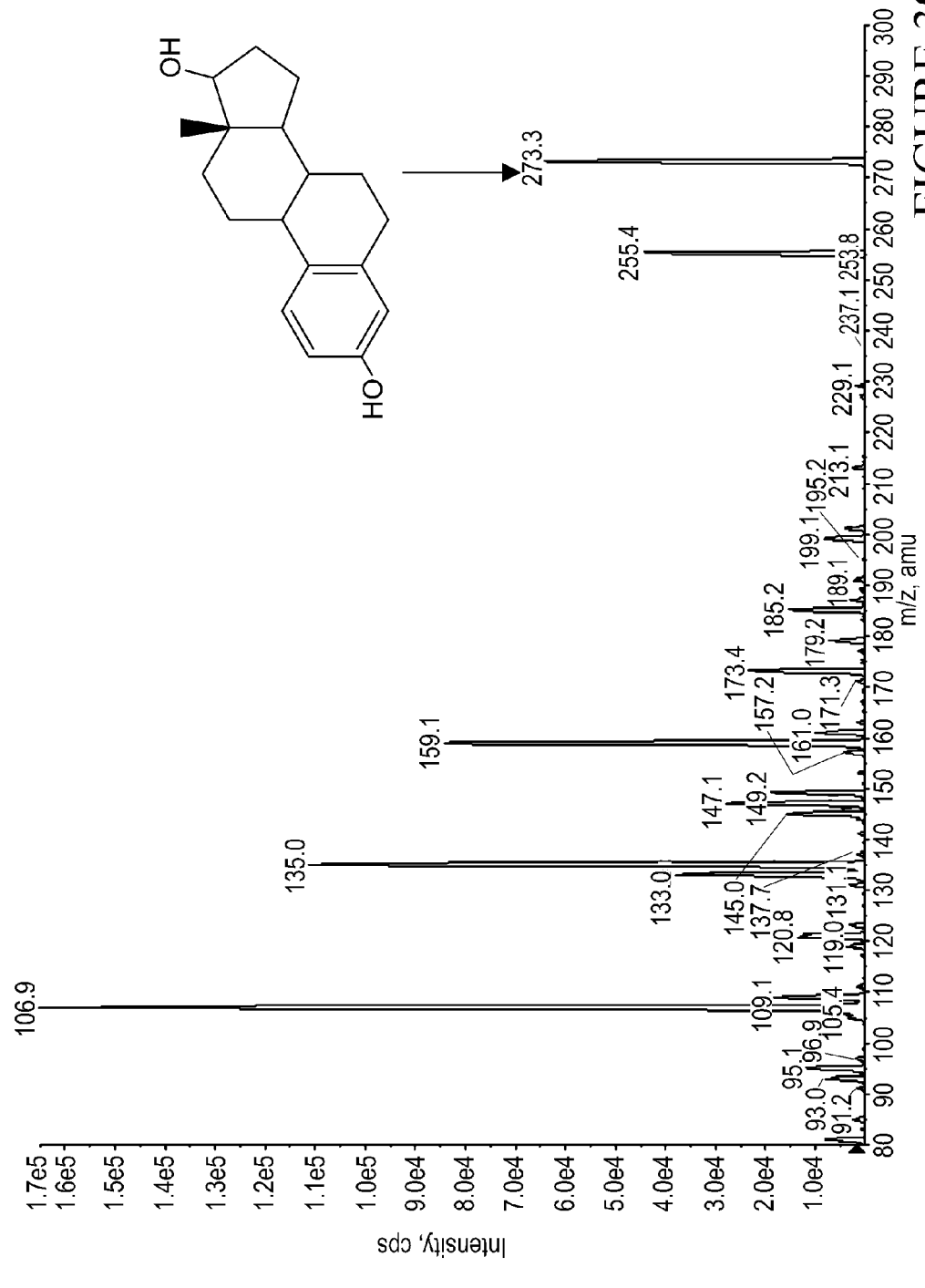

FIGS. 39A-39E schematically depict experimental data of Example 5. FIG. 39A schematically depicts a chromatogram of a labeled estradiol sample. FIGS. 39B and 39C schematically depict, respectively, electrospray (ESI) mass spectra of the eluent at approximately 5.0 minutes and at 5.3 minutes in FIG. 39A. FIGS 39D and 39E schematically depict, respectively, ESI-MS/MS spectra of the eluent at approximately 5.02 minutes and at 5.3 minutes in FIG. 39A. FIG. 39F schematically depicts an ESI-MS/MS spectra of unlabeled estradiol.

Figures 40A, 40B:
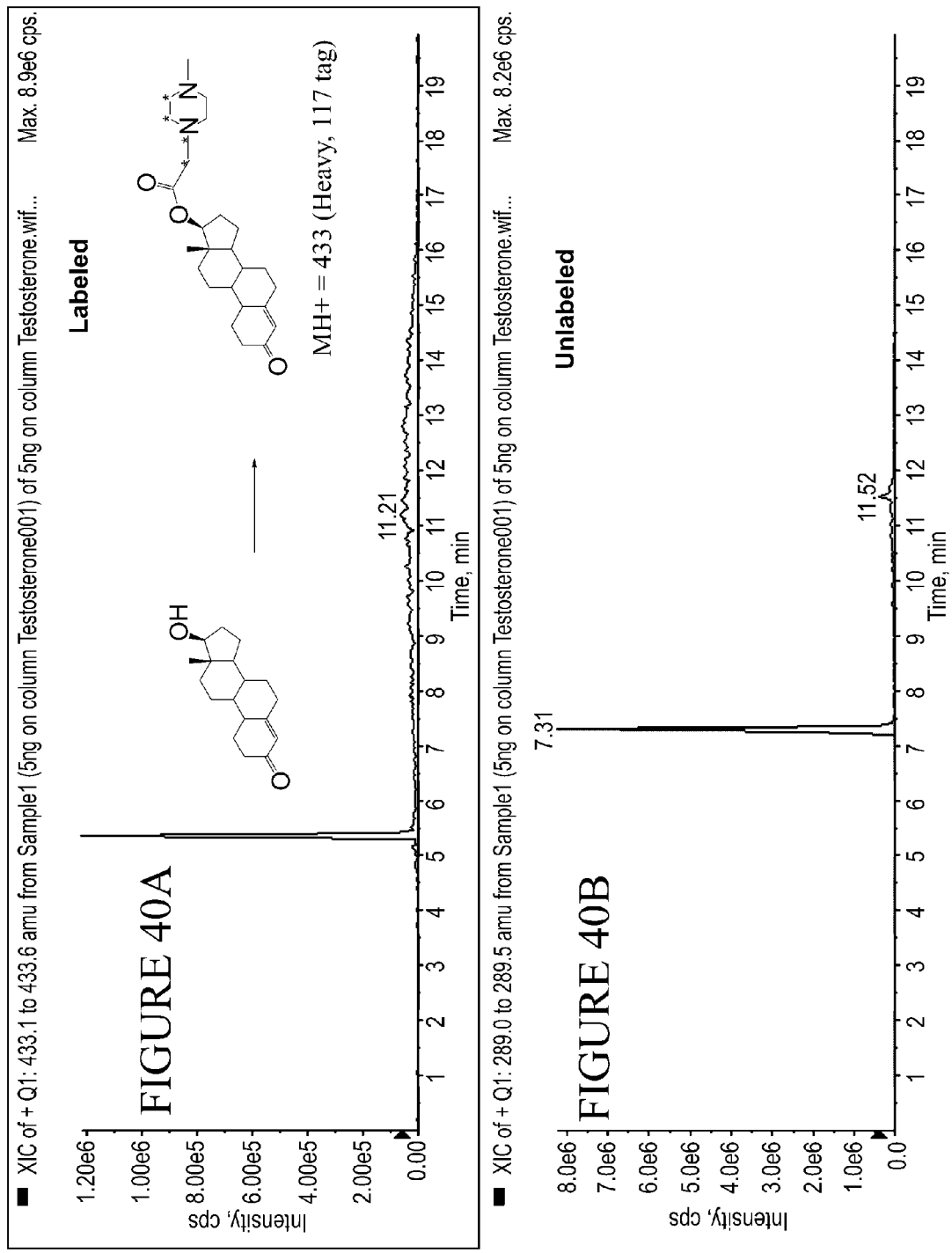

FIGS. 40A-40D schematically depict experimental data of Example 6. FIGS. 40A and 40B schematically depict, respectively, chromatograms of labeled and unlabeled testosterone. FIGS. 40C and 40D schematically depict, respectively, ESI-MS/MS spectra of unlabeled and labeled testosterone.

Figures 41A, 41B:
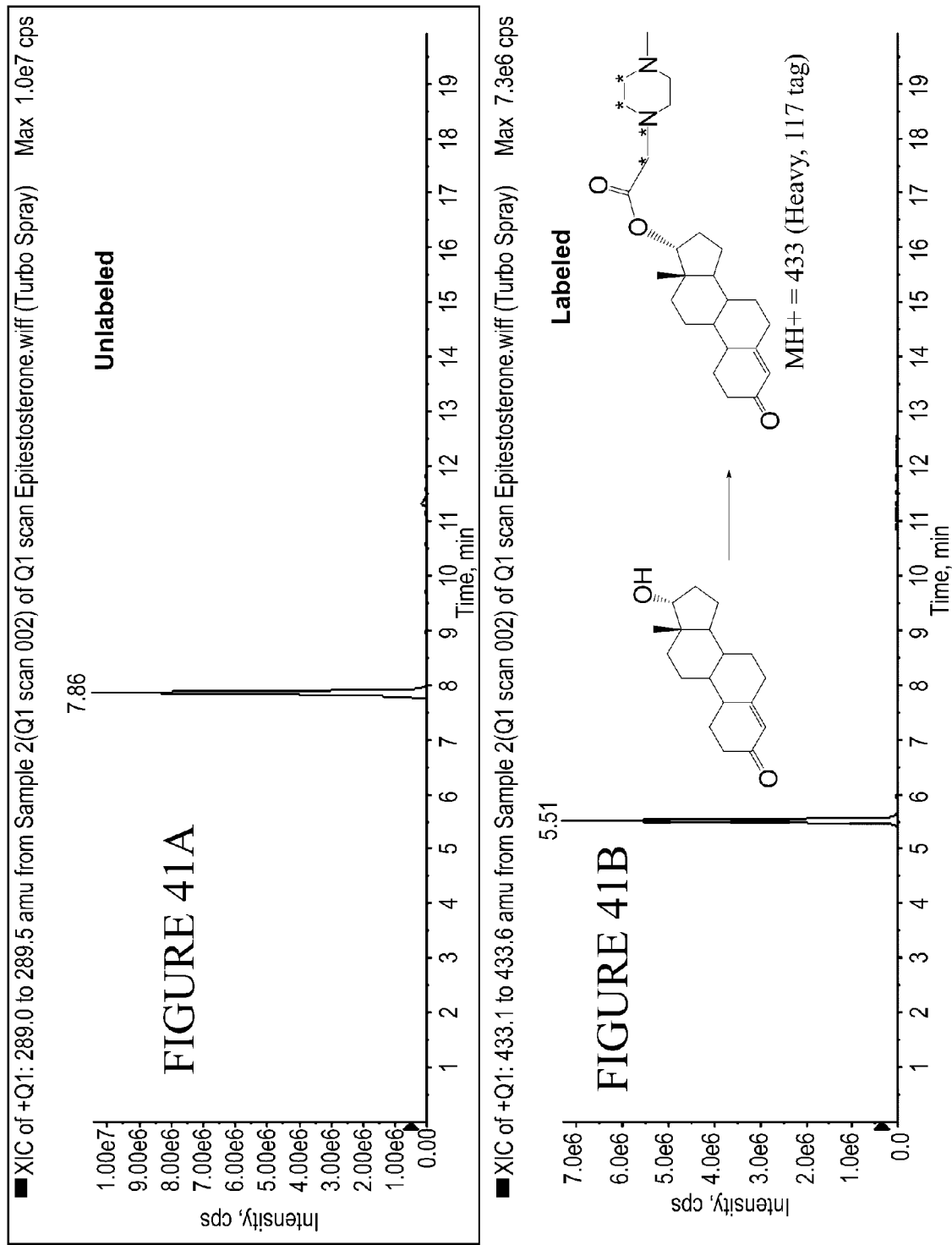
Figures 41C, 41D:
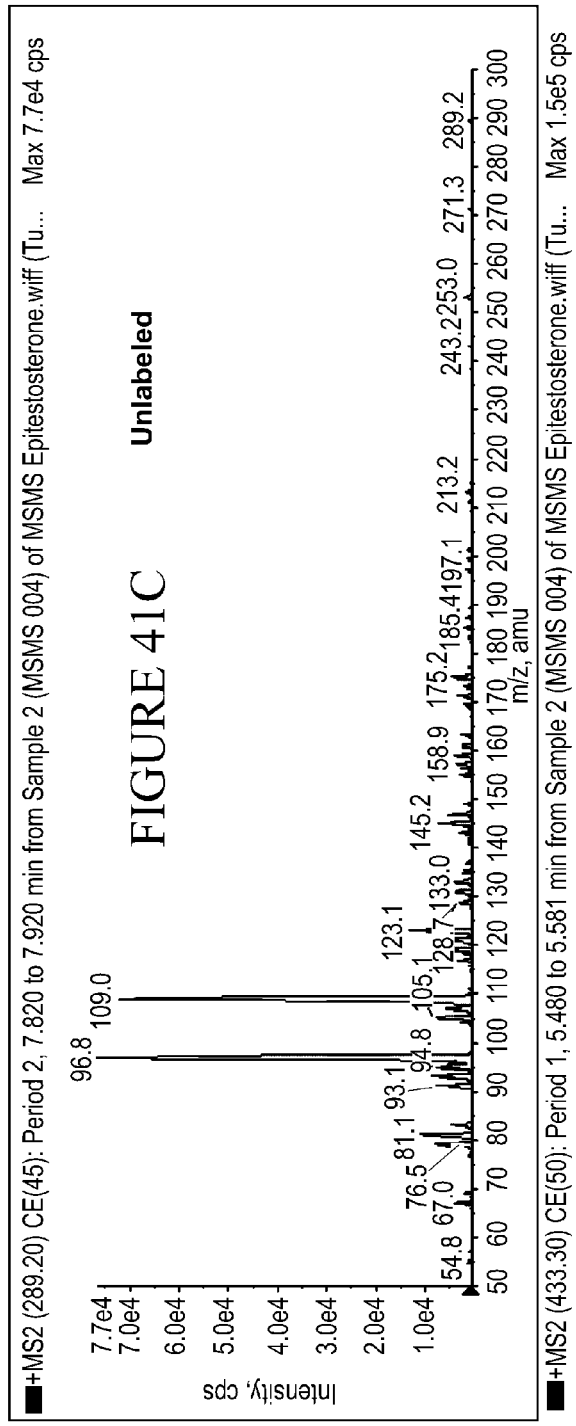

FIGS. 41A-41D schematically depict experimental data of Example 6. FIGS. 41A and 41B schematically depict, respectively, chromatograms of unlabeled and labeled epitestosterone. FIGS. 41C and 41D schematically depict, respectively, ESI-MS/MS spectra of unlabeled and labeled epitestosterone.

Figure 42C:
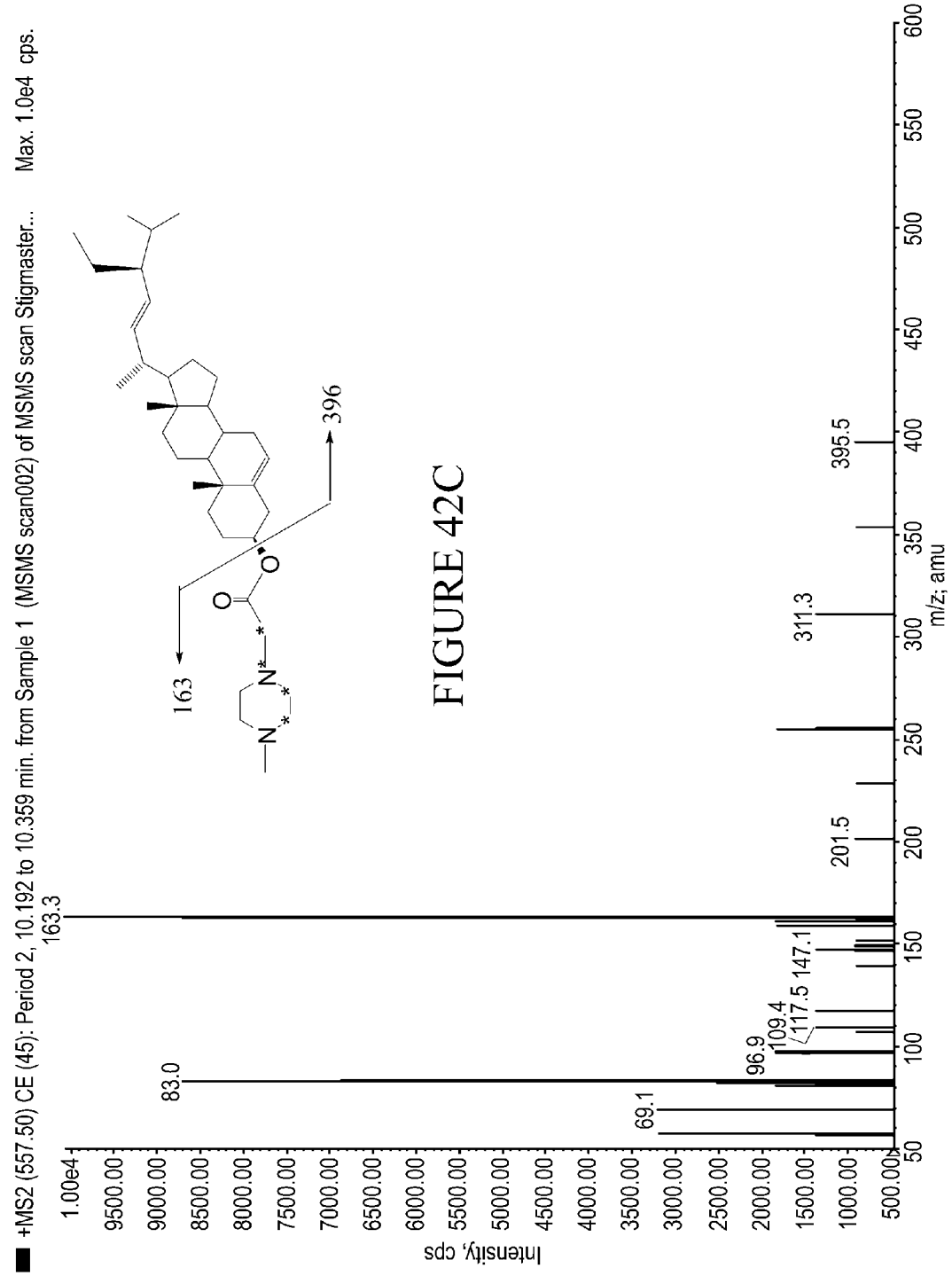

FIGS. 42A-42C schematically depict experimental data of Example 7. FIGS. 42A and 42B schematically depict, respectively, chromatograms of unlabeled and labeled sigmasterol. FIG. 42C schematically depicts an ESI-MS/MS spectra of labeled sigmasterol.

Figure 43A:
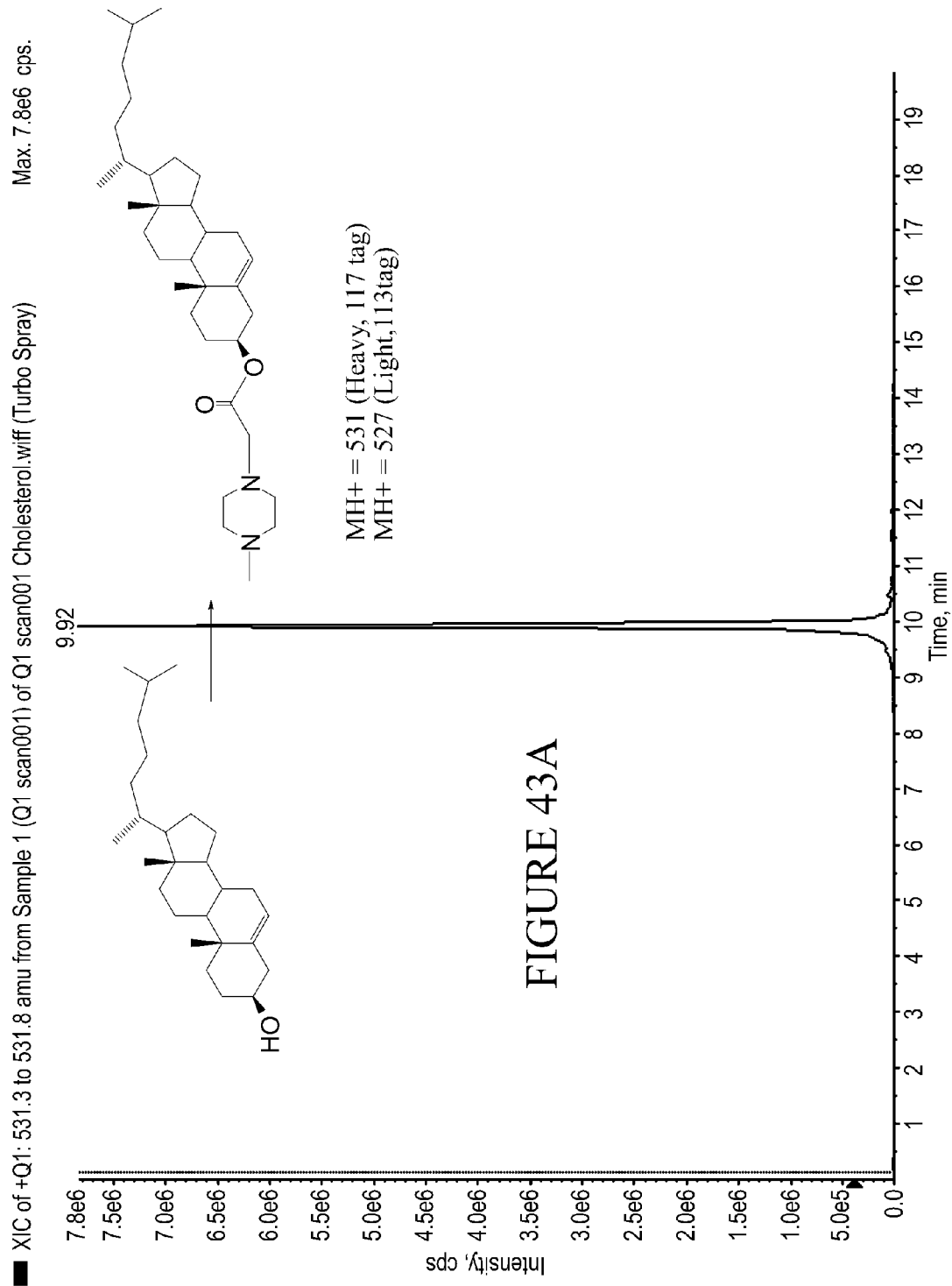
Figure 43B:
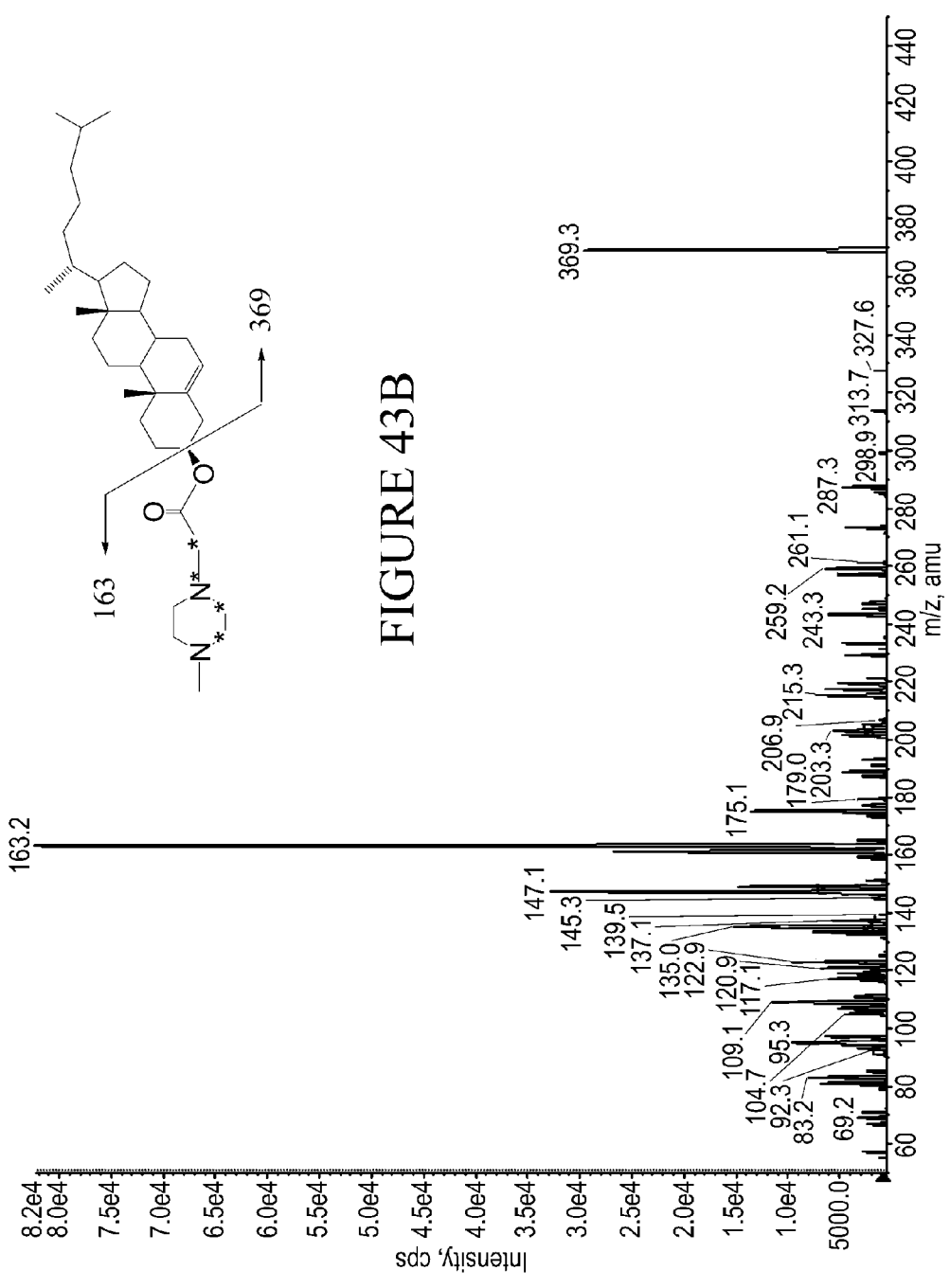
Figure 43E:
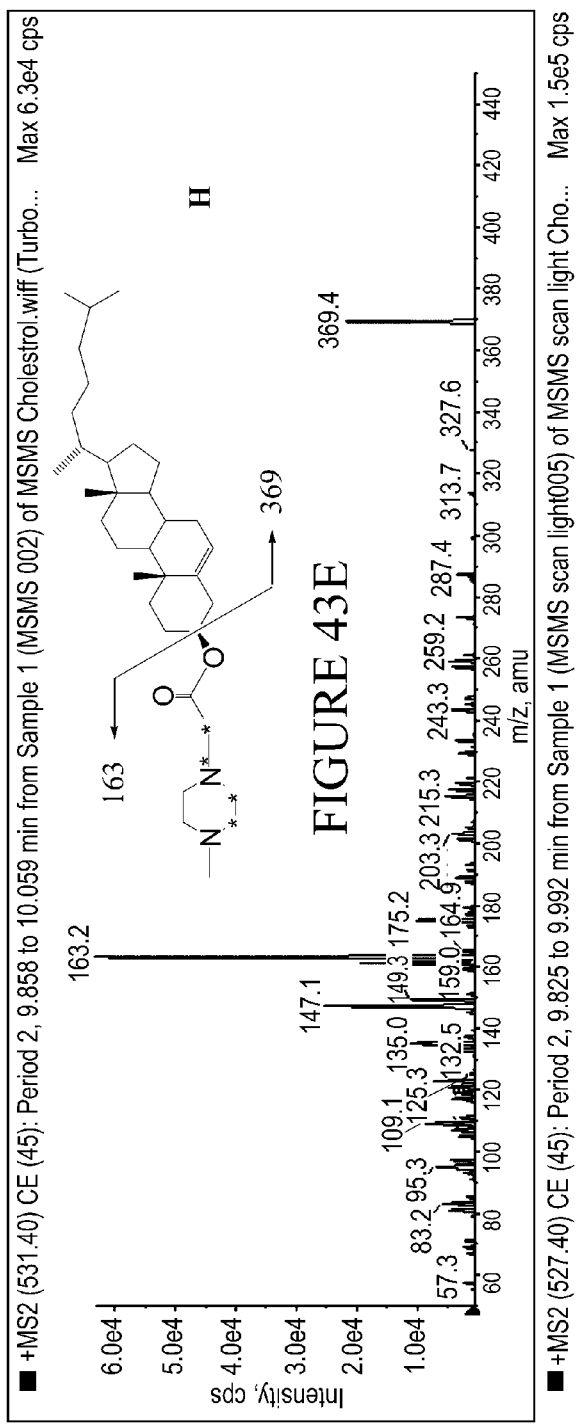
Figure 43F:
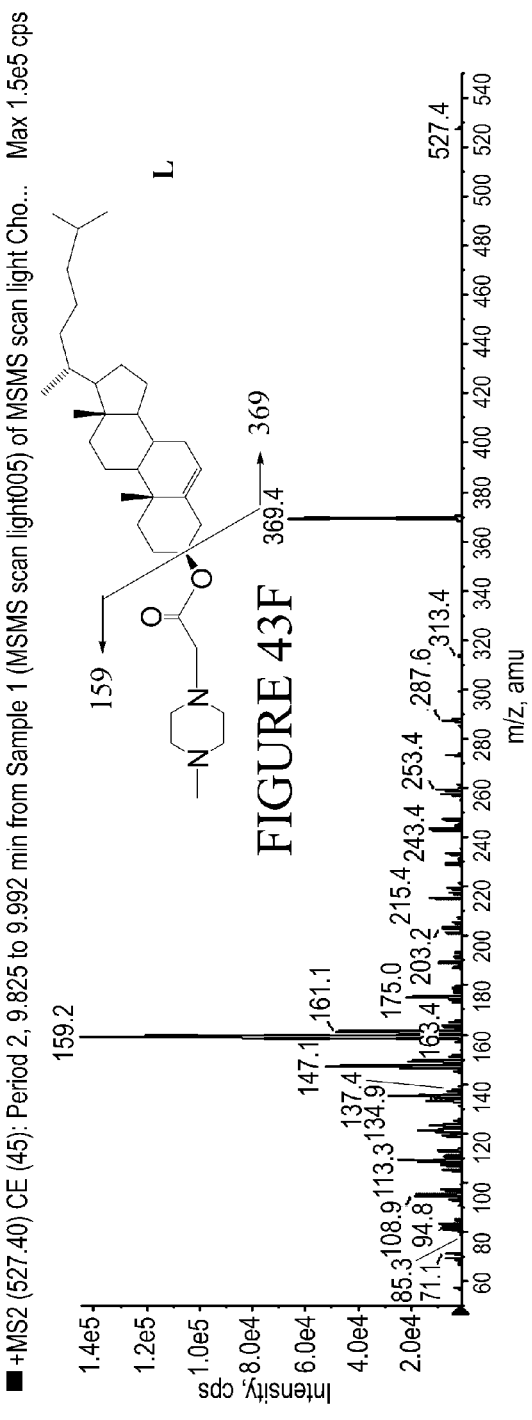
Figure 43G:
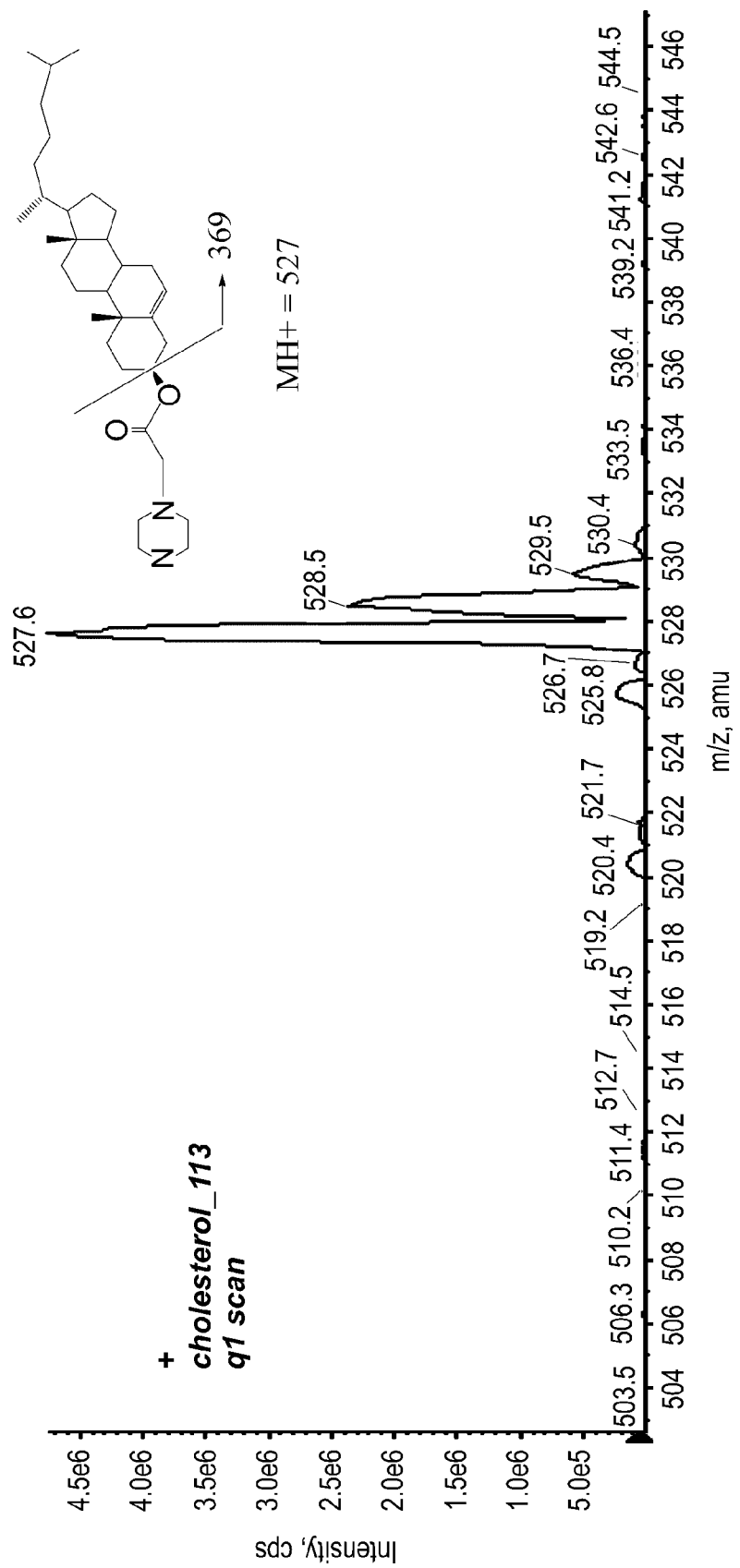
Figure 43H:
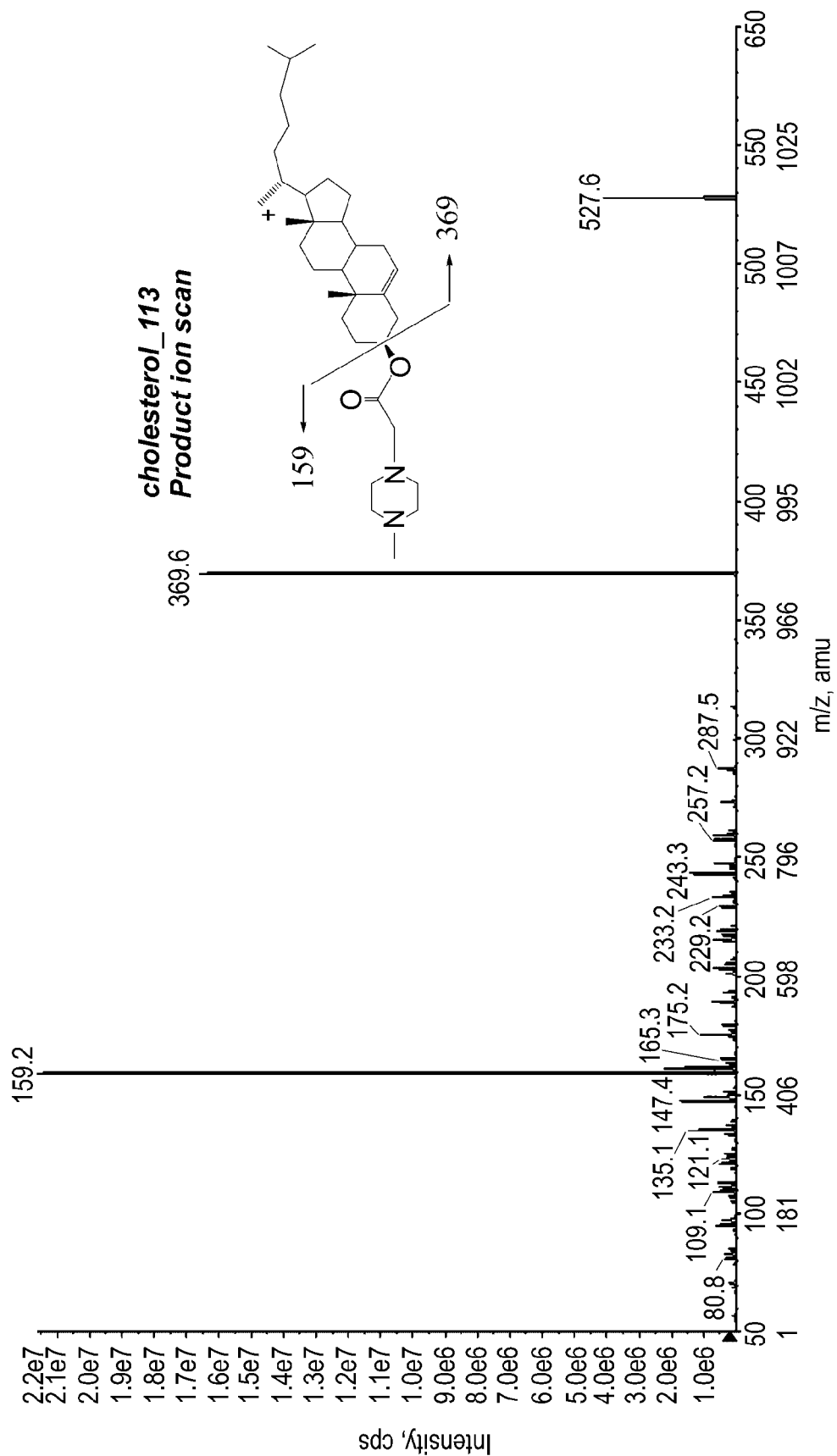
Figure 43I:
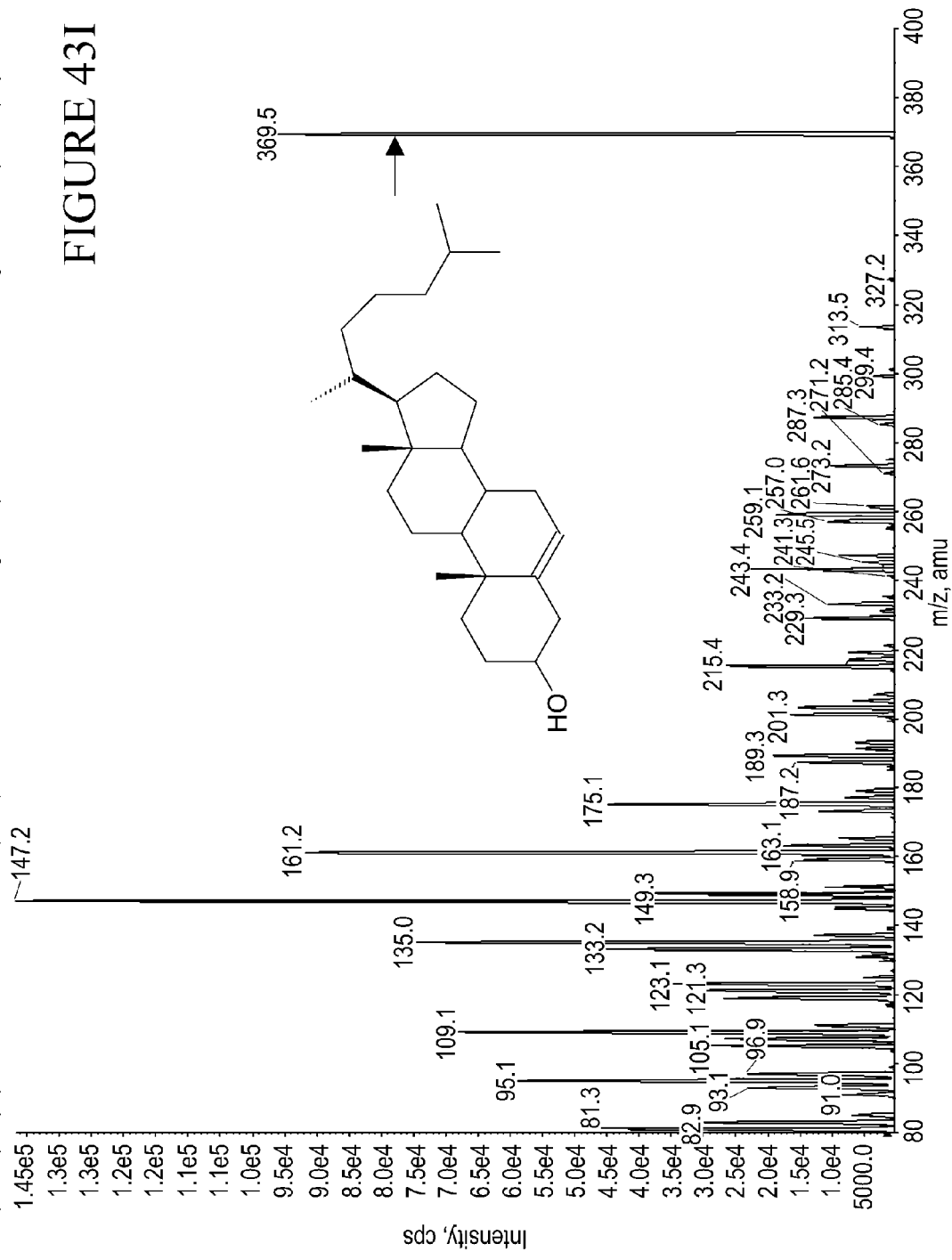

FIGS. 43A-43I schematically depict experimental data of Example 8. FIG. 9A schematically depicts a chromatogram of labeled cholesterol. FIG. 43B schematically depicts an ESI-MS-MS spectra of labeled cholesterol. FIGS. 43C and 43D schematically depict for comparison ESI-MS spectra of cholesterol labeled with mass differential tags from a set of mass differential tags. FIGS. 43E and 43F schematically depict for comparison ESI-MS/MS spectra of cholesterol labeled with mass differential tags from a set of mass differential tags. FIGS. 43G and 43H show finer and broader details of ESI-MS and ESI-MS/MS spectra respectively and FIG. 43I shows an ESI-MS/MS spectra for an unlabeled cholesterol.

Figure 44A:
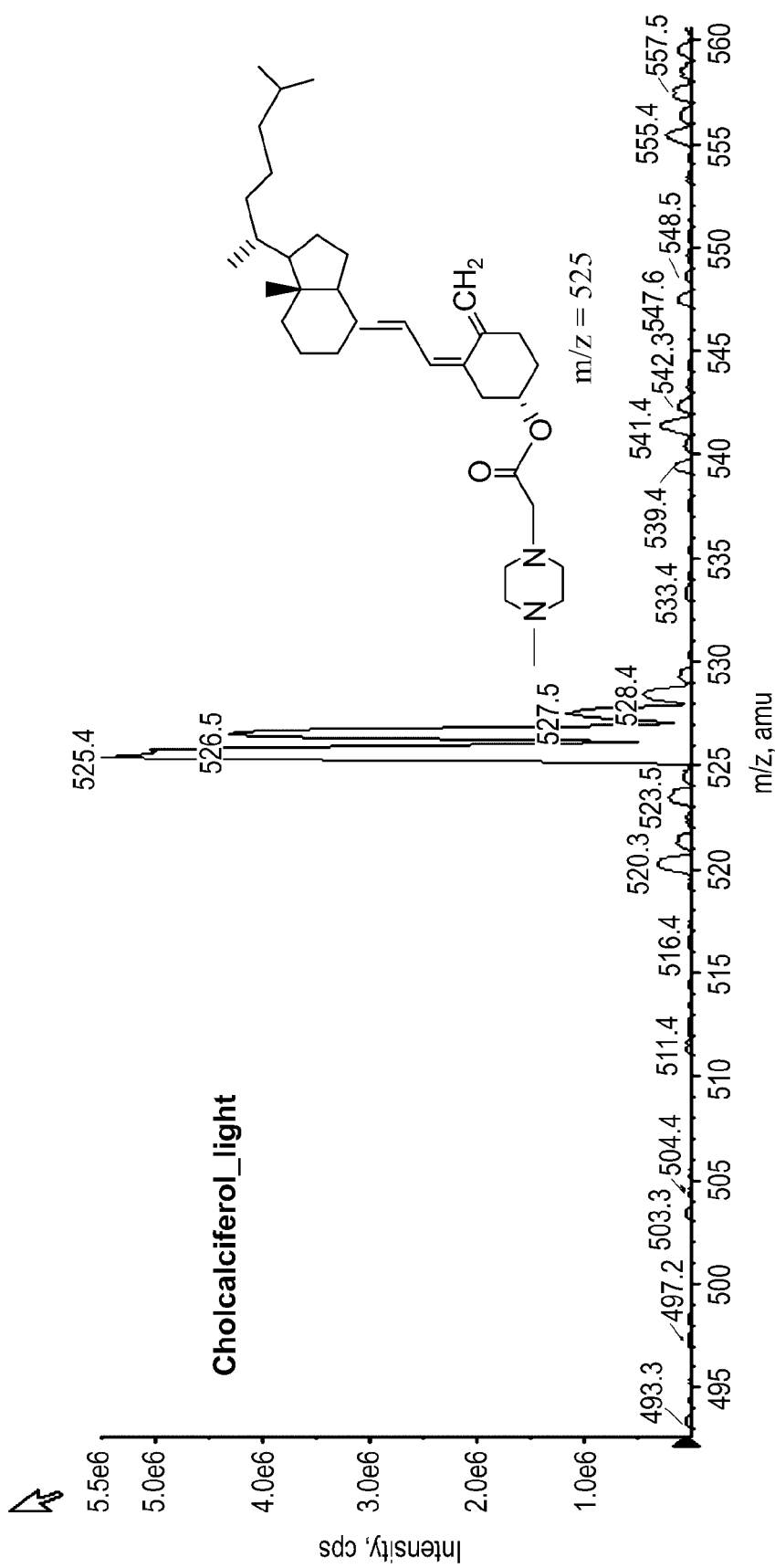
Figure 44B:
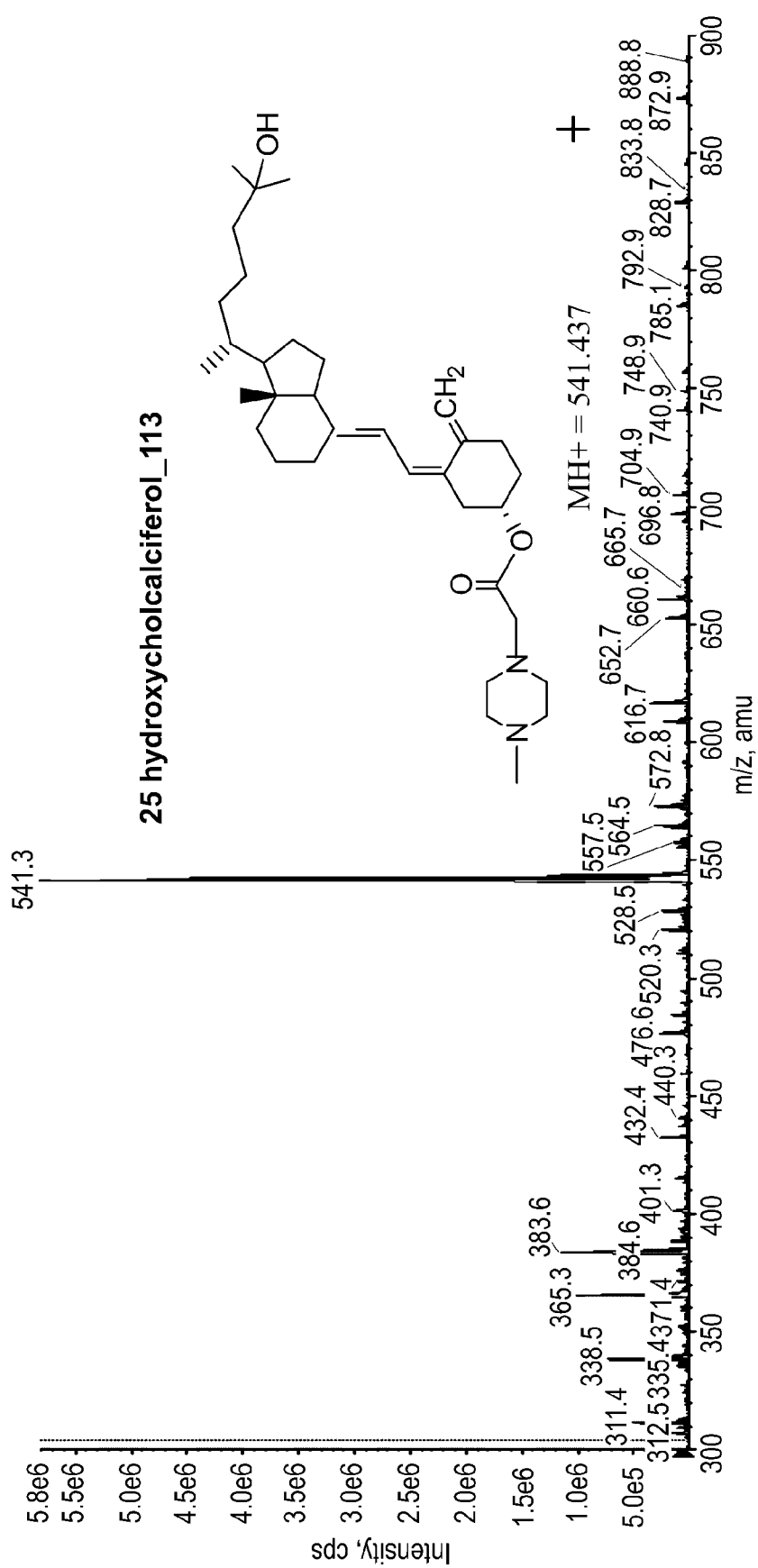
Figure 44C:
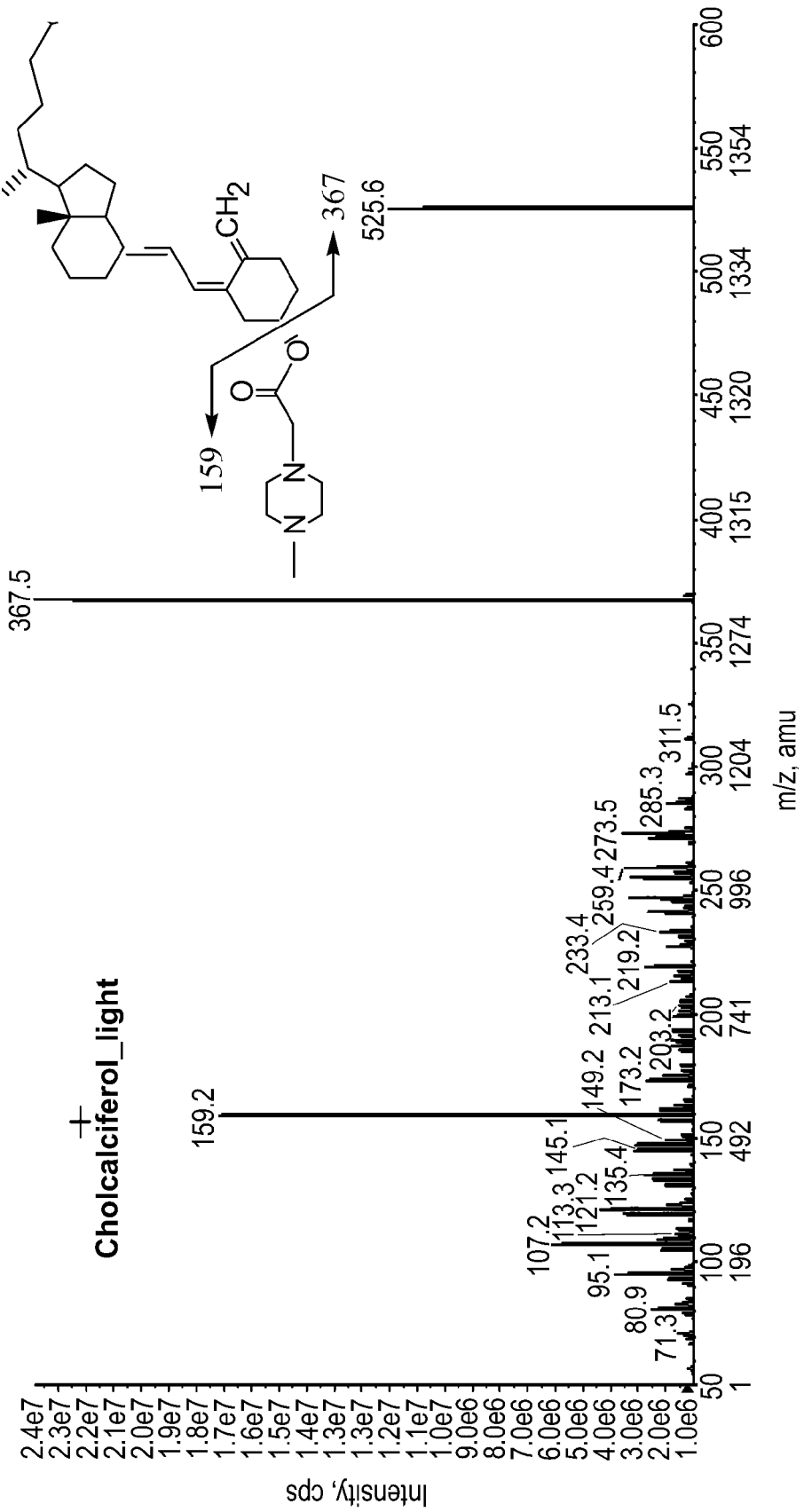
Figure 44D:
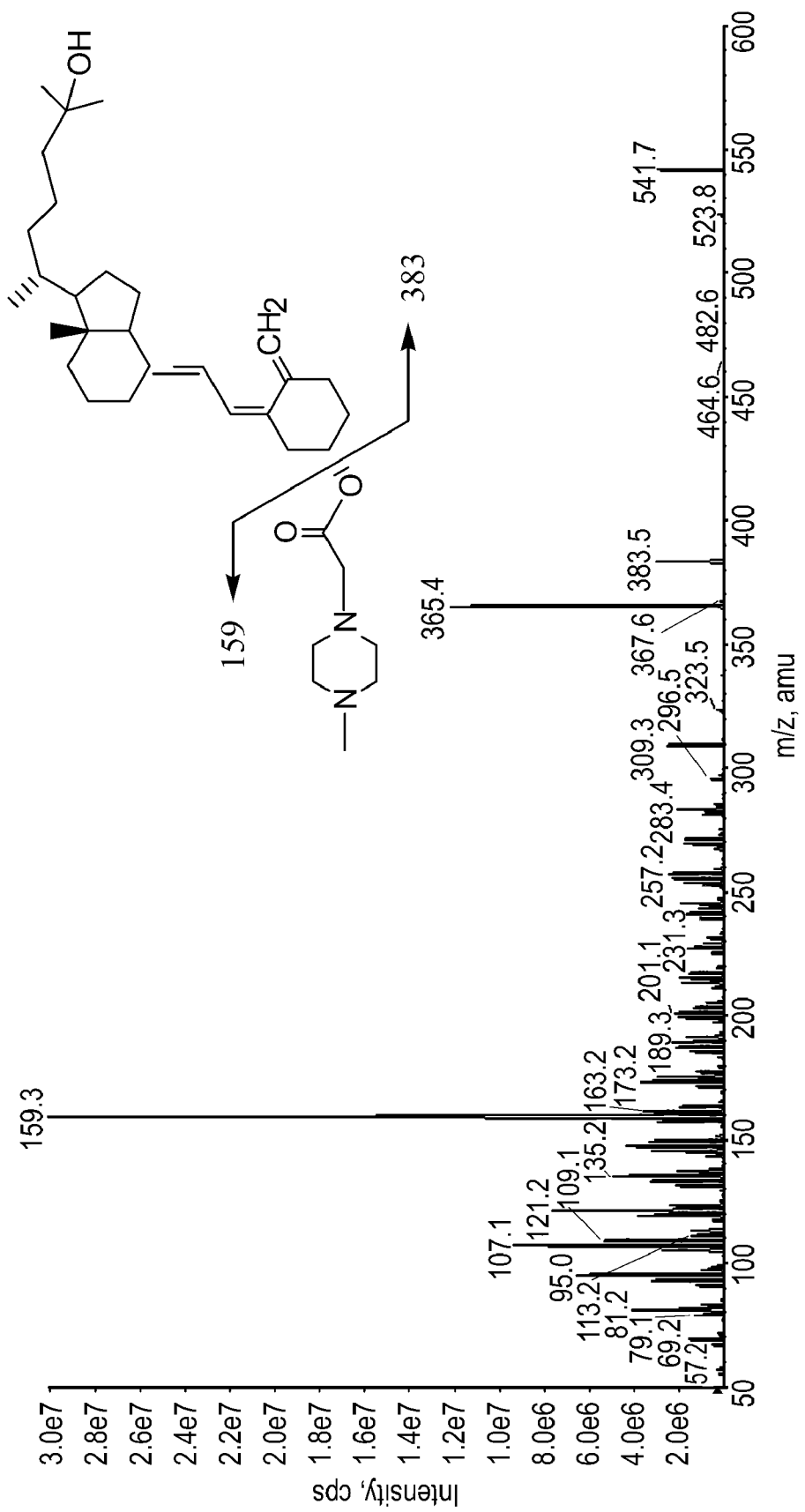

FIGS. 44A-44D schematically depict experimental data of Example 9. FIGS. 44A and 44B schematically depict, respectively, ESI-MS spectra of of labeled cholecalciferol (vitamin $D_3$) and labeled 25-hydroxycholcalciferol (a metabolite of vitamin $D_3$). FIGS. 44C and 44D schematically depict, respectively, ESI-MS/MS spectra for the labeled cholecalciferol (vitamin $D_3$) and labeled 25-hydroxycholcalciferol.

Figure 45A:
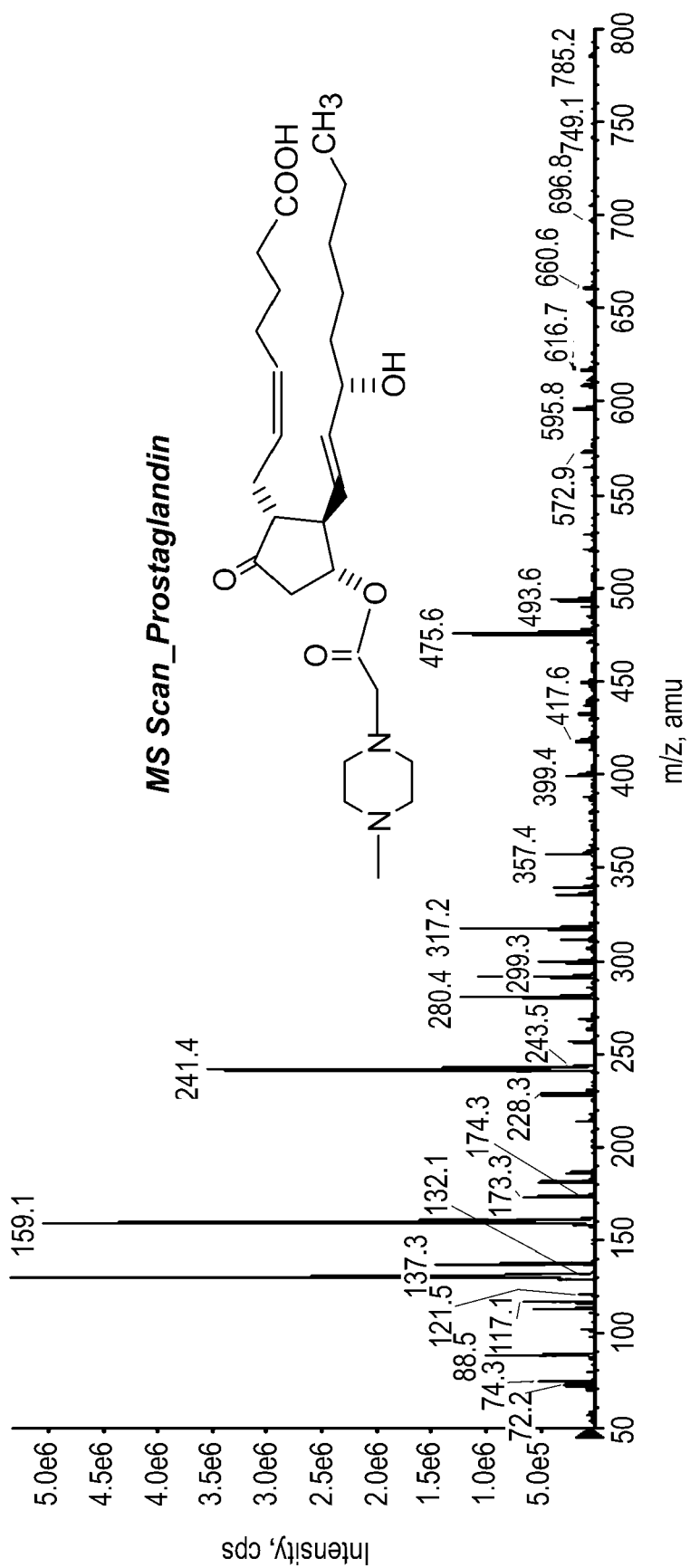
Figure 45B:
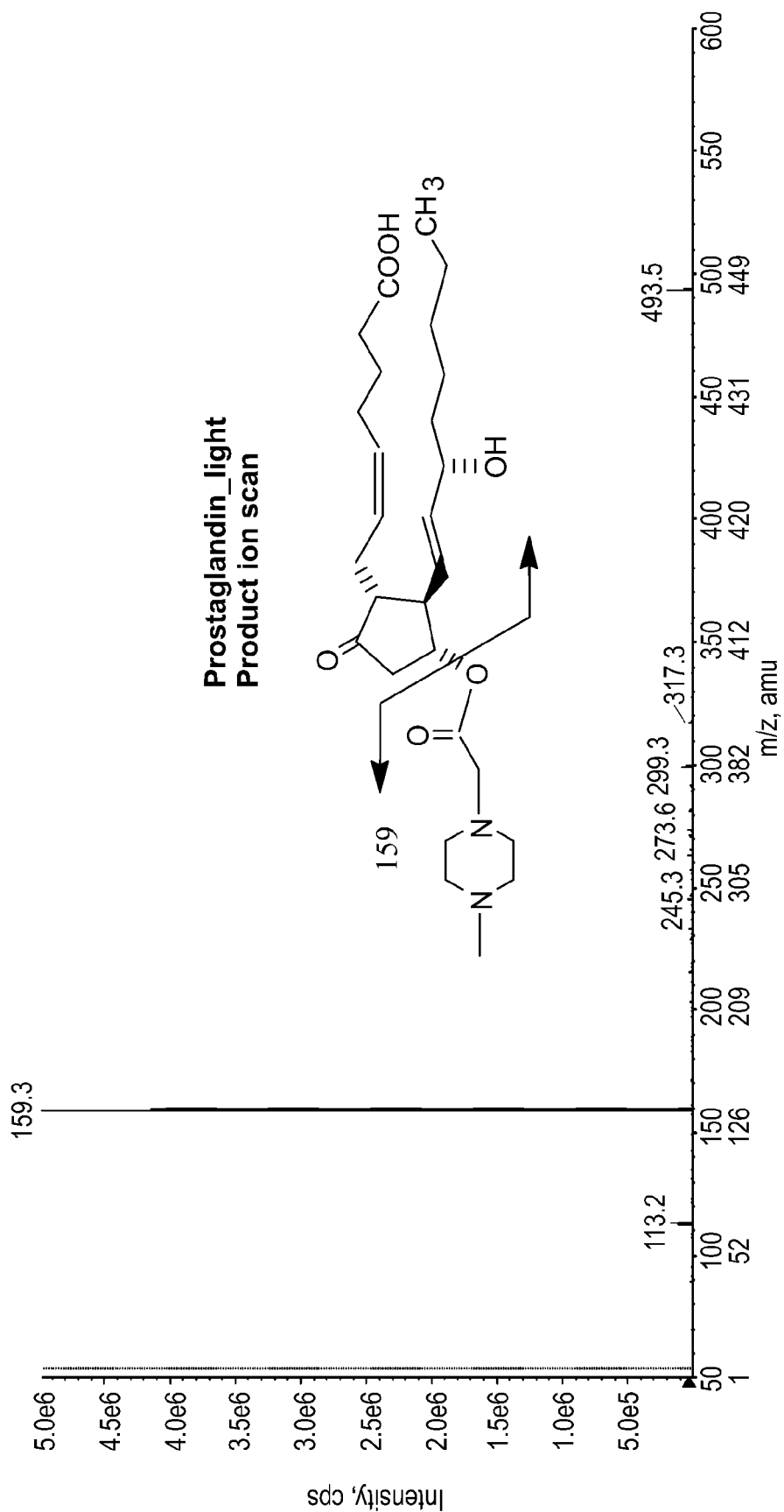

FIGS. 45A and 45B schematically depict experimental data of Example 10. FIG. 45A schematically depicting an ESI-MS spectra and FIG. 45B an ESI-MS/MS spectra for labeled prostaglandin.

Figure 46:
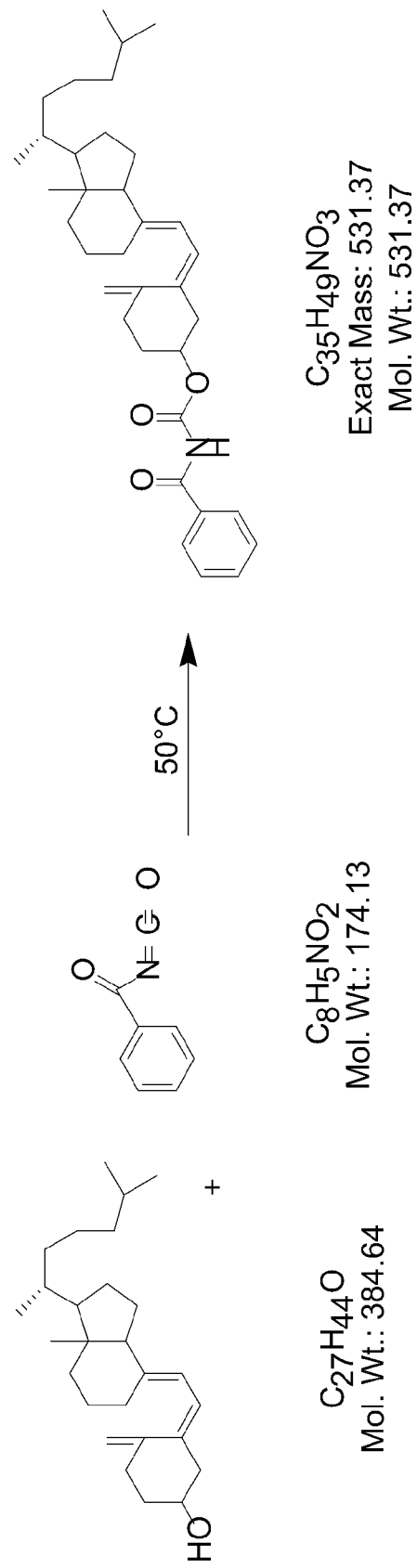

FIG. 46 schematically illustrates a reaction for forming the labeled analyte of Examples 11.

Figure 47:
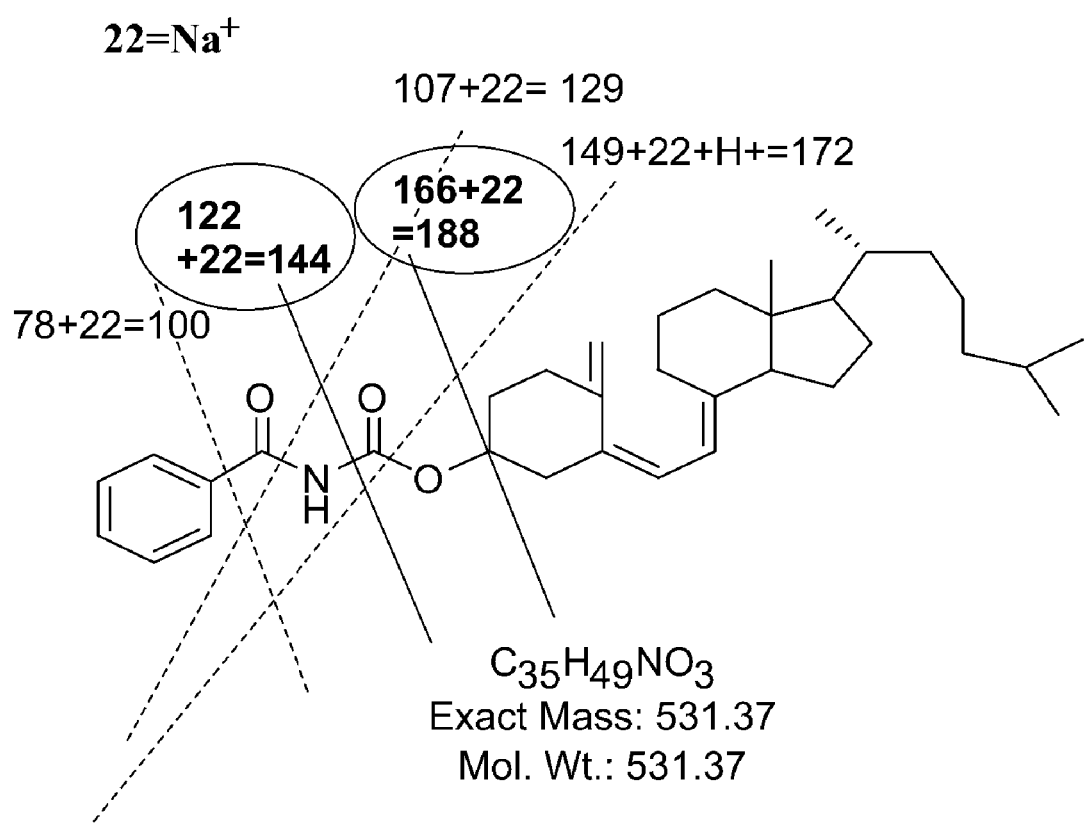

FIG. 47 schematically illustrates for Example 11 various theoretical fragmentation points (dashed lines) of labeled analytes and the potential reporter ion rough base mass resulting from fragmentation at that point (number associated with dashed line). In Example 11, the fragments were seen to be abducted with sodium ion.

Figure 48A:
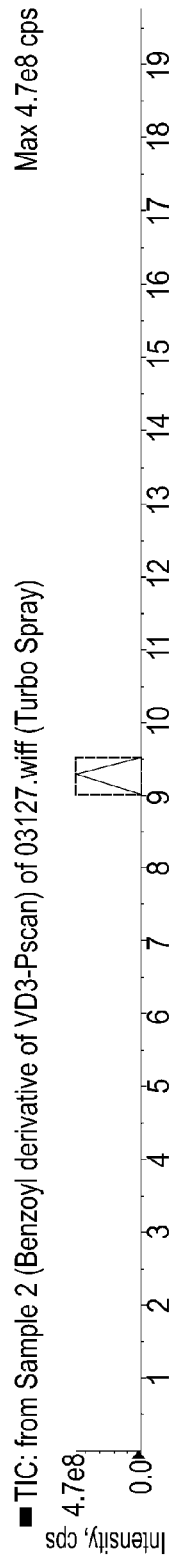
Figure 48B:
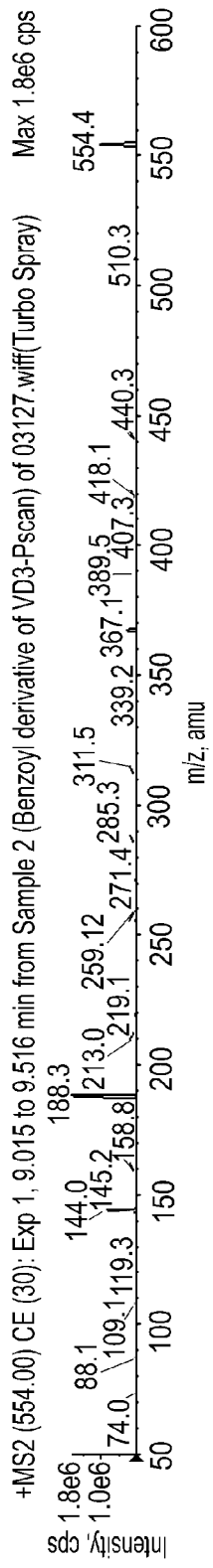
Figure 48C:
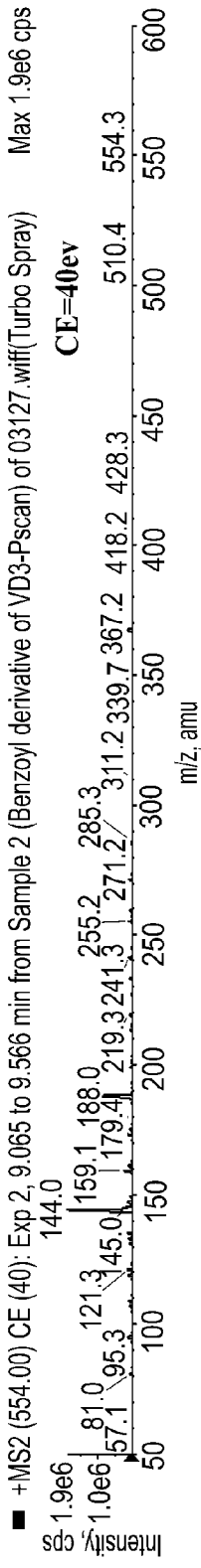
Figure 48D:
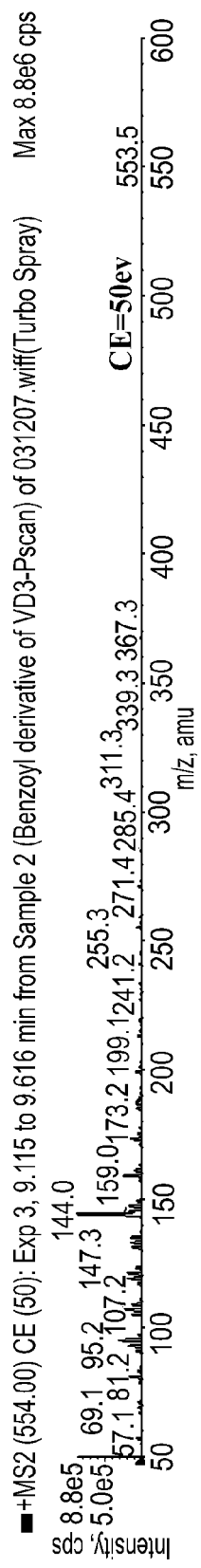
Figure 48E:
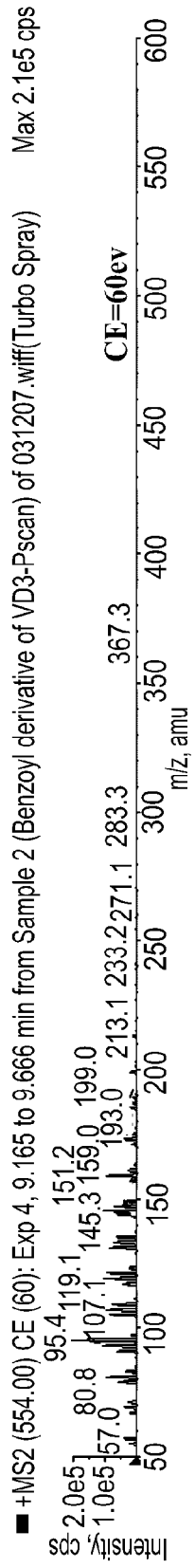
Figure 48F:
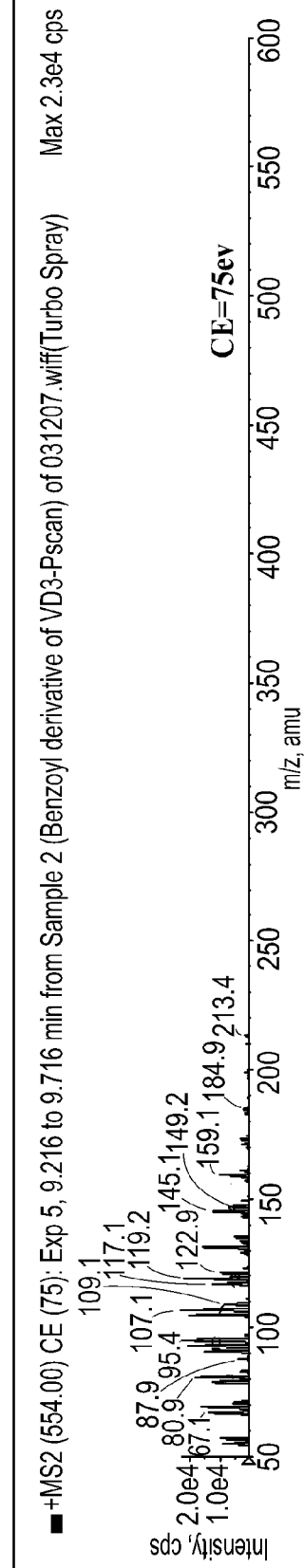

FIGS. 48A-F schematically depict experimental data of Example 11; FIG. 48A depicting total ion current (TIC) as a function of time; and FIGS. 48B-F depicting experimental LC/MS/MS data for various collision energies (CE).

Figure 49:
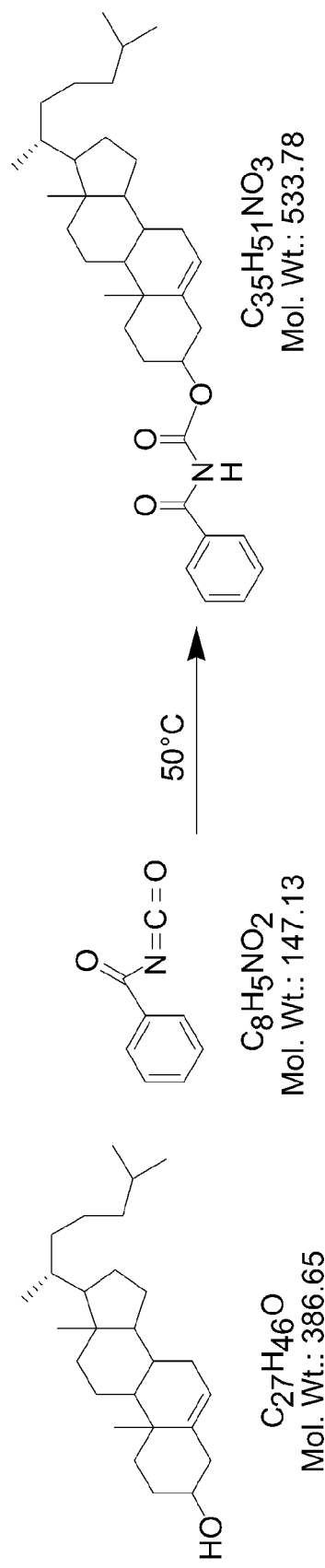

FIG. 49 schematically illustrates a reaction for forming the labeled analyte of Examples 12.

Figure 50:
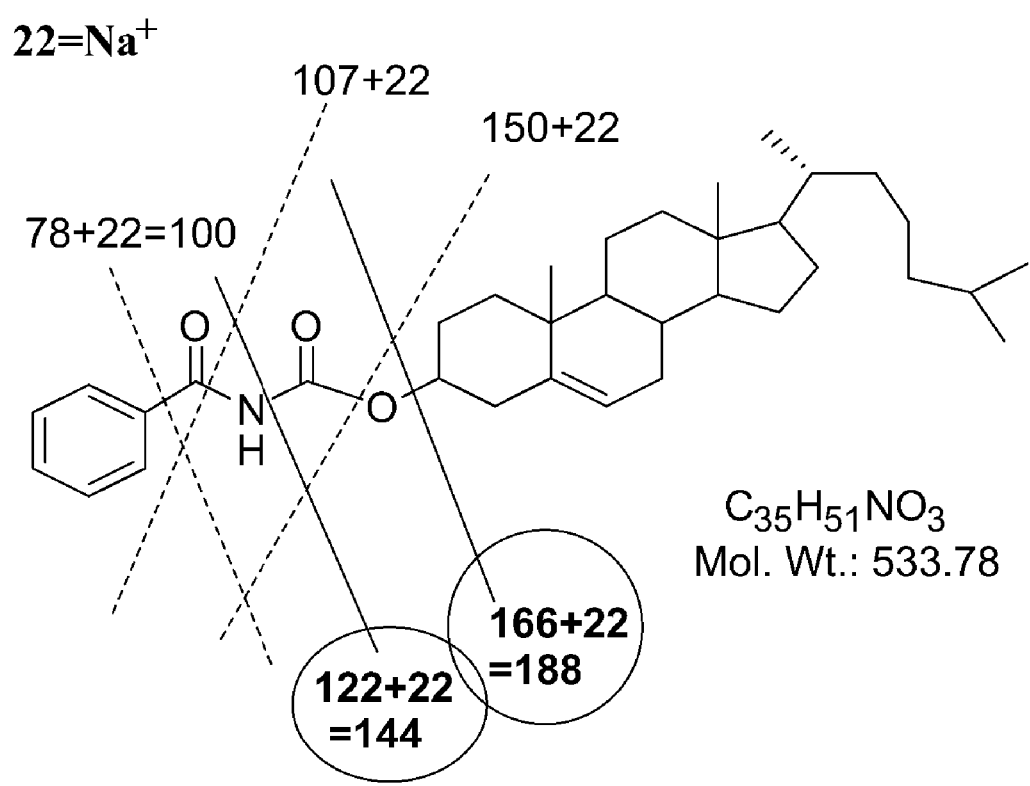

FIG. 50 schematically illustrates for Example 12 various theoretical fragmentation points (dashed lines) of labeled analytes and the potential reporter ion rough base mass resulting from fragmentation at that point (number associated with dashed line). In Example 12, the fragments were seen to be abducted with sodium ion.

Figure 51A:
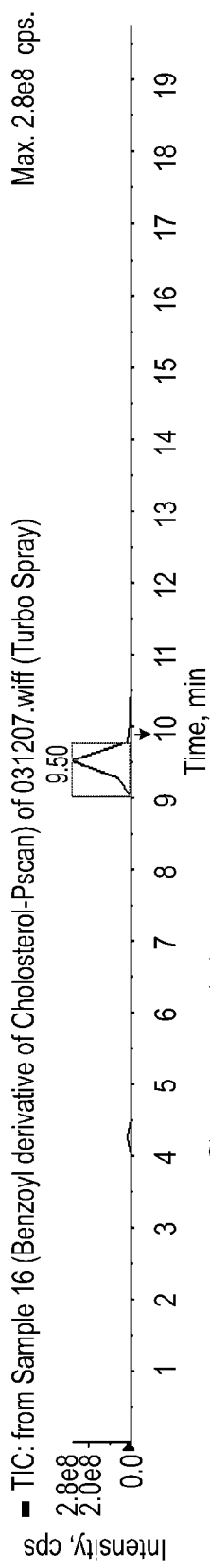
Figure 51B:
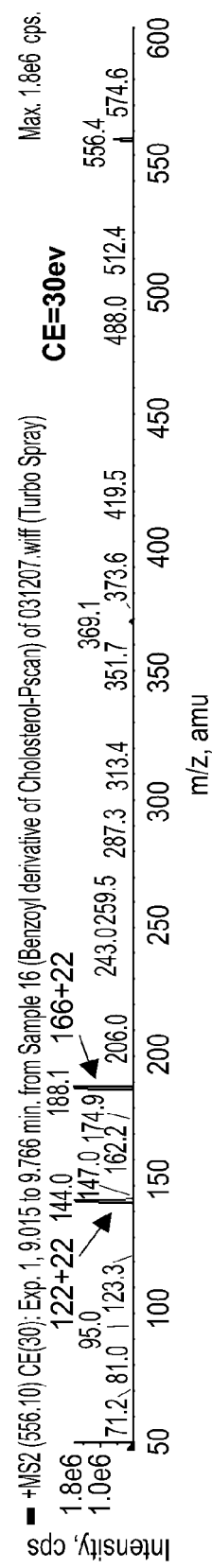
Figure 51C:
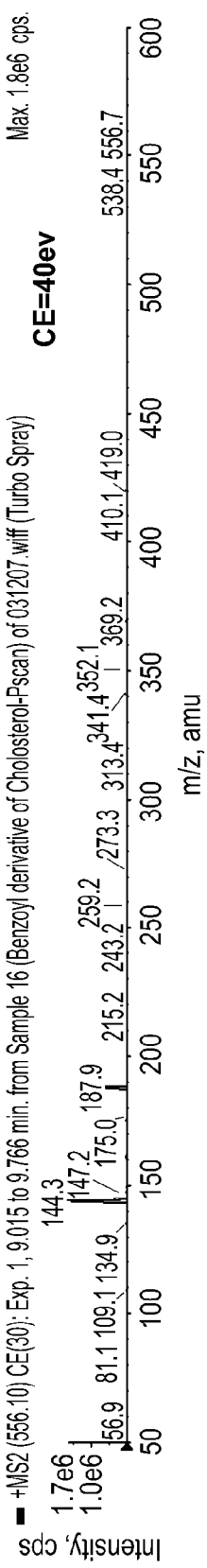
Figure 51D:
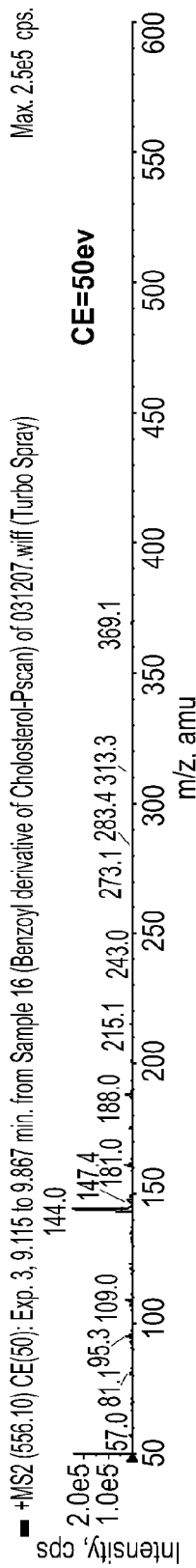
Figure 51E:
Figure 51F:
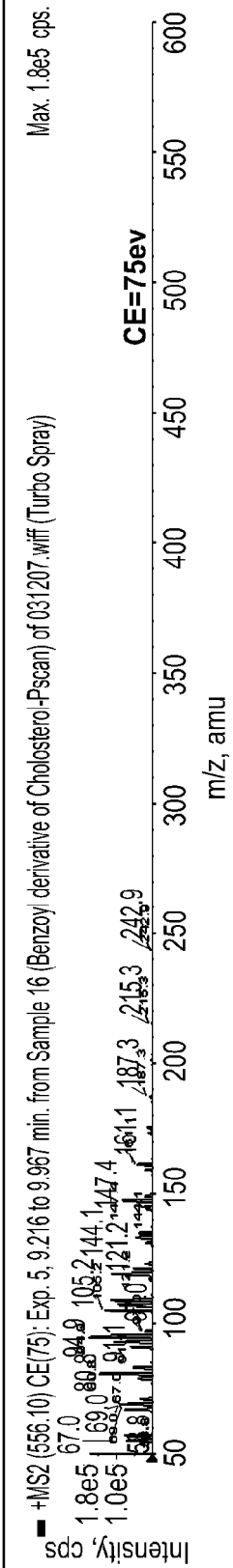

FIGS. 51A-F schematically depict experimental data of Example 12; FIG. 51A depicting total ion current (TIC) as a function of time; and FIGS. 51B-F depicting experimental LC/MS/MS data for various collision energies (CE).

Figure 52:
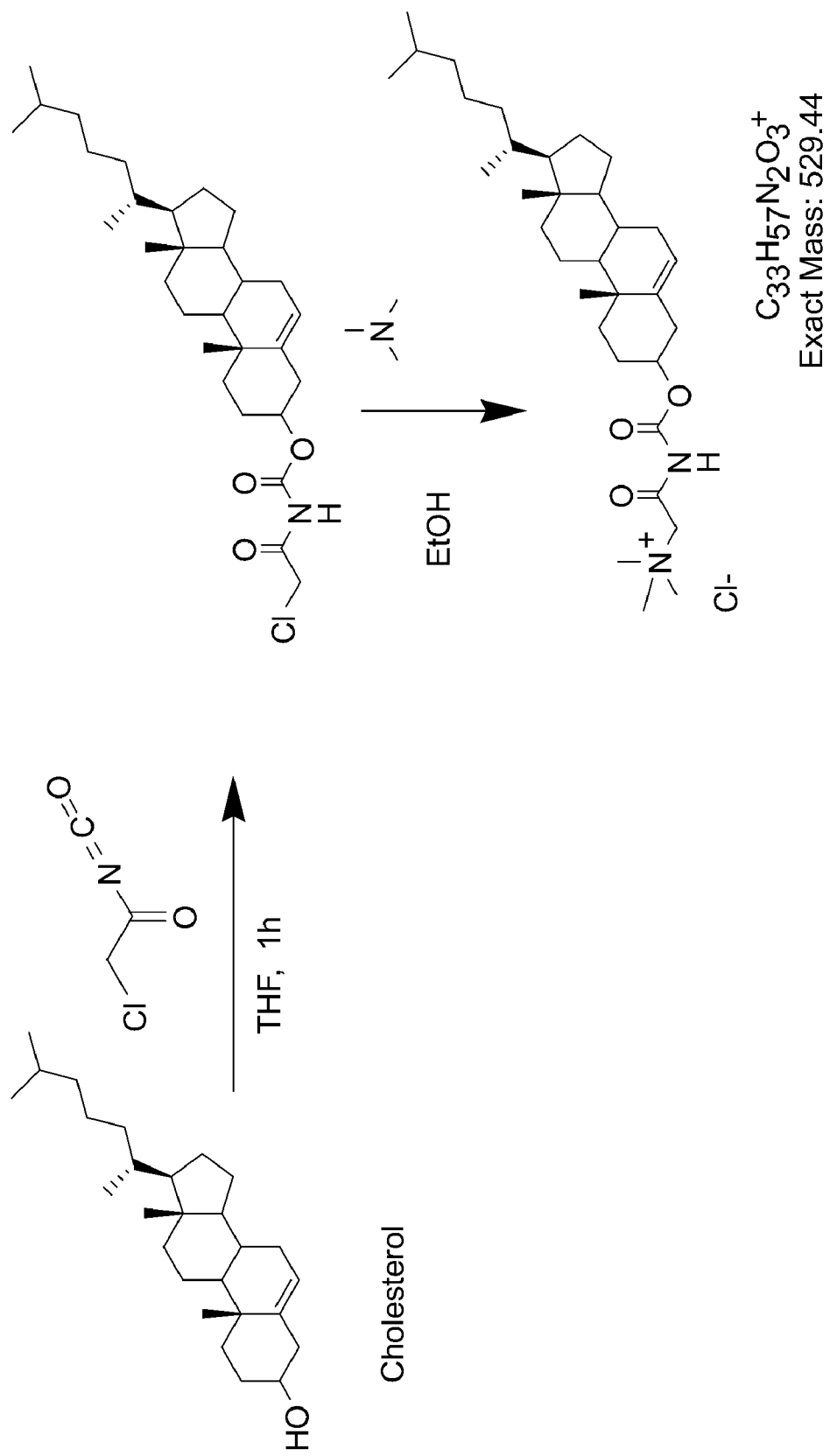

FIG. 52 schematically illustrates a reaction for forming the labeled analyte of Examples 13.

Figure 53:
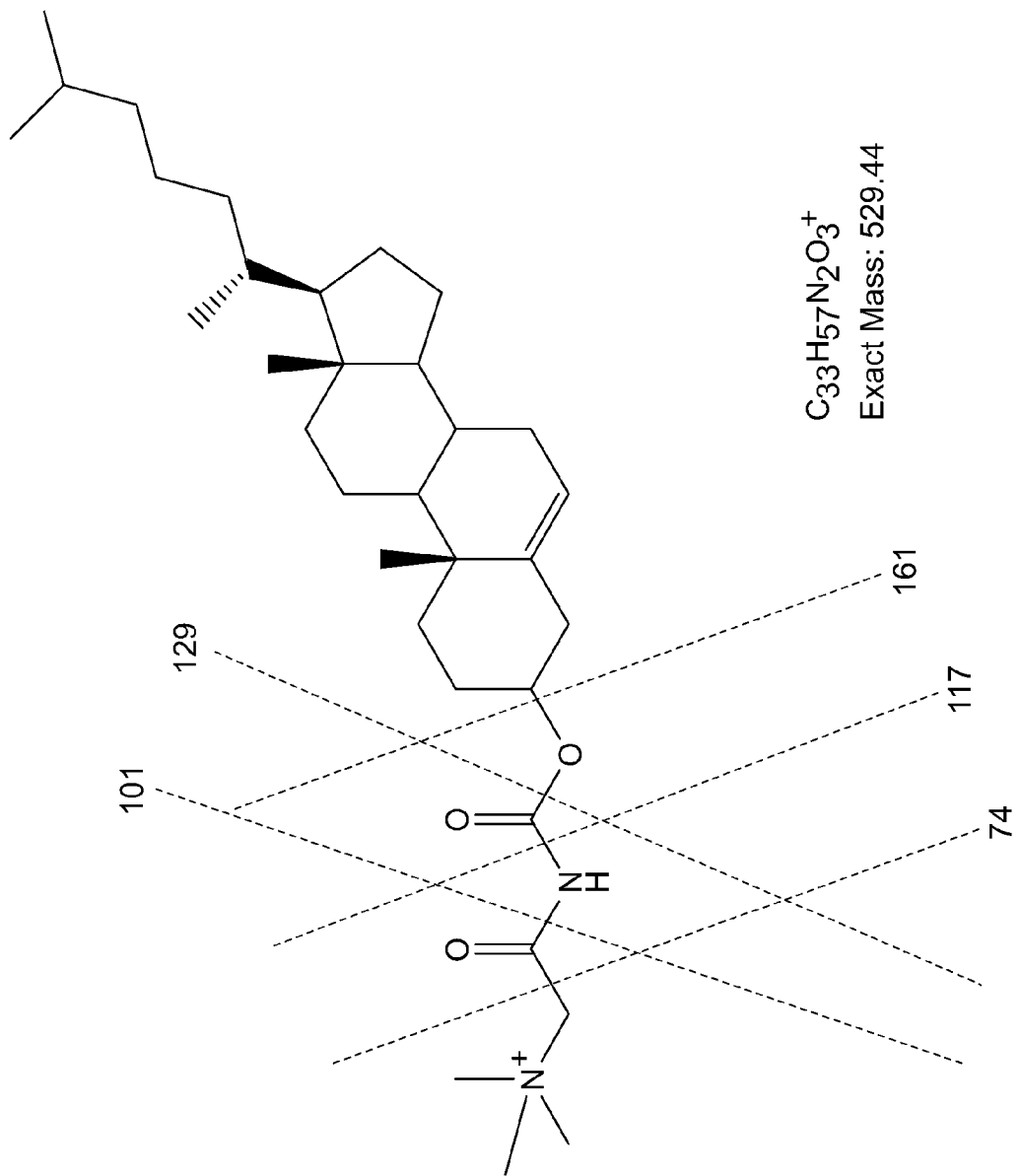

FIG. 53 schematically illustrates for Example 13 various theoretical fragmentation points (dashed lines) of labeled analytes and the potential reporter ion rough base mass resulting from fragmentation at that point (number associated with dashed line).

Figure 54A:
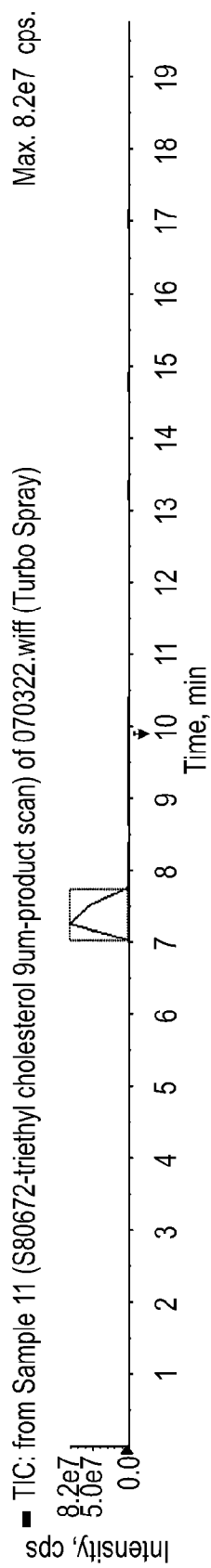
Figure 54B:
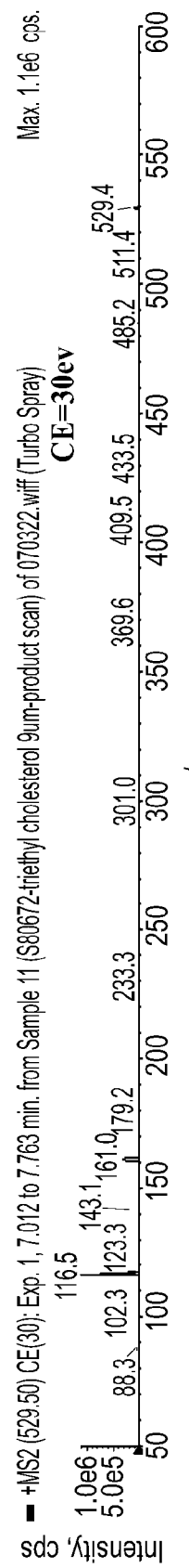
Figure 54C:
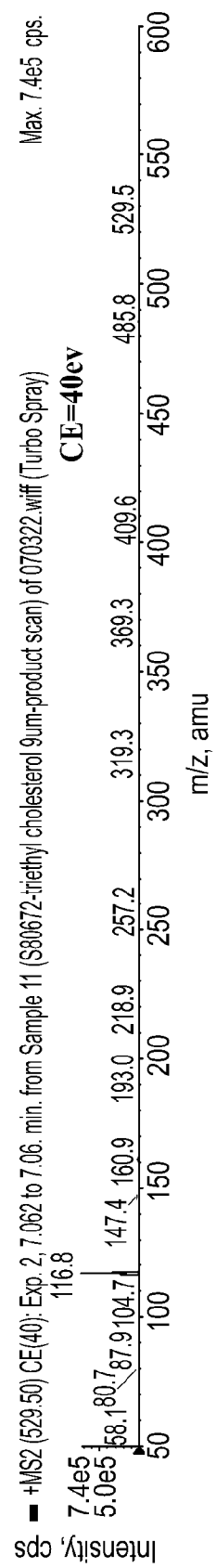
Figure 54D:
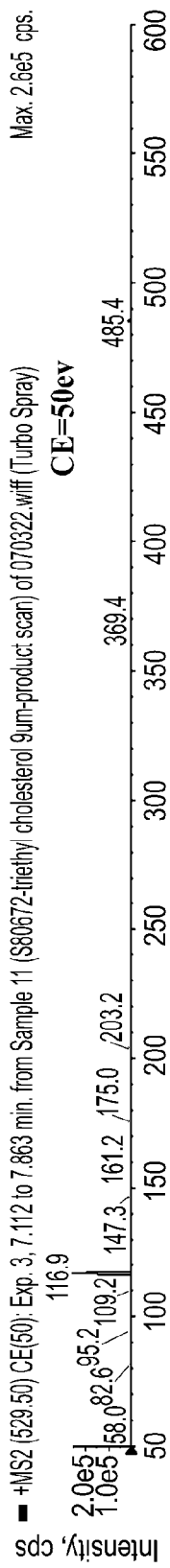
Figure 54E:
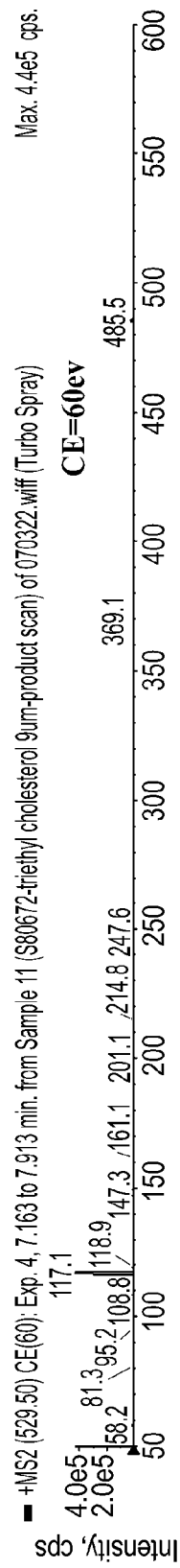
Figure 54F:
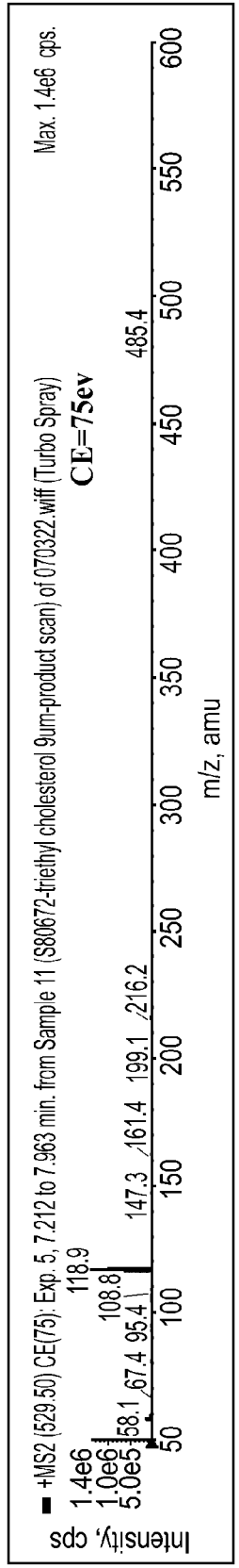

FIGS. 54A-F schematically depict experimental data of Example 13; FIG. 54A depicting total ion current (TIC) as a function of time; and FIGS. 54B-F depicting experimental LC/MS/MS data for various collision energies (CE).

Figure 55:
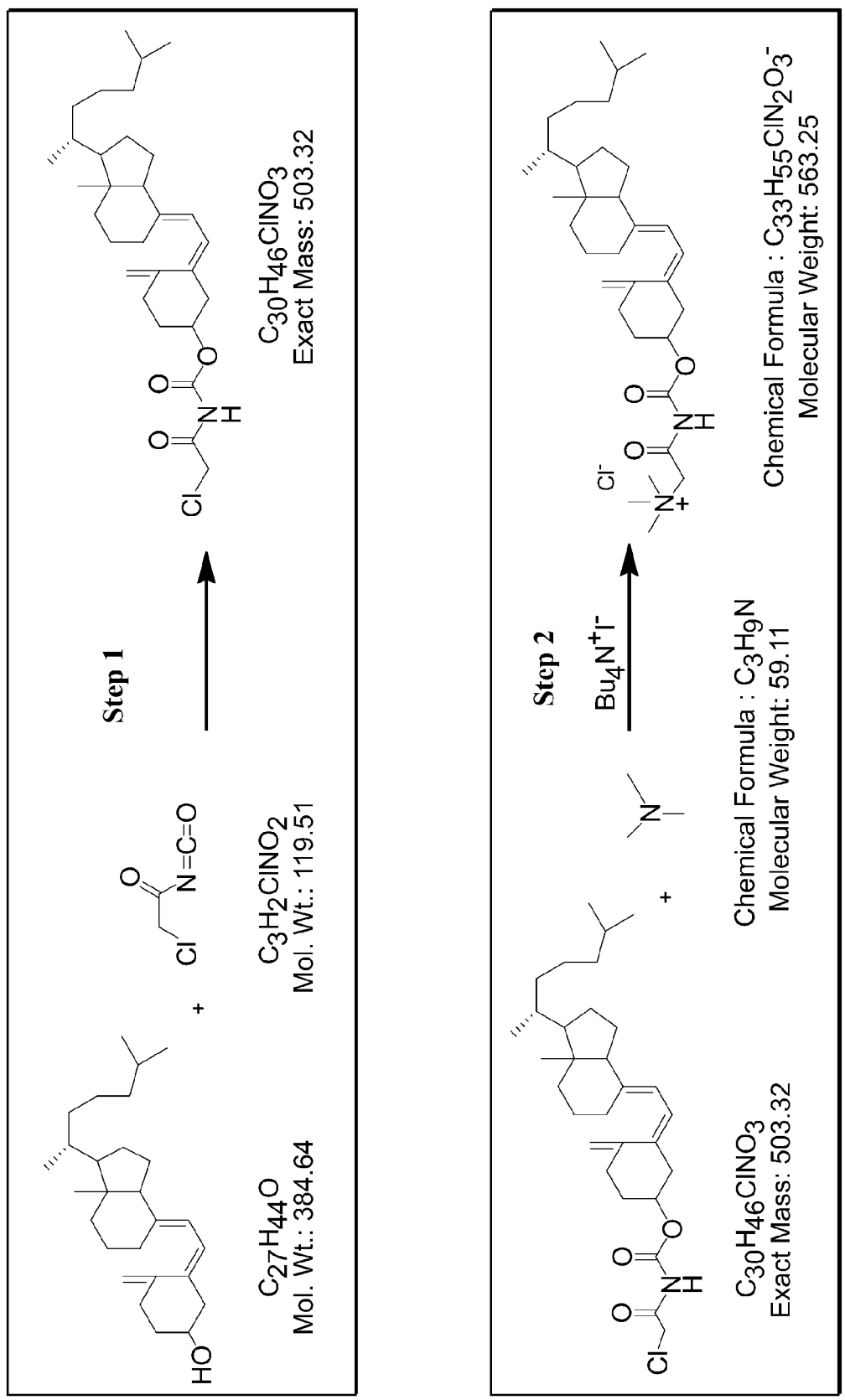

FIG. 55 schematically illustrates a reaction for forming the labeled analyte of Examples 14.

Figure 56:
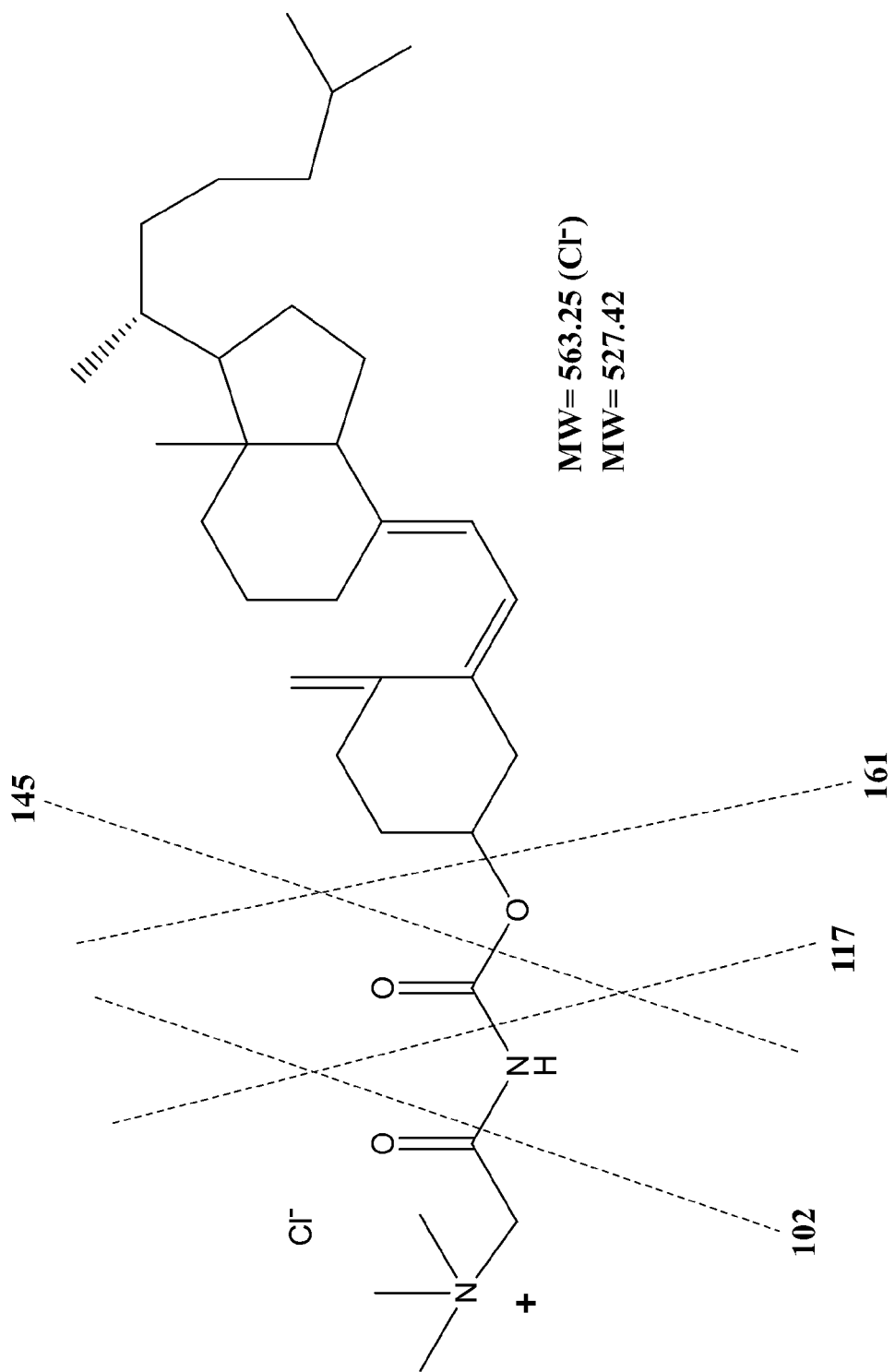

FIG. 56 schematically illustrates for Example 14 various theoretical fragmentation points (dashed lines) of labeled analytes and the potential reporter ion rough base mass resulting from fragmentation at that point (number associated with dashed line).

Figure 57A:
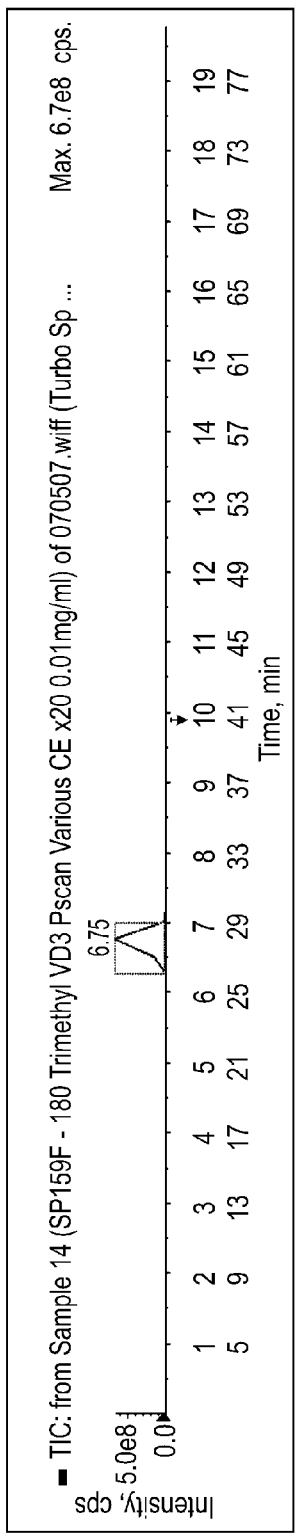
Figure 57B:
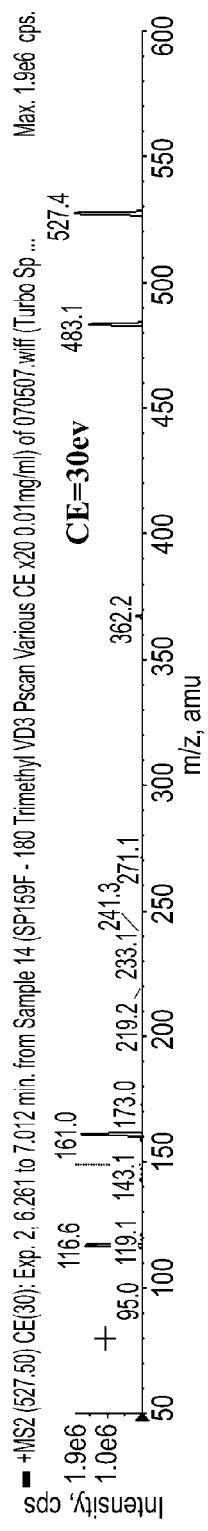
Figure 57C:
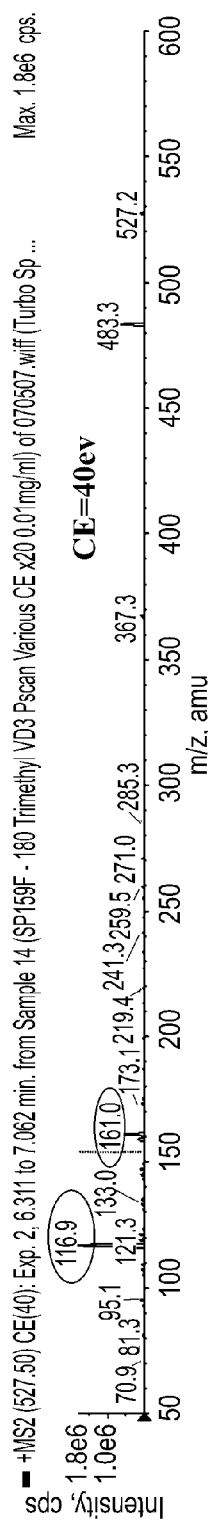
Figure 57D:
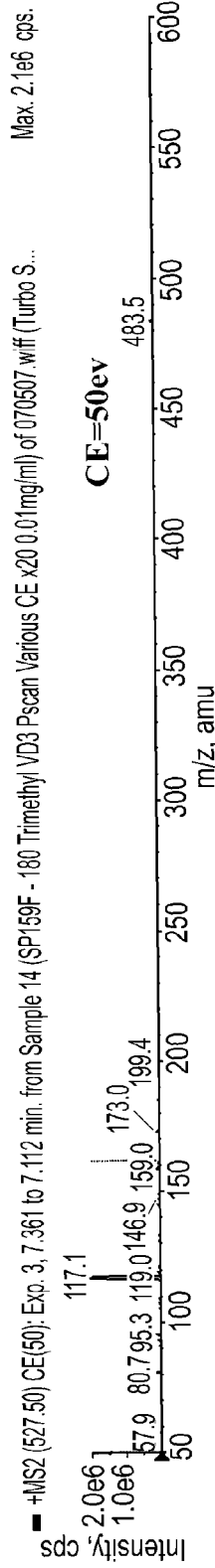
Figure 57E:
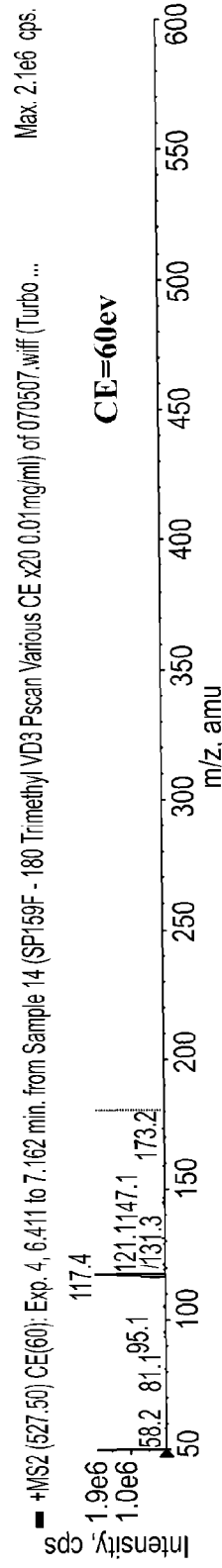
Figure 57F:
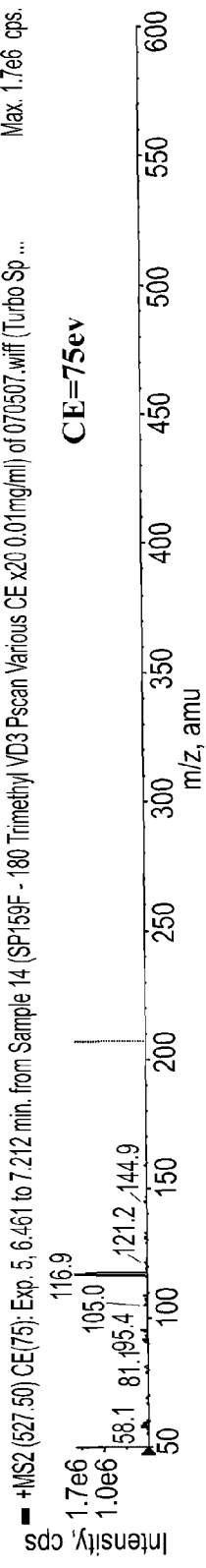

FIGS. 57A-F schematically depict experimental data of Example 14; FIG. 57A depicting total ion current (TIC) as a function of time; and FIGS. 57B-F depicting experimental LC/MS/MS data for various collision energies (CE).

Figure 58:
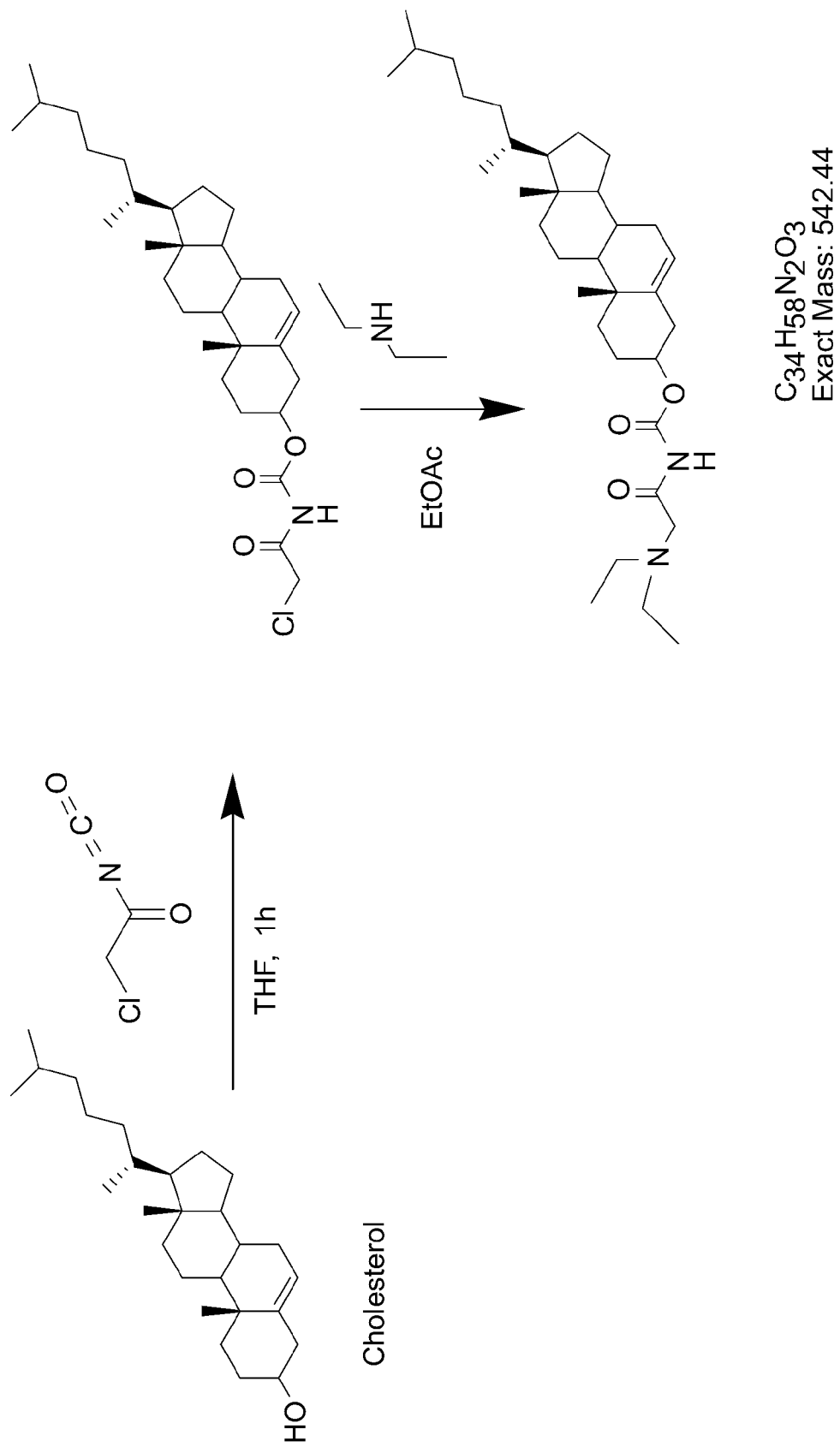

FIG. 58 schematically illustrates a reaction for forming the labeled analyte of Examples 15.

Figure 59:
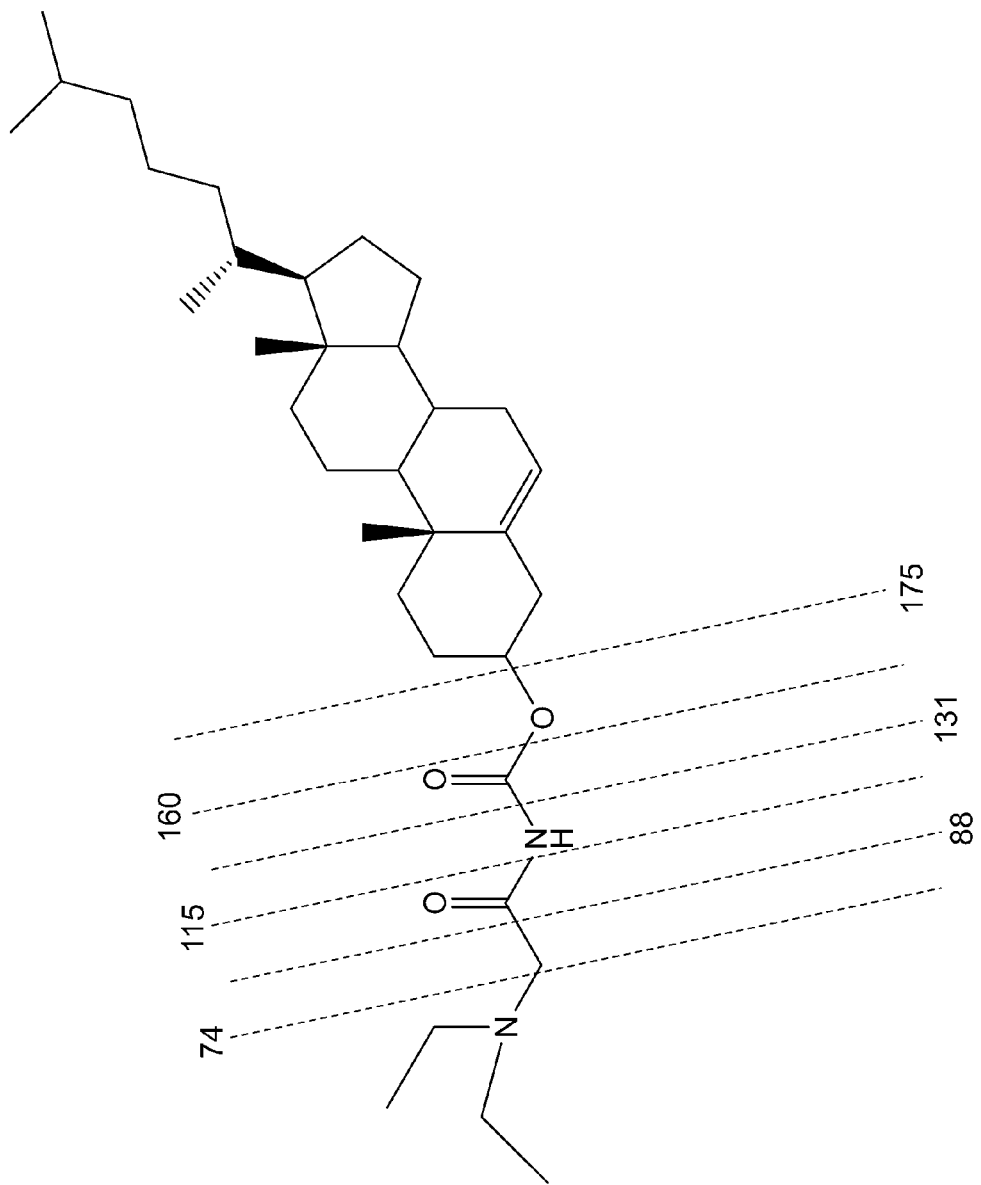

FIG. 59 schematically illustrates for Example 15 various theoretical fragmentation points (dashed lines) of labeled analytes and the potential reporter ion rough base mass resulting from fragmentation at that point (number associated with dashed line).

Figure 60A:
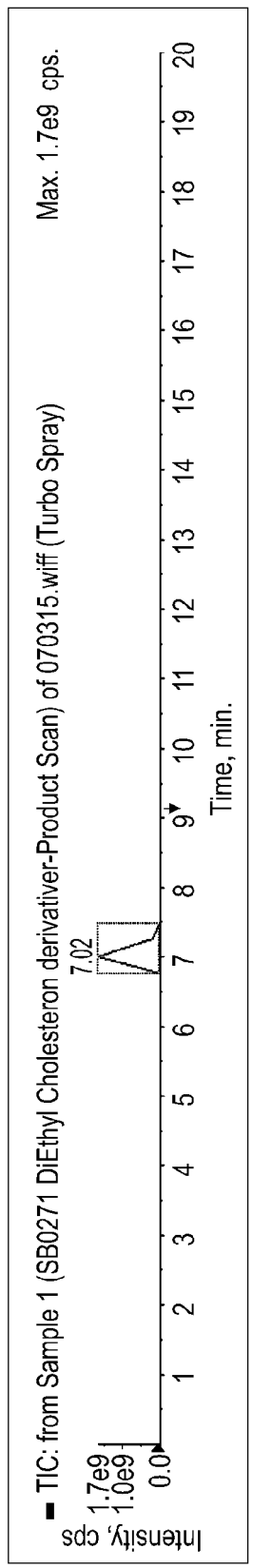
Figure 60B:
Figure 60C:
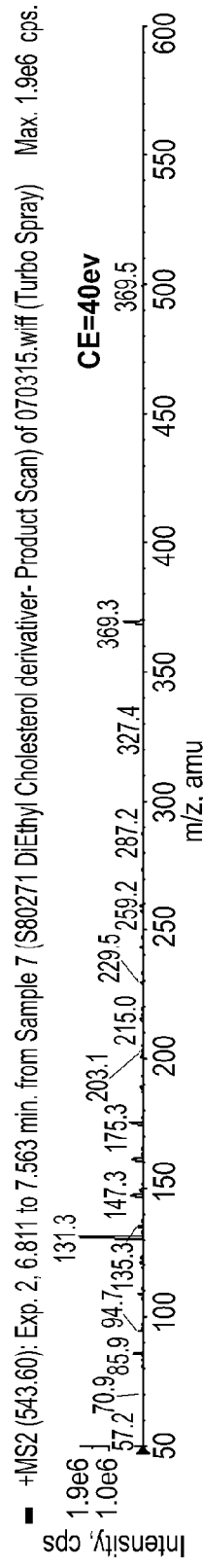
Figure 60D:
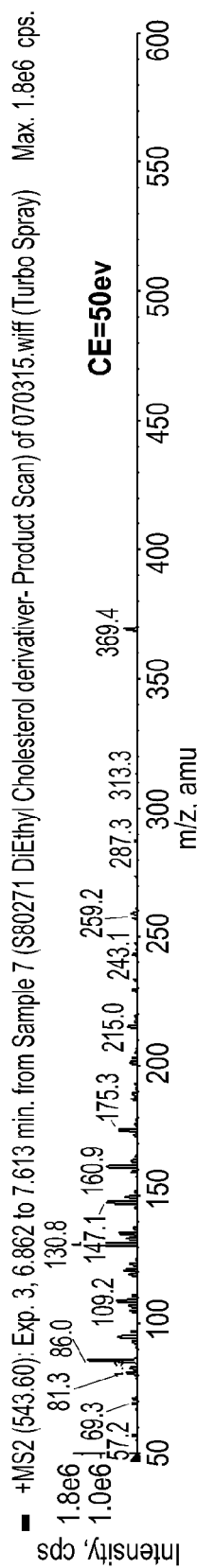
Figure 60E:
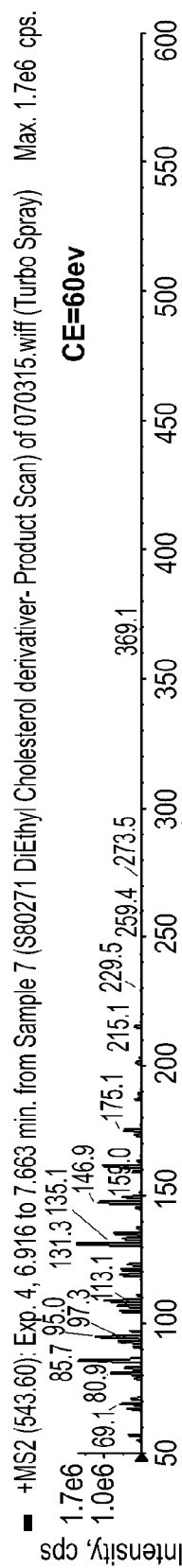
Figure 60F:
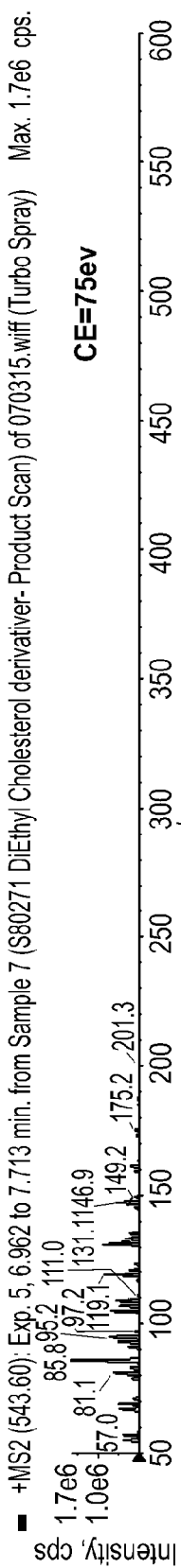

FIGS. 60A-F schematically depict experimental data of Example 15; FIG. 60A depicting total ion current (TIC) as a function of time; and FIGS. 60B-F depicting experimental LC/MS/MS data for various collision energies (CE).

Figure 61:
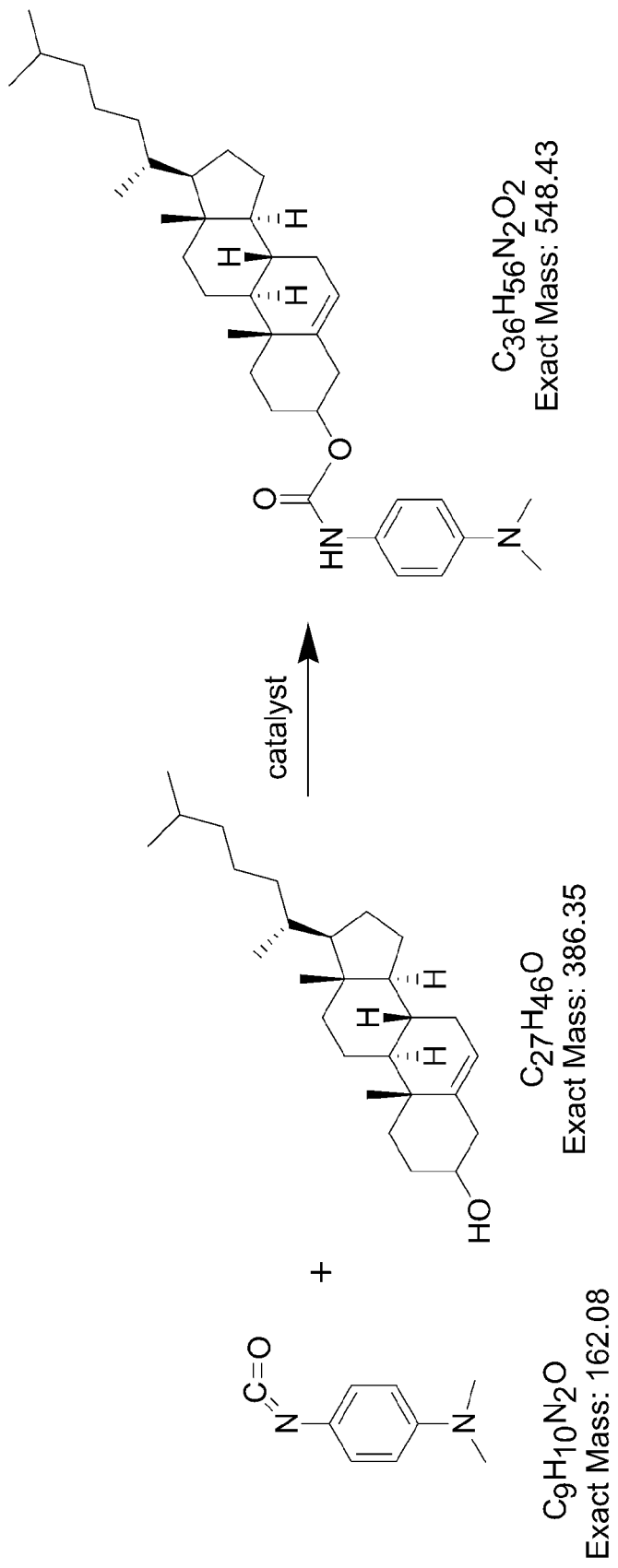

FIG. 61 schematically illustrates a reaction for forming the labeled analyte of Examples 16.

Figure 62:
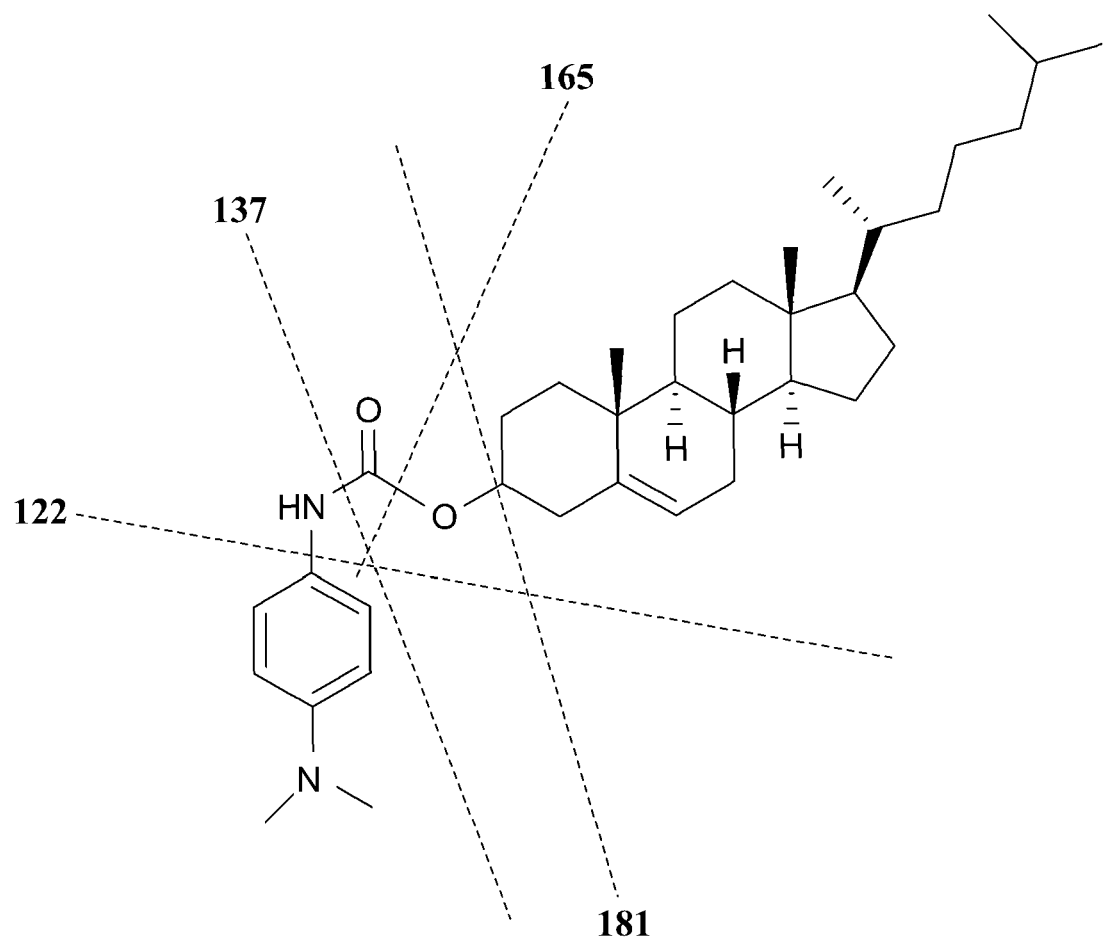

FIG. 62 schematically illustrates for Example 16 various theoretical fragmentation points (dashed lines) of labeled analytes and the potential reporter ion rough base mass resulting from fragmentation at that point (number associated with dashed line).

Figure 63A:
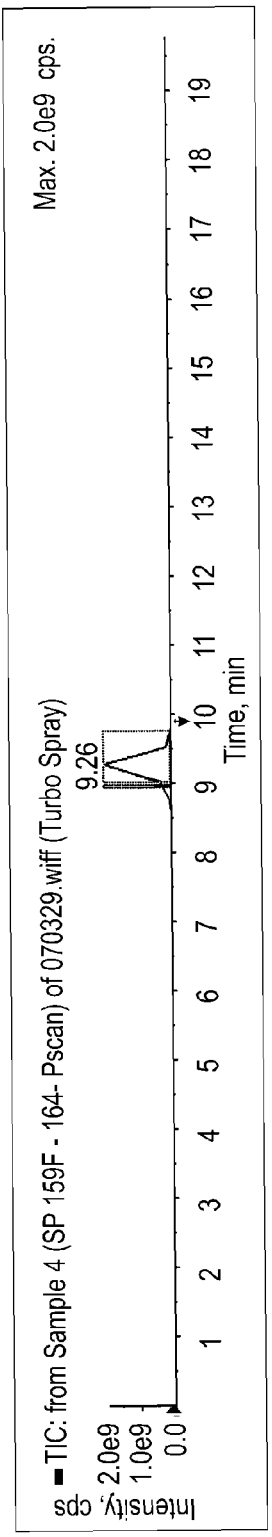
Figure 63B:
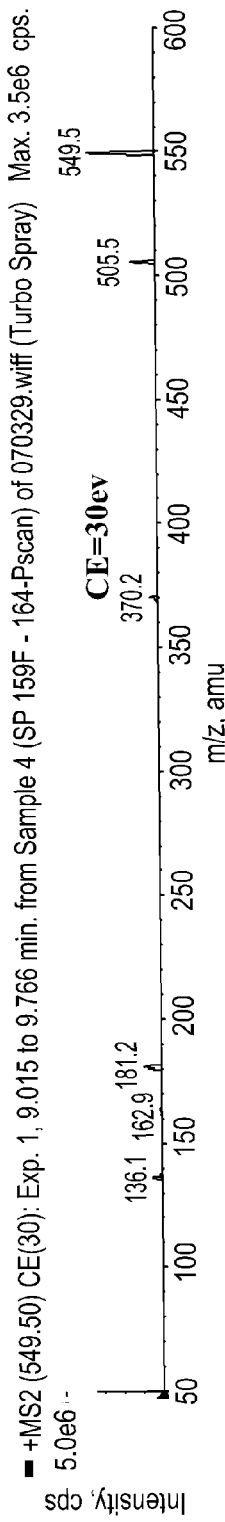
Figure 63C:
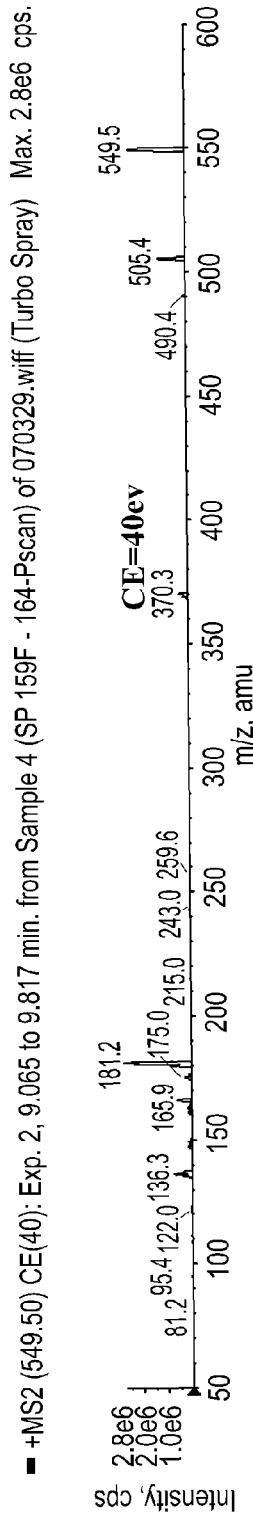
Figure 63D:
Figure 63E:
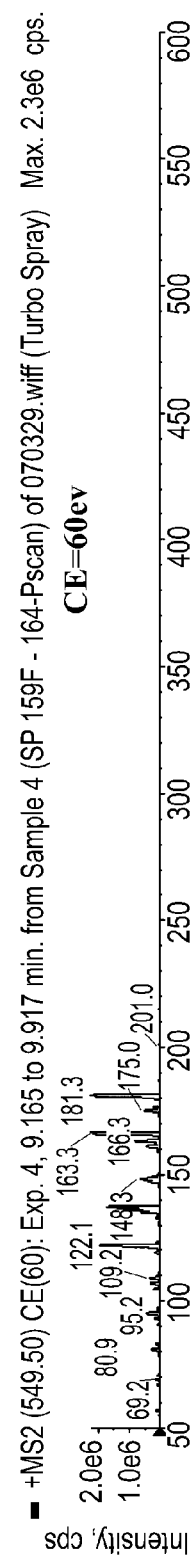
Figure 63F:
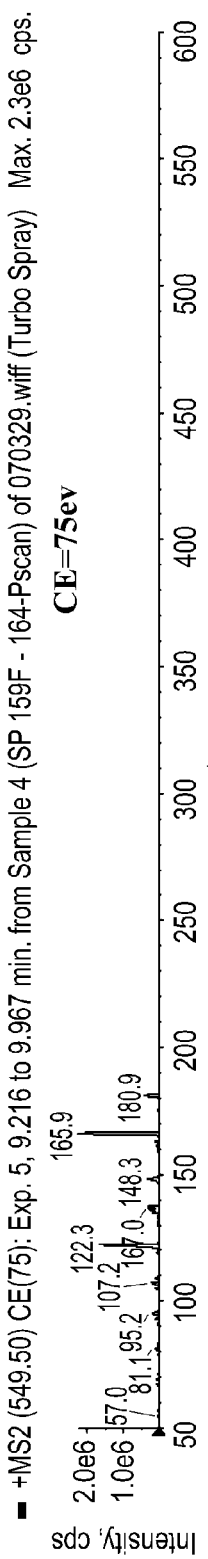

FIGS. 63A-F schematically depict experimental data of Example 16; FIG. 63A depicting total ion current (TIC) as a function of time; and FIGS. 63B-F depicting experimental LC/MS/MS data for various collision energies (CE).

Figure 64:
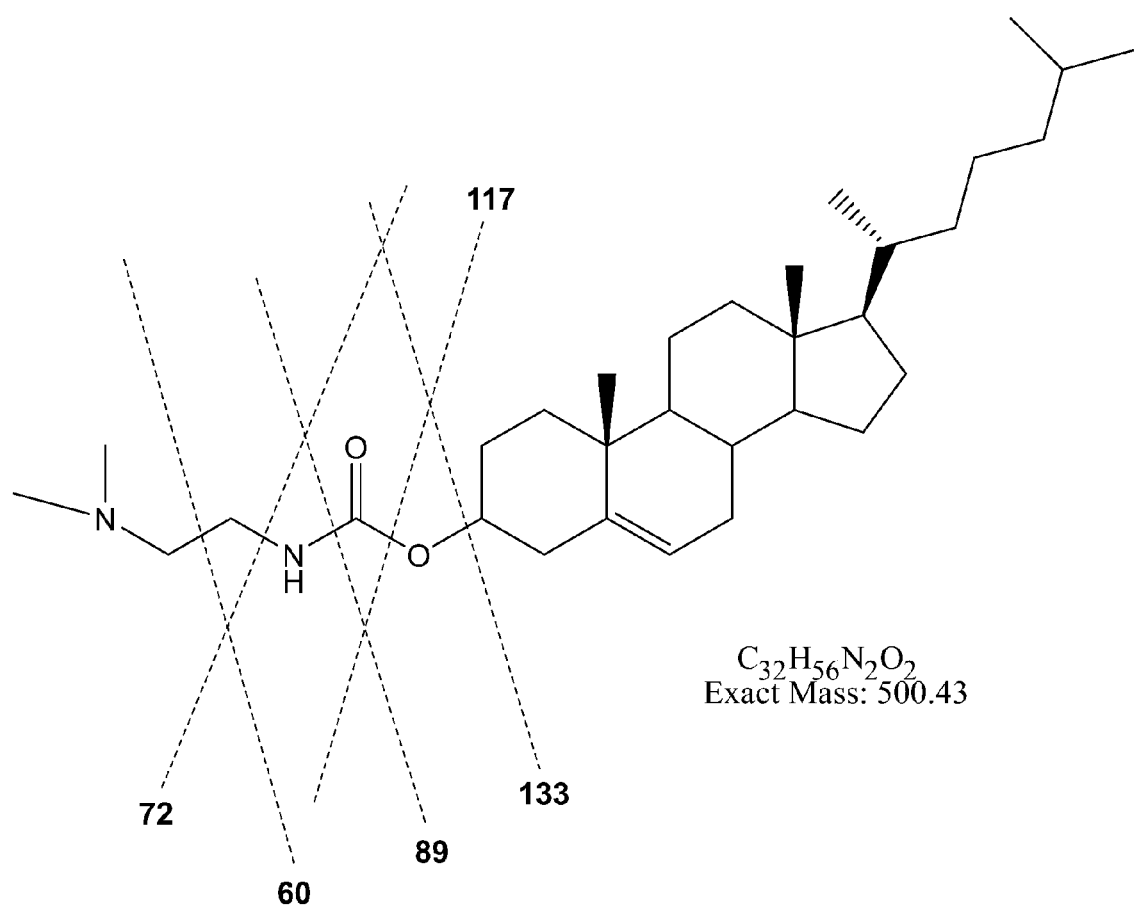

FIG. 64 schematically illustrates for Example 17 various theoretical fragmentation points (dashed lines) of labeled analytes and the potential reporter ion rough base mass resulting from fragmentation at that point (number associated with dashed line).

Figure 65A:
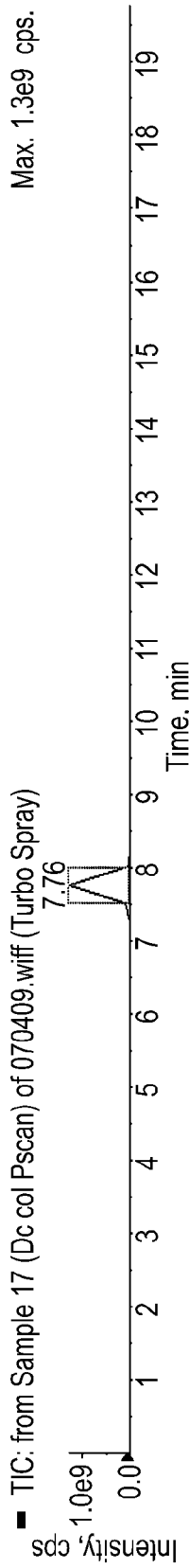
Figure 65B:
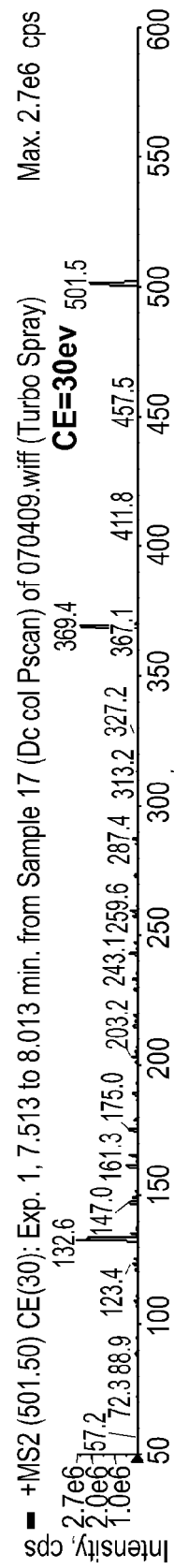
Figure 65C:
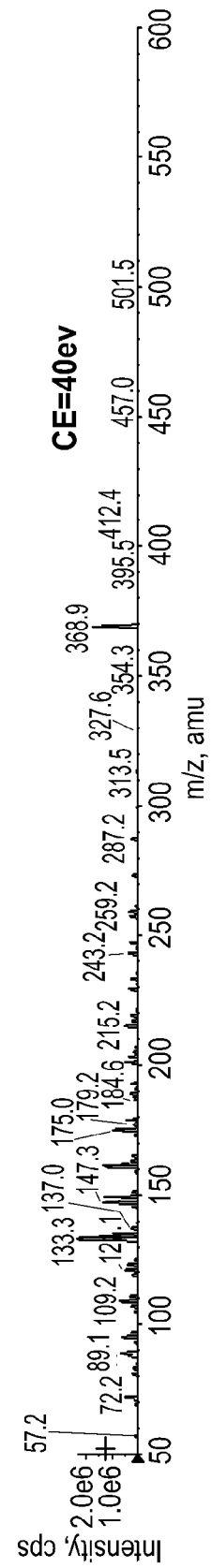
Figure 65D:
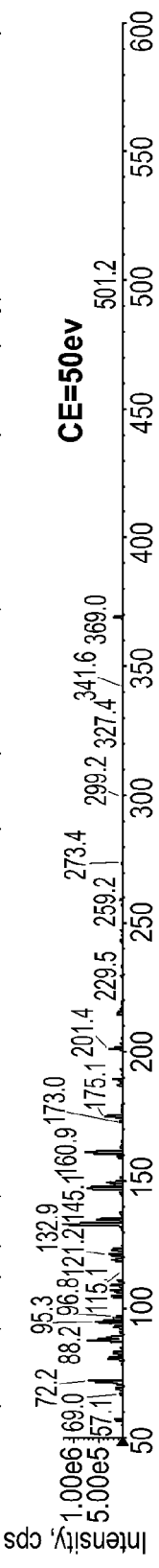
Figure 65E:
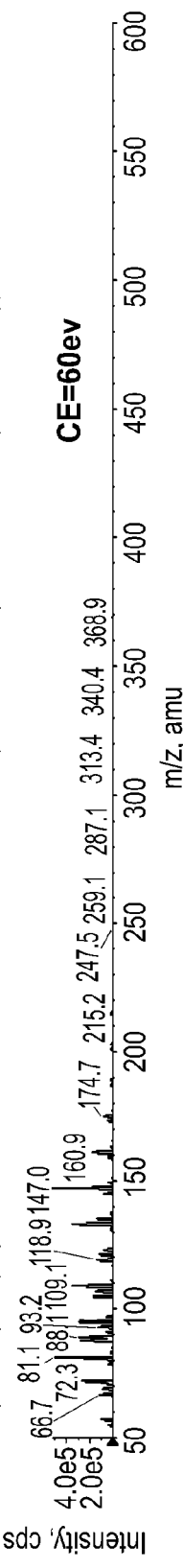
Figure 65F:
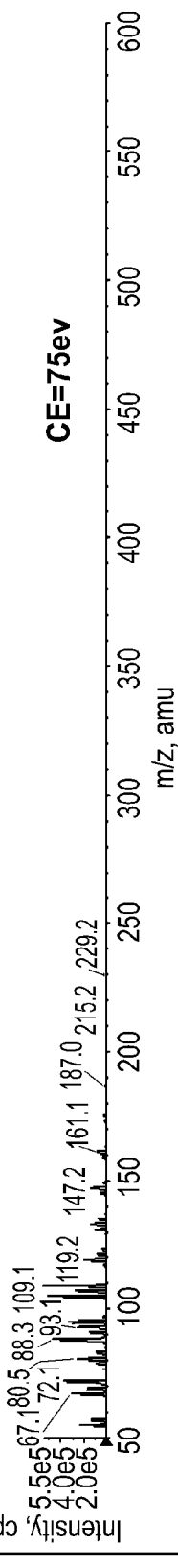

FIGS. 65A-F schematically depict experimental data of Example 17; FIG. 65A depicting total ion current (TIC) as a function of time; and FIGS. 65B-F depicting experimental LC/MS/MS data for various collision energies (CE).

DESCRIPTION OF VARIOUS EMBODIMENTS

Prior to further describing the present teachings, it may be helpful to provide an understanding thereof to set forth definitions of certain terms to be used herein.

As used herein, the article "a" is used in its indefinite sense to mean "one or more" or "at least one." That is, reference to any element of the present teachings by the indefinite article "a" does not exclude the possibility that more than one of the element is present.

The terms "labels", "tags" and "labeling reagents" are used interchangeably herein.

The phrases "mass differential labels", "mass differential tags" and "mass differential labeling reagents" are used interchangeably herein. The phrases "set of mass differential labels", "set of mass differential tags" are used interchangeably and refer to, for example, a set of reagents or chemical moieties where the members of the set (i.e., an individual "mass differential label" or "mass differential tag") have substantially similar structural and chemical properties but differ in mass due to differences in heavy isotope enrichment between members of the set. Each member of the set of mass differential tags can produce a different daughter ion signal upon being subjected to ion fragmentation. Ion fragmentation can be, for example, by collisions with an inert gas (e.g., collision induced dissociation (CID), collision a activated dissociation (CAD), etc.), by interaction with photons resulting in dissociation, (e.g., photoinduced dissociation (PID)), by collisions with a surface (e.g., surface induced dissociation (SID)), by interaction with an electron beam resulting in dissociation (e.g., electron induced dissociation (EID), electron capture dissociation (ECD)), thermal/black body infrared radiative dissociation (BIRD), post source decay, or combinations thereof. A daughter ion of a mass differential tag or label that can be used to distinguish between members of the set can be referred to as a reporter ion of the mass differential tag or label. In various embodiments, a set of mass differential tags comprises compounds of formula (I), or a salt or a hydrate form thereof, that differ only in mass due to differences in heavy isotope enrichment between the members of the set.

The phrases "isobaric labels", "isobaric tags" and "isobaric labeling reagents" are used interchangeably. The phrases "set of isobaric labels", "set of isobaric tags" and "set of isobaric labeling reagents" are used interchangeably and refer to, for example, a reagents or chemical moieties where the members of the set (an individual "isobaric label," "isobaric tag," or "isobaric labeling reagent") have substantially the same mass but where each member of the set can produce a different daughter ion signal upon being subjected to ion fragmentation (e.g., by collision induced dissociation (CID), photoinduced dissociation (PID), etc.). In various embodiments, a set of isobaric tags comprises compounds of formula (I), or a salt or a hydrate form thereof. A daughter ion of an isobaric tag that can be used to distinguish between members of the set can be referred to as a reporter ion of the isobaric tag. In various embodiments, a set of isobaric tags is used to label hydroxylated ring containing compounds and produced labeled compounds that are substantially chromatographically indistinguishable and substantially indistinguishable mass spectrometrically in the absence of fragmentation, but which produce signature ions following CID.

It is to be understood that the mass of an atom or molecule can be approximated to the nearest whole number atomic mass unit or the nearest tenth or hundredth of an atomic mass unit. As used herein, "mass" refers to the absolute mass as well as to the approximate mass within a range where the use of isotopes of different atom types are so close in mass that they are functional equivalents for, e.g., the purpose of balancing the mass of the reporter and balance reactive portions of a isobaric label (so that the gross mass of the isobaric labels within a set or kit of isobaric labels are substantially the same) whether or not differences in the mass of the different isotopes types used can be detected.

For example, the two most common terrestrial isotopes of oxygen have a gross mass of 16 (actual mass 15.9949) and 18 (actual mass 17.9992), the two most common terrestrial isotopes of carbon have a gross mass of 12 (actual mass 12.00000) and 13 (actual mass 13.00336) and two most common terrestrial isotopes of nitrogen have a gross mass of 14 (actual mass 14.003 1) and 15 (actual mass 15.0001). Although these values are approximate, one of ordinary skill in the art will appreciate, e.g., that using a $^{18}$O atom instead of an $^{16}$O atom, is the functional mass equivalent of using two carbon $^{13}$C atoms instead of two $^{12}$C atoms; two $^{15}$N atoms instead of two $^{14}$N atoms; and/or one $^{13}$C atom and one $^{15}$N atom instead of a $^{12}$C and a $^{14}$N.

As used herein, "isotopically enriched" means that a compound (e.g., labeling reagent) has been enriched synthetically with one or more heavy atom isotopes (e.g. stable isotopes such as Deuterium, $^{13}$C, $^{15}$N, $^{18}$O, $^{37}$Cl, or $^{81}$Br). Because isotopic enrichment is not 100% effective, there can be impurities of the compound that are of lesser states of enrichment and these will have a lower mass. Likewise, because of over-enrichment (undesired enrichment) and because of natural isotopic abundance variations, there can be impurities of greater mass.

As used herein, "natural isotopic abundance" refers to the level (or distribution) of one or more isotopes found in a compound based upon the natural terrestrial prevalence of an isotope or isotopes in nature. For example, a natural compound obtained from living plant matter will typically contain about 0.6% $^{13}$C.

The term "substituted" is intended to describe groups having substituents replacing a hydrogen on one or more atoms, e.g. carbon, nitrogen, oxygen, etc., of a molecule. Substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, nitro, trifluoromethyl, cyano, azido, heterocyclyl, alkylaryl, or an aromatic or heteroaromatic group. Accordingly, the phrase "a substituent as described herein" or the like refers to one or more of the above substituents, and combinations thereof.

The term "alkyl" includes saturated aliphatic groups, which includes both "unsubstituted alkyls" and "substituted alkyls", the latter of which refers to alkyl groups having substituents replacing a hydrogen on one or more carbons of the hydrocarbon backbone. The term "alkyl" includes straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and cycloalkyl substituted alkyl groups. The term "alkyl" also includes the side chains of natural and unnatural amino acids.

An "alkylaryl" or an "aralkyl" group is an alkyl substituted with an aryl (e.g., phenylmethyl (benzyl)).

The term "aryl" includes 5- and 6-membered single-ring aromatic groups, as well as multicyclic aryl groups, e.g. tricyclic, bicyclic, e.g., naphthalene, anthracene, phenanthrene, etc.). The aromatic ring(s) can be substituted at one or more ring positions with such substituents as described above. Aryl groups can also be fused or bridged with, e.g. alicyclic or heterocyclic rings which are not aromatic so as to form, e.g. a polycycle.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl includes both "unsubstituted alkenyls" and "substituted alkenyls", the latter of which refers to alkenyl groups having substituents replacing a hydrogen on one or more carbons of the hydrocarbon backbone.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

The term "acyl" includes compounds and groups which contain the acyl radical (CH$_3$CO—) or a carbonyl group. The term "substituted acyl" includes acyl groups having substituents replacing a one or more of the hydrogen atoms.

The term "acylamino" includes groups wherein an acyl group is bonded to an amino group. For example, the term includes alkylcarbonylamino, arylcarbonylamino, carbamoyl and ureido groups.

The term "aroyl" includes compounds and groups with an aryl or heteroaromatic group bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g. oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or groups that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "carbonyl" or "carboxy" includes compounds and groups which contain a carbon connected with a double bond to an oxygen atom, and tautomeric forms thereof. Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "ether" includes compounds or groups that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and groups that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O⁻.

The term "halogen" includes fluorine, bromine, chlorine, iodine, etc. The term "perhalogenated" generally refers to a group wherein all hydrogens are replaced by halogen atoms.

The term "heteroatom" includes atoms of any element other than carbon or hydrogen. Preferred heteroatoms are nitrogen, and oxygen. The term "heterocycle" or "heterocyclic" includes saturated, unsaturated, aromatic ("heteroaryls" or "heteroaromatic") and polycyclic rings which contain one or more heteroatoms. The heterocyclic may be substituted or unsubstituted. Examples of heterocyclics include, for example, benzodioxazole, benzofuran, benzoimidazole, benzothiazole, benzothiophene, benzoxazole, chromene, deazapurine, furan, indole, indolizine, imidazole, isoxazole, isoindole, isoquinoline, isothiaozole, methylenedioxyphenyl, napthridine, oxazole, purine, pyran, pyrazine, pyrazole, pyridazine, pyridine, pyrimidine, pyrrole, quinoline, tetrazole, thiazole, thiophene, and triazole. Other heterocycles include morpholino, piprazine, piperidine, thiomorpholino, and thioazolidine.

The terms "polycyclic ring" and "polycyclic ring structure" include groups with two or more rings (e.g., cycloalkyls, cycloalkenyls, cycloalkynyls, aryls and/or heterocyclyls) in which two or more carbons are common to two adjoining rings, e.g. the rings are "fused rings". Rings that are joined through non-adjacent atoms are termed "bridged" rings. Each of the rings of the polycyclic ring can be substituted with such substituents as described above.

The term "hydroxylated ring containing compound" refers to a compound having at least one hydrogen atom of a ring replaced by a hydroxyl group.

The term "hydroxylated compound" refers to a compound having at least one hydrogen atom replaced by a hydroxyl group.

The term "hydroxylated polycyclic ring containing compound" refers to a compound having at least one hydrogen atom of at least one ring replaced by a hydroxyl group.

As used herein, the term "salt form" includes a salt of a compound or a mixture of salts of a compound. In addition, zwitterionic forms of a compound are also included in the term "salt form." Salts of compounds having an amine, or other basic group can be obtained, for example, by reaction with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

As used herein, "hydrate form" refers to any hydration state of a compound or a mixture or more than one hydration state of a compound. For example, a labeling reagent discussed herein can be a hemihydrate, a monohydrate, a dihydrate, etc. Moreover, a sample of a labeling reagent described herein can comprise monohydrate, dihydrate and hemihydrate forms.

Labeling Reagents

In various aspects the present teachings provide labeling reagents, sets of labels and labeled analytes. In various embodiments, provided are sets of mass differential labels of general formula (I). In various embodiments, provided are sets of isobaric labels of general formula (I) in their unsalted and/or unhydrated form. In various embodiments, the masses of the labels differ by less than about 0.05 amu in the unsalted and/or unhydrated form. The sets of labels provided comprise two or more compounds of the general formula (I):

$$Z-R_1 \qquad (I),$$

or a salt or hydrate form thereof, wherein one or more of the compounds in the set of labels contains one or more heavy atom isotopes. In various embodiments, the heavy atom isotopes are each independently $^{13}C$, $^{15}N$, $^{18}O$, $^{33}S$, or $^{34}S$.

In formula (I) Z represents a substituted or unsubstituted straight, branched or cyclic alkyl; a substituted or unsubstituted aryl; a substituted or unsubstituted hetero aryl; a substituted or unsubstituted amino; or a substituted or unsubstituted thio; $R_1$ represents a substituted or unsubstituted

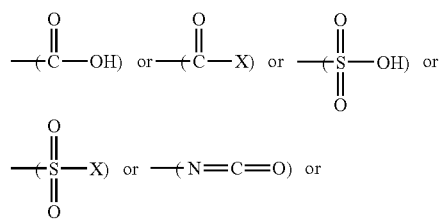

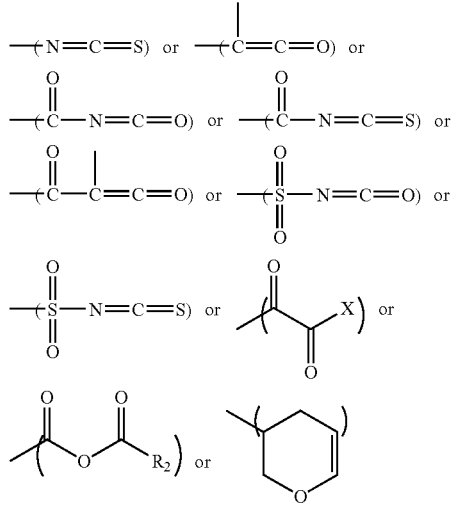

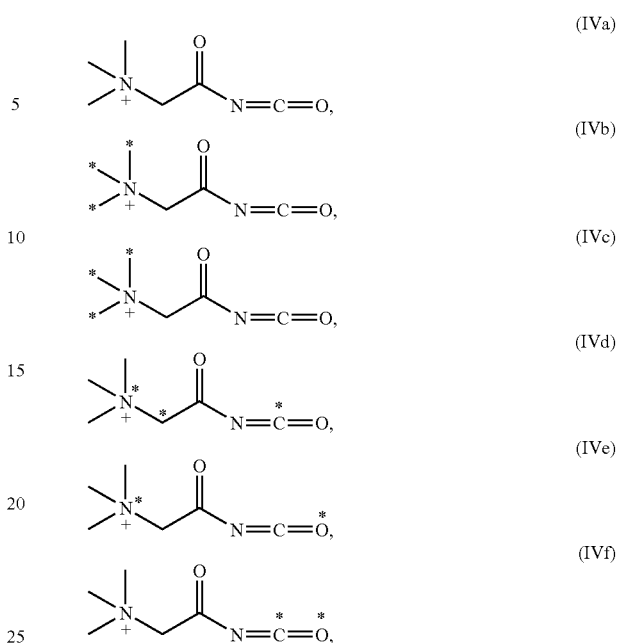

X represents Cl, Br, I or an acetyl; and $R_2$ represents a substituted or unsubstituted alkyl; a substituted or unsubstituted halogenated alkyl; or a substituted or unsubstituted aryl.

The compounds of formula (I) can be provided in a wide variety of salt and hydrate forms including, but not limited to, a mono-TFA salt, a mono HCl salt, a bis-HCl salt, or a bis-TFA salt, or a hydrate thereof.

In various embodiments, the one or more of the compounds of the set of labels is isotopically enriched with two or more heavy atoms; three or more heavy atoms; and/or with four or more heavy atoms. In various embodiments, a set of labels of formula incorporated heavy atom isotope such that the isotopes are present in at least 80 percent isotopic purity, at least 93 percent isotopic purity, and/or at least 96 percent isotopic purity.

In various embodiments, the set of labels comprises trimethylammonium compounds of the general formula (IV):

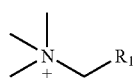

(IV)

or a salt or hydrate form thereof, where $R_1$ can be as described for formula (I). In various embodiments, $R_1$ represents

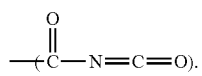

It is to be understood that a set of labels of formula (I) or formula (IV), for example, can be a set of mass differential labels, a set of isobaric labels, or combine both mass differential and isobaric labels. For example, a set of mass differential labels within the present teachings could comprise two or more compounds selected from compounds of the general formulas (IVa)-(IVb) and a set of isobaric labels within the present teachings could comprise two or more compounds selected from compounds of the general formulas (IVc)-(IVf):

where the asterisk denotes a heavy atom substitution.

The members of a set of tags of the present teachings can have substantially similar structural properties even where they are mass differential tags, differing in mass due to differences in heavy isotope enrichment between members of the set. Accordingly, in various embodiments, although two identical compounds each labeled with different label from the set of tags can have different masses, the labeled compounds can have substantially similar chemical reactivity and chromatographic separation properties, such that, for example, differences in chromatographic separation, ionization, etc. do not lead to substantial differences in the relative amount of label compound transmitted to a mass analyzer. In the present teachings, each member of a set of tags, mass differential as well as isobaric, can produce a different daughter ion signal upon being subjected to ion fragmentation (e.g., by collision induced dissociation (CID), photoinduced dissociation (PID), etc.). Such daughter ions can be used to distinguish between members of the set and can be referred to as a reporter ion of the tag or label. In various embodiments, a given tag may produced more than one reporter ion signal.

In various embodiments, the set of labels comprises two or more 5, 6 or 7 membered heterocyclic ring of the general formula (V):

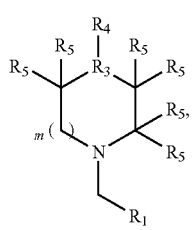

or a salt or a hydrate form thereof In formula (V) m=0, 1, or 2 (providing, respectively, a 4, 5, 6 or 7 membered ring), $R_1$ can be as described for formula (I), and $R_3$ represents C, N, O or S; $R_4$ represents hydrogen, a straight chain or branched $C_1$-$C_6$ alkyl group, or a straight chain or branched $C_1$-$C_6$ alkoxy group; and each $R_5$ represent independently hydrogen, deuterium, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently are bonded to one or more hydrogen, deuterium or fluorine atoms.

In various embodiments, the set of labels comprises two or more N-substituted piperidine, piperazine or morpholine compounds of the general formula (VI):

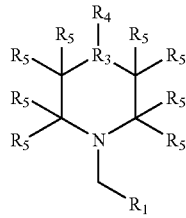
(VI)

or a salt or a hydrate form thereof. In formula (VI) $R_1$, $R_3$, $R_4$, and $R_5$ can be as described for formula (I) and/or formula (V)

In various embodiments, $R_1$ represents

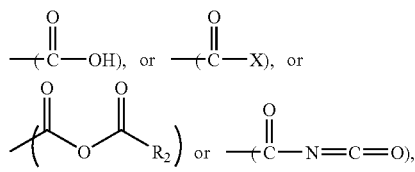

where X and $R_2$ can be as described for formula (I).

It is also to be understood that a set of labels of formulas (V) and (VI), for example, can be a set of mass differential labels, a set of isobaric labels, or combine both mass differential and isobaric labels.

In various embodiments, provided are a set of mass differential tags comprising two or more N-substituted piperazine compounds of the general formula (VII):

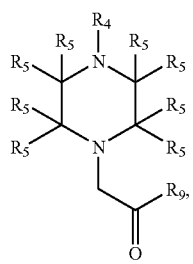
(VII)

where $R_9$ represents a halide, —OH, or —OC(=O)$R_{11}$, where $R_{11}$ is a hydrogen or a straight chain or branched alkyl group; $R_4$, and $R_5$ can be as described previously. In various embodiments, the set of mass differential tags comprises N-substituted piperazine compounds of the general formula (VIII) or (IX):

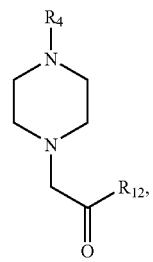
(VIII)

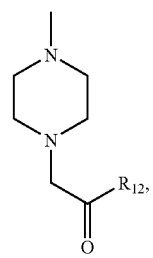
(IX)

where $R_9$ and $R_4$ are as described previously. In various embodiments, the heavy atom isotope enrichment used to distinguish tags in a set of tags uses tags where such isotopic enrichment is of an atom of the piperazine ring, an atom directly bonded to an atom of the piperazine ring, an atom of $R_4$, or combinations thereof.

It is to be understood that not every member of a set of mass differential tags is heavy atom isotopically enriched according to the present teaching. For example, a set of mass differential tags within the present teachings could comprise two or more compounds selected from compounds of the general formulas (IXa)-(IXl):

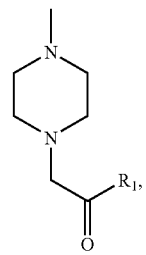
(IXa)

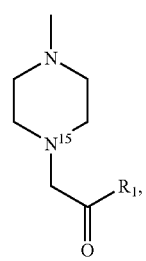
(IXb)

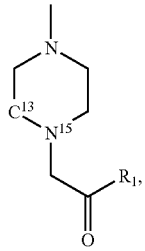 (IXc)

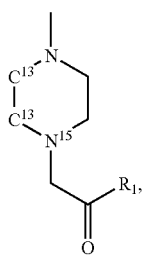 (IXd)

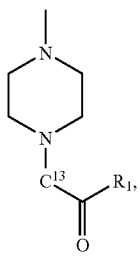 (IXe)

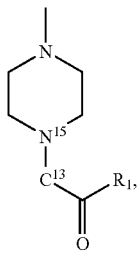 (IXf)

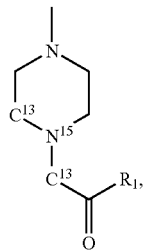 (IXg)

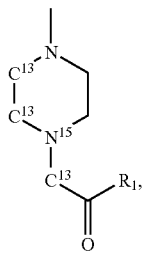 (IXh)

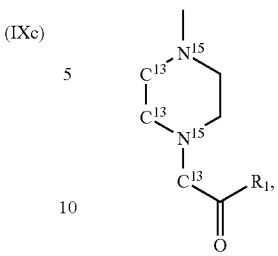 (IXi)

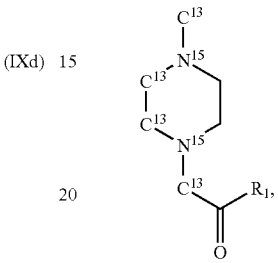 (IXj)

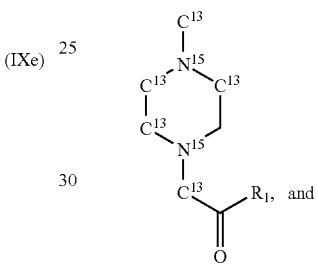 (IXk)

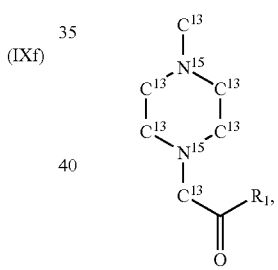 (IXl)

or salt or hydrate forms thereof, where member (IXa), for example, is not isotopically enriched.

In various embodiments, provide are sets of isobaric tags comprising two or more N-substituted piperazine compounds of the general formula (X):

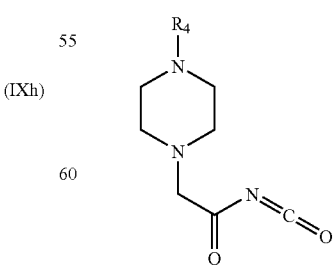 (X)

wherein $R_4$ is methyl, n-propyl, isopropyl, n-butyl, sec-butyl, or tert-butyl, and each member of the set of isobaric tags is heavy atom isotopically enriched. In various embodiments, a set isobaric tags comprises two or more tags of the general formulas (Xa)-(Xd):

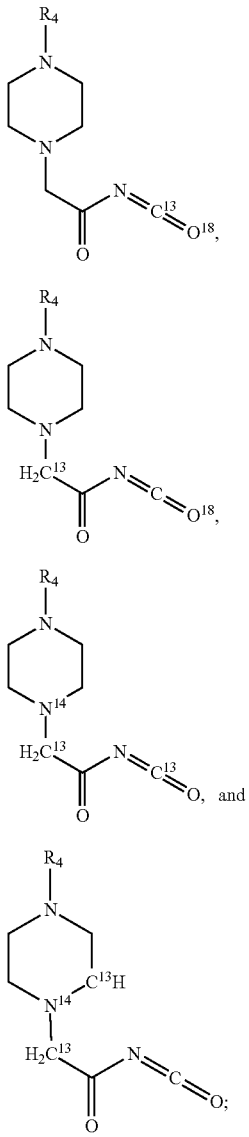

wherein $R_4$ is methyl, ethyl, n-propyl, isopropyl, n-butyl, sec-butyl, or tert-butyl.

Isobaric Labels

In various embodiments, the present teachings provide isobaric labeling reagents, labeled analytes, methods of labeling and analysis for hydroxylated compounds. In general, an isobaric label of the present teachings comprises at least one reporter group portion and a balance group portion. For example, FIGS. 13, 14 and 16 provide various non-limiting examples of label structures that can serve as isobaric labels in various embodiments of the present teachings.

Referring to FIG. 13, in various embodiments, the reporter group portion (1302) comprises an N-substituted piperidine, piperazine or morpholine linked to a balance group portion (1304) by a nitrogen atom (1306) of the reporter group portion. A variety of balance group moieties can be used to provide an isobaric tag. In various embodiments, the balance group comprises a reactive center for reaction with a hydroxyl on an analyte of interest. For example, in various embodiments the balance group comprises a carbonyl (C=O) reactive center that forms a bond to the analyte through and oxygen atom of the analyte.

In various embodiments, when a labeled analyte (1308) is subjected to fragmentation, at least the bond between the nitrogen (1306) and the balance group portion (1310) of the labeled analyte (1308) breaks producing a reporter ion that in various embodiments is an ion of the acetamide N-substituted piperidine, piperazine or morpholine (1312).

Referring to FIG. 14, in various embodiments of isobaric tags of the present teachings and various embodiments of their associated reporter ions are schematically illustrated. Depicted are four isobaric tags of a set of isobaric tags each tag comprising a reporter portion (RP) and a balance group portion (BG). In this example each tag is a (4-Methyl-piperazin-1-yl)-acetyl isocyanate with various heavy atom isotope substitutions (indicated by an asterisk). In various embodiments, one or more analytes from one or more samples are labeled with an isobaric tag, the labeled analytes mass filtered (e.g., with a TOF MS, a RF Multipole MS, a ion mobility MS, etc.) and subjected to fragmentation (e.g., collision induced dissociation (CID), photodissociation, etc.) to produce a reporter ion (1422, 1424, 1426, 1428) that can be detected by mass spectrometry.

Reporter Groups & Ions

The reporter group portion of an isobaric tag of the present teachings can be a group that produces a reporter ion from a labeled analyte when the labeled analyte is subjected to fragmentation; this reporter ion having a substantially consistent mass and/or mass-to-charge ratio that can be determined by mass spectrometry. In the present teachings, the reporter ions of different isobaric tags in set of isobaric tags have different masses and/or mass-to-charge ratios (m/z). Different reporter groups and ions can comprise one or more heavy atom isotopes to achieve the differences in mass or m/z between different tags. For example, heavy atom isotopes of carbon ($^{12}C$, $^{13}C$ and $^{14}C$), nitrogen ($^{14}N$ and $^{15}N$), oxygen ($^{16}O$ and $^{18}O$), sulfur ($^{32}S$, $^{33}S$ and $^{34}S$), and/or hydrogen (hydrogen, deuterium and tritium) can be used in the preparation of a diverse group of reporter groups and ions.

A reporter ion can be associated with a sample of interest thereby labeling one or multiple analytes of that sample with an isobaric tag of the present teachings having the corresponding reporter group. In this way, e.g., information about the reporter ion can be associated with information about one or all of the analytes of the sample. In various embodiments, ions of the labeled analyte are fragmented to thereby produce daughter fragment ions and detectable reporter ions. The detected reporter ion signal can be used, e.g., to identify the sample from which an analyte originated. The detected reporter ion signal can be used, e.g., to determine the relative or absolute amount (often expressed as a concentration and/or quantity) of analyte in the sample or samples. For example, the amount of a labeled analyte in a sample can be determined by comparing the reporter ion signal to those of other reporter ions, a calibration standard, etc. In various embodiments, information such as the amount of one or more analytes in a particular sample, can be associated with the reporter ion that corresponds to the reporter group of the isobaric tag used to label each particular sample. In various embodiments, information on the identity of the analyte or analytes can be correlated with information pertaining to the different reporter ions to thereby facilitate the determination of the identity and amount of each labeled analyte in one or a plurality of samples.

The reporter group can comprise a fixed charge or can be capable of becoming ionized. In various embodiments, use can be made of a reporter group having a fixed charge or being capable of being ionized, to isolate and/or use the isobaric tag to label an analyte in a salt, in a mixture of salts), in zwitterionic form, or a combination thereof Ionization of the reporter group facilitates its determination in a mass spectrometer. When ionized, the reporter group can comprise one or more net positive or negative charges. Thus, the reporter group can comprise one or more acidic groups or basic groups since various embodiments of such groups can be easily ionized in a mass spectrometer. For example, the reporter group can comprise one or more basic nitrogen atoms (positive charge) or one or more ionizable acidic groups such as a carboxylic acid group, sulfonic acid group or phosphoric acid group (negative charge). Examples of reporter groups comprising a basic nitrogen include, but are not limited to, substituted or unsubstituted, morpholines, piperidines or piperazines.

The reporter group can be selected so that it produces a reporter ion that does not substantially sub-fragment under conditions typical for the analysis of an analyte. In various embodiments, the reporter ion can be chosen so that it does not substantially sub-fragment under conditions of dissociative energy applied to cause fragmentation of the bond between the nitrogen of the alkyl amide of the reporter group and the balance group. By "does not substantially sub-fragment" we mean that fragments of the reporter ion are difficult or impossible to detect above background noise when applied to the successful analysis of the analyte of interest.

The mass of a reporter ion can be selected to be different as compared with the mass of the analyte of interest and/or any of the expected fragments of the analyte. For example, where proteins or peptides are the analytes, the reporter ion's mass can be chosen to be different as compared with any naturally occurring amino acid or peptide, or expected fragments thereof.

In various embodiments of the present teachings, the parent ion is a steroid labeled with an isobaric tag and the daughter ion is a reporter ion of the isobaric tag; accordingly, the ion signal of a reporter ion that is measured at a detector for a given isobarically labeled steroid parent ion can be referred to as a "labeled steroid-reporter ion transition signal". Similarly, the ion signal of a reporter ion that is measured at a detector for a given isobarically labeled standard compound can be referred to as a "labeled standard-reporter ion transition signal".

Balance Groups

In various embodiments, the isobaric tags of the present teachings comprise a reporter group and a balance group where the combined mass of the reporter and balance group is such that each tag of a set of isobaric tags has substantially the same mass. In various embodiments, the balance group comprises one or more carbonyl groups (C=O). In various embodiments, an analyte is linked to the tag by an oxygen atom through a carbonyl carbon of the balance group to form a labeled compound.

In various embodiments, the balance group also acts as a leaving group upon subjecting a labeled analyte to fragmentation. For example, in various embodiments the balance group comprises a carbonyl moiety, bound to the analyte through an oxygen atom of the analyte, which upon fragmentation leaves as carbon dioxide.

The present teachings provide many embodiments of labeling reagents. FIG. 5 illustrates just a few of the many possible reagents illustrating the labeling of cholesterol with three different labels (502). FIGS. 6A-9E provide further non-limiting illustrations of various labeling methods and labeled analyte compounds within the present teachings.

It is to be understood that herein the methods of labeling, of adding labels to compounds and the descriptions of, e.g., providing and adding labels include both single step reaction of, e.g., a compound of formula (I) or addition of a compound of formula (I) by a multi-step reaction (see, e.g., FIGS. 6B, 17, 19 and 52). For example, in various embodiments, the step of adding a label of formula (I), or a salt or a hydrate form thereof, to a compound to label the compound comprises a two step reaction where a first portion of the label (e.g., a moiety comprising portion $R_1$ in formula (I)) followed by a second step adding a second portion of the label (e.g., a moiety comprising portion Z in formula (I)) to effect the labeling of a standard compound.

FIG. 10 schematically depicts a label comprising a reporter group (1002) and a balance group (1004), according to various embodiments of general formula (I) and a labeled analyte compound (1008) according to various embodiments of general formula (II) and illustrates various embodiments of bond breakage upon CID of the labeled compound. In various embodiments, the labeled compound produces a reporter ion by fragmentation of bond between the amine (1006) and carbonyl (1010). In various embodiments, the labeled compound can fragment at two or more points.

Labeled Analytes

In various aspects, the present teachings provide labeled hydroxyl containing compounds that can be represented by the general formula (XI):

RP—BX-LG-O—BY-AR (XI), where AR is a ring containing compound, LG represents a linker group, BX represents a bond between RP and an atom of LG, O is an oxygen, and BY represents a bond between the oxygen O and a carbon of AR that was hydroxylated prior to the labeling reaction. In various embodiments, LG acts as a balance group (BG). In various embodiments, LG and O together act as a balance group (BG). In various embodiments, BX represents a bond that breaks upon subjecting the labeled polycyclic ring containing compound to collision induced dissociation (CID). In various embodiments, Both BX and BY represent bonds that breaks upon subjecting the labeled polycyclic ring containing compound to collision induced dissociation (CID).

In various embodiments, a labeled analyte containing compound can produce more than one reporter ion mass per member of the set of tags. For example, in various embodiments, a sample of labeled compounds subjected to CID produces reporter ions of two different m/z values: those produced by fragmentation of bond BX, and those produced by fragmentation of bond BY.

FIG. 11 schematically depicts a labeled analyte compound according to various embodiments of the present teachings and illustrates various embodiments of bond breakage upon CID of the labeled compound. In various embodiments, the labeled compound produces a reporter ion, RP fragment 1, by fragmentation of bond BX (scheme 1101). In various embodiments, the labeled compound can fragment at two or more points. In scheme 1102 the labeled compound can fragment by dissociation of bond BX, bond BY, or both; breakage of bond BY producing a different reporter ion, RP fragment 2. In various embodiments it is thus preferred that heavy atom isotope enrichment, to distinguish members of the set of tags, is of an atom of the RP Fragment 2 portion of the compound.

FIGS. 16A-B schematically depict various embodiments of labeled ring containing compounds (labeled cholesterols) FIG. 16A depicts a cholesterol labeled an isobaric tag where the BG (1604) is a carbonyl —C═O, and bond BX (1606) is the bond between the nitrogen and carbon of the carbonyl; another potential fragmentation point, bond BY, is also indicated. FIG. 16B depicts a cholesterol labeled an isobaric tag where the BG (1614) is a carbonyl —C═O, and bond BX (1616) is the bond between the carbons of the carbonyl groups; another potential fragmentation point, bond BY, is also indicated. In various embodiments, the labeled compound can fragment at two or more points.

In various aspects, the present teachings provide labeled analytes, wherein the analyte comprised at least one hydroxyl group to labeling with a label of the present teachings. In various embodiments, the labeled compounds can be represented by the general formula (II):

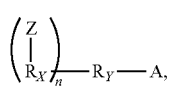

(II)

and can be provided and/or used as a salt or hydrate form thereof In general formula (II): (a) Z can be as given for formula (I); (b) A represents the compound that contained one or more hydroxyl groups prior to formation of the labeled compound; (c) $R_Y$ represents an oxygen atom forming a bond to a carbon atom of A that contained a hydroxyl group prior to formation of the labeled compound; (d) n represents an integer from 1 up to the number of hydroxyl groups in A prior to formation of the labeled compound; and (e) $R_X$ represents a substituted or unsubstituted

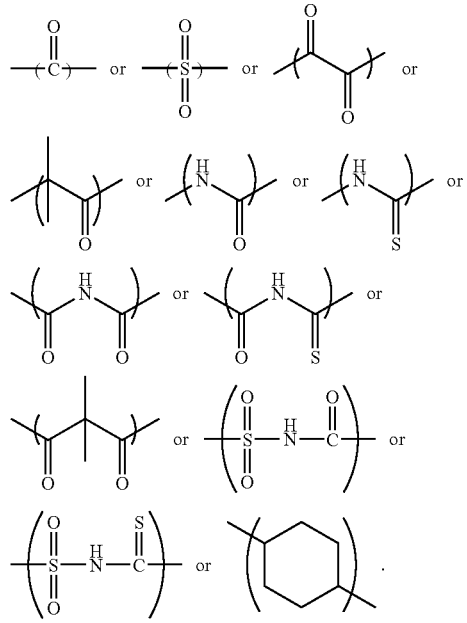

The present teachings are not limited to the analysis of hydroxylated compounds, but can be applied to non-hydroxylated carbonyl bearing compounds by reduction of the carbonyl group prior to labeling with a tag of an embodiments of the present teachings; by reduction in situ with the labeling reaction; or combinations thereof.

In various embodiments, the Z—$R_X$ is of the general formula (IIa)

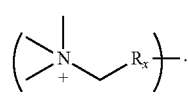

(IIa)

and, in various embodiments, wherein $R_X$ represents

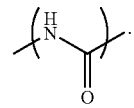

In various embodiments, the labeled analyte compound comprises a tetracyclic ring. In various embodiments, the tetracyclic ring can be represented by the general formula (III)

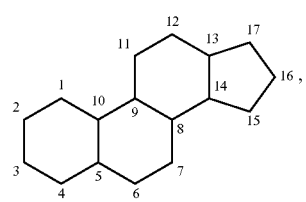

(III)

wherein one or more of the positions on the tetracyclic ring that do not form a bond with $R_Y$ are each independently substituted with a hydrogen, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, alkoxyl, cyano, alkylaryl, or an aromatic or heteroaromatic group. The numbers given in general formula (III) are for positional reference purposes only. In various embodiments, the hydroxylated compound from which A derives comprises a polycyclic ring structure of formula (III) hydroxylated at the 3 position, the 17 position or both.

In various embodiments, a hydroxylated ring containing compound can be a hydroxylated polycyclic ring containing compounds. In various embodiments, the hydroxylated polycyclic ring containing compound can be a tetracyclic compound such as, for example, a sterol, a steroid, etc., including naturally produced as well as synthetic steroids, sterols etc. Examples of steroids containing a hydroxyl bearing ring, include, but are not limited to, cortisol, 11-desoxycortisol (compound S), corticosterone, DHT, testosterone, epitestosterone, desoxymethyltestosterone (DMT), tetrahydrogestrinone (THG), estradiol, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, D4A (delta 4 androstenedione), stigmasterol, and cholesterol. The present teachings are not limited to the analysis of hydroxylated steroids, but can be applied to non-hydroxylated carbonyl bearing steroids by hydroxylation of the carbonyl group prior to labeling with a tag of an embodiments of the present teachings; by hydroxylation in situ with the labeling reaction; or combinations thereof.

In various embodiments, the polycyclic compound comprises a polycyclic ring linked to an aryl, cycloalkyl, or cycloalkene, examples include, but are not limited to, vitamin $D_2$ (sometimes referred to as ergocalciferol), vitamin $D_3$ (sometimes referred to a cholecalciferol), metabolites, and analogs thereof.

In various embodiments, the hydroxylated ring containing compounds include ring containing hormone-like compounds, including, but not limited to, prostaglandin, metabolites, and analogs thereof. In various embodiments, the hydroxylated ring containing compounds include ring containing vitamins including, but not limited to, vitamin $B_2$, vitamin $B_6$, vitamin A, vitamin $A_2$, vitamin E, vitamin K, and metabolites, and analogs thereof.

The hydroxylated compounds to which various aspects and embodiments of the present teachings can be applied can come from a wide variety of source types such as, for example, physiological fluid samples, cell or tissue lysate samples, protein samples, cell culture samples, fermentation broth media samples, agricultural product samples, animal product samples, animal feed samples, samples of food or beverage for human consumption, and combinations thereof. The samples can be from different sources, conditions, or both; for example, control vs. experimental, samples from different points in time (e.g. to form a sequence), disease vs. normal, experimental vs. disease, contaminated vs. non-contaminated, etc. Examples of physiological fluids, include, but are not limited to, blood, serum, plasma, sweat, tears, urine, peritoneal fluid, lymph, vaginal secretion, semen, spinal fluid, ascetic fluid, saliva, sputum, breast exudates, and combinations thereof.

Methods of Labeling

In various aspects, the present teachings provide methods for labeling a hydroxylated compound to form a labeled analyte compound. In various embodiments, the methods comprise reacting a labeling compound of the general formula (I), or a salt or a hydrate form thereof, with a hydroxylated ring containing compound in the presence of one or more coupling agents to form a labeled ring containing compound of the general formula (II). In various embodiments, the step of adding a label of formula (I), or a salt or a hydrate form thereof, to a hydroxylated compound to label it comprises a two step reaction where a first portion of the label (e.g., a moiety comprising portion $R_1$ in formula (I)) is added followed by a second step adding a second portion of the label (e.g., a moiety comprising portion Z in formula (I)) to effect the labeling of the compound with a label of formula (I).

In various embodiments, a hydroxylated compound can be labeled by reacting a compound of the general formula (XIIa):

(XIIa), or a salt or hydrate form thereof, with the hydroxylated compound to form a precursor labeled compound of the general formula (XIIIa):

(XIIIa); and reacting a compound of the general formula (XIVb):

(XIVb), or a salt or hydrate form thereof, with the precursor labeled compound to form a labeled compound of the general formula (II):

(II)

or a salt or hydrate form thereof, where L represents a leaving group; and $R_8$ represents a leaving group, counter ion, or hydrogen. A, Z, n, $R_X$, $R_Y$, X, $R_1$ and $R_2$ can be as described previously for formulas (I) and (II).

In various embodiments, a hydroxylated compound can be labeled by reacting a compound of the general formula (I):

$$Z-R_1 \quad \quad (I),$$

or a salt or hydrate form thereof, with a hydroxylated compound to form a labeled compound of the general formula (II):

(II)

or a salt or hydrate form thereof. A, Z, n, $R_X$, $R_Y$, X, $R_1$ and $R_2$ can be as described previously for formulas (I) and (II).

In various embodiments the methods can include first forming one or more hydroxyl groups on a compound of interest to produce a hydroxylated compound for subsequent labeling. For example, in various embodiments, the methods comprise a step of converting a carbonyl group on the compound into a hydroxyl group. In various embodiments, a base is used in conjunction with the one or more coupling reagents to facilitate the labeling reaction.

A wide variety of coupling agents can be used in various embodiments of the labeling reactions including, but not limited to, hexafluorophosphate compounds (e.g., HATU (2-(1H-7-Azabenzotriazol-1-yl)-1,1,3,3-tetramethyl uronium hexafluorophosphate), HBTU (O-Benzotriazole-N,N,N',N'-tetramethyl-uronium-hexafluorophosphate), HCTU(1H-Benzotriazolium 1-[bis(dimethylamino)methylene]-5 chloro-,hexafluorophosphate (1-),3-oxide)), tetrafuoroborate compound (e.g., TBTU (O-(Benzotriazol-1-yl)-N,N,N',N'-tetramethyluronium tetrafluoroborate)), and a ethyldiethylaminopropylcarbodiimide compounds (e.g., EDC (1-Ethyl-3-(3-dimethylaminopropyl)-carbodiimide)). A wide variety of bases can be used to further facilitate the labeling reaction, including, but not limited to, diisopropylethyl amines (e.g., DIPEA (N,N-diisopropylethylethylamine)).

The labeled analyte compounds of the present teachings can comprise a wide variety of hydroxylated compounds including, but not limited to, polycyclic ring containing compounds. The methods of the present teachings can be applied to a wide variety of hydroxylated compounds to form labeled analyte compounds. FIGS. 3A-3H schematically illustrates several hydroxylated polycyclic ring containing compounds amiable to various embodiments of the methods of the present teachings and FIGS. 3I-3K several hydroxylated ring containing compounds amiable to various embodiments of the methods of the present teachings.

The present teachings, in various embodiments, can be applied to both naturally produced as well as synthetic steroids. Examples of steroids, include, but not limited to, cortisol, 11-desoxycortisol (compound S), corticosterone, DHT, testosterone, epitestosterone, desoxymethyltestosterone (DMT), tetrahydrogestrinone (THG), estradiol, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, D4A (delta 4 androstenedione), stigmasterol, and cholesterol. The present teachings can be applied to bridged polycyclic ring containing compounds as well as fused ring compounds. For example, in various embodiments, the present teachings can be applied to vitamin $D_3$ and its metabolites, see for example FIGS. 3F-3H.

Referring to FIGS. 12A-12B, an example of labeling testosterone and epitestosterone with member of a set of mass differential tags is shown. Schemes 1201-1204 labeling testosterone by reaction with a (4-Methyl-piperazin-1-yl) acetic acid tag in the presence of HATU and DIPEA. Schemes 1205-1208 illustrate the labeling of epistestosterone. In the illustrated reactions, the acetic acid portion of the (4-Methyl-piperazin-1-yl) acetic acid reacts with the hydroxyl on the testosterone or epitestosterone compound to form a labeled compound.

Schemes 1201 and 1205 utilize a non-isotopically encriched (4-Methyl-piperazin-1-yl) acetic acid while the other Schemes use a heavy atom isotope enriched tags from the set of tags. Such mass differential labeling provides a means to distinguish between different samples. For example, the testosterone and epitestosterone subjected to the reactions, respectively, of Schemes 1201 and 1205 may be from a reference sample and that of the remaining Schemes may be from samples under investigation, for example for potential performance enhancing steroid use.

Referring to FIG. 15, various embodiments of labeled cholesterol analytes that have been labeled with an isobaric tag of general formula (X) to form a labeled analyte compound are shown, together with various embodiments of associated reporter ions. FIG. 15 illustrates the labeling (Scheme 1500 to 1503) of cholesterol from 4 samples where different isobaric labels, each comprising an isotopically substituted (4-Methyl-piperazin-1-yl)-acetyl isocyanate, are used between samples. In various embodiments, such labeled samples can be subjected to MS/MS analysis, e.g., passing the labeled compounds through a first mass filter to an ion fragmentor (e.g., a collision cell), subjecting the labeled compounds to dissociate energy, and passing the resulting fragments through a mass filter, detecting the reporter ions, and determining the relative and/or absolute concentration of one or more of the analytes based on the reporter ion signals. In various embodiments where the isobaric tags comprise a N-substituted piperidine, piperazine or morpholine, acetyl isocyanate or acetyl hydrazyl, the resultant reporter ion is an ion of a N-substituted piperidine, piperazine or morpholine carboxy amine, e.g., an ammonium ion. Although a coupling agent is used in the scheme of FIG. 15 such an agent can be omitted but is generally used when the leaving group of the reaction is OH.

In FIG. 15, schemes 1500 and 1503 utilize an isotopically enriched (4-Methyl-piperazin-1-yl)-acetyl isocyanate which differ in the mass of the reporter portion between tags in the set of isobaric tags. Such labeling provides a means to distinguish between different samples. For example, where the ring containing compound of Scheme 1500 and 1501 is testosterone, instead of cholesterol, and that of Scheme 1502 and 1503 is epitestosterone, instead of cholesterol, the monitoring of the various reporter ions, where, e.g., the steroids of Scheme 1500 and 1503 come form a sample to be analyzed, and the steroids of Scheme 1501 and 1503 come from a standard, can be used, e.g., to detect potential performance enhancing steroid use.

A variety of synthetic techniques can be used to form labels of the present teachings with the desired heavy atom isotopic substitutions. Referring to FIG. 17, in various embodiments, an isotopically enriched label of the present teachings can be made by reacting a isotopically enriched substituted or unsubstituted piperidine, piperazine or morpholine (1702), where n=0, 1, or 2 (providing, respectively, a 5, 6 or 7 membered ring); and $R_2$ in FIG. 17 is a substituted or unsubstituted carbon, nitrogen or oxygen. For example, the $R_2$ in FIG. 17 can be substituted with a straight chain or branched $C_1$-$C_6$ alkyl group, or a straight chain or branched $C_1$-$C_6$ alkoxy group. The carbon atoms of the ring can be substituted in one or more positions with, independently, fluorine, chlorine, bromine, iodine, an amino acid side chain, a straight chain or branched $C_1$-$C_6$ alkyl group that may optionally contain a substituted or unsubstituted aryl group. The isotopically enriched substituted or unsubstituted piperidine, piperazine or morpholine (1702) is reacted with an isotopically enriched acetamide (1704) having a leaving group (LG) to form a carboxy amine (1706) containing compound. The carboxy amine (1706) can then be reacted with an electrophile, for example phosgene (1708) to form an isobaric tag (1710).

Referring to FIG. 18, various embodiments of forming a set of (4-Methyl-piperazin-1-yl)-acetyl isocyanate isobaric tags are depicted (Scheme 1800-1803), the asterisks in FIGS. 17 and 18 indicating a heavy atom isotopic substitution.

Methods of Analysis

In various aspects, the present teachings provide methods for analyzing one or more hydroxylated compounds in one or more samples using labels of formula (I) and parent-daughter ion transition monitoring (PDITM).

In various embodiments, the present teachings provide methods for determining the concentration of one or more hydroxylated compounds in two or more samples by adding a different label to each sample, combining the differentially labeled samples and using PDITM to determine concentration of one or more of the hydroxylated compounds in the samples. In various embodiments, one of the samples comprises a standard sample, such as, for example, a control sample, a reference sample, sample with a compound of known concentration, etc. The methods can thus provide an analysis of multiple compounds from multiple samples.

For example, referring to FIG. 4A, in various embodiments, the methods comprises the steps of labeling one or more hydroxylated compounds in two or more samples of interest by adding to each sample of interest a different tag from a set of tags of formula (I), or salt or hydrate forms thereof (step 410a), to form labeled analyte compounds, each tag from the set of tags comprising a reporter ion portion. The labeled analyte compounds being differentially labeled with respect to the sample they come from. In various embodiments, the step of adding a label of formula (I), or a salt or a hydrate form thereof, to label a hydroxylated compound it comprises a two step reaction where a first portion of the label (e.g., a moiety comprising portion $R_1$ in formula (I)) is added followed by a second step adding a second portion of the label (e.g., a moiety comprising portion Z in formula (I)) to effect the labeling of the compound with a label of formula (I).

The methods then combine at least a portion of each of the samples to produce a combined sample (step 420a) and subject at least a portion of the combined sample to parent-daughter ion transition monitoring (where the transmitted parent ion m/z range includes a m/z value of the labeled analyte compound and the transmitted daughter ion m/z range includes a m/z value of a reporter ion corresponding to the tag of the labeled analyte compound) and measuring the ion signal of one or more of the transmitted reporter ions (step 430a). The concentration of one or more of the labeled analyte compounds can then be determined based at least on a comparison of the measured ion signal of the corresponding reporter ion to one or more measured ion signals of a standard compound (step 440a). The ion signal(s) can, for example, be based on the intensity (average, mean, maximum, etc.) of the ion peak, an area of the ion peak, or a combination thereof. In various embodiments, one or more of the two or more samples of interest can be a standard sample containing one or more the standard compounds.

In various embodiments, the concentration of a hydroxylated compound is determined by comparing the measured ion signal of the corresponding labeled analyte compound-reporter ion transition signal to one or more of:

(i) a concentration curve for a standard compound-reporter ion transition; and (ii) a standard compound-reporter ion transition signal for a standard compound in the combined sample with the labeled analyte compound.

In various embodiments, PDITM can be performed on a mass analyzer system comprising a first mass separator, and ion fragmentor and a second mass separator. The transmitted parent ion m/z range of a PDITM scan (selected by the first mass separator) is selected to include a m/z value of one or more of the labeled analyte compounds and the transmitted daughter ion m/z range of a PDITM scan (selected by the second mass separator) is selected to include a m/z value one or more of the reporter ions corresponding to the tag of the transmitted labeled analyte compound.

In various embodiments, the tags added to the two or more samples are selected from a set of tags of formula (I), or salt or hydrate forms thereof, so that, for example, within one experimental measurement: (i) multiple hydroxylated compounds from different samples (e.g., a control, treated, time sequence of samples) can be compared and/or quantified; (ii) multiple concentration measurements can be determined on the same hydroxylated compound from different samples; (iii) different isolates of a blood sample can be evaluated against a baseline sample; etc.

Referring again to FIG. 4A, in various embodiments, the step of subjecting at least a portion of the combined sample to PDITM comprises introducing the combined sample directly into a mass analyzer system (workflow path 421a and step 430a), e.g., by introduction of the combined sample in a suitable solution using an electrospray ionization (ESI) ion source.

In various embodiments, the step of subjecting at least a portion of the combined sample to PDITM comprises loading the portion of the combined sample on a chromatographic column (e.g., a LC column, a gas chromatography (GC) column, or combinations thereof) (workflow path 422a and step 425a), subjecting at least a portion of the eluent from the chromatographic column to parent-daughter ion transition monitoring and measuring the ion signal of one or more of the transmitted reporter ions (workflow path 423a and step 430a).

In various embodiments, the combined sample is cleaned up (e.g., to remove, e.g., interfering sample, buffer artifacts, etc; by high performance liquid chromatography (HPLC), reverse phase (RP)-HPLC, exchange fractionation, cation exchange, high resolution cation exchange, etc., and combinations thereof) before it is used to measure a reporter ion signal.

In various embodiments, the chromatographic column is used to separate two or more labeled analyte compounds, which differ in the analyte portion of the labeled compound. For example, in various embodiments, a first labeled analyte compound found in one or more of the samples is separated by the chromatographic column from a second labeled analyte compound found in one or more of the samples. In various embodiments, two or more different labeled analyte compounds are separated such that the different compounds do not substantially co-elute. Such chromatographic separation can further facilitate the analysis of multiple compounds in multiple samples by, for example, providing chromatographic retention time information on a compound.

Referring again to FIG. 4A, the one or more measured ion signals of a standard compound used in the step of determining the concentration of one or more of the labeled analyte compounds (step 440a) can be provided in many ways. In various embodiments, one or more non-isotopically enriched standard compounds are labeled with an tag from the set of tags of formula (I), or salt or hydrate forms thereof, and at least a portion of one or more of the one or more labeled standard compounds is combined with at least a portion of each of the labeled analyte compounds to produce a combined sample (step 450a); followed by subjecting at least a portion of this combined sample to PDITM and measuring the ion signal of one or more of the transmitted reporter ions (step 430a).

In various embodiments, a tag from the set of tags is added to one or more standard samples to provide one or more labeled standard samples, each standard sample containing one or more non-isotopically enriched standard compounds that are labeled by the tag, the tag added to the one or more standard samples being different from the tags added to the samples of interest. In various embodiments, at least a portion of one or more of the one or more labeled standard samples is combined with at least a portion of each of the samples of interest to produce a combined sample (step 450a); followed by subjecting at least a portion of this combined sample to PDITM and measuring the ion signal of one or more of the transmitted reporter ions (step 430a).

The measured ion signals of one or more of the reporters ions corresponding to one or more of the one or more labeled standard compounds in the combined sample can then be used in determining the concentration of one or more of the labeled analyte compounds. Accordingly, in various embodiments, determining the concentration of a labeled analyte compound is based at least on a comparison of the measured ion signal of the corresponding reporter ion to the measured ion signal of one or more reporter ions corresponding to one or more of the one or more labeled standard compounds in the combined sample (step 440a). The step of subjecting at least a portion of this combined sample to PDITM can comprise, e.g., a direct introduction into a mass analyzer system (workflow path 452a and step 430a); first loading at least a portion of this combined sample on a chromatographic column (workflow path 453a and step 425a) followed by subjecting at least a portion of the eluent from the chromatographic column to PDITM and measuring the ion signal of one or more of the transmitted reporter ions (workflow path 423a and step 430a); or combinations thereof.

In various embodiments, two or more of the labeled standard compounds in one or more standard samples are separated by the chromatographic column such that they substantially co-elute with the compound or compounds for which they are a standard.

In various embodiments, determining the concentration of one or more of the labeled analyte compounds (step 440a) is based at least on a comparison of the measured ion signal of the corresponding reporter ion to the measured ion signal of one or more reporter ions corresponding to one or more concentration curves of one or more standard compounds. In various embodiments, a non-isotopically enriched standard compound is provided having a first concentration (step 460a) and labeled with an tag from the set of tags of formula (I), or salt or hydrate forms thereof (step 470a). At least a portion of the labeled standard compound is subjected to parent-daughter ion transition monitoring (where the transmitted parent ion m/z range includes a m/z value of the labeled standard compound and the transmitted daughter ion m/z range includes a m/z value of a reporter ion corresponding to the tag of the labeled standard compound) and the ion signal of the reporter ion is measured (step 480a). The steps of labeling (step 470a) and the steps of PDITM and measuring the ion signal of the transmitted reporter ions (step 480a) are repeated for at least one more standard compound concentration different from the first concentration to generate a concentration curve for the standard compound (step 490a).

The step of subjecting at least a portion of the labeled standard compound to PDITM can comprise, e.g., a direct introduction into a mass analyzer system (workflow path 471a and step 480a) (e.g., by introduction of the combined sample in a suitable solution using an ESI ion source, or mixing the combined sample with a suitable matrix and introducing the sample using a suitable MALDI ion source); first loading at least a portion of this combined sample on a chromatographic column (workflow path 472a and step 475) followed by subjecting at least a portion of the eluent from the chromatographic column to PDITM and measuring the ion signal of one or more of the transmitted reporter ions (workflow path 473a and step 480a); or combinations thereof.

In various embodiments, PDITM on a standard compound can be performed on a mass analyzer system comprising a first mass separator, and ion fragmentor and a second mass separator. The transmitted parent ion m/z range of a PDITM scan (selected by the first mass separator) is selected to include a m/z value of one or more of the labeled standard compounds and the transmitted daughter ion m/z range of a PDITM scan (selected by the second mass separator) is selected to include a m/z value one or more of the reporter ions corresponding to the transmitted standard compound.

In various embodiments, the generation of a concentration curve can use one or more internal standards included in at least a portion of the standard compound to, e.g., facilitate concentration determination, account for differences in injection volumes, etc.

In various embodiments, a concentration curve can be generated by using PDITM to measure the ion signal of a reporter ion associated with the corresponding standard compound and generating a concentration curve by linear extrapolation of the measured concentration such that zero concentration corresponds to zero reporter ion signal. In various embodiments, a concentration curve can be generated by using PDITM to measure the ion signal of a reporter ion associated with the corresponding standard compound at two or more known concentrations and generating a concentration curve by fitting a function to the measured reporter ion signals. Suitable fitting functions can depend, for example, on the response of the detector (e.g., detector saturation, non-linearity, etc.). In various embodiments, the fitting function is a linear function.

Referring again to FIG. 4A, in various embodiments, determining the concentration of one or more of the labeled analyte compounds (step 440a) is based at least on both: (i) a comparison of the measured ion signal of the corresponding reporter ion to the measured ion signal of one or more reporter ions corresponding to one or more concentration curves of one or more standard compounds, and (ii) a comparison of the measured ion signal of the corresponding reporter ion to the measured ion signal of one or more reporter ions corresponding to one or more labeled standard compounds combined with the labeled analyte compounds. In various embodiments, a non-isotopically enriched standard compound is provided having a first concentration (step 460a) and labeled with an tag from the set of tags of formula (I), or salt or hydrate forms thereof (step 470a). A portion of the labeled standard compound is combined with at least a portion of each of the labeled samples to produce a combined sample (workflow path 476a and step 450a), and this combined sample can then be further analyzed as described herein. In various embodiments, a portion of the same labeled standard compound used to produce the combined sample is also used in generating a concentration curve, as described herein.

In various embodiments, the present teachings provide methods for determining the concentration of one or more hydroxylated analyte compounds in one or more samples. For example, referring to FIG. 4B, in various embodiments, the methods comprise the steps of labeling one or more hydroxylated compounds each with a different tag from a set of tags of formula (I), or salt or hydrate forms thereof (step 410b), each tag from the set of tags comprising a reporter ion portion; combining at least a portion of each of the labeled analyte compound to produce a combined sample (step 420b) and subjecting at least a portion of the combined sample to parent-daughter ion transition monitoring (where the transmitted parent ion m/z range includes a m/z value of the labeled analyte compound and the transmitted daughter ion m/z range includes a m/z value of a reporter ion corresponding to the tag of the labeled analyte compound) and measuring the ion signal of one or more of the transmitted reporter ions (step 430b); then determining the concentration of one or more of the labeled analyte compounds based at least on a comparison of the measured ion signal of the corresponding reporter ion to one or more measured ion signals of a standard compound (step 440b). The ion signal(s) can, for example, be based on the intensity (average, mean, maximum, etc.) of the ion peak, an area of the ion peak, or a combination thereof.

In various embodiments, PDITM can be performed on a mass analyzer system comprising a first mass separator, and ion fragmentor and a second mass separator. The transmitted parent ion m/z range of a PDITM scan (selected by the first mass separator) is selected to include a m/z value of one or more of the labeled analyte compounds and the transmitted daughter ion m/z range of a PDITM scan (selected by the second mass separator) is selected to include a m/z value one or more of the reporter ions corresponding to the tag of the transmitted labeled analyte compound.

In various embodiments, the one or more hydroxylated compound samples are labeled with one or more of tags selected from a set of mass differential tags of formula (I), or salt or hydrate forms thereof, so that, for example, within one experimental measurement: (i) multiple hydroxyl containing compounds from different samples (e.g., a control, treated) can be compared and/or quantified; (ii) multiple concentration measurements can be determined on the same hydroxylated compound from the same sample; (iii) different isolates of a blood sample can be evaluated against a baseline sample; etc.

Referring again to FIG. 4B, in various embodiments, the step of subjecting at least a portion of the combined sample to PDITM comprises introducing the combined sample directly into a mass analyzer system (workflow path 421b and step

430b), e.g., by introduction of the combined sample in a suitable solution using an electrospray ionization (ESI) ion source.

In various embodiments, the step of subjecting at least a portion of the combined sample to PDITM comprises loading the portion of the combined sample on a chromatographic column (e.g., a LC column, a gas chromatography (GC) column, or combinations thereof) (workflow path 422b and step 425b), subjecting at least a portion of the eluent from the chromatographic column to parent-daughter ion transition monitoring and measuring the ion signal of one or more of the transmitted reporter ions (workflow path 423b and step 430b).

In various embodiments, the combined sample is cleaned up (e.g., to remove, e.g., interfering sample, buffer artifacts, etc; by high performance liquid chromatography (HPLC), reverse phase (RP)-HPLC, exchange fractionation, cation exchange, high resolution cation exchange, etc., and combinations thereof) before it is used to measure a reporter ion signal.

In various embodiments, the concentration of a hydroxylated compound is determined by comparing the measured ion signal of the corresponding labeled analyte compound-reporter ion transition signal to one or more of:

(i) a concentration curve for a standard compound-reporter ion transition; and (ii) a standard compound-reporter ion transition signal for a standard compound in the combined sample with the labeled analyte compound.

Referring again to FIG. 4, the one or more measured ion signals of a standard compound used in the step of determining the concentration of one or more of the labeled analyte compounds (step 440b) can be provided in many ways. In various embodiments, one or more non-isotopically enriched standard compounds are labeled with an tag from the set of mass differential tags of formula (I), or salt or hydrate forms thereof, and at least a portion of one or more of the one or more labeled standard compounds is combined with at least a portion of each of the labeled analyte compounds to produce a combined sample (step 450b); followed by subjecting at least a portion of this combined sample to PDITM and measuring the ion signal of one or more of the transmitted reporter ions (step 430b).

The measured ion signals of one or more of the reporters ions corresponding to one or more of the one or more labeled standard compounds in the combined sample can then be used in determining the concentration of one or more of the labeled analyte compounds. Accordingly, in various embodiments, determining the concentration of a labeled analyte compound is based at least on a comparison of the measured ion signal of the corresponding reporter ion to the measured ion signal of one or more reporter ions corresponding to one or more of the one or more labeled standard compounds in the combined sample (step 440b). The step of subjecting at least a portion of this combined sample to PDITM can comprise, e.g., a direct introduction into a mass analyzer system (workflow path 452b and step 430b); first loading at least a portion of this combined sample on a chromatographic column (workflow path 453b and step 425b) followed by subjecting at least a portion of the eluent from the chromatographic column to PDITM and measuring the ion signal of one or more of the transmitted reporter ions (workflow path 423b and step 430b); or combinations thereof.

In various embodiments, determining the concentration of one or more of the labeled analyte compounds (step 440b) is based at least on a comparison of the measured ion signal of the corresponding reporter ion to the measured ion signal of one or more reporter ions corresponding to one or more concentration curves of one or more standard compounds. In various embodiments, a non-isotopically enriched standard compound is provided having a first concentration (step 460b) and labeled with an tag from the set of tags of formula (I), or salt or hydrate forms thereof (step 470b). At least a portion of the labeled standard compound is subjected to parent-daughter ion transition monitoring (where the transmitted parent ion m/z range includes a m/z value of the labeled standard compound and the transmitted daughter ion m/z range includes a m/z value of a reporter ion corresponding to the tag of the labeled standard compound) and the ion signal of the reporter ion is measured (step 480b). The steps of labeling (step 470b) and the steps of PDITM and measuring the ion signal of the transmitted reporter ions (step 480b) are repeated for at least one more standard compound concentration different from the first concentration to generate a concentration curve for the standard compound (step 490b).

The step of subjecting at least a portion of the labeled standard compound to PDITM can comprise, e.g., a direct introduction into a mass analyzer system (workflow path 471b and step 480b) (e.g., by introduction of the combined sample in a suitable solution using an ESI ion source, or mixing the combined sample with a suitable matrix and introducing the sample using a suitable MALDI ion source); first loading at least a portion of this combined sample on a chromatographic column (workflow path 472b and step 475b) followed by subjecting at least a portion of the eluent from the chromatographic column to PDITM and measuring the ion signal of one or more of the transmitted reporter ions (workflow path 473b and step 480b); or combinations thereof.

In various embodiments, PDITM on a standard compound can be performed on a mass analyzer system comprising a first mass separator, and ion fragmentor and a second mass separator. The transmitted parent ion m/z range of a PDITM scan (selected by the first mass separator) is selected to include a m/z value of one or more of the labeled standard compounds and the transmitted daughter ion m/z range of a PDITM scan (selected by the second mass separator) is selected to include a m/z value one or more of the reporter ions corresponding to the transmitted standard compound.

In various embodiments, the generation of a concentration curve can use one or more internal standards included in at least a portion of the standard compound to, e.g., facilitate concentration determination, account for differences in injection volumes, etc.

In various embodiments, a concentration curve can be generated by using PDITM to measure the ion signal of a reporter ion associated with the corresponding standard compound and generating a concentration curve by linear extrapolation of the measured concentration such that zero concentration corresponds to zero reporter ion signal. In various embodiments, a concentration curve can be generated by using PDITM to measure the ion signal of a reporter ion associated with the corresponding standard compound at two or more known concentrations and generating a concentration curve by fitting a function to the measured reporter ion signals. Suitable fitting functions can depend, for example, on the response of the detector (e.g., detector saturation, non-linearity, etc.). In various embodiments, the fitting function is a linear function.

In various embodiments, determining the concentration of one or more of the labeled analyte compounds (step 440b) is based at least on both: (i) a comparison of the measured ion signal of the corresponding reporter ion to the measured ion signal of one or more reporter ions corresponding to one or more concentration curves of one or more standard compounds, and (ii) a comparison of the measured ion signal of the corresponding reporter ion to the measured ion signal of one or more reporter ions corresponding to one or more labeled standard compounds combined with the labeled analyte compounds. In various embodiments, a non-isotopically enriched standard compound is provided having a first concentration (step 460b) and labeled with an tag from the set of tags of formula (I), or salt or hydrate forms thereof (step 470b). A portion of the labeled standard compound is combined with at least a portion of each of the labeled analyte compounds to produce a combined sample (workflow path 476b and step 450b), and this combined sample can then be further analyzed as described herein. In various embodiments, a portion of the same labeled standard compound used to produce the combined sample is also used in generating a concentration curve, as described herein.

In various embodiments of the present teachings, including but not limited to the embodiments discussed in the context of FIGS. 4A and 4B, the same standard compound portion used to measure a reporter ion signal, or another portion, can be used to determine parent-daughter ion transition monitoring conditions for the mass analyzer. For example, where the mass analyzer system comprises a liquid chromatography (LC) component, the standard compound can be used to determine chromatography retention times. In various embodiments, the standard compound can be used to determine for a hydroxylated compound its ionization efficiency in the ion source and fragmentation efficiency in the ion fragmentor under various conditions.

The hydroxylated compounds to which various embodiments of the present teachings can be applied can come from a wide variety of source types such as, for example, physiological fluid samples, cell or tissue lysate samples, protein samples, cell culture samples, fermentation broth media samples, agricultural product samples, animal product samples, animal feed samples, samples of food or beverage for human consumption, and combinations thereof. The samples can be from different sources, conditions, or both; for example, control vs. experimental, samples from different points in time (e.g. to form a sequence), disease vs. normal, experimental vs. disease, contaminated vs. non-contaminated, etc. Examples of physiological fluids, include, but are not limited to, blood, serum, plasma, sweat, tears, urine, peritoneal fluid, lymph, vaginal secretion, semen, spinal fluid, ascetic fluid, saliva, sputum, breast exudates, and combinations thereof.

A wide variety of compounds can be used as standard compounds. In various embodiments, a standard compound comprises a non-isotopically enriched hydroxylated compound of interest. In various embodiments, the standard compound can be one or more compounds present in one or more control samples, samples of known concentration, or combinations thereof. In various embodiments, a standard compound is provided for each hydroxylated compound of interest in the analysis.

In various embodiments, a concentration curve for a standard compound can be generated using PDITM to measure the ion signal of a reporter ion associated with the standard compound at two or more known concentrations. In various embodiments, a histological profile of one or more compounds derived, for example, from a time series of samples can be used as a concentration curve over time to determine one or more of a qualitative, relative, or quantitative concentration of one or more compounds. In various embodiments, a histological profile can be used to ascertain, for example, the presence of disease state or increased disposition to a disease state, a genetic or metabolic condition, steroid use, etc.

Any suitable combination of one or more labeled standard compounds, one or more standard samples containing one or more labeled standard compounds, one or more labeled analyte compounds, one or more samples containing one or more labeled analyte compounds, or combinations thereof, can be used in the methods of the present teachings to provide, for example, a combined sample. For example, in general, the number of different labeled components in a combined sample, N, is less than or equal to the number, T, of tags in the set of tags. In any one combined sample, the possible combinations of labeled standard components and one or more labeled analyte components can be expressed as:

$$(S+C) \leq T \quad (1),$$

where T represents the number of tags in the set of tags; S represents the number of labeled standard components with different labels and ranges from 0 to T inclusive; and C represents the number of labeled analyte components with different labels and ranges from 0 to T inclusive. As used here, a component can refer to a compound and can refer to all the compound in a sample where, for example, all compounds in the sample are labeled with the same tag from the set of tags.

For example, in various embodiments, one or more labeled standard compounds (e.g., from a control sample, from a sample of known concentration, etc.) is combined with one or more labeled analyte compounds of interest, the one or more labeled standard compounds providing one or more reporter ion signals that can serve, e.g., as internal concentration standards. In various embodiments, the addition of a labeled standard compound can serve as an internal standard for one or more hydroxyl containing compounds of interest in the combined sample. In various embodiments, a different labeled standard compound is added for each different hydroxylated compound of interest in the combined sample (e.g., S=C), each different labeled standard compound, for example, serving as an internal standard for a different hydroxylated compound of interest.

In various embodiments, two or more of the hydroxylated compounds to be analyzed in the combined sample comprise the same hydroxylated compounds of interest. For example, hydroxylated compounds #1 to #X (where X>1) can comprise the same hydroxylated compound of interest but, e.g., from different samples with a different label being used for each of the different samples. For example, the different samples can be from different points in time for the same system (e.g., athlete, patient, location, etc.) and used e.g., to monitor the progression of some process, e.g., disease, fermentation, etc., the use of performance enhancing steroids, etc. Accordingly, in various embodiments, substantially all labeled compounds in a first sample will be labeled with a first tag from the set of tags; substantially all labeled compounds in a second sample will be labeled with a second tag from the set of tags different from the first; etc. In various embodiments, one or more of the samples comprises a standard sample, wherein in the labeled compounds in the standard sample are labeled with a tag from the set of tags different from that used on the other samples.

In various embodiments, a sample is processed with different I tags used for the same hydroxylated compound. For example, a sample is processed in triplicate, a different tag being used for each of the three portions which are then combined to provide at least in part the combined sample (which can also include one or more standard compounds); to provide, e.g, three measurements of the concentration of the hydroxylated compound in a single experimental analysis of the combined sample. Triplicate, or more generally multiplicate measures, are often required to provide statistically significant and/or accurate results. The ability of various embodiments of the present teachings to provide multiple measures of a hydroxylated compound concentration in a single experimental run can facilitate reducing the inaccuracy due to run-to-run variations.

In various embodiments, a labeled standard compound is not added to the combined sample and, in various embodiments, e.g., the concentration of one or more of the hydroxylated compounds of interest can be determined based at least on a comparison of the corresponding reporter ion signal of the hydroxylated compound to a concentration curve of a standard compound, a standard sample, or both. In various embodiments, a combined sample is cleaned up (e.g., to remove, e.g., interfering sample, buffer artifacts, etc; by high performance liquid chromatography (HPLC), reverse phase (RP)-HPLC, exchange fractionation, cation exchange, high resolution cation exchange, etc., and combinations thereof) before it is used to measure a reporter ion signal.

In various embodiments, provided are method for analyzing one or more steroid containing compounds, sterol containing compounds or analogs thereof in two or more samples. In various embodiments the methods comprise: (a) adding to each of one or more samples of interest a different mass differential tag from a set of mass differential of tags to provide labeled samples, such that a tag labels one or more steroid containing compounds in one or more of the samples of interest to produce a labeled steroid of the general formula (XI):

RP—BX-LG-O—BY-AR  (XI), wherein RP is a reporter portion of a mass differential tag or an isobaric tag, LG is a linking group, O is an oxygen, AR is a ring containing compound of a steroid containing compound, a sterol containing compound, or an analog thereof, wherein BX represents a bond between RP and an atom of LG, and BY represents a bond between the oxygen O and a carbon of A that was hydroxylated prior to the labeling reaction. In various embodiments, LG comprises one or more carbonyl groups.

The labeled samples are combined to provide a combined sample and the combined sample loaded on a chromatographic column. Eluent from the chromatographic column is subjected to parent-daughter ion transition monitoring wherein, (i) a transmitted parent ion m/z range for a given labeled steroid containing compound includes a m/z value of one or more of the labeled ring containing compounds and a first transmitted daughter ion m/z range includes a m/z value of at least one reporter ion corresponding to at least one of the tags of the labeled steroid containing compounds and the ion signal of one or more of the transmitted reporter ions is measured. The concentration of one or more of the labeled steroid containing compounds is determined based at least on a comparison of the measured ion signal of the corresponding reporter ion to the measured ion signal of a reporter ion corresponding to a standard compound.

Kits

In various aspects, this present teachings provide kits for the analysis of hydroxylated compounds. In various embodiments, a kit comprises a set of two or more isobaric tags of a set of isobaric tags of the general formula (I), or a salt or hydrate form thereof, and one or more reagents, containers, enzymes, buffers and/or instructions for use.

In various embodiments, kits of the present teachings comprise one or more sets of supports, each support comprising a different isobaric labeling reagent of the general formula (I), or a salt or hydrate form thereof, cleavably linked to the support through a cleavable linker. Examples of cleavable linkages include, but are not limited to, a chemically or photolytically cleavable linker. The supports can be reacted with different samples thereby labeling the analytes of a sample with the isobaric tag associated with the respective support. For example analytes from different samples can be contacted with different supports and thus labeled with different reporter/linker combinations.

Mass Analyzers

A wide variety of mass analyzer systems can be used in the present teachings to perform PDITM. Suitable mass analyzer systems include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, by interaction with an electron beam (e.g., electron induced dissociation (EID), electron capture dissociation (ECD)), interaction with thermal radiation (e.g., thermal/black body infrared radiative dissociation (BIRD)), post source decay, or combinations thereof.

Examples of suitable mass spectrometry systems for the mass analyzer include, but are not limited to, those which comprise one or more of a triple quadrupole, a quadrupole-linear ion trap (e.g., 4000 Q TRAP® LC/MS/MS System, Q TRAP® LC/MS/MS System), a quadrupole TOF (e.g., QSTAR® LC/MS/MS System), and a TOF-TOF.

Suitable ion sources for the mass spectrometry systems include, but are not limited to, an electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. One of several desirable features of ESI is that fractions from the chromatography column can proceed directly from the column to the ESI ion source.

In various embodiments, the mass analyzer system comprises a MALDI ion source. In various embodiments, at least a portion of the combined sample is mixed with a MALDI matrix material and subjected to parent-daughter ion transition monitoring using a mass analyzer with a MALDI ionization source. In various embodiments, at least a portion of the combined sample loaded on chromatographic column and at least a portion of the eluent mixed with a MALDI matrix material and subjected to parent-daughter ion transition monitoring using a mass analyzer with a MALDI ionization source.

In various embodiments, the mass spectrometer system comprises a triple quadrupole mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can include an ion trap disposed between the ion source and the triple quadrupoles. The ion trap can be set to collect ions (e.g., all ions, ions with specific m/z ranges, etc.) and after a fill time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

In various embodiments, one or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

In various embodiments, the mass spectrometer system comprises two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

In various embodiments, the mass spectrometer system comprises two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

In various embodiments, the mass spectrometer system comprises a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

EXAMPLES

Aspects of the present teachings may be further understood in light of the following examples, which are not exhaustive and which should not be construed as limiting the scope of the present teachings in any way.

Examples 1-4

In Examples 1-4 the following materials and methods were used unless stated otherwise.

The labeling reagent was added in a two-step reaction substantially as illustrated in FIG. 19. The first step was conducted in a THF (tetrahydrofuran) solution. The second step was conducted in ethyl acetate (EtOAc), in the presence of a tetrabutylammonium iodide ($Bu_4N^+I^-$) catalyst.

An Applied Biosystems/MDS Sciex 3200 Q Trap® brand or 5000 Q Trap® brand LC/MS/MS system was used to obtain the chromatographic and mass spectral data. The MS/MS data was obtained using a nitrogen collision gas (at a pressure in the range between about 1 millitorr to 10 millitorrs). The chromatographic set-up comprised a binary gradient HPLC system equipped with an autosampler, C18 reverse phase column and column heater.

Table 1 further summarizes various experimental conditions for Examples 1-4, where the notation N-M-PIP before a compound name refers to the labeled analyte.

TABLE 1

| Compound | LC gradient | MRM transition | DP (V) | CE (V) |
|---|---|---|---|---|
| N-M-PIP Vitamin D3 | 20-90% B in 7 min (A = MeOH/water 9/1 B = IPA/MeOH 1/1) | 568.4→158.1 (DT = 333 msec) | 45.6 | 32 |
| Vitamin D3 | 65-95% B in 7 min | 385.37→259.15 (DT = 333 msec) | 25 | 23 |
| N-M-PIP Estradiol | 5-80% B in 7 min, | 456.2→113.08 456.2→158.11 (DT = 400 and 350 msec) | 44.8 | 65 35 |
| Estradiol | 35-95% B in 7 min | 255.13→159.07 (DT = 350 msec) | 27 | 29 |
| N-M-PIP Cholesterol | 20-90% B in 7 min | 570.38→158.07 (DT = 350 msec) | 43.4 | 35.9 |
| Cholesterol | 56-95% B in 7 min | 369.38→147.12 (DT = 800 msec) | 46 | 37 |

Examples 1-3

Piperzine Isocyanate Labels

Examples 1-3 present data on the effect of CID collision energy (CE) with the nitrogen collision gas on the fragmentation of various analytes labeled with a piperzine isocyante label of and according to the present teachings. Example 1 presents data on labeled estradiol; Example 2 on labeled cholesterol; and Example 3 on various labeled vitamin D compounds and metabolites.

The labeled analytes were subjected to PDITM where the parent ion was the labeled analyte, see e.g., FIGS. 21, 23 and 25 for, respectively examples 1, 2 and 3, and the product ions were scanned. FIGS. 21, 23, and 25 also indicate the fragmentation point (bond broken) to produce various fragments observed in the mass spectra of Example 1 (FIGS. 22A-C); and Example 2 (FIGS. 24A-B). FIG. 26 of Example 3, provides an overview of the signal intensity of various parent daughter ion transitions (where the notation 568-158 in FIG.

26, for example, indicates a parent ion transmission of about 568 amu and a daughter ion transmission of about 158 amu). The arrow in FIG. 27 indicating the very small 184 amu peak observed at CE=45 eV.

Example 3 also illustrates that in various embodiments the piperzine isocyanate label can be used to determine, e.g., the concentration of vitamin D3 and one or more of its metabolites in one or more samples. For example, in various embodiments a set of isobaric piperzine isocyanate labels could be used to determine the concentration of vitamin D3 and one or more of its metabolites in one or more samples according to methods of the present teachings.

Example 4

Chromatographic Improvement

In various aspects, the present teachings provide methods for improving the detection limit of analytes subjected to a chromatographic separation. With out being held to theory, it is believed that various embodiments of labeled analytes of the present teachings facilitate improving the detection limit by reducing system carry over.

Figure 34:
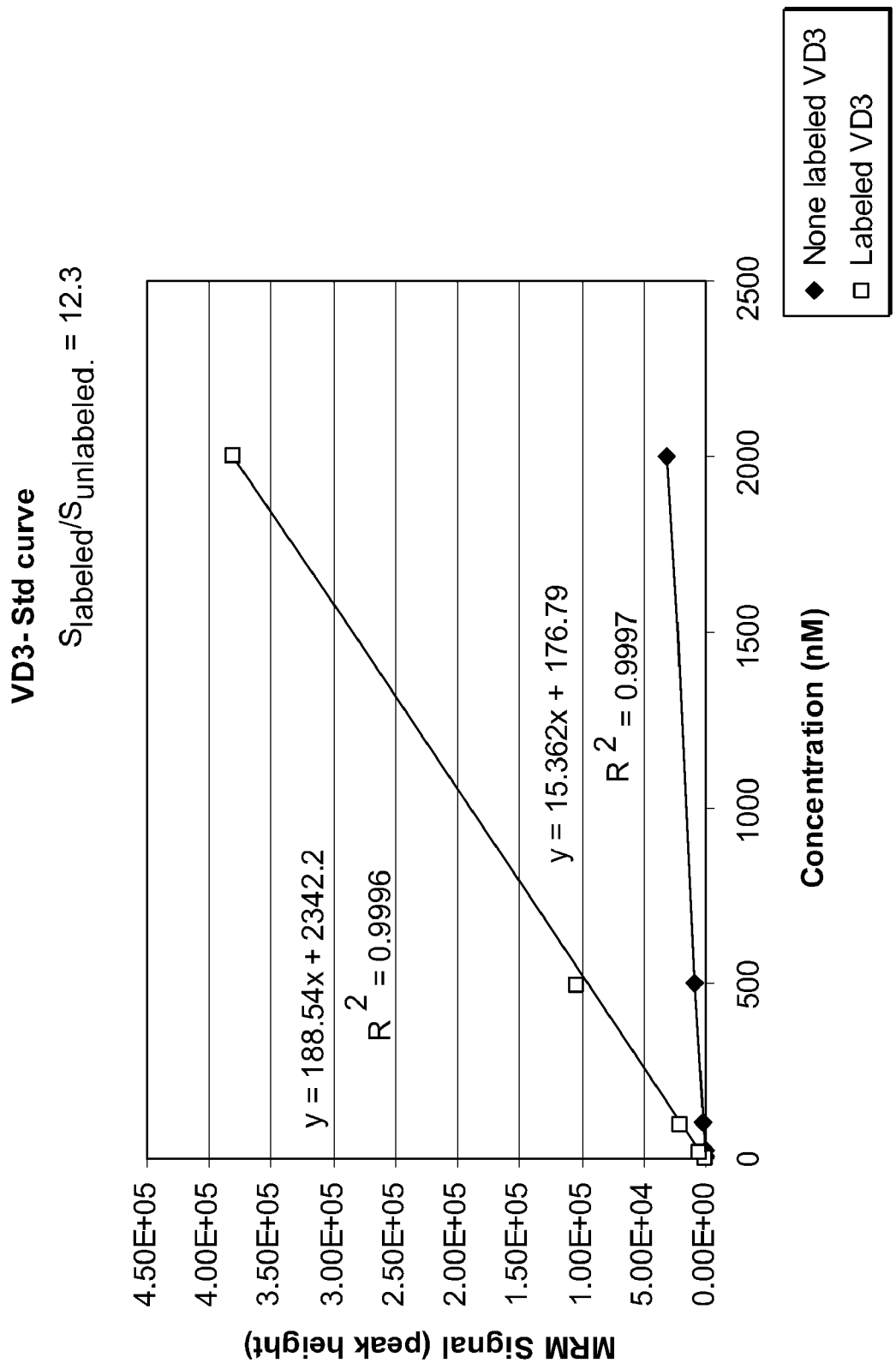

Example 4 presents data on the ability of various embodiments of the present labels to facilitate improving chromatographic signals. FIG. 34 compares signal enhancement obtained with labeled analytes; showing at least an order of magnitude enhancement over a wide range of analyte and labeled analyte concentrations (x-axis in FIG. 34). For example in FIG. 34 the ratio of labeled signal to unlabeled signal is greater than about 12:1. In FIG. 34, the solid diamonds represent unlabeled analyte data and the solid squares represent labeled analyte data.

Figure 36:
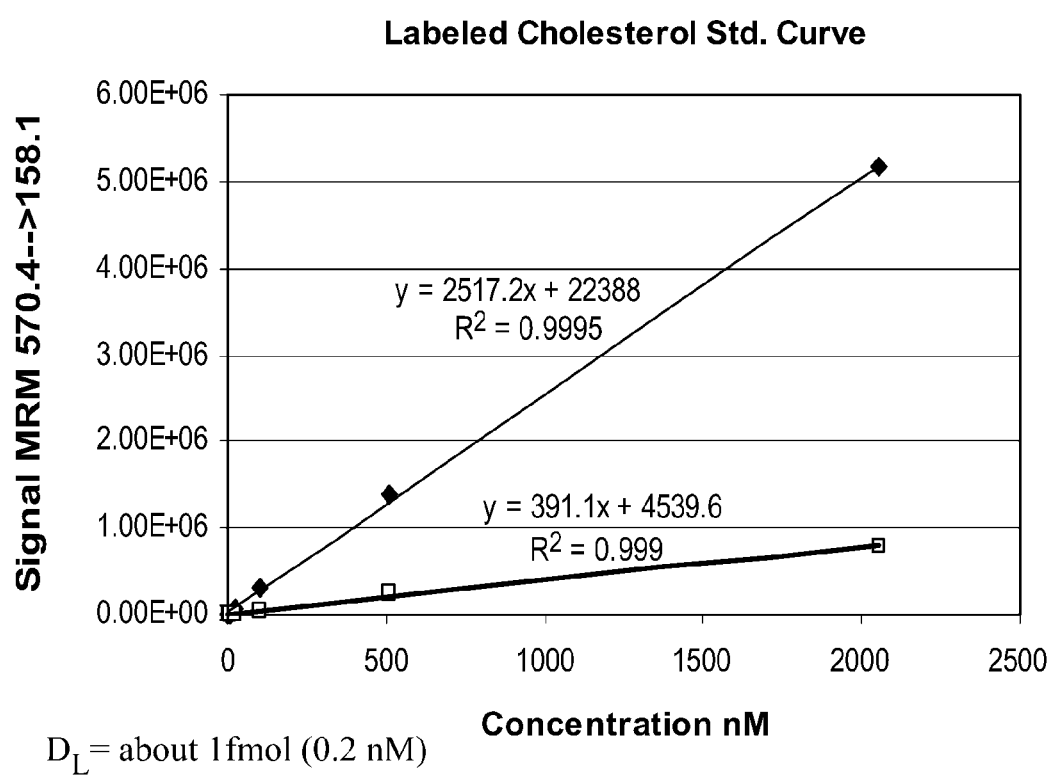
Figure 38:
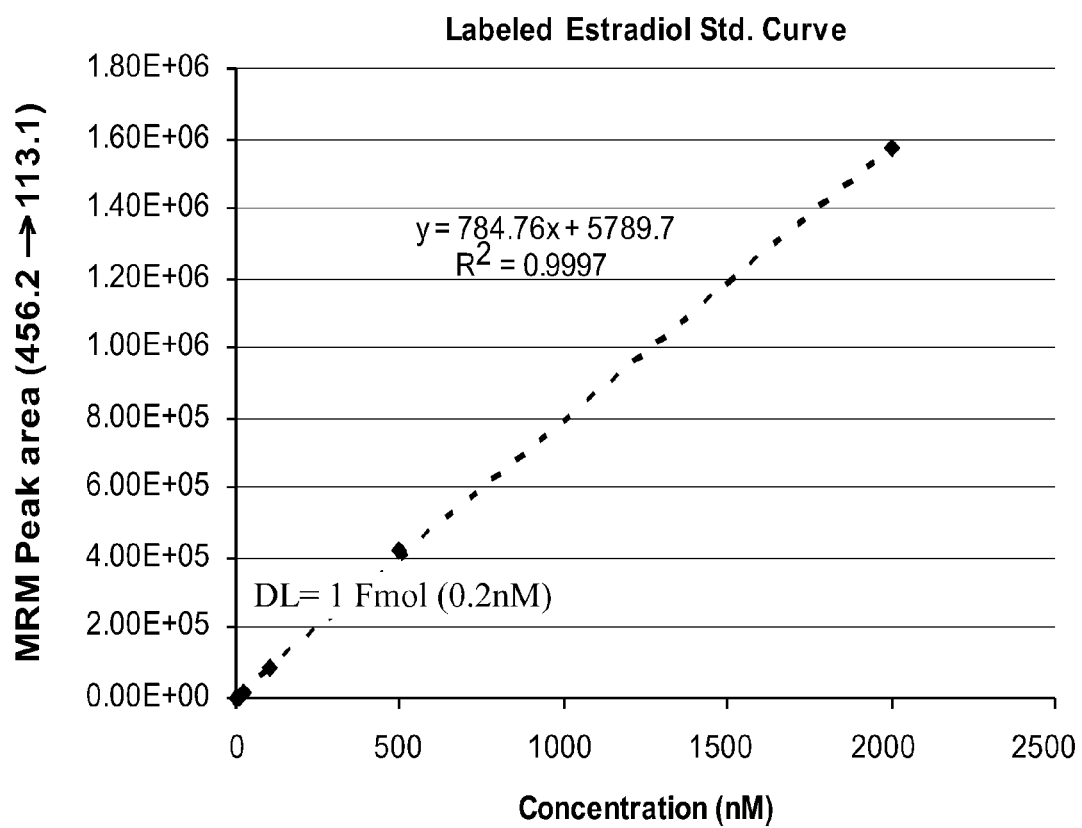

In FIGS. 36 and 38 present data for labeled analyte only; FIG. 36 providing data on peak area and height of the monitored MRM transition. Estimated detection limits (DL) for the labeled analytes are also indicated in the FIGS. 36 and 38.

Figures 37A, 37B:
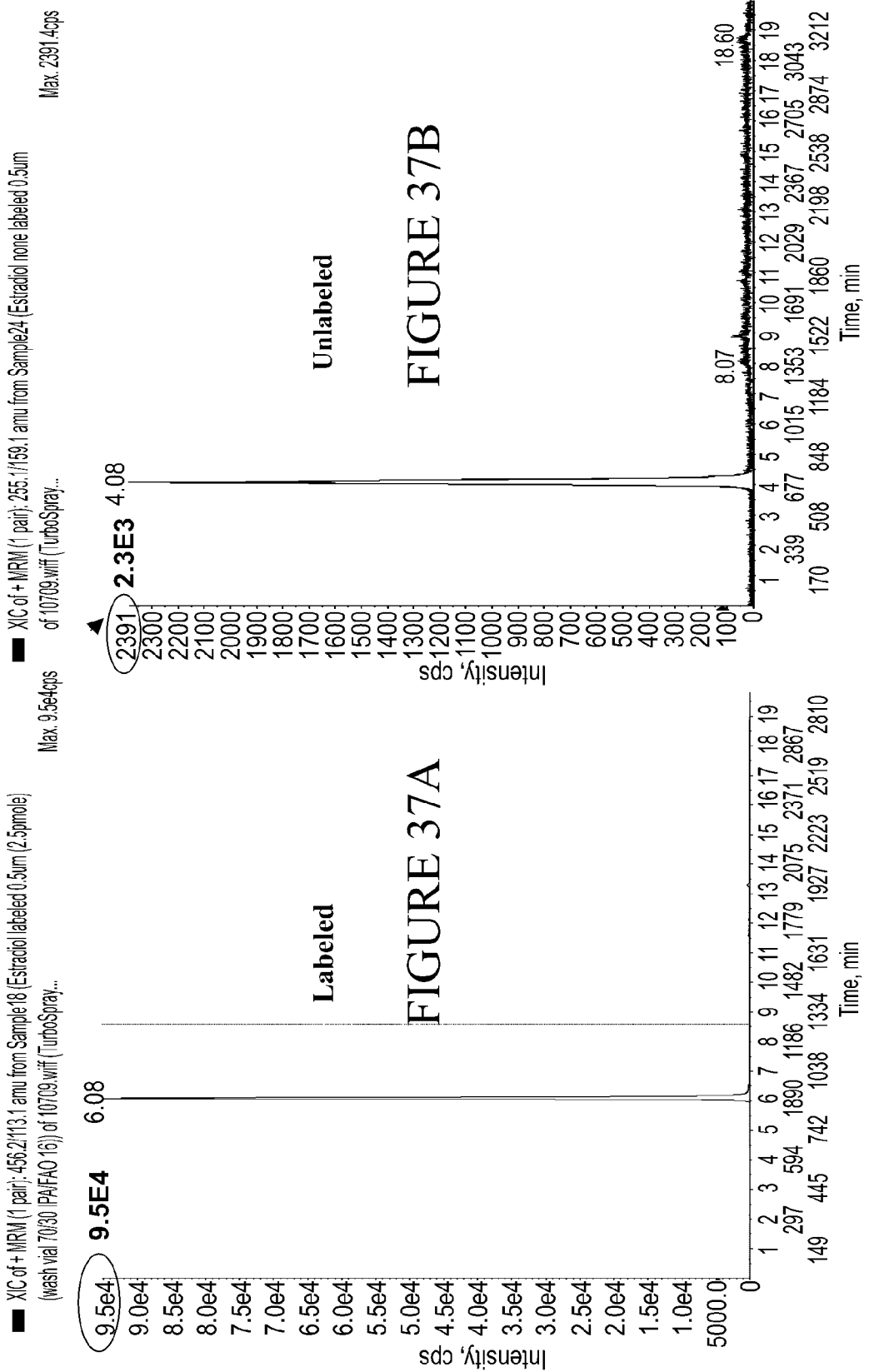

FIGS. 35 and 37 compare MRM spectra for labeled and unlabeled analytes.

Examples 5-10

Mass Differential Data

In the following Examples 5-10, two mass differential tags having a specific and pre-determined Amass are used to label two ring containing compound sample sets (e.g. a standard and a test sample) to give modified ring containing compound derivatives which can be separated by a Amass when analyzed by a mass spectrometer. In various embodiments, the ratio of the intensities of the two m/z peaks can give the relative quantitation of the analyte in the two sample sets. CID can be used to generate one or more reporter ions from the labeled ring containing compounds. The ratio of the intensities of reporter fragments from different tags can also provide information on the relative quantitation of the analyte in the two sample sets. The analyte could thus, for example, be subjected to PDITM monitoring for identification, quantitation, or both.

Although Examples 5-10 present data on mass differential labels, the methods are applicable to the use of isobaric labels by appropriate isotopic substitution in the labels.

In Examples 5-10 the following materials and methods were used unless stated otherwise.

The labeling reaction was conducted in a DMF (dimethylformamide) solution comprising the hydroxyl-containing compound at 0.1M, DIPEA at 1M, and HATU at 0.5 M. The labeling reagents comprised a methylpiperazine acetic acid; the specific reagent(s) used are indicated in the various examples.

Preparation of an activated methylpiperazine acetic acid for the labeling reaction was conducted substantially as follows. Weigh out the methylpiperazine acetic acid and to the methylpiperazine acetic acid add 2 equivalents of 1 M diisopropylethylamine in DMF and vortex to dissolve the acid. Then add 1 equivalent of 0.5 M HATU in DMF, vortex, and let sit for 20 minutes. Examples of various methylpiperazine acetic acid labels are illustrated in general formulas (IXa)-(IXl).

Preparation of labeled hydroxylated ring containing compounds was conducted substantially as follows. Prepare a 0.1 M solution of the hydroxylated ring containing compound in DMF. Add 3 equivalents of the activated methylpiperazine acetic acid prepared above and vortex. Allow to react overnight at room temperature. Dry and redissolve in methanol to a concentration of 1 mg/mL.

An Applied Biosystems/MDS Sciex 3200 Q Trap® brand or 5000 Q Trap® brand LC/MS/MS system was used to obtain the chromatographic and mass spectral data. The MS/MS data was obtained using a nitrogen collision gas (at a pressure in the range between about 1 millitorr to 10 millitorrs). The chromatographic set-up comprised a binary gradient HPLC system equipped with an autosampler, C18 reverse phase column and column heater.

Example 5

Estradiol

The following example illustrates the labeling and mass spectrometric measurements on labeled (labeled with a mass differential tag) estradiol. The inset structures of FIG. 39A illustrate that estradiol either, or both, of the hydroxyl groups on estradiol, at the 3 and 17 positions, can receive the mass differential label.

The estradiol came from Sigma Chemical Co. The labeled estradiol was labeled by reaction with a tag of formula (IXh).

FIG. 39A schematically depicts a chromatogram of a labeled estradiol sample. Two eluent peaks are observed are due to two different labeling possibilities for estradiol at the 3 and 17 position of the tetracyclic ring FIGS. 39B and 39C schematically depict, respectively, electrospray (ESI) mass spectra of the eluent at approximately 5.0 minutes and at 5.3 minutes in FIG. 39A. The peaks at about an m/z value of 417 corresponding to labeled estradiol.

FIGS. 39D and 39E schematically depict, respectively, ESI-MS/MS spectra of the eluent at approximately 5.0 minutes and at 5.3 minutes in FIG. 39A. The peaks at about an m/z value of 117 correspond to the reporter ion of the tag when fragmentation occurs at bond Y, as illustrated in the inset in FIG. 39D. The peaks at about an m/z value of 159 and 163 correspond to the reporter ion of the tag when fragmentation occurs at bond X.

The MS data in this example confirms the mass of the labeled hydroxylated ring containing compound and the MS/MS data shows the production of a reporter ion upon fragmentation by CID and the consistency in the production of the reporter ions indicated by a substantial fraction of the ion signal residing in a reporter ion fragment signal, i.e., m/z values of about 117, 159, and/or 163.

For comparison, FIG. 39F shows an ESI-MS/MS spectra of unlabeled estradiol. It can be seen that the fragmentation of unlabled estradiol is driven through numerous pathways, reducing MRM sensitivity enormously.

Example 6

Testosterone and Epitestoterone

The following example illustrates the labeling and mass spectrometric measurements on labeled (labeled with a mass differential tag) and unlabeled (unlabeled) testosterone and epitestosterone. The inset structures of FIGS. 40A and 41A illustrating the labeling at the 17 position.

The testosterone and epitestosterone came from Sigma Chemical Co. The labeled testosterone and labeled epitestosterone was labeled by reaction with a tag of formula (IXh)

FIGS. 40A and 40B compare, respectively, chromatograms of labeled and unlabeled testosterone, showing earlier elution of the labeled testostrone. FIGS. 40C and 40D schematically depict, respectively, ESI-MS/MS spectra of unlabeled and labeled testosterone. The peak at about an m/z value of 117 corresponds to the reporter ion of the tag when fragmentation occurs as illustrated in the inset, and the peak at about an m/z value of 159 163 correspond to the reporter ion of the tag when fragmentation occurs as illustrated in the inset in FIG. 40D.

FIGS. 41A and 41B compare, respectively, chromatograms of unlabeled and labeled epitestosterone, showing earlier elution of the labeled epitestostrone. FIGS. 41C and 41D schematically depict, respectively, ESI-MS/MS spectra of unlabeled and labeled epitestosterone. The peak at about an m/z value of 117 corresponds to the reporter ion of the tag when fragmentation occurs as illustrated in the inset, and the peak at about an m/z value of 163 corresponds to the reporter ion of the tag when fragmentation occurs as illustrated in the inset in FIG. 41D.

The MS data in this example confirms the mass of the labeled hydroxylated ring containing compound and the MS/MS data shows the production of a reporter ion upon fragmentation by CID and the consistency in the production of the reporter ions indicated by a substantial fraction of the ion signal residing in a reporter ion fragment signal, i.e., m/z values of about 117, 159, and/or 163.

Example 7

Stigmasterol

The following example illustrates the labeling and mass spectrometric measurements on labeled (labeled with a mass differential tag) and unlabeled (unlabeled) stigmasterol. The inset structure of FIG. 42B illustrating the labeling at the 3 position.

The stigmasterol came from a Sigma Chemical Co. The labeled stigmasterol was labeled by reaction with a tag of formula (IXh).

FIGS. 42A and 42B compare, respectively, chromatograms of unlabeled and labeled stigmasterol, showing earlier elution of the labeled stigmasterol. FIG. 42C schematically depicts an ESI-MS/MS spectra of labeled stigmasterol. The peak at about an m/z value of 163 corresponds to the reporter ion of the tag when fragmentation occurs as illustrated in the inset in FIG. 42C.

The MS data in this example confirms the mass of the labeled hydroxylated ring containing compound and the MS/MS data shows the production of a reporter ion upon fragmentation by CID and the consistency in the production of the reporter ions is indicated the fraction of the ion signal residing in a reporter ion fragment signal at an m/z value of about 163.

Example 8

Cholesterol

The following example illustrates the labeling and mass spectrometric measurements on labeled (labeled with a mass differential tag) cholesterol with two different mass differential tags. The inset structure of FIG. 43A illustrating the labeling at the 3 position.

The cholesterol came from Sigma Chemcial Co. Two different tags were used to label cholesterol the "heavy" reagent labeled cholesterol (H) was labeled by reaction with a tag of formula (IXh), and the "light" reagent labeled cholesterol (L) with a tag of formula (IXa).

The data corresponding to the cholesterol labeled using the (IXa) tag is designated as light or L, and that corresponding to the cholesterol labeled using the (IXh) tag is designated as heavy or H.

FIG. 43A schematically depicts a chromatogram of both H and L labeled cholesterol, the components substantially co-elueting. FIG. 43B schematically depicts an ESI-MS/MS spectra of a labeled cholesterol. The peak at about an m/z value of 163 correspond to the reporter ion of the tag when fragmentation occurs at bond X, as illustrated in the inset in FIG. 43B. FIGS. 43C and 43D compare, respectively, ESI-MS spectra of H labeled cholesterol and L labeled cholesterol. FIGS. 43E and 43F compare, respectively, ESI-MS/MS of H labeled cholesterol and L labeled cholesterol.

Finer and broader details can be seen in FIG. 43G and 43H. FIG. 43G shows an smaller portion of n ESI-MS spectra of L labeled cholesterol, while FIG. 43H shows a larger portion of an ESI-MS/MS spectra of L labeled cholesterol.

The MS data in this example confirms the mass of the labeled hydroxylated ring containing compound and the MS/MS data shows the production of a reporter ion upon fragmentation by CID and the consistency in the production of the reporter ions indicated by a substantial fraction of the ion signal residing in a reporter ion fragment signal, i.e., m/z values of about 117, 159, and/or 163.

FIG. 43I shows an ESI-MS/MS spectra of unlabeled cholesterol were it can be seen that the fragmentation of unlabeled cholesterol is driven through numerous pathways, reducing MRM sensitivity enormously.

Example 9

Vitamin D

The following example illustrates the labeling and mass spectrometric measurements on labeled (labeled with a mass differential tag) cholecalciferol (vitamin $D_3$) labeled 25-hydroxycholcalciferol (a metabolite of vitamin $D_3$). The inset structures in FIGS. 44A and 44B illustrating the labeling position.

The cholecalciferol and 25-hydroxycholcalciferol came from Sigma Chemical Co. The cholecalciferol and 25-hydroxycholcalciferol were labeled by reaction with a tag of formula (IXa)

FIGS. 44A and 44B schematically depict, respectively, ESI-MS spectra of labeled cholecalciferol (vitamin $D_3$) and. FIGS. 44C and 44D schematically depict, respectively, ESI-MS/MS spectra for the labeled cholecalciferol (vitamin $D_3$) and labeled 25-hydroxycholcalciferol.

The peak at about an m/z value of 159 corresponds to the reporter ion of the tag when fragmentation occurs as illustrated in the inset in FIGS. 44C and 44D.

Example 10

Prostaglandin

The following example illustrates the labeling and mass spectrometric measurements on a labeled (labeled with a mass differential tag) prostaglandin. The prostaglandin came from Sigma Chemical Co. and was labeled by reaction with a tag of formula (IXa). The inset structures in FIGS. 45A and 45B illustrating the labeling position.

FIG. 45A schematically depicts an ESI-MS spectra and FIG. 45B an ESI-MS/MS spectra for the labeled prostaglandin. The peak at about an m/z value of 159 corresponds to the reporter ion of the tag when fragmentation occurs as illustrated in the inset in FIG. 45B.

The MS data in this example confirms the mass of the labeled hydroxylated ring containing compound and the MS/MS data shows the production of a reporter ion upon fragmentation by CID and the consistency in the production of the reporter ions indicated by a substantial fraction of the ion signal residing in a reporter ion fragment signal at a m/z value of about 159.

Examples 11-12

Benzoyl Isocyante Labels

In Examples 11-12 the following materials and methods were used unless stated otherwise.

The labeling was conducted in a one step reaction substantially as illustrated in FIGS. 46 and 49 for Examples 11 and 12 respectively.

An Applied Biosystems/MDS Sciex 3200 Q Trap® brand or 5000 Q Trap® brand LC/MS/MS system was used to obtain the chromatographic and mass spectral data. The MS/MS data was obtained using a nitrogen collision gas (at a pressure in the range between about 1 millitorr to 10 millitorrs). The chromatographic set-up comprised a binary gradient HPLC system equipped with an autosampler, C18 reverse phase column and column heater.

In both Examples 11 and 12, sodium ions were observed to be added to all the fragments, shifting base fragment mass by about 22 amu. The 122+22=144 amu reporter ion was observable over a range of collision energies, and the 166+>=188 amu reporter was substantially reduced at collision energies above about 30 eV.

Examples 13-14

Trimethylammonium Labels

In Examples 13-14 the following materials and methods were used unless stated otherwise.

The labeling reagent was added in a two-step reaction substantially as illustrated in FIGS. 52 and 55 for Examples 13 and 14 respectively.

Preparation of labeled analyte compounds was conducted substantially as follows in Example 13, to a solution of cholesterol (0.65 mmol) in THF (3 mL) at room temperature chloroacetyl isocyanate (2.6 mmol) was added, mixed by vortexing and then heated at 50° C. for 1 h. Reaction then was allowed to equilibrate to ambient temperature and partitioned between water (4 mL) and EtOAc (10 mL). The EtOAc layer containing the chloroacetyl isocyanate labeled cholesterol was treated with 25 mL of Me$_3$N solution (35% in EtOH) and allowed to react for 40 min at ambient temperature. The reaction mixture was then concentrated in a rotary evaporator and purified by silica gel column chromatography using dichloromethane-methanol-1% Et$_3$N solvent system. Purified material was isolated as chloride salt was a while solid. ES-MS: Calculated M$^+$=529.44, observed=529.40.

Preparation of labeled analyte compounds was conducted substantially as follows in Example 14. In step 1, the chloroacetyl carbamate of vitamin D3 was prepared substantially as follows, to a solution of vitamin D3 (20 mg, 0.052 mmol) in anhydrous THF (500 uL), 4 equivalents of chloroacetyl isocyanate (25 mg, 0.21 mmoL) was added. The reaction mixture was then heated at 50° C. in heating block for 1 hr. A TLC at this point confirmed the completion of the reaction. The reaction mixture was diluted to 5 mL with ethyl acetate and 5 mL of water was added. The resultant mixture was then vortexed for 2 minutes to afford a turbid solution. Layers were separated by centrifugation. The upper organic layer was carefully drawn out using a Pasteur pipette and dried over Na$_2$SO$_4$, filtered and filtrate was concentrated in a speedvac. The resultant yellow solid was directly used for the next step without further purification.

Step 2, was conducted substantially as follows, crude chloroacetyl carbamate of vitamin D3 from the above step was dissolved in ethyl acetate (1 ml) and a solution of trimethyl amine in ethanol (24.5 mg, 99 uL, 0.42 mmol) was added. The mixture was then agitated at RT overnight. An aliquot was analyzed by TLC to confirm the completion of the reaction. The mixture was then concentrated in a speedvac and the residue was triturated with ether. Ether was decanted out after spinning down. The residue was dried under high vacuum to afford a white solid (24 mg, 83% over-all yield) (MS 527 (M+H))

An Applied Biosystems/MDS Sciex 3200 Q Trap® brand or 5000 Q Trap® brand LC/MS/MS system was used to obtain the chromatographic and mass spectral data. The MS/MS data was obtained using a nitrogen collision gas (at a pressure in the range between about 1 millitorr to 10 millitorrs). The chromatographic set-up comprised a binary gradient HPLC system equipped with an autosampler, C18 reverse phase column and column heater.

Example 13 presents data on a labeled cholesterol analyte. A primary reporter ion signal at 117 amu was seen over the ranges of collision energies of this example. Example 14 presents data on a labeled vitamin D3. In Example 14, reporter ion at 117 amu was also the primary ion reporter ion signal seen over the ranges of collision energies of this example. Thus monitoring the ion signal at 117 amu can serve as the reporter ion in various embodiments employing a trimethylammonium label.

Examples 15-17

Examples 15-17 present further data on the labeling of hydroxylated compounds in various embodiments of the present teachings and fragmentation data of labeled analyte compounds. In Examples 15-17, an Applied Biosystems/MDS Sciex 3200 Q Trap® brand or 5000 Q Trap® brand LC/MS/MS system was used to obtain the chromatographic and mass spectral data. The MS/MS data was obtained using a nitrogen collision gas (at a pressure in the range between about 1 millitorr to 10 millitorrs). The chromatographic set-up comprised a binary gradient HPLC system equipped with an autosampler, C18 reverse phase column and column heater.

Example 15

Diethyamino Labels

A diethyamino labeling reagent was added in a two-step reaction substantially as illustrated in FIGS. 58, various theoretical fragmentations are illustrated in FIG. 59 for the labeled analyte, and data on the fragmentation is presented in FIGS. 60A-F.

Example 16

4-Dimethyl Aminophenyl Labels

A 4-dimethyl aminophenyl labeling reagent was added in a two-step reaction substantially as illustrated in FIG. 61, various theoretical fragmentations are illustrated in FIG. 62 for the labeled analyte, and data on the fragmentation is presented in FIGS. 63A-F.

Example 17

N,N Dimethyl Ethylamino Labels

A N,N dimethyl ethylamino labeling reagent was added to a cholesterol, various theoretical fragmentations are illustrated in FIG. 64 for the labeled analyte, and data on the fragmentation is presented in FIGS. 65A-F.

All literature and similar material cited in this application, including, but not limited to, patents, patent applications, articles, books, treatises, and web pages, regardless of the format of such literature and similar materials, are expressly incorporated by reference in their entirety for all purposes. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

The teachings should not be read as limited to the described order or elements unless stated to that effect. It should be understood that various changes in form and detail may be made without departing from the scope of the present teachings. By way of example, any of the disclosed method steps can be combined with any of the other disclosed steps to provide a method of analyzing ring-containing compounds in accordance with various embodiments of the present teachings. Therefore, all embodiments that come within the scope and spirit of the present teachings and equivalents thereto are claimed.

What is claimed is:

1. A set of isobaric labels comprising two or more compounds of the general formula (XIV):

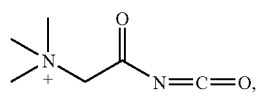

(XIV)

or a salt or hydrate form thereof, wherein each of the isobaric labels of the set of isobaric labels contains one or more heavy atom isotopes.

2. The set of labels of claim 1, wherein each label of the set of labels is isotopically enriched with two or more heavy atom isotopes.

3. The set of labels of claim 1, wherein each label of the set of labels is isotopically enriched with three or more heavy atom isotopes.

4. The set of labels of claim 1, wherein each label of the set of labels is isotopically enriched with four or more heavy atom isotopes.

5. The set of labels of claim 1, wherein the heavy atom isotopes are each independently $^{13}C$, $^{15}N$, $^{18}O$.

6. The set of labels of claim 1, wherein the two or more compounds of the general formula (I) are in the form of a mono-TFA salt, a mono HCl salt, a bis-HCl salt, or a bis-TFA salt, or a hydrate thereof.

7. A set of isobaric labels comprising two or more N-substituted piperidine, piperazine or morpholine compounds of the general formula (XVII):

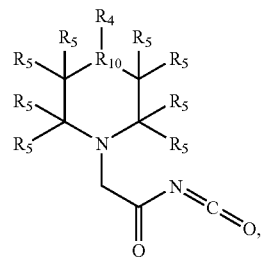

(XVII)

or a salt or hydrate form thereof, wherein each of the isobaric labels of the set of isobaric labels contains one or more heavy atom isotopes, and wherein, $R_{10}$ represents C, N or O;

$R_4$ represents hydrogen, a straight chain or branched $C_1$-$C_6$ alkyl group, or a straight chain or branched $C_1$-$C_6$ alkoxy group; and each $R_5$ represents independently hydrogen, deuterium, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently are bonded to one or more hydrogen, deuterium or fluorine atoms.

8. The set of labels of claim 7, wherein each label of the set of labels is isotopically enriched with four or more heavy atom isotopes.

9. The set of labels of claim 7, wherein the heavy atom isotopes are each independently $^{13}C$, $^{15}N$, $^{18}O$.

10. The set of labels of claim 7, wherein $R_{12}$ represents =C=O.

11. The set of labels of claim 7, wherein $R_{10}$ represents nitrogen.

12. The set of labels of claim 7, wherein $R_4$ represents methyl, ethyl, n-propyl, isopropyl, n-butyl, sec-butyl, or tert-butyl.

13. The set of labels of claim 7, wherein each $R_5$ represents independently hydrogen, methyl or methoxy.

14. The set of labels of claim 7, wherein the two or more N-substituted piperidine, piperazine or morpholine compounds are of the general formula (XVIII):

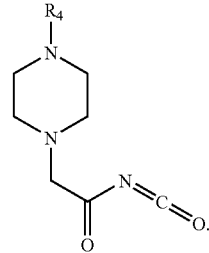

(XVIII)

15. The set of labels of claim 14, wherein $R_4$ is methyl, ethyl, n-propyl, isopropyl, n-butyl, sec-butyl, or tert-butyl.

16. A set of labels comprising two or more compounds of the general formula (I):

$$Z—R_1 \tag{I}$$

or a salt or hydrate form thereof, wherein one or more of the compounds in the set of labels contains one or more heavy atom isotopes and wherein, Z represents a substituted or unsubstituted straight, branched or cyclic alkyl; a substituted or unsubstituted aryl; a substituted or unsubstituted hetero aryl; a substituted or unsubstituted amino; or a substituted thio;

wherein the two or more compounds are of the general formula (V):

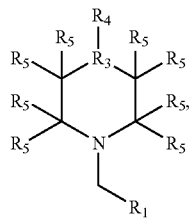

or a salt or a hydrate form thereof, wherein:
$R_1$ represents

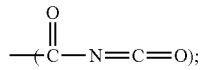

$R_2$ represents a substituted or unsubstituted alkyl; a substituted or unsubstituted halogenated alkyl; or a substituted or unsubstituted aryl, $R_3$ represents C, N, O or S;

$R_4$ represents hydrogen, a straight chain or branched $C_1$-$C_6$ alkyl group, or a straight chain or branched $C_1$-$C_6$ alkoxy group; and each $R_5$ represent independently hydrogen, deuterium, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently are bonded to one or more hydrogen, deuterium or fluorine atoms.

17. The set of labels of claim 16, wherein the labels are isobaric in the unsalted or unhydrated form, and each of the isobaric labels contains one or more heavy atom isotopes.

18. The set of labels of claim 16, wherein the masses of the labels differ by less than about 0.05 amu in the unsalted or unhydrated form.

19. A set of labels comprising two or more compounds of the general formula (I):

$$Z—R_1 \tag{I}$$

or a salt or hydrate form thereof, wherein one or more of the compounds in the set of labels contains one or more heavy atom isotopes and wherein, Z represents a substituted or unsubstituted straight, branched or cyclic alkyl; a substituted or unsubstituted aryl; a substituted or unsubstituted hetero aryl; a substituted or unsubstituted amino; or a substituted thio;

wherein the two or more compounds are of the general formula (IV)

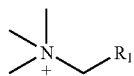

or a salt or hydrate form thereof;
$R_1$ represents

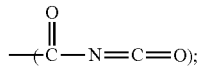

and $R_2$ represents a substituted or unsubstituted alkyl; a substituted or unsubstituted halogenated alkyl; or a substituted or unsubstituted aryl.

20. A set of labels comprising two or more compounds of the general formula (I):

$$Z—R_1 \tag{I}$$

or a salt or hydrate form thereof, wherein one or more of the compounds in the set of labels contains one or more heavy atom isotopes and wherein, Z represents a substituted or unsubstituted straight, branched or cyclic alkyl; a substituted or unsubstituted aryl; a substituted or unsubstituted hetero aryl; a substituted or unsubstituted amino; or a substituted thio;

wherein the two or more compounds are of the general formula (V):

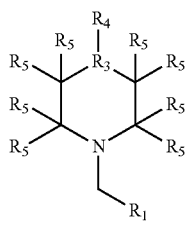

or a salt or a hydrate form thereof, wherein:
$R_1$ represents

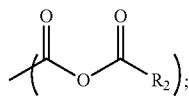

$R_2$ represents a substituted or unsubstituted alkyl; a substituted or unsubstituted halogenated alkyl; or a substituted or unsubstituted aryl;

$R_3$ represents C, N, O or S;

$R_4$ represents hydrogen, a straight chain or branched $C_1$-$C_6$ alkyl group, or a straight chain or branched $C_1$-$C_6$ alkoxy group; and each $R_5$ represent independently hydrogen, deuterium, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently are bonded to one or more hydrogen, deuterium or fluorine atoms.

21. The set of labels of claim 20, wherein each label in the set of labels being differentiated from the another label in the set by a mass difference greater than about 1 amu.

22. A set of labels comprising two or more N-substituted piperidine, piperazine or morpholine compounds of the general formula (XV):

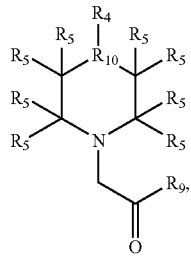

(XV)

or a salt or a hydrate form thereof, wherein:

$R_9$ represents —OC(=O)$R_{11}$, where $R_{11}$ is a straight chain or branched alkyl group;

$R_{10}$ represents C, N or O;

$R_4$ represents hydrogen, a straight chain or branched $C_1$-$C_6$ alkyl group, or a straight chain or branched $C_1$-$C_6$ alkoxy group; and each $R_5$ represents independently hydrogen, deuterium, fluorine, chlorine, bromine, iodine, an amino acid side chain, a straight chain or branched $C_1$-$C_6$ alkyl group that may optionally contain a substituted or unsubstituted aryl group wherein the carbon atoms of the alkyl and aryl groups each independently are bonded to one or more hydrogen, deuterium or fluorine atoms;

wherein one or more of the compounds in the set of tags contains one or more heavy atom isotopes.

* * * * *